(12) United States Patent
Bethune et al.

(10) Patent No.: US 12,215,347 B2
(45) Date of Patent: Feb. 4, 2025

(54) CHIMERIC ANTIGEN RECEPTORS WITH ENHANCED SIGNALING AND ACTIVITIES AND USES THEREOF

(71) Applicant: Allogene Therapeutics, Inc., South San Francisco, CA (US)

(72) Inventors: Michael Thomas Bethune, Castro Valley, CA (US); Yi Zhang, Foster City, CA (US); Thomas John Van Blarcom, Oakland, CA (US); Siler Panowski, Barkeley, CA (US); Barbra Johnson Sasu, San Francisco, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 165 days.

(21) Appl. No.: 17/381,693

(22) Filed: Jul. 21, 2021

(65) Prior Publication Data

US 2022/0023346 A1 Jan. 27, 2022

Related U.S. Application Data

(60) Provisional application No. 63/219,710, filed on Jul. 8, 2021, provisional application No. 63/054,701, filed on Jul. 21, 2020.

(51) Int. Cl.
*C12N 5/0783* (2010.01)
*A61K 39/00* (2006.01)
(Continued)

(52) U.S. Cl.
CPC ........ *C12N 5/0636* (2013.01); *A61K 39/4611* (2023.05); *A61K 39/4631* (2023.05);
(Continued)

(58) Field of Classification Search
CPC ................ A61K 35/17; A61K 39/0011; A61K 2039/5156; C07K 14/7051;
(Continued)

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| WO | WO2012058458 A2 | 5/2012 |
| WO | WO2013153391 A1 | 10/2013 |

(Continued)

OTHER PUBLICATIONS

Palacios, E., Weiss, A. Function of the Src-family kinases, Lck and Fyn, in T-cell development and activation. Oncogene 23, 7990-8000 (2004). (Year: 2004).*

(Continued)

*Primary Examiner* — Jeremy C Flinders
*Assistant Examiner* — Thomas R. Amick
(74) *Attorney, Agent, or Firm* — Allogene Therapeutics, Inc.

(57) ABSTRACT

Provided herein are recombinant antigen receptors, for example chimeric antigen receptors (CARs), that comprise modified cytoplasmic domains that provide improved signalling and thereby provide improved performance and safety. Also provided are polynucleotides encoding the recombinant antigen receptors, vectors comprising the polynucleotides, and engineered immune cells comprising the vectors and/or polynucleotides. The invention further provides methods for engineering immune cells to express the recombinant antigen receptors. Improved recombinant antigen receptor signalling is also provided by co-expressing a first recombinant antigen receptor and a second recombinant (Continued)

antigen receptor or co-expressing a recombinant antigen receptor and a protein involved in transducing the signal from the activated recombinant antigen receptor. Also provided are methods of treating a variety of conditions, including, but not limited to, blood cancers and cancers characterized by solid tumors, by administering the engineered cells to patients suffering from such a condition.

12 Claims, 16 Drawing Sheets

Specification includes a Sequence Listing.

(51) Int. Cl.
   *C07K 14/725* (2006.01)
   *C12N 15/86* (2006.01)
(52) U.S. Cl.
   CPC .. *A61K 39/464402* (2023.05); *C07K 14/7051* (2013.01); *C12N 15/86* (2013.01); *A61K 2239/22* (2023.05)
(58) Field of Classification Search
   CPC .......... C07K 2317/622; C07K 2317/73; C07K 16/28; C07K 2319/33; C07K 2319/03; C12N 5/0636; C12N 15/86; A61P 35/00
   See application file for complete search history.

(56) References Cited

U.S. PATENT DOCUMENTS

| | | | |
|---|---|---|---|
| 4,754,065 | A | 6/1988 | Levenson et al. |
| 4,800,159 | A | 1/1989 | Mullis et al. |
| 4,975,278 | A | 12/1990 | Senter et al. |
| 5,037,743 | A | 8/1991 | Welch et al. |
| 5,143,830 | A | 9/1992 | Holland et al. |
| 5,545,806 | A | 8/1996 | Lonberg et al. |
| 5,545,807 | A | 8/1996 | Surami et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Loneberg |
| 5,750,373 | A | 5/1998 | Garrard et al. |
| 5,858,358 | A | 1/1999 | June et al. |
| 5,883,223 | A | 3/1999 | Gray et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Brenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 2006/0121005 | A1 | 6/2006 | Berenson et al. |
| 2019/0002521 | A1* | 1/2019 | Maher .............. C07K 14/70517 |
| 2019/0365875 | A1 | 12/2019 | Brander et al. |
| 2020/0048618 | A1* | 2/2020 | Cordoba .......... C07K 14/70578 |
| 2021/0107979 | A1* | 4/2021 | Zhang .................... C12N 15/63 |

FOREIGN PATENT DOCUMENTS

| | | | |
|---|---|---|---|
| WO | WO2014039523 | A1 | 3/2014 |
| WO | WO2014184143 | A1 | 11/2014 |
| WO | WO2014184741 | A1 | 11/2014 |
| WO | WO2014184744 | A1 | 11/2014 |
| WO | WO2014191128 | A1 | 12/2014 |
| WO | WO-2018208849 | A1 * | 11/2018 ......... A61K 39/0011 |
| WO | WO-2019165116 | A1 * | 8/2019 ............ A61K 35/17 |
| WO | WO2019210081 | A2 | 12/2019 |
| WO | WO-2020078925 | A1 * | 4/2020 ............ A61K 35/17 |
| WO | WO2020180591 | A1 | 9/2020 |
| WO | WO2020180664 | A1 | 9/2020 |
| WO | WO2020180694 | A1 | 9/2020 |
| WO | WO2021041806 | A1 | 3/2021 |
| WO | WO2020068702 | A1 | 4/2021 |
| WO | WO2022020456 | A2 | 1/2022 |

OTHER PUBLICATIONS

Huston, J. S.; Levinson, D.; Mudgett-Hunter, M.; Tai, M. S.; Novotný, J.; Margolies, M. N.; Crea, R. (1988). Proceedings of the National Academy of Sciences of the United States of America. 85 (16): 5879-5883.) (Year: 1988).*
Perlmutter, R.M., Marth, J.D., Lewis, D.B., Peet, R., Ziegler,S.F. and Wilson, C.B. Structure and expression of lck transcripts in human lymphoid cells). Journal J. Cell. Biochem. 38 (2), 117-126 (1988) (Year: 1988).*
Genseq database search result for WO2019165116-A1, matching Sequence 59 of present application. (Year: 2019).*
Abate-Daga, Daniel , et al., "CAR models: next-generation CAR modifications for enhanced T-cell function", Mol Ther Oncolytics; May 18, 2016;3:16014. doi: 10.1038/mto.2016.14. eCollection 2016.
Al-Lazikani, Bissan , et al., "Standard Conformations for the Canonical Structures of Immunoglobulins", J. Mol. Biol. (1997) 273, 927-948.
Bettini, Matthew L., et al., "CD3 ITAM diversity is required for optimal T cell receptor signaling and thymocyte development", J Immunol. Sep. 1, 2017; 199(5): 1555-1560, doi: 10.4049/jimmunol.1700069.
Bird, Robert E., et al., "Single Chain Antigen-Binding Proteins", Science, vol. 242, Issue 4877, Oct. 21, 1988; DOI: 10.1126/science.3140379.
Boerner, P , et al., "Production of Antigen-Specific Human Monoclonal Antibodies From in Vitro-Primed Human Splenocytes", J Immunol 1991; 147:86-95; http://www.jimmunol.org/content/147/1/86.
Brenner, Malcom K., et al., "Adoptive T Cell Therapy of Cancer", Curr Opin Immunol. Apr. 2010 ; 22(2): 251-257. doi:10.1016/j.coi.2010.01.020.
Capel, Peter J.A., et al., "Heterogeneity of Human IgG Fc Receptors", Immunomethods 4, 25-34 (1994).
Chothia, Cyrus , et al., "Structural Repertoire of the Human VH Segments", J. Mol. Biol. (1992) 227, 799-917.
Cole, S. P.C., et al., "The EBV-Hybridoma Technique and Its Application to Human Lung Cancer", Monoclonal Antibodies and Cancer Therapy pp. 77-96 1985, Alan R. Liss, Inc.
Davenport, A. J., et al., "Chimeric antigen receptor T cells form nonclassical and potent immune synapses driving rapid cytotoxicity", Proc Natl Acad Sci U S A. Feb. 27, 2018;115(9):E2068-E2076. doi: 10.1073/pnas.1716266115. Epub Feb. 12, 2018.
Dayhoff, M. O., "A model of evolutionary change in proteins—Matrices for detecting distant relationships", Atlas of Protein sequence and structure, pp. 345-352, 1978.
De Haas, Masja , et al., "Fc gamma receptors of phagocytes", J Lab Clin Med; Oct. 1995; 126(4):330-41.
EPO , "International Search Report & Written Opinion", mailed on Feb. 4, 2022 for PCT/US2021/042555.
Eshhar, Zelig , et al., "Specific activation and targeting of cytotoxic lymphocytes through chimeric single chains consisting of antibody-binding domains and the gamma or zeta subunits of the immunoglobulin and T-cell receptors.", Immunology; Proc Natl Acad Sci U S A. Jan. 15, 1993; 90(2): 720-724.
Fellouse, F. A., "High-throughput Generation of Synthetic Antibodies from Highly Functional Minimalist Phage-displayed Libraries", J. Mol. Biol.; 2007; 373; 924-940.
Feucht, Judith , et al., "Calibration of CAR activation potential directs alternative T cell fates and therapeutic potency", Nat Med. Jan. 2019 ; 25(1): 82-88. doi: 10.1038/s41591-018-0290-5.
Gait, M. J., "Oligonucleotide Synthesis: A Practical Approach", IRL Press Ltd., Oxford, England, 1984 (TOC).

(56) References Cited

OTHER PUBLICATIONS

Genbank, accession No. CR541888.1 Homo sapiens full open reading frame cDNA clone RZPDo834D06333D for gene CD160, CD160 antigen; complete cds, without stopcodon, 2 total pages.
Genbank, accession No. AAA53133 4-1BB Homo sapiens; total 2 pages.
Genbank, accession No. AY358337.1, Homo sapiens clone DNA54002 SIGLEC10 (UNQ477) mRNA, complete cds, 2 total pages.
Genbank, accession No. NP_006130.1, T-cell-specific surface glycoprotein CD28 isoform 1 precursor, Homo sapience, total 4 pages.
Genbank, accession No. CR542051.1, Home sapiens full open reading frame cDNA clone RZPDo834C0736D for gene LAIR1, leukocyte-associated ig-like receptor 1; complete cds, without stopcodon, 2 total pages.
Genbank, accession No. NM001166664.1, Homo sapiens CD244 molecule (CD244), transcript variant 3, mRNA, 4 total pages.
Genbank, accession No. NM-022153.1, Homo sapiens V-set immunoregulatory receptor (VSIR), mRNA, 5 total pages.
Genbank, accession No. NM-173799.4, Homo sapients T cell immunoreceptor with Ig and ITIM domains (TIGIT), mRNA, 5 total pages.
Genbank, accession No. NM-181780.3, Homo sapiens B and T lymphocyte associated (BTLA), transcript variant 1, mRNA, complete cds, 2 total pages.
Genbank, accession No. NPP_001139345.1, T-cell surface glycoprotein CD8 alpha chain isoform 1 precurse (Home sapiens), 3 total pages.
Gudipati, Venugopal, et al., "Inefficient CAR-proximal signaling blunts antigen sensitivity", Nature Immunology; 21, 848-856 (2020). https://doi.org/10.1038/s41590-020-0719-0.
Guyer, Ruth, et al., "Immunoglobulin Binding by Mouse Intestinal Epithelial Cell Receptors", The Journal of Immunology; vol. 117, No. 2, Aug. 1976.
Hartl, Frederike A., et al., "Noncanonical binding of Lck to CD3ε promotes TCR signaling and CAR function", Nat Immunol; Aug. 2020;21(8):902-913. doi: 10.1038/s41590-020-0732-3. Epub Jul. 20, 2020.
Hoogenboom, Hennie R., et al., "By-passing Immunisation Human Antibodies from Synthetic Repertoires of Germline VH Gene Segments Rearranged in Vitro", J. Mol. Hid. (1!)92) 227. 381-:388.
Jayasena, S. D., et al., "Aptamers: an emerging class of molecules that rival antibodies in diagnostics", Clin Chem. Sep. 1999;45(9):1628-50.
Kabat, Elvin A., et al., "Sequences of Proteins of Immunological Interest", 5th Ed. NIH publication, No. 91-3242; 1992 (TOC).
Kim, Jin-Kyoo, et al., "Localization of the site of the murine IgG1 molecule that is invoiced in binding to the murine Intestinal Fc receptor", Eur. J. Immunol. 1994. 24: 2429-2434.
Köhler, G., et al., "Continuous cultures of fused cells secreting antibody of predefined specificity", Nature, vol. 256, 1975, 495-497.
Sadelain, Michel, et al., "The promise and potential pitfalls of chimeric antigen receptors", Current Opinion in Immunology 2009, 21:215-223.
Li, Lunyi, et al., "Ionic CD3-Lck interaction regulates the initiation of T-cell receptor signaling", PNAS Jul. 18, 2017 114 (29) E5891-E5899; first published Jun. 28, 2017; https://doi.org/10.1073/pnas.1701990114.
Liu, Haiyan, et al., "On the dynamics of TCR:CD3 complex cell surface expression and downmodulation", Immunity; .Nov. 2000;13(5):665-75. doi: 10.1016/s1074-7613(00)00066-2.
MacCallum, Robert M., et al., "Antibody-antigen Interactions: Contact Analysis and Binding Site Topography", J. Mol. Biol. (1996) 262, 732-745.
Majzner, Robbie G., et al., "Tuning the Antigen Density Requirement for CAR T-cell Activity", Cancer Discov.; May 2020;10(5):702-723. doi: 10.1158/2159-8290.CD-19-0945. Epub Mar. 19, 2020.
Makabe, Koki, et al., "Thermodynamic Consequences of Mutations in Vernier Zone Residues of a Humanized Anti-human Epidermal Growth Factor Receptor Murine Antibody, 528", The Journal of Biological Chemistry vol. 283, No. 2, pp. 1156-1166, Jan. 11, 2008.
Marks, James D., et al., "By-passing Immunization Human Antibodies from V-gene Libraries Displayed on Phage", J. Mol. Biol. (1991) 222, 581-597.
McCafferty, John, et al., "Phage antibodies: filamentous phage displaying antibody variable domains", Nature vol. 348, pp. 552-554 (1990).
Mukhopadhyay, Himadri, et al., "Systems Model of T Cell Receptor Proximal Signaling Reveals Emergent Ultrasensitivity", PLoS Comput Biol 9(3):2013; e1003004. doi: 10.1371/journal.pcbi.1003004.
Payne, Gillian, "Progress in immunoconjugate cancer therapeutics", Pipeline, Cancer Cell, vol. 3, pp. 207-212, (2003).
Purbhoo, Marco A., et al., "T cell killing does not require the formation of a stable mature immunological synapse", Nature Immunology; vol. 5, No. 5, 2004, 524-530.
Ravtech, Jefferey V., et al., "Fc Receptors", Annu. Rec. Immunol. 1991 9:457-92.
Remington, "The Science and Practice of Pharmacy", 21st Ed. Mack Publishing, 2005, Table of Contents.
Rosenberg, Steven A., et al., "Adoptive cell transfer: a clinical path to effective cancer immunotherapy", Nat Rev Cancer. Apr. 2008 ; 8(4): 299-308. doi:10.1038/nrc2355.
Sambrook, J., et al., "Molecular Cloning: A Laboratory Manual", Second Ed., Cold Spring Harbor Laboratory Press, 1989 (TOC).
Saitou, Naruya, et al., "The neighbor-joining method: a new method for reconstructing phylogenetic trees", Molecular Biology and Evolution, vol. 4, Issue 4, Jul. 1987, pp. 406-425, https://doi.org/10.1093/oxfordjournals.molbev.a040454.
Sneath, Peter H.A., et al., "Numerical Taxonomy—The Principles and Practice of Numerical Classification", Nature 193, 855-860 (1962) W. H. Freeman and Co. (TOC).
Sun, Chuang, et al., "THEMIS-SHP1 Recruitment by 4-1BB Tunes LCKMediated Priming of Chimeric Antigen Receptor-Redirected T Cells", Cancer Cell 37, 216-225; 202; Elsevier Inc.; https://doi.org/10.1016/j.ccell.2019.12.014.
Sunder-Plassmann, Raute, "Functional analysis of immunoreceptor tyrosinebased activation motif (1TAM)-mediated signal transduction: the two YxxL segments within a single CD3c-ITAM are functionally distinct", Eur. J. Immunol. 1997.27: 2001-2009.
Syrigos, Konstantinos, et al., "Antibody Directed Enzyme Prodrug Therapy (ADEPT): A Review of the Experimental and Clinical Considerations", Review, Anticancer Research 19: 605-614 (1999).
Trail, Pamela A., et al., "Monoclonal antibody drug immunoconjugates for targeted treatment of cancer", Symposium in Writing, Cancer Immunol Immunother (2003) 52: 328-337.
Vaughan, Tristan, et al., "Huinan Antibodies with Sub-nanon1olar Affinities Isolated fron1 a Large Non-In1n1unized Phage Display Library", Nature Biotechnology, vol. 14 1996, 309-314.
Wilbur, W. J., et al., "Rapid Similarity Searches of Nucleic Acid and Protein Data Banks", 1983, Proc. Natl. Acad. Sci. USA vol. 80, pp. 726-730.
Xu, Hua, et al. "A Kinase-Independent Function of Lck in Potentiating Antigen-Specific T Cell Activation"; Cell, vol. 74, 633-643, Aug. 27, 1993.

* cited by examiner

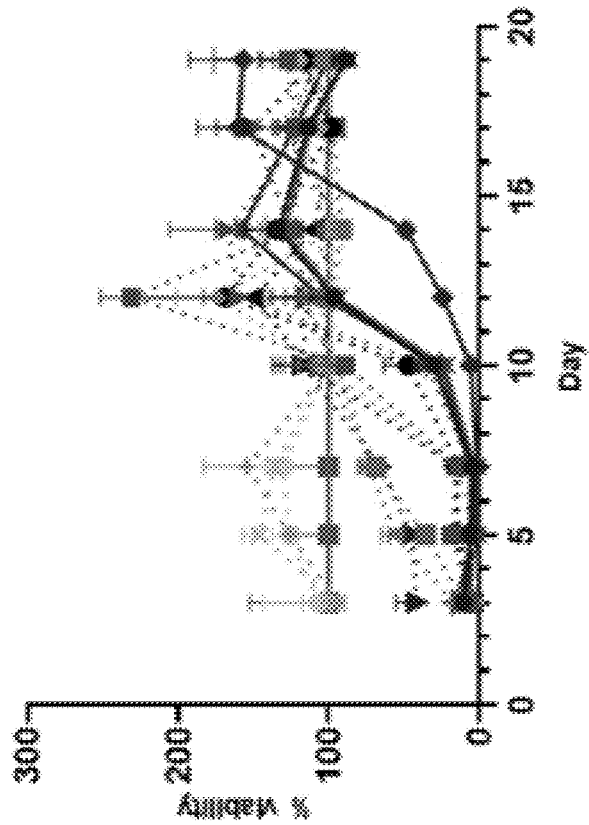
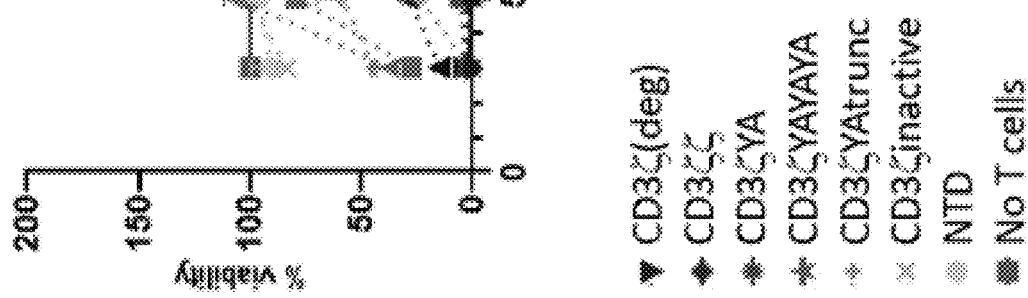
FIG. 3A
FIG. 3B

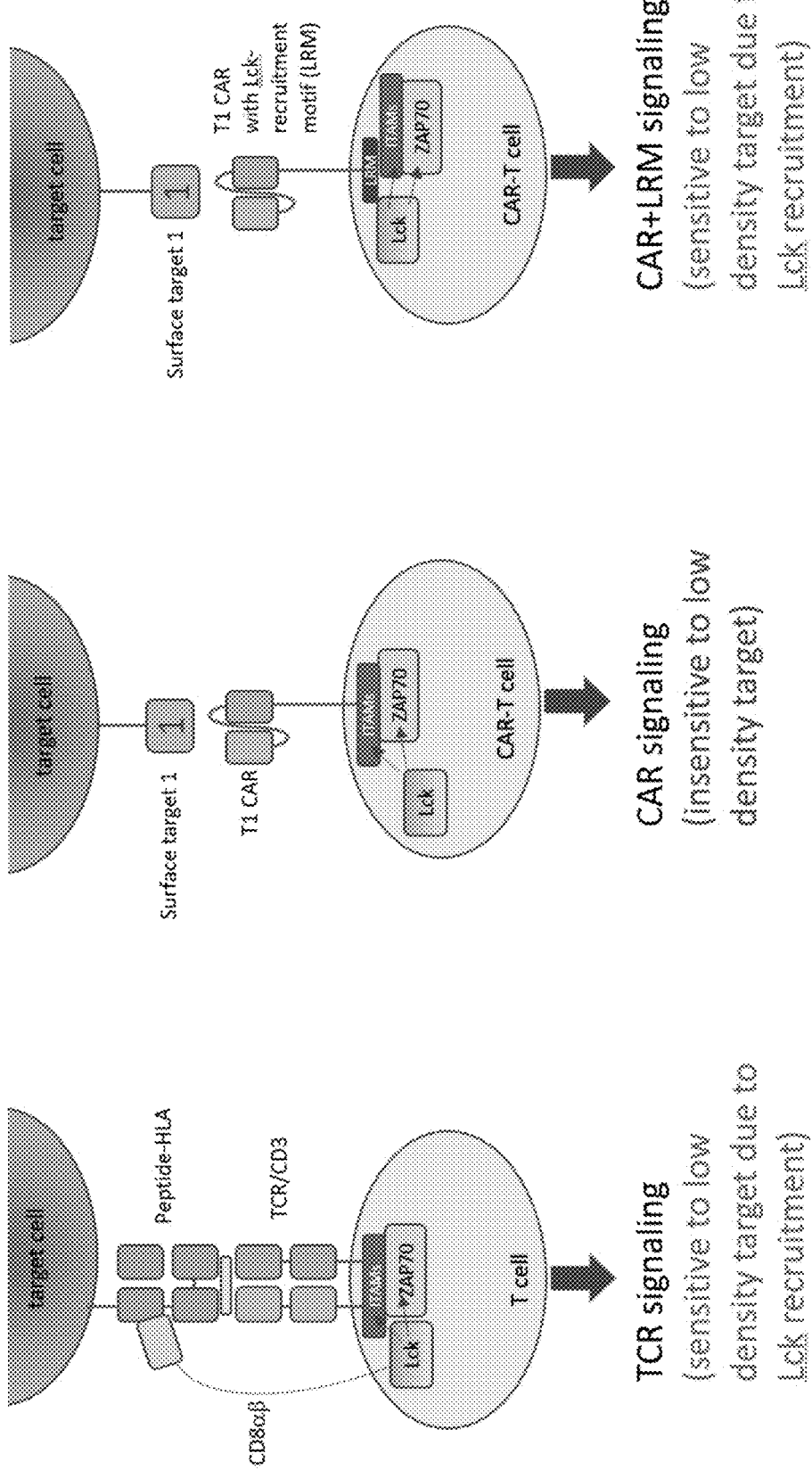

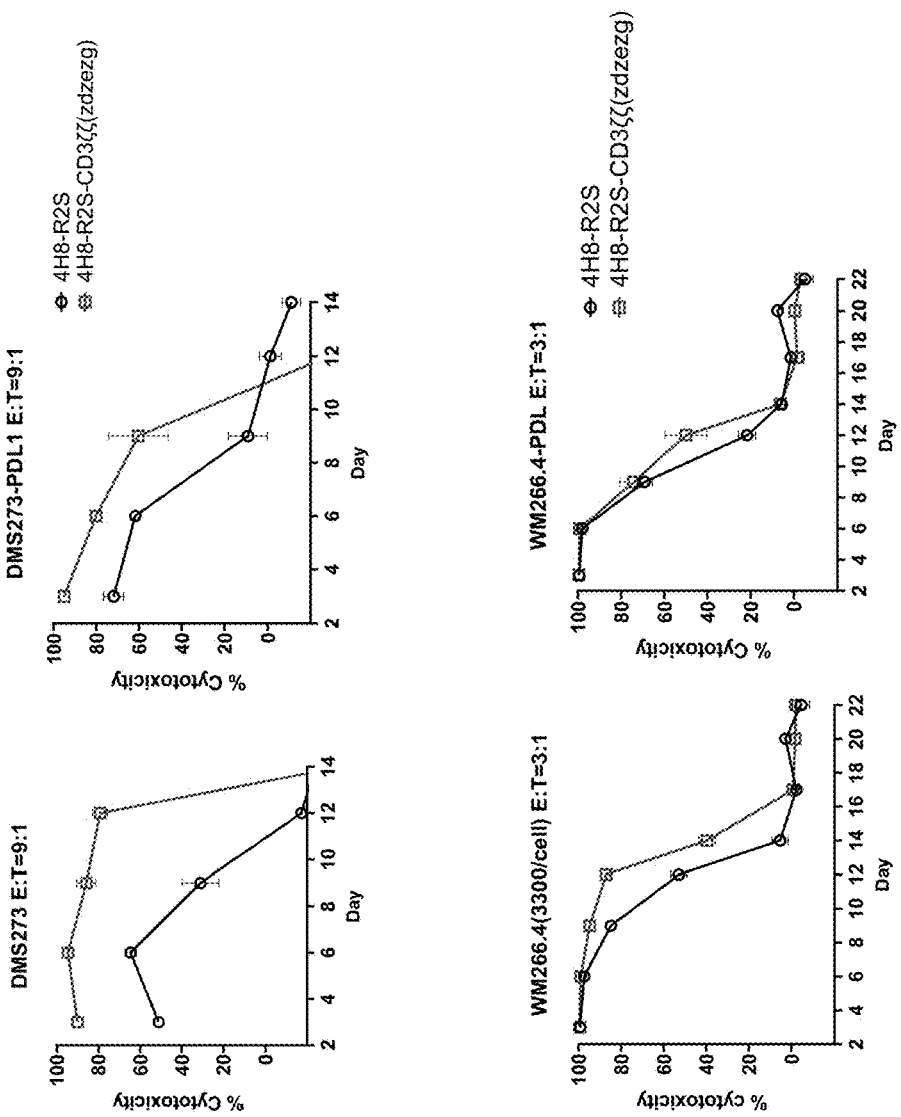
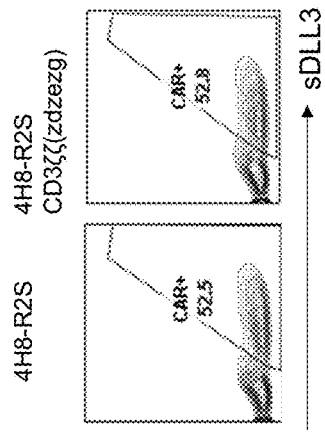
FIG. 9A
FIG. 9B

CHIMERIC ANTIGEN RECEPTORS WITH ENHANCED SIGNALING AND ACTIVITIES AND USES THEREOF

CROSS REFERENCE TO RELATED APPLICATIONS

The present application claims the benefit of priority to U.S. Provisional Application No. 63/054,701, filed on Jul. 21, 2020; and U.S. Provisional Application No. 63/219,710, filed on Jul. 8, 2021, the contents of all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 19, 2021, is named AT-03903US_SL.txt and is 407,932 bytes in size.

FIELD

The invention relates to improvements in signalling by recombinant antigen receptors such as chimeric antigen receptors. The improvements include modifications to the intracellular signaling domain of the recombinant antigen receptors and other methods for enhancing signal transduction when the recombinant antigen receptor is activated by ligand or antigen binding. The invention also relates to the incorporation of these improvements into engineered immune cells and the use of such cells to treat cancer and other maladies.

BACKGROUND

Adoptive transfer of immune cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). T cells can be genetically modified to express chimeric antigen receptors (CARs), fusion proteins comprised of an antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)).

While CARs present various therapeutic advantages, they lack some of the complexities that contribute to the sensitivity, specificity and strength of the natural interaction between T cells and their targets. For example, the co-receptor (CD4 or CD8)-associated Lck kinase that is central to TCR signaling is coordinated with target recognition for the TCR synapse but is not for the CAR synapse (FIG. 2A). See, e.g., Davenport, A. J. et al. *Chimeric antigen receptor T cells form nonclassical and potent immune synapses driving rapid cytotoxicity*. Proc. Natl. Acad. Sci. U.S.A. 115, E2068-E2076 (2018). Further, a CD3 zeta CAR has only 3 ITAMs, all of which derive from CD3 zeta, whereas the TCR/CD3 holocomplex has 10 ITAMs comprising contributions from all four CD3 chains (delta, epsilon, gamma, and zeta). Reducing the number or diversity of ITAMs modulates both TCR and CAR function. See, e.g., Bettini, M. L. et al. Cutting Edge: *CD3 ITAM Diversity Is Required for Optimal TCR Signaling and Thymocyte Development*. J. Immunol. 199, 1555-1560 (2017); Feucht, J. et al. *Calibration of CAR activation potential directs alternative T cell fates and therapeutic potency*. Nature Medicine 25, 82-88 (2019). Thus, the quantity and quality of ITAMs and the complement of proximate signaling mediators differ between CARs and TCRs. Perhaps resultingly, TCRs are more sensitive to low-density antigens than are CARs, with the former mediating killing of target cells expressing as few as three cognate peptide-MHC complexes. See, e.g., Purbhoo, M. A., Irvine, D. J., Huppa, J. B. & Davis, M. M. *T cell killing does not require the formation of a stable mature immunological synapse*. Nat. Immunol. 5, 524-530 (2004).

Accordingly, there is a need for improvements in CAR-based therapy. Provided herein are methods and compositions that address this need.

SUMMARY

In one aspect, the present invention provides a recombinant antigen receptor comprising an extracellular antigen binding domain, a transmembrane domain, and an intracellular domain that comprises a co-stimulatory domain and an ITAM-containing domain, wherein
  (a) the ITAM-containing domain comprises one, two or three or more ITAM domains selected from the group consisting of a wildtype CD3g ITAM, CD3d ITAM, CD3e ITAM, CD3z1 ITAM, CD3z2 ITAM, CD3z3 ITAM, and a variant thereof, and wherein if the ITAM-containing domain comprises only three wildtype ITAM domains, the three ITAMs domains are not CD3z1, CD3z2 and CD3z3; and/or
  (b) the intracellular domain further comprises a Lck recruiting motif (LRM).

In an embodiment of the recombinant antigen receptor described herein, the recombinant antigen receptor comprises a chimeric antigen receptor (CAR). In an embodiment of the recombinant antigen receptor described herein, the antigen binding domain comprises a heavy chain variable domain (VH) and a light chain variable domain (VL). In any of the recombinant antigen receptor embodiments disclosed herein, the variant ITAM domain may comprise an Ala substitution at the second position in the canonical YXX(L/I) ITAM motif of a wildtype CD3z1, CD3z2, CD3z3, CD3d, CD3e, or CD3g. In an embodiment, the co-stimulatory domain comprises 4-1BB co-stimulatory domain. In an embodiment, the number of ITAM domains is a multiple of three. For example, the ITAM-containing domain may consist of three ITAM domains or six ITAM domains. In an embodiment, the ITAM-containing domain comprises from N-terminus to C-terminus:
  (a) CD3d ITAM, CD3z2 ITAM, CD3z3 ITAM;
  (b) CD3e ITAM, CD3z2 ITAM, CD3z3 ITAM;
  (c) CD3g ITAM, CD3z2 ITAM, CD3z3 ITAM;
  (d) CD3d ITAM, CD3e ITAM, CD3g ITAM;
  (e) CD3z1 ITAM, CD3z2 ITAM, CD3z3 ITAM, CD3z1 ITAM, CD3z2 ITAM, CD3z3 ITAM;
  (f) CD3z1 ITAM, CD3d ITAM, CD3z2 ITAM, CD3e ITAM, CD3z3 ITAM, CD3g ITAM;
  (g) CD3d ITAM, CD3z1 ITAM, CD3e ITAM, CD3z2 ITAM, CD3g ITAM, CD3z3 ITAM;
  (h) CD3z1 ITAM, CD3z2 ITAM, CD3z3 ITAM, CD3d ITAM, CD3e ITAM, CD3g ITAM;
  (i) CD3d ITAM, CD3e ITAM, CD3g ITAM, CD3z1 ITAM, CD3z2 ITAM, CD3z3 ITAM;
  (j) CD3z1 (YAEL (SEQ ID NO: 152)) ITAM, CD3z2 ITAM, CD3z3 ITAM;
  (k) CD3z1 (YAEL (SEQ ID NO: 152)) ITAM, CD3z2 (YAEL (SEQ ID NO: 152)) ITAM, CD3z3 (YAGL (SEQ ID NO: 153)) ITAM;

(l) CD3z1 (YAEL (SEQ ID NO: 152));
(m) CD3z1 (YAEL (SEQ ID NO: 152)) ITAM, CD3d (YAPL (SEQ ID NO: 154)) ITAM, CD3z2 (YAEL (SEQ ID NO: 152)) ITAM, CD3e (YAPI (SEQ ID NO: 155)) ITAM, CD3z3 (YAGL (SEQ ID NO: 153)) ITAM, CD3g (YAPL (SEQ ID NO: 154)) ITAM; or
(n) CD3d (YAPL (SEQ ID NO: 154)) ITAM, CD3z1 (YAEL (SEQ ID NO: 152)) ITAM, CD3e (YAPI (SEQ ID NO: 155)) ITAM, CD3z2 (YAEL (SEQ ID NO: 152)) ITAM, CD3g (YAPL (SEQ ID NO: 154)) ITAM, CD3z3 (YAGL (SEQ ID NO: 153)) ITAM.

In certain embodiments, the ITAM-containing domain is derived from or based on a CD3z ITAM-containing domain framework.

In certain embodiments, the ITAM-containing domain comprises an ITAM domain comprising the amino acid sequence selected from SEQ ID NOs: 20-25, 65-70. In certain embodiments, the ITAM-containing domain comprises an amino acid sequence selected from SEQ ID NOs: 26-38.

In an embodiment, the LRM comprises an LRM of CD4, CD8 or CD28. In an embodiment, the LRM comprises a CD4LRM, CD8 LRM-1, 2×CD8LRM-1, CD8LRM-2, CD28LRM or a CD28LRMY3, or comprises an LRM derived from one of AXL, CD2, CD5, CD44, CD45, and CD122. In an embodiment, the LRM comprises an amino acid sequence selected from the group consisting of SEQ ID NOs: 55, 56, 57, 58, 59, and 64.

In an embodiment, the recombinant antigen receptor comprises an intracellular domain that comprises an amino acid sequence selected from the group consisting of SEQ ID NOs:26-38, SEQ ID NOs: 55-59, and SEQ ID NOs: 64-70. In an embodiment, the recombinant antigen receptor comprises an amino acid sequence selected from the group consisting of SEQ ID NOs:26-38, SEQ ID NOs: 55-59, and SEQ ID NOs: 64-70. In an embodiment, the recombinant antigen receptor comprises the amino acid sequence of one or more of SEQ ID NOs:26-38, SEQ ID NOs: 55-59, and SEQ ID NOs: 64-70. In an embodiment, the recombinant antigen receptor comprises the amino acid sequence of one or more of SEQ ID NOs: 30-35, 37-38, 57 and 59. In an embodiment, the recombinant antigen receptor comprises the amino acid sequence of one or more of SEQ ID NOs: 30, 35, 37, 57 and 59.

In certain embodiments, the recombinant antigen receptor binds to an antigen expressed on a tumor cell. In certain embodiments, the antigen is expressed at a low density on the tumor cell. In certain embodiments, the low-density antigen is expressed at or below about 10,000 copies per cell. In certain embodiments, the antigen is expressed at a low level naturally. In some embodiments, the expression of the antigen is reduced after the cells are exposed to CAR T treatment. In an embodiment, the recombinant antigen receptor binds to DLL3. In another embodiment, the recombinant antigen receptor binds to CD19. In an embodiment, the recombinant antigen receptor binds to BCMA.

In another aspect, the present invention provides a polynucleotide comprising a DNA sequence encoding the recombinant antigen receptor as described herein.

In another aspect, the present invention provides a vector comprising a herein-described polynucleotide.

In another aspect, the present invention provides an engineered immune cell comprising any one or more of the recombinant antigen receptors described herein. In an embodiment, one or more of the recombinant antigen receptors binds to DLL3.

In an embodiment, the present invention provides an engineered immune cell comprising a recombinant antigen receptor described herein. In an embodiment, the present invention provides an engineered immune cell comprising a recombinant antigen receptor described herein wherein the recombinant antigen receptor binds to DLL3.

In an embodiment, the antigen binding domain binds to DLL3 and comprises a heavy chain variable domain (VH) and a light chain variable domain (VL), and wherein (1) the VH comprises the amino acid sequence of SEQ ID NO: 44 and the VL comprises the amino acid sequence of SEQ ID NO: 45, or (2) the VH comprises the amino acid sequence of SEQ ID NO: 47 and the VL comprises the amino acid sequence of SEQ ID NO: 48, or (3) the VH comprises the amino acid sequence of SEQ ID NO: 50 and the VL comprises the amino acid sequence of SEQ ID NO: 51.

In an embodiment, the recombinant antigen receptor comprises the amino acid sequence selected from SEQ ID NOs: 91-146, with or without a signal peptide.

In an embodiment, the present invention provides an engineered immune cell comprising a first recombinant antigen receptor as described herein and further comprises a second recombinant antigen receptor comprising an extracellular antigen binding domain and an intracellular domain that comprises Lck, LAT, ZAP70, or a variant thereof, e.g. a functional variant thereof. In an embodiment, the first recombinant antigen receptor comprises an amino acid sequence selected from SEQ ID NOs: 26-38, SEQ ID NOs: 55-59, and SEQ ID NOs: 64-70. In an embodiment, the first recombinant antigen receptor comprises an amino acid sequence selected from SEQ ID NOs: 43, 46, 49, and 91-146. In an embodiment, the intracellular domain of the second recombinant antigen receptor comprises the amino acid sequence of one or more of SEQ ID NOs: 1, 2, 3, and 8. In an embodiment, the antigen binding domain of the first recombinant antigen receptor binds to DLL3. In an embodiment of either of the above, either the antigen binding domain of the second recombinant antigen receptor binds to the same antigen as the first recombinant antigen receptor (for example, DLL3), or the antigen binding domain of the second recombinant antigen receptor binds to an antigen different from the antigen that the first recombinant antigen receptor binds to (for example, DLL3).

In another aspect, the present invention provides an engineered immune cell comprising a recombinant antigen receptor, for example, a CAR, and expressing an exogenous downstream mediator of T cell signaling. In an embodiment, the exogenous downstream mediator of T cell signaling comprises the amino acid sequence of ZAP70, Lck, Fyn, Syk, LAT or UNC119 (e.g. the amino acid sequence of SEQ ID NOs: 1, 2, 4, 6, 8 or 9, respectively), or the amino acid sequence of a variant thereof, e.g. a functional variant thereof, for example the amino acid sequence of truncated Lck, truncated Fyn, or of truncated Syk (e.g. the amino acid sequence of SEQ ID NOs: 3, 5 or 7, respectively). In another embodiment, the exogenous downstream mediator of T cell signaling is ZAP70, Lck, Fyn, Syk, LAT, or UNC119 or a variant thereof, e.g. a functional variant thereof, such as truncated Lck, truncated Fyn, or truncated Syk. In an embodiment, the CAR comprises an amino acid sequence selected from SEQ ID NOs: 26-38, SEQ ID NOs: 55-59, and SEQ ID NOs: 64-70. In an embodiment, the CAR comprises an antigen binding domain that binds to DLL3. In an embodiment, the CAR comprises an amino acid sequence selected from SEQ ID NOs: 43, 46, 49, and 91-146.

In another aspect, the invention provides an engineered immune cell comprising a first recombinant antigen receptor and a second recombinant antigen receptor, wherein the first recombinant antigen receptor comprises a CAR and the second recombinant receptor comprises an extracellular antigen binding domain and an intracellular domain that comprises Lck, LAT, Fyn, Syk, UNC119, or ZAP70, or a variant thereof, e.g. a functional variant thereof. In an embodiment, the intracellular domain of the second recombinant antigen receptor comprises the amino acid sequence of one or more of SEQ ID NOs:1-9. In an embodiment, the intracellular domain of the second recombinant antigen receptor comprises the amino acid sequence of one or more of SEQ ID NOs: 1, 2, 3, and 8. In an embodiment, the first recombinant antigen receptor comprises an amino acid sequence selected from SEQ ID NOs: 26-38, SEQ ID NOs: 55-59, and SEQ ID NOs: 64-70. In an embodiment, the antigen binding domain of the first recombinant antigen receptor binds to DLL3. In an embodiment of any of the above, the antigen binding domain of the second recombinant antigen receptor binds to the same antigen as the first recombinant antigen receptor (e.g. DLL3), or the antigen binding domain of the second recombinant antigen receptor binds to an antigen different from the antigen that the first recombinant antigen receptor binds to (e.g. DLL3). In an embodiment, the first recombinant antigen receptor comprises an amino acid sequence selected from SEQ ID NOs: 43, 46, 49, and 91-146.

In various embodiments, any of the engineered immune cells described above is a T cell. In an embodiment, the T cell comprises one or more genomic modifications, such as a genomic modification to the TCRa gene.

In an embodiment, the present invention provides an engineered immune cell that comprises a first recombinant antigen receptor as described herein and further comprises a second recombinant antigen receptor comprising an extracellular antigen binding domain and an intracellular domain that comprises Lck, LAT, Fyn, Syk, UNC119, or ZAP70, or a variant thereof, e.g. a functional variant thereof, and the antigen binding domain of the first recombinant antigen receptor and the antigen binding domain of the second recombinant antigen receptor both bind to DLL3. In an embodiment, the intracellular domain of the second recombinant antigen receptor comprises the amino acid sequence of one or more of SEQ ID NOs:1-9. In an embodiment, the intracellular domain of the second recombinant antigen receptor comprises the amino acid sequence of one or more of SEQ ID NOs: 1, 2, 3, and 8.

In an embodiment, the present invention provides an engineered immune cell that comprises a first recombinant antigen receptor as described herein and further comprises a second recombinant antigen receptor comprising an extracellular antigen binding domain and an intracellular domain that comprises Lck, LAT, Fyn, Syk, UNC119, or ZAP70, or a variant thereof, e.g. a functional variant thereof, and the antigen binding domain of the first recombinant antigen receptor binds to DLL3 and the antigen binding domain of the second recombinant antigen receptor binds to an antigen other than DLL3 and does not bind to DLL3. In an embodiment, the intracellular domain of the second recombinant antigen receptor comprises the amino acid sequence of one or more of SEQ ID NOs:1-9. In an embodiment, the intracellular domain of the second recombinant antigen receptor comprises the amino acid sequence of one or more of SEQ ID NOs: 1, 2, 3, and 8.

In another aspect, the present invention provides a pharmaceutical composition comprising any of the engineered immune cells described herein.

In another aspect, the present invention provides a method of treating cancer comprising administering to a patient in need thereof an effective amount of any of the engineered immune cells described herein and/or a pharmaceutical composition described herein.

In another aspect, the present invention provides a method of making any of the engineered immune cells described herein comprising introducing into an immune cell a polynucleotide that encodes a recombinant antigen receptor and/or CAR described herein, and/or a vector comprising such a polynucleotide, optionally together with another polynucleotide that encodes an exogenous downstream mediator or any of the second recombinant antigen receptors described herein and/or a vector comprising such a polynucleotide. In an embodiment, any one of the polynucleotides or vectors can encode one or more of a recombinant antigen receptor, CAR, exogenous downstream mediator, and/or second recombinant antigen receptors described herein. In an embodiment, the immune cell is a T cell. In an embodiment, the immune cell is an NK cell.

BRIEF DESCRIPTION OF THE DRAWINGS

FIG. 1A shows multiple CAR constructs that contain a different number and/or sequence of CD3 ITAMs selected from γ (gamma), δ (delta), ε (epsilon), and ζ1, ζ2, and ζ3 (zeta 1-3) ITAMs. FIG. 1B shows a CAR construct comprising the CD3zeta wildtype ITAM-containing domain and multiple CAR constructs that have mutations in the canonical ITAM YXXL sequence. FIG. 1B discloses SEQ ID NOS 156, 156-157, 152, 156-157, 152, 152-153 and 152, respectively, in order of appearance. FIG. 1C shows constructs that combine the strategies from FIGS. 1A and 1B (first construct comprises ITAM domains ζ1-YA, δ-YA, ζ2-YA, ε-YA, ζ3-YA, γ-YA; second construct comprises ITAM domains δ-YA, ζ1-YA, ε-YA, ζ2-YA, γ-YA, ζ2-YA). FIG. 1C discloses SEQ ID NOS 152, 154, 152, 155, 153-154, 154, 152, 155, 152, 154 and 153, respectively, in order of appearance.

FIG. 2A-top shows schematic diagram of expression construct used in the experiments reported in FIG. 2A-bottom panels and FIG. 2B to FIG. 2G; FIG. 2A, bottom panels are a series of plots (BFP on vertical axis, sDLL3 on horizontal axis) showing the detection of conventional or modified DLL3 CAR expressed on primary human T cells. sDLL3, soluble DLL3. The DLL3 CAR T cells shown in FIG. 2A-bottom panels were co-incubated in a cell killing assay with high antigen density WM266.4 targets at an effector:target ratio of 1:3 (FIG. 2B), or high antigen density WM266.4 targets at an effector:target ratio of 1:1 (FIG. 2C), or low antigen density DMS273 targets at an effector:target ratio of 3:1 (FIG. 2D). The number of target cells was counted every 6 hours for a total of 180 hours. FIG. 2E shows a series of plots showing the detection of conventional or modified DLL3 CAR expressed on primary human T cells from a donor different from the donor for the CAR T cell data shown in the FIG. 2A-bottom panels. The DLL3 CAR T cells shown in FIG. 2E were co-incubated with low antigen density DMS273 targets at an effector:target ratio of 3:1 (FIG. 2F), or high antigen density WM266.4 targets at an effector:target ratio of 1:3 (FIG. 2G). The number of target cells was counted every 6 hours for a total of 120 hours.

FIGS. 3A-3B show that altering the quality and quantity of CD3ζ ITAMs improved CAR T function in a long-term cytotoxicity assay. Primary human T cells were modified to express a conventional or modified CAR, in some cases co-expressing an indicated T cell signaling component. These CAR T effector cells were co-incubated for 19 days with either low antigen density DMS273 tumor targets at an effector:target ratio of 3:1 (FIG. 3A), or high antigen density WM266.4 tumor targets at an effector:target ratio of 1:1 (FIG. 3B). Every 2-3 days, the viability of the luciferase-expressing target cells was measured by luminescence and half of the effectors were transferred to fresh target cells to continue killing. CD3ζ inactive, all 6 Tyr residues in the 3 ITAMs of CD3ζ were mutated to Phe. NTD, untransduced T cells. % viability was determined based on baselining luminescence data to "No T cells" wells (only target cells added to wells).

FIGS. 4A-4B are schematic representations that show insertion of Lck recruitment motifs (LRM) as a strategy to enable recruitment of Lck to CAR synapses in a more TCR-like manner. The left diagram of FIG. 4A is a schematic representation showing binding of both the CD8 co-receptor (CD4 co-receptor can function the same way) and the TCR to the target cell MHC results in a convergence of CD8-associated Lck and CAR ITAMs, resulting in more efficient signaling. The right diagram of FIG. 4A illustrates that this convergence does not occur in CAR synapses due to the lack of involvement of co-receptors in CAR-antigen binding. As a result, the CAR signaling may be insensitive or ineffective to low density target. FIG. 4B is a schematic representation showing addition of a binding motif sequence for Lck (identified as "LRM") (other signaling enzymes or adaptors may be used in place of the LRM shown) to the CAR intracellular domain may improve efficiency of CAR signaling due to the directed inclusion of Lck in the CAR synapse.

FIG. 5A is a schematic representation showing LRMs can be inserted at different positions of a conventional CAR construct. FIG. 5B are a series of plots (BFP on vertical axis, sDLL3 on horizontal axis) showing the detection of DLL3 CARs with LRMs inserted between the transmembrane domain and 4-1BB co-stimulation domain (FL: full-length). FIG. 5C shows modified DLL3 CARs depicted in FIG. 5B did not perform as well as the DLL3 CAR without the LRM (CD3ζWT). FIG. 5D shows DLL3 CARs with LRMs at the C-terminus of the construct have better cytotoxicity against low antigen density DMS273 targets (effector:target ratio of 3:1) and high antigen density WM266.4 targets (effector:target ratio of 1:3) than the DLL3 CAR without the LRM.

FIG. 6A is a schematic representation mimicking the natural convergence of TCR and coreceptors on binding to MHC, with a CAR (T1 CAR) and a second "LckCAR" that bind to the same target on a tumor cell to improve Lck recruitment to the CAR synapse and thus CAR T performance. FIG. 6B is a schematic representation showing targeting the T1 CAR and the "T2 LckCAR" to different targets on a tumor cell to impose the requirement that an otherwise Lck-deficient CAR T cell must engage both targets to achieve functional signaling. This requisite combinatorial targeting (a so-called "AND" logic gate) may enable specific tumor targeting even when one of the targets is present on normal, non-tumor cells.

DETAILED DESCRIPTION

Figure 1A:
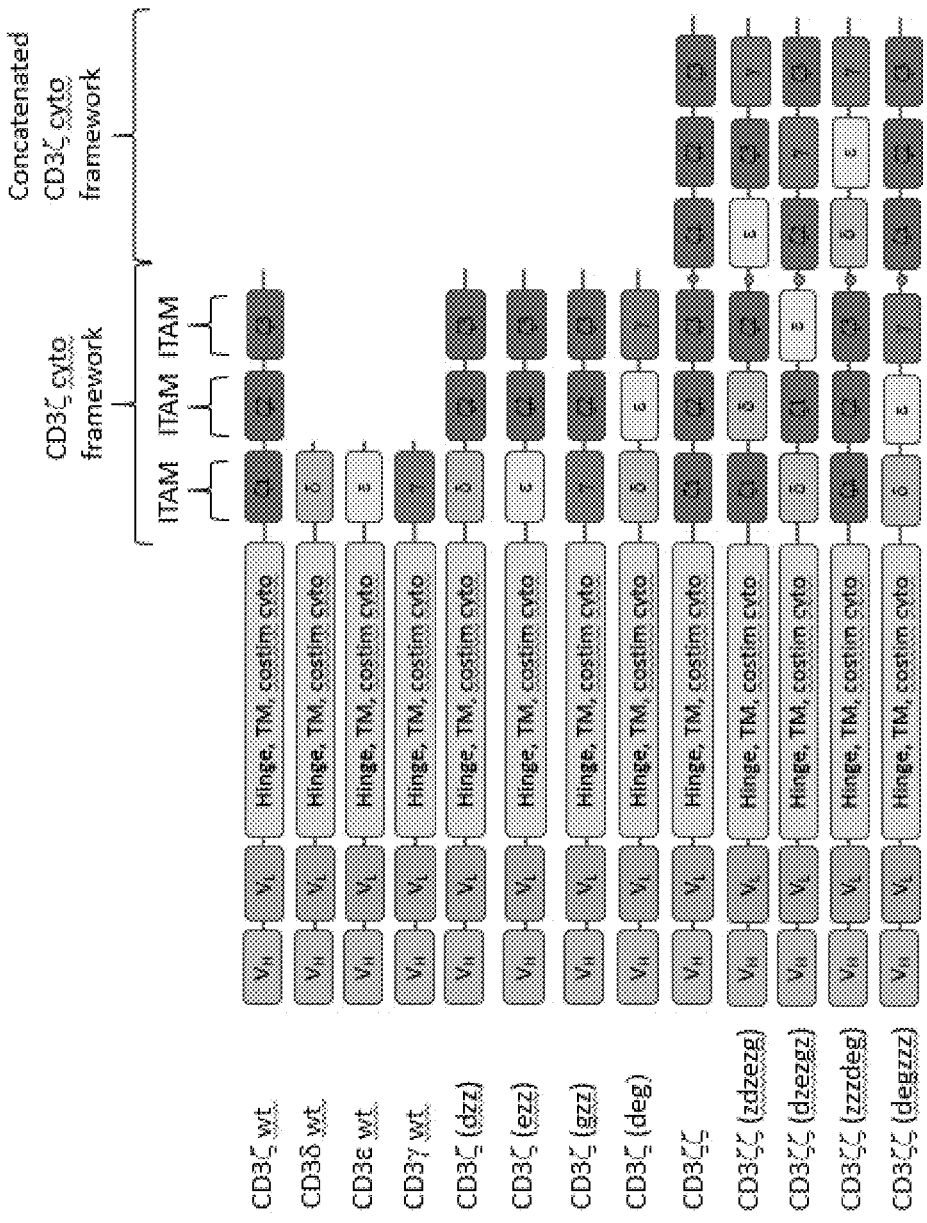
FIGS. 1A-1C show altering the quality and quantity of CD3 ITAMs to improve CAR signaling.

In one aspect, the invention disclosed herein provides improved chimeric antigen receptors (CARs) that have novel cytoplasmic domains that improve CAR T cell performance and engineered immune cells comprising the CARs (e.g. CAR-T cells). The invention also provides polynucleotides encoding these CARs, compositions comprising immune cells expressing these CARs, and methods of making and using these CARs and CAR expressing immune cells. The invention also provides methods for treating a subject having a condition that is treatable using CAR T technology such as cancer, including conditions associated with DLL3, such as small cell lung cancer, by using the improved CARs and immune cells expressing these CARs as described herein. The invention also provides compositions comprising the engineered immune cells and methods of using these compositions. For example, provided herein are methods for treating a condition such as cancer in a subject using these compositions.

General Techniques

The practice of the invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The term "recombinant antigen receptor" as used herein refers broadly to a non-naturally occurring surface receptor that comprises an extracellular antigen-binding domain or an extracellular ligand-binding domain, a transmembrane domain and an intracellular domain. In some embodiments, the recombinant antigen receptor is a chimeric antigen receptor (CAR). In some embodiments, the intracellular domain of a recombinant antigen receptor comprises a co-stimulatory domain and an ITAM-containing domain. In some embodiments, the intracellular domain of a recombinant antigen receptor comprises an intracellular protein or a functional variant thereof (e.g., truncation(s), insertion(s), deletion(s) or substitution(s)).

The term "extracellular ligand-binding domain" or "extracellular antigen-binding domain" as used herein refers to a polypeptide that is capable of binding a ligand or an antigen or capable of interacting with a cell surface molecule, such as a ligand or a surface antigen. For example, the extracellular ligand-binding or antigen-binding domain may be chosen to recognize a ligand that acts as a cell surface marker on target cells associated with a particular disease state, e.g., a tumor-specific antigen. In some embodiments, the antigen-binding domain comprises an antibody, or an antigen binding fragment or an antigen binding portion of an antibody. In some embodiments, the antigen binding domain comprises an Fv or scFv, an Fab or scFab, an F(ab')2 or a scF(ab')2, an Fd, a monobody, a affibody, a camelid antibody, a VHH antibody, a single domain antibody, or a darpin. In some embodiments, the ligand-binding domain comprises a partner of a binding pair, such as a ligand that binds to a surface receptor, or an ectodomain of a surface receptor that binds to a ligand.

The term "stalk domain" or "hinge domain" are used interchangeably herein to refer to any polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

A "co-stimulatory molecule" as used herein refers to the cognate binding partner on immune cells, e.g. T cells, that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, M1CB, HVEM, lymphotoxin β receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, IgE, IgD, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., DLL3). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antigen binding fragment, an antibody conjugate, or a polypeptide that "specifically binds" to a target (e.g., DLL3 protein) is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. For example, an antibody that specifically binds to a DLL3 epitope is an antibody that binds this epitope with greater affinity, avidity, more readily, and/or with greater duration than it binds to other DLL3 epitopes or non-DLL3 epitopes. It is also understood that, for example, an antibody (or moiety or epitope) that specifically binds to a first target may or may not specifically bind to a second target. As such, "specific binding" does not necessarily require (although it can include) exclusive binding. Generally, but not necessarily, reference to binding means specific binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen binding subsequences of antibodies) that contain minimal sequence derived from non-human immunoglobulin. In one aspect, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "monovalent antibody" comprises one antigen binding site per molecule (e.g., IgG or Fab). In some instances, a monovalent antibody can have more than one antigen binding sites, but the binding sites are from different antigens.

A "bivalent antibody" comprises two antigen binding sites per molecule (e.g., IgG). In some instances, the two binding sites have the same antigen specificities. However, bivalent antibodies may be bispecific.

Recombinant antigen receptors e.g. chimeric antigen receptors (CARs) of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art, a "constant region" of an antibody refers to the constant region of the antibody light chain or the constant region of the antibody heavy chain, either alone or in combination.

As used herein, "substantially pure" refers to material which is at least 50%, at least 60%, at least 70%, at least 80%, at least 90%, at least 95%, at least 97%, at least 98%, or even at least 99% pure (i.e., free from contaminants).

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein "autologous" means that cells, a cell line, or population of cells used for treating patients are originating from said patient.

As used herein "allogeneic" means that cells or population of cells used for treating patients are not originating from said patient but from a donor.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of a tumor, remission of a disease (e.g., cancer), decreasing symptoms resulting from a disease e.g. (e.g., cancer), increasing the quality of life of those suffering from a disease (e.g., cancer), decreasing the dose of other medications required to treat a disease (e.g., cancer), delaying the progression of a disease (e.g., cancer), curing a disease (e.g., cancer), and/or prolonging survival of patients having a disease (e.g., cancer).

"Ameliorating" means a lessening or improvement of one or more symptoms as compared to not administering a CAR or engineered cell of the invention. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various diseases or conditions (such as for example cancer), decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual", "patient" or a "subject" are used interchangeably herein and is a mammal. Mammals include, but are not limited to, humans, monkeys, pigs, other farm animals, sport animals, pets, primates, horses, dogs, cats, rodents including mice, rats, guinea pigs, etc. A subject is a mammal and these terms are used interchangeably herein. In some embodiments, the subject is a human. In some embodiments, the subject is a non-human primate. In some embodiments, the subject is a human or a monkey, e.g. a cynomolgus monkey.

As used herein, "vector" means a construct, which is capable of delivering, and, in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutically acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration include phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

The term "$k_{on}$", as used herein, refers to the rate constant for association of an antibody or scFv of a CAR to an antigen.

The term "$k_{off}$", as used herein, refers to the rate constant for dissociation of an antibody or scFv of a CAR from the antibody/antigen complex.

The term "$K_D$", as used herein, refers to the equilibrium dissociation constant of an antibody-antigen interaction or an scFv-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the invention encompasses not only the entire group listed as a whole, but each member of the group individually and all possible subgroups of the main group, but also the main group absent one or more of the group members. The invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the invention. The materials, methods, and examples are illustrative only and not intended to be limiting.

Recombinant Antigen Receptors

The present invention provides recombinant antigen receptors comprising an extracellular antigen binding domain, a transmembrane domain, and an intracellular domain that comprises a co-stimulatory domain and an ITAM-containing domain. The intracellular signaling domain of a recombinant antigen receptor e.g. CAR according to the invention is responsible for intracellular signaling following the binding of an extracellular ligand-binding domain to the target resulting in the activation of the immune cell and immune response. The intracellular signaling domain has the ability to activate at least one of the normal effector functions of the immune cell in which the recombinant antigen receptor e.g. CAR is expressed. For example, the effector function of a T cell can be a cytolytic activity or helper activity including the secretion of cytokines.

In some embodiments, an intracellular signaling domain for use in a recombinant antigen receptor e.g. CAR of the invention can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Non-limiting examples of ITAM domains used in the invention can include as non-limiting examples those derived from TCRζ, FcRγ, FcRβ, FcRε, CD3γ, CD3δ, CD3ε, CD5, CD22, CD79a, CD79b and CD66d. In some embodiments the intracellular signaling domain of the CAR of the invention comprises a domain of a co-stimulatory molecule.

In some embodiments, the intracellular signaling domain of a CAR of the invention comprises a part of a co-stimulatory molecule selected from the group consisting of a fragment of 41BB (GenBank: AAA53133.) and CD28 (NP_006130.1).

In one aspect, the present invention provides recombinant antigen receptors comprising an extracellular antigen binding domain, a transmembrane domain, and an intracellular domain that comprises a co-stimulatory domain and an ITAM-containing domain, wherein:
(1) the ITAM-containing domain comprises one or more ITAM domains, e.g. three or more ITAM domains selected from the group consisting of a wildtype CD3g ITAM, CD3d ITAM, CD3e ITAM, CD3z1 ITAM, CD3z2 ITAM, CD3z3 ITAM, FcgRI ITAM, FcgRIIA ITAM, FcgRIIC ITAM, FcgRIIIA ITAM, FceRIG ITAM, and FceRIBITAM, and a variant of any one of the above, and wherein if the ITAM-containing domain comprises only three wildtype ITAM domains, the three ITAMs domains are not CD3z1, CD3z2 and CD3z3; and/or
(2) the intracellular domain further comprises one or more Lck recruiting motifs (LRM).

As used herein, CD3g refers to CD3 gamma (CD3γ), CD3d refers to CD3 delta (CD3δ), CD3e refers to CD3 epsilon (CD3ε), CD3z1 refers to CD3 zeta 1 (CD3ζ1), CD3z2 refers to CD3 zeta 2 (CD3ζ2), CD3z3 refers to CD3 zeta 3 (CD3ζ3).

As recited herein, the ITAM-containing domain can comprise a variety of configurations of the recited ITAMs, but does not include the configuration that is present in the wildtype CD3zeta ITAM-containing domain, which is only three ITAM domains, being CD3z1, CD3z2, CD3z3, in the order listed (amino to carboxy). In various embodiments, the ITAM-containing domain may have one or more ITAM domains, three or more ITAM domains (i.e., 3, 4, 5, 6, 7, 8, 9, 10 or more), and ITAM domains in multiples of three (e.g. an ITAM-containing domain comprising the six ITAMS CD3z1, CD3z2, CD3z3, CD3z1, CD3z2, CD3z3; in an embodiment, this ITAM-containing domain comprises the amino acid sequence of SEQ ID NO: 16). In various embodiments, the ITAM domains comprise the respective amino acid sequence set forth in Table 1: wildtype CD3g ITAM (SEQ ID NO: 25), CD3d ITAM (SEQ ID NO: 23), CD3e ITAM (SEQ ID NO: 24), CD3z1 ITAM (SEQ ID NO: 20), CD3z2 ITAM (SEQ ID NO: 21), CD3z3 ITAM (SEQ ID NO: 22).

In various embodiments, the ITAM-containing domain comprises the amino acid sequence of the wildtype CD3 zeta ITAM-containing domain (e.g. SEQ ID NO: 15 (also termed "CD3ζ cytoplasmic domain")) except that at least one ITAM domain is replaced with a different ITAM domain. For example, in an embodiment of the invention, the ITAM-containing domain comprises the amino acid sequence of SEQ ID NO: 26, which is referred to as "CD3ζ (dzz)," indicating that it comprises the amino acid sequence of the wildtype CD3 zeta ITAM-containing domain except that it comprises the ITAM configuration CD3d ITAM, CD3z2 ITAM, CD3z3 ITAM instead of the ITAM configuration CD3z1 ITAM, CD3z2 ITAM, CD3z3 ITAM. In such an embodiment, the intervening amino acid sequences between the ITAM domains are the same as or comprise the corresponding amino acid sequences of the wildtype CD3 zeta ITAM-containing domain (e.g. the amino acid sequences of SEQ ID NO: 61 (intervening sequence between the first and second ITAM domains) and SEQ ID NO: 62 (intervening sequence between the second and third ITAM domains)). Similarly, in such an embodiment, the N-terminal amino acid sequence and C-terminal amino acid sequence of the ITAM-containing domain are the same as or comprise the corresponding N- and C-terminal amino acid sequence of the wildtype CD3 zeta ITAM-containing domain (e.g. the amino acid sequences of SEQ ID NO: 60 (N-terminal amino acid sequence) and SEQ ID NO: 63 (C-terminal amino acid sequence).

In the above example, the CD3d (or "delta") ITAM domain is the replacement ITAM domain. In embodiments of the invention, the replacement ITAM domain can be any of those listed above (CD3g ITAM, CD3d ITAM, CD3e ITAM, CD3z1 ITAM, CD3z2 ITAM, CD3z3 ITAM, or a variant of any of these). The replacement ITAM domain can also be that of a protein other than the CD3 holocomplex, such as FcγRI, FcγRIIA, FcγRIIC, FcγRIIIA In various embodiments, the wildtype CD3 zeta ITAM-containing domain provides a framework that comprises three ITAM "slots," a first ITAM slot, a second ITAM slot, and a third ITAM slot. For example, in the wildtype CD3 zeta ITAM-containing domain, the first ITAM slot contains CD3zeta ITAM zeta1 (e.g. comprising the amino acid sequence of SEQ ID NO: 20), the second ITAM slot contains CD3zeta ITAM zeta2 (e.g. comprising the amino acid sequence SEQ ID NO: 21), and the third ITAM slot contains CD3zeta ITAM zeta 3 (e.g. comprising the amino acid sequence SEQ ID NO: 22). Various embodiments of the recombinant antigen receptors of the invention comprise a variant of the wildtype CD3 zeta ITAM-containing domain, the variant differing from the wildtype in that the variant contains a different ITAM domain in at least one of the three slots. For example, in the example given above, the CD3 delta ITAM replaces the CD3zeta1 ITAM in the first ITAM slot, and the rest of the ITAM-containing domain retains the amino acid sequence of the wildtype CD3 zeta ITAM-containing domain.

In embodiments of the invention, any ITAM-containing domain can be inserted into any one or more slot to produce an ITAM-containing domain of the recombinant antigen receptors of the invention. For example, the ITAM-containing domain referred to herein as "CD3zeta (deg)" (e.g. comprising the amino acid sequence of SEQ ID NO: 29) has the CD3 delta ITAM delta domain in the first slot (e.g. comprising the amino acid sequence of SEQ ID NO: 23), the CD3 epsilon ITAM epsilon domain in the second slot (e.g. comprising the amino acid sequence of SEQ ID NO: 24), and the CD3 gamma ITAM gamma domain in the third slot (e.g. comprising the amino acid sequence of SEQ ID NO: 25).

In embodiments of the invention, the ITAM-containing domain of the recombinant antigen receptor comprises amino acid sequences in addition to the ITAM domain sequences. In an embodiment, the CD3 zeta cytoplasmic domain is the framework that provides the initial or N-terminal amino acid sequence amino to the first ITAM (e.g. comprising the amino acid sequence of SEQ ID NO: 60), C-terminal amino acid sequence carboxy to the last ITAM (e.g. comprising the amino acid sequence of SEQ ID NO: 63), sequence between the first and second ITAM domains, if there is a second ITAM domain (e.g. comprising the amino acid sequence of SEQ ID NO: 61), and sequence between the second and third ITAM domains, if there is a third ITAM domain (e.g. comprising the amino acid sequence of SEQ ID NO: 62). This pattern is applied to each set of three ITAMs. An example of this pattern is the amino acid sequence comprising SEQ ID NO: 16. As exemplified in SEQ ID NO: 16, one or more amino acids can be interposed between groups of ITAMs. For example, in SEQ ID NO: 16. a glycine is between the first group of three ITAMs and the second group of three ITAMs. In embodiments of the invention, a group of ITAMs has a sequence comprising the amino acid sequence of SEQ ID NO: 60 at the amino terminus of the group of ITAMs and has a sequence comprising the amino acid sequence of SEQ ID NO: 63 at the carboxy terminus of the group of ITAMs. In preferred embodiments, a group of ITAMs has three ITAMs with intervening sequences as set forth above.

In an embodiment in which the ITAM-containing domain comprises only one ITAM domain, the amino acid sequence of the ITAM-containing domain may comprise the amino acid sequence of SEQ ID NO: 60 amino to the ITAM amino acid sequence and the amino acid sequence of SEQ ID NO: 63 carboxy to the ITAM amino acid sequence. In embodiments that comprise a multiple of three ITAMs plus one ITAM (e.g. 4 ITAMs, 7 ITAMs), the same rule may apply to the ITAM outside the groups of three ITAMs (e.g. [3-ITAM group as described herein][SEQ ID NO: 60-single ITAM domain-SEQ ID NO: 63]).

In an embodiment in which the ITAM-containing domain comprises only two ITAM domains, the amino acid sequence may comprise the amino acid sequence of SEQ ID NO: 60 amino to the first ITAM amino acid sequence, the amino acid sequence of SEQ ID NO: 61 between the first and second ITAMs, and the amino acid sequence of SEQ ID NO: 63 carboxy to the second ITAM amino acid sequence. In embodiments that comprise a multiple of three ITAMs plus two ITAMs (e.g. 5 ITAMs, 8 ITAMs), the same rule may apply to the 2 ITAMs outside the groups of three ITAMs (e.g. [3-ITAM group as described herein][SEQ ID NO: 60-first ITAM domain-SEQ ID NO: 61-second ITAM domain-SEQ ID NO: 63]).

In an embodiment of the recombinant antigen receptors of the invention, the recombinant antigen receptor is a chimeric antigen receptor (CAR). In an embodiment, the CAR comprises an scFv. In an embodiment, the scFv has an amino acid sequence that comprises the amino acid sequence of SEQ ID NO: 43, 46 or 49. In certain embodiments, the scFv has binding affinity for DLL3. In certain embodiments, the scFv comprises an amino acid sequence which comprises at least 70%, for example at least 80%, or at least 90%, 95%, 97%, or 99% sequence identity with the amino acid sequence of SEQ ID NO: 43, 46 or 49.

In an embodiment of the recombinant antigen receptors of the invention, the antigen binding domain comprises a heavy chain variable domain (VH) and a light chain variable domain (VL). In some embodiments, the VH comprises the amino acid sequence of SEQ ID NO: 44 and the VL comprises the amino acid sequence of SEQ ID NO: 45, or the VH comprises the amino acid sequence of SEQ ID NO: 47 and the VL comprises the amino acid sequence of SEQ ID NO: 48, or the VH comprises the amino acid sequence of SEQ ID NO: 50 and the VL comprises the amino acid sequence of SEQ ID NO: 51. In some embodiments, a VH-VL linker amino acid sequence joins the VH and VL domains. In some embodiments, the VH-VL linker comprises between 1 and 5 copies of the amino acid sequence of SEQ ID NO: 52, e.g. 4 copies of SEQ ID NO: 52, as in SEQ ID NOs: 43, 46 and 49. In some embodiments, the VH is amino to the VL, and in some embodiments the VL is amino to the VH. In some embodiments, the antigen binding domain has binding affinity for DLL3. See WO2020/180591, which is incorporated herein by reference.

In an embodiment of the recombinant antigen receptors of the invention, the antigen binding domain is connected to the transmembrane domain by a hinge domain. In some embodiments, the hinge domain comprises the CD8 alpha hinge, for example the hinge domain comprises the amino acid sequence of SEQ ID NO: 11. In an embodiment, a linker sequence links the transmembrane domain to the intracellular domain. In an embodiment, the linker sequence comprises the amino acid sequence of SEQ ID NO: 13.

In an embodiment of the recombinant antigen receptors of the invention, the recombinant antigen receptor initially comprises a signal sequence, e.g the CD8 alpha signal sequence, e.g. the signal sequence comprises the amino acid sequence of SEQ ID NO: 10.

In an embodiment of the recombinant antigen receptor of the invention, the transmembrane domain comprises a CD8 alpha transmembrane domain, e.g. the transmembrane domain comprises the amino acid sequence of SEQ ID NO: 12.

Figure 5A:
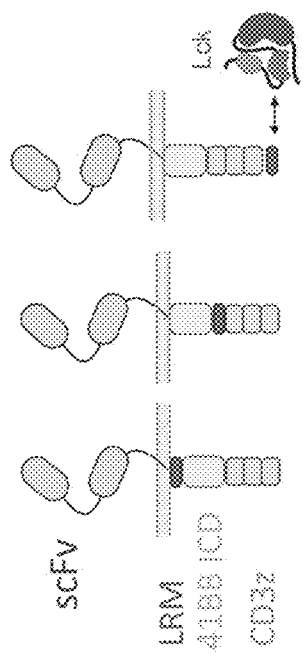
FIGS. 5A-5D show adding Lck recruitment motif (LRM) to the conventional CAR construct may improve CAR T function as demonstrated in a short-term kinetic killing assay.

In an embodiment of the recombinant antigen receptor of the invention, the recombinant antigen receptor comprises an Lck recruiting motif (LRM). In an embodiment, a linker sequence connects the LRM positioned N-terminal to the intracellular domain of the recombinant antigen receptor as shown in FIG. 5A. In an embodiment, the amino terminal linker comprises from 1 to 4 copies e.g. 1 copy of the amino acid sequence of SEQ ID NO: 53 (termed "Linker 3"). In an embodiment, a linker sequence connects LRM positioned C-terminal to the intracellular domain of the recombinant antigen receptor. In an embodiment, the carboxy terminal linker comprises from 1 to 4 copies, e.g. 1 copy, of the amino acid sequence of SEQ ID NO: 52 (termed "Linker 2") as shown in FIG. 5A.

In an embodiment of the recombinant antigen receptor of the invention, the intracellular domain comprises an LRM of CD4, CD8 or CD28. In an embodiment, the LRM comprises a CD4LRM (e.g. comprising the amino acid sequence of SEQ ID NO: 64), CD8 LRM-1 (e.g. comprising the amino acid sequence of SEQ ID NO: 55), 2×CD8LRM-1 (e.g. comprising the amino acid sequence of SEQ ID NO: 56), CD8LRM-2 (e.g. comprising the amino acid sequence of SEQ ID NO: 57), CD28LRM (e.g. comprising the amino acid sequence of SEQ ID NO: 58) or a CD28LRMY3 (e.g. comprising the amino acid sequence of SEQ ID NO: 59).

In an embodiment of the recombinant antigen receptors of the invention, the variant of a wildtype ITAM comprises an Ala substitution at the second position in the canonical YXX(L/I) ITAM motif (i.e., the Y+1 position) of a wildtype CD3z1, CD3z2, CD3z3, CD3d, CD3e, or CD3g. In some embodiments, the variant ITAM domain comprises the Ala substitution at the Y+1 position in the N-terminal YXX(L/I) motif. In some embodiments, the variant ITAM domain comprises the Ala substitution at the Y+1 position in the C-terminal YXX(L/I) motif. The variant ITAM domain can comprise the sequence of, for example, any one of SEQ ID NO: 65 (termed "CD3zeta ITAM zeta1 YA"), SEQ ID NO: 66 (termed "CD3zeta ITAM zeta2 YA"), SEQ ID NO: 67 (termed "CD3zeta ITAM zeta3 YA"), SEQ ID NO: 68 (termed "CD3 delta ITAM delta YA"), SEQ ID NO: 69 (termed "CD3 epsilon ITAM epsilon YA"), and SEQ ID NO: 70 (termed "CD3gamma ITAM gamma YA").

An example of an ITAM-containing domain that comprises this variant of each of CD3z1, CD3z2, and CD3z3 comprises the amino acid sequence of SEQ ID NO: 35 (termed "CD3zeta YAYAYA"). An example of an ITAM-containing domain that comprises this variant of each of CD3z1, CD3z2, CD3z3, CD3d, CD3e, and CD3g comprises the amino acid sequence of SEQ ID NO: 37 (termed "CD3zeta zeta (zdzezg-6×YA)").

In an embodiment of the recombinant antigen receptors of the invention, the co-stimulatory domain comprises a 4-1BB co-stimulatory domain. In an embodiment, the 4-1BB co-stimulatory domain comprises the amino acid sequence of SEQ ID NO: 14.

In an embodiment of the recombinant antigen receptors of the invention, the ITAM-containing domain consists of three ITAM domains or six ITAM domains, or generally a multiplicity of three ITAM domains, such as three, six or nine ITAM domains. One or more amino acids, for example, a single glycine, can join or link neighboring groups of three ITAM domains.

In an embodiment of the recombinant antigen receptors of the invention, the ITAM-containing domain comprises from N-terminus to C-terminus:

(a) CD3d ITAM, CD3z2 ITAM, CD3z3 ITAM (e.g. the ITAM-containing domain comprises the amino sequence of SEQ ID NO: 26);

(b) CD3e ITAM, CD3z2 ITAM, CD3z3 ITAM (e.g. the ITAM-containing domain comprises the amino sequence of SEQ ID NO: 27);

(c) CD3g ITAM, CD3z2 ITAM, CD3z3 ITAM (e.g. the ITAM-containing domain comprises the amino sequence of SEQ ID NO: 28);

(d) CD3d ITAM, CD3e ITAM, CD3g ITAM (e.g. the ITAM-containing domain comprises the amino sequence of SEQ ID NO: 29);

(e) CD3z1 ITAM, CD3z2 ITAM, CD3z3 ITAM, CD3z1 ITAM, CD3z2 ITAM, CD3z3 ITAM (e.g. the ITAM-containing domain comprises the amino sequence of SEQ ID NO: 16);

(f) CD3z1 ITAM, CD3d ITAM, CD3z2 ITAM, CD3e ITAM, CD3z3 ITAM, CD3g ITAM (e.g. the ITAM-containing domain comprises the amino sequence of SEQ ID NO: 30);

(g) CD3d ITAM, CD3z1 ITAM, CD3e ITAM, CD3z2 ITAM, CD3g ITAM, CD3z3 ITAM (e.g. the ITAM-containing domain comprises the amino sequence of SEQ ID NO: 31);

(h) CD3z1 ITAM, CD3z2 ITAM, CD3z3 ITAM, CD3d ITAM, CD3e ITAM, CD3g ITAM (e.g. the ITAM-containing domain comprises the amino sequence of SEQ ID NO: 32);

(i) CD3d ITAM, CD3e ITAM, CD3g ITAM, CD3z1 ITAM, CD3z2 ITAM, CD3z3 ITAM (e.g. the ITAM-containing domain comprises the amino sequence of SEQ ID NO: 33);
(j) CD3z1 (YAEL (SEQ ID NO: 152)) ITAM, CD3z2 ITAM, CD3z3 ITAM (e.g. the ITAM-containing domain comprises the amino sequence of SEQ ID NO: 34);
(k) CD3z1 (YAEL (SEQ ID NO: 152)) ITAM, CD3z2 (YAEL (SEQ ID NO: 152)) ITAM, CD3z3 (YAGL (SEQ ID NO: 153)) ITAM (e.g. the ITAM-containing domain comprises the amino sequence of SEQ ID NO: 35);
(l) CD3z1 (YAEL (SEQ ID NO: 152)) (e.g. the ITAM-containing domain comprises the amino sequence of SEQ ID NO: 36);
(m) CD3z1 (YAEL (SEQ ID NO: 152)) ITAM, CD3d (YAPL (SEQ ID NO: 154)) ITAM, CD3z2 (YAEL (SEQ ID NO: 152)) ITAM, CD3e (YAPI (SEQ ID NO: 155)) ITAM, CD3z3 (YAGL (SEQ ID NO: 153)) ITAM, CD3g (YAPL (SEQ ID NO: 154)) ITAM (e.g. the ITAM-containing domain comprises the amino sequence of SEQ ID NO: 37); or
(n) CD3d (YAPL (SEQ ID NO: 154)) ITAM, CD3z1 (YAEL (SEQ ID NO: 152)) ITAM, CD3e (YAPI (SEQ ID NO: 155)) ITAM, CD3z2 (YAEL (SEQ ID NO: 152)) ITAM, CD3g (YAPL (SEQ ID NO: 154)) ITAM, CD3z3 (YAGL (SEQ ID NO: 153)) ITAM (e.g. the ITAM-containing domain comprises the amino sequence of SEQ ID NO: 38).

TABLE 1

| Plasmid Feature | Amino acid sequence | SEQ ID NO: |
|---|---|---|
| ZAP70 | MPDPAAHLPFFYGSISRAEAEEHLKLAGMADGLFLLRQCLRSLGG YVLSLVHDVRFHHFPIERQLNGTYAIAGGKAHCGPAELCEFYSRDP DGLPCNLRKPCNRPSGLEPQPGVFDCLRDAMVRDYVRQTWKLEG EALEQAIISQAPQVEKLIATTAHERMPWYHSSLTREEAERKLYSGA QTDGKFLLRPRKEQGTYALSLIYGKTVYHYLISQDKAGKYCIPEGT KFDTLWQLVEYLKLKADGLIYCLKEACPNSSASNASGAAAPTLPA HPSTLTHPQRRIDTLNSDGYTPEPARITSPDKPRPMPMDTSVYESPY SDPEELKDKKLFLKRDNLLIADIELGCGNFGSVRQGVYRMRKKQI DVAIKVLKQGTEKADTEEMMREAQIMHQLDNPYIVRLIGVCQAE ALMLVMEMAGGGPLHKFLVGKREEIPVSNVAELLHQVSMGMKY LEEKNFVHRDLAARNVLLVNRHYAKISDFGLSKALGADDSYYTA RSAGKWPLKWYAPECINFRKFSSRSDVWSYGVTMWEALSYGQKP YKKMKGPEVMAFIEQGKRMECPPECPPELYALMSDCWIYKWEDR PDFLTVEQRMRACYYSLASKVEGPPGSTQKAEAACA | 1 |
| Lck | MGCGCSSHPEDDWMENIDVCENCHYPIVPLDKGTLLIRNGSEVR DPLVTYEGSNPPASPLQDNLVIALHSYEPSHDGDLGFEKGEQLRIL EQSGEWWKAQSLTTGQEGFIPFNFVAKANSLEPEPWFFKNLSRKD AERQLLAPGNTHGSFLIRESESTAGSFSLSVRDFDQNQGEVVKHYK IRNLDNGGFYISPRITFPGLHELVRHYTNASDGLCTRLSRPCQTQKP QKPWWEDEWEVPRETLKLVERLGAGQFGEVWMGYYNGHTKVA VKSLKQGSMSPDAFLAEANLMKQLQHQRLVRLYAVVTQEPIYIIT EYMENGSLVDFLKTPSGIKLTINKLLDMAAQIAEGMAFIEERNYIH RDLRAANILVSDTLSCKIADFGLARLIEDNEYTAREGAKFPIKWTA PEAINYGTFTIKSDVWSFGILLTEIVTHGRIPYPGMTNPEVIQNLERG YRMVRPDNCPEELYQLMRLCWKERPEDRPTFDYLRSVLEDFFTAT EGQYQPQP | 2 |
| Truncated Lck | MGCGCSSHPEDDWMENIDVCENCHYPIVPLDKGTLLIRNGSEVR DPLVTYEGSNPPASPLQDNLVIALHSYEPSHDGDLGFEKGEQLRIL EQSGEWWKAQSLTTGQEGFIPFNFVAKANSLEPEPWFFKNLSRKD AERQLLAPGNTHGSFLIRESESTAGSFSLSVRDFDQNQGEVVKHYK IRNLDNGGFYISPRITFPGLHELVRHYTNASDGLCTRLSRPCQTQKP QKPWWEDEWEVPRET | 3 |
| Fyn | MGCVQCKDKEATKLTEERDGSLNQSSGYRYGTDPTPQHYPSFGV TSIPNYNNFHAAGGQGLTVFGGVNSSSHTGTLRTRGGTGVTLFVA LYDYEARTEDDLSFHKGEKFQILNSSEGDWWEARSLTTGETGYIPS NYVAPVDSIQAEEWYFGKLGRKDAERQLLSFGNPRGTFLIRESETT KGAYSLSIRDWDDMKGDHVKHYKIRKLDNGGYYITTRAQFETLQ QLVQHYSERAAGLCCRLVVPCHKGMPRLTDLSVKTKDVWEIPRE SLQLIKRLGNGQFGEVWMGTWNGNTKVAIKTLKPGTMSPESFLEE AQIMKKLKHDKLVQLYAVVSEEPIYIVTEYMNKGSLLDFLKDGEG RALKLPNLVDMAAQVAAGMAYIERMNYIHRDLRSANILVGNGLI CKIADFGLARLIEDNEYTARQGAKFPIKWTAPEAALYGRFTIKSDV WSFGILLTELVTKGRVPYPGMNNREVLEQVERGYRMPCQDCPIS LHELMIHCWKKDPEERPTFEYLQSFLEDYFTATEPQYQPGENL | 4 |
| Truncated Fyn | MGCVQCKDKEATKLTEERDGSLNQSSGYRYGTDPTPQHYPSFGV TSIPNYNNFHAAGGQGLTVFGGVNSSSHTGTLRTRGGTGVTLFVA LYDYEARTEDDLSFHKGEKFQILNSSEGDWWEARSLTTGETGYIPS NYVAPVDSIQAEEWYFGKLGRKDAERQLLSFGNPRGTFLIRESETT KGAYSLSIRDWDDMKGDHVKHYKIRKLDNGGYYITTRAQFETLQ QLVQHYSERAAGLCCRLVVPCHKGMPRLTDLSVKTKDVWEIPRE S | 5 |

TABLE 1-continued

| Plasmid Feature | Amino acid sequence | SEQ ID NO: |
|---|---|---|
| Syk | MASSGMADSANHLPFFFGNITREEAEDYLVQGGMSDGLYLLRQSR NYLGGFALSVAHGRKAHHYTIERELNGTYAIAGGRTHASPADLCH YHSQESDGLVCLLKKPFNRPQGVQPKTGPFEDLKENLIREYVKQT WNLQGQALEQAIISQKPQLEKLIATTAHEKMPWFHGKISREESEQI VLIGSKTNGKFLIRARDNNGSYALCLLHEGKVLHYRIDKDKTGKL SIPEGKKFDTLWQLVEHYSYKADGLLRVLTVPCQKIGTQGNVNFG GRPQLPGSHPATWSAGGIISRIKSYSFPKPGHRKSSPAQGNRQESTV SFNPYEPELAPWAADKGPQREALPMDTEVYESPYADPEEIRPKEV YLDRKLLTLEDKELGSGNFGTVKKGYYQMKKVVKTVAVKILKNE ANDPALKDELLAEANVMQQLDNPYIVRMIGICEAESWMLVMEMA ELGPLNKYLQQNRHVKDKNIIELVHQVSMGMKYLEESNFVHRDL AARNVLLVTQHYAKISDFGLSKALRADENYYKAQTHGKWPVKW YAPECINYYKFSSKSDVWSFGVLMWEAFSYGQKPYRGMKGSEVT AMLEKGERMGCPAGCPREMYDLMNLCWTYDVENRPGFAAVELR LRNYYYDVVN | 6 |
| Truncated Syk | MASSGMADSANHLPFFFGNITREEAEDYLVQGGMSDGLYLLRQSR NYLGGFALSVAHGRKAHHYTIERELNGTYAIAGGRTHASPADLCH YHSQESDGLVCLLKKPFNRPQGVQPKTGPFEDLKENLIREYVKQT WNLQGQALEQAIISQKPQLEKLIATTAHEKMPWFHGKISREESEQI VLIGSKTNGKFLIRARDNNGSYALCLLHEGKVLHYRIDKDKTGKL SIPEGKKFDTLWQLVEHYSYKADGLLRVLTVPCQKIGTQGNVNFG GRPQLPGSHPATWSAGGIISRIKSYSFPKPGHRKSSPAQGNRQESTV SFNPYEPELAPWAADKGPQREALPMDTEVYESPYADPEEIRPKEV YLDRKLL | 7 |
| LAT | MEEAILVPCVLGLLLLPILAMLMALCVHCHRLPGSYDSTSSDSLYP RGIQFKRPHTVAPWPPAYPPVTSYPPLSQPDLLPIPRSPQPLGGSHR TPSSRRDSDGANSVASYENEGASGIRGAQAGWGVWGPSWTRLTP VSLPPEPACEDADEDEDDYHNPGYLVVLPDSTPATSTAAPSAPALS TPGIRDSAFSMESIDDYVNVPESGESAEASLDGSREYVNVSQELHP GAAKTEPAALSSQEAEEVEEEGAPDYENLQELN | 8 |
| Unc119 | MKVKKGGGGAGTATESAPGPSGQSVAPIPQPPAESESGSESEPDAG PGPRPGPLQRKQPIGPEDVLGLQRITGDYLCSPEENIYKIDFVRFKIR DMDSGTVLFEIKKPPVSERLPINRRDLDPNAGRFVRYQFTPAFLRL RQVGATVEFTVGDKPVNNFRMIERHYFRNQLLKSFDFHFGFCIPSS KNTCEHIYDFPPLSEELISEMIRHPYETQSDSFYFVDDRLVMHNKA DYSYSGTP | 9 |
| CD8α [alpha] signal sequence | MALPVTALLLPLALLLHAARP | 10 |
| CD8α [alpha] hinge | TTTPAPRPPTPAPTIASQPLSLRPEACRPAAGGAVHTRGLDFACD | 11 |
| CD8α [alpha] transmembrane | IYIWAPLAGTCGVLLLSLVIT | 12 |
| CD8α [alpha] cytoplasmic sequence (truncated) | LYC | 13 |
| 4-1BB (TNFRSF9, CD137) cytoplasmic domain | KRGRKKLLYIFKQPFMRPVQTTQEEDGCSCRFPEEEEGGCEL | 14 |
| CD3zeta cytoplasmic domain | RVKFSRSADAPAYQQGQNQLYNELNLGRREEYDVLDKRRGRDPE MGGKPRRKNPQEGLYNELQKDKMAEAYSEIGMKGERRRGKGHD GLYQGLSTATKDTYDALHMQALPPR | 15 |
| CD3zeta zeta concatenated cytoplasmic domain | RVKFSRSADAPAYQQGQNQLYNELNLGRREEYDVLDKRRGRDPE MGGKPRRKNPQEGLYNELQKDKMAEAYSEIGMKGERRRGKGHD GLYQGLSTATKDTYDALHMQALPPRGRVKFSRSADAPAYQQGQN QLYNELNLGRREEYDVLDKRRGRDPEMGGKPRRKNPQEGLYNEL QKDKMAEAYSEIGMKGERRRGKGHDGLYQGLSTATKDTYDALH MQALPPR | 16 |
| CD3 delta cytoplasmic domain | GHETGRLSGAADTQALLRNDQVYQPLRDRDDAQYSHLGGNWAR NK | 17 |

TABLE 1-continued

| Plasmid Feature | Amino acid sequence | SEQ ID NO: |
|---|---|---|
| CD3 epsilon cytoplasmic domain | KNRKAKAKPVTRGAGAGGRQRGQNKERPPPVPNPDYEPIRKGQRDLYSGLNQRRI | 18 |
| CD3 gamma cytoplasmic domain | GQDGVRQSRASDKQTLLPNDQLYQPLKDREDDQYSHLQGNQLRRN | 19 |
| CD3 zeta ITAM zeta1 | APAYQQGQNQLYNELNLGRREEYDVLDKR | 20 |
| CD3 zeta ITAM zeta2 | PRRKNPQEGLYNELQKDKMAEAYSEIGM | 21 |
| CD3 zeta ITAM zeta3 | ERRRGKGHDGLYQGLSTATKDTYDALHMQ | 22 |
| CD3 delta ITAM delta | DTQALLRNDQVYQPLRDRDDAQYSHLGGN | 23 |
| CD3 epsilon ITAM epsilon | ERPPPVPNPDYEPIRKGQRDLYSGLNQR | 24 |
| CD3 gamma ITAM gamma | DKQTLLPNDQLYQPLKDREDDQYSHLQGN | 25 |
| CD3 zeta (dzz) | RVKFSRSADDTQALLRNDQVYQPLRDRDDAQYSHLGGNRGRDPEMGGKPRRKNPQEGLYNELQKDKMAEAYSEIGMKGERRRGKGHDGLYQGLSTATKDTYDALHMQALPPR | 26 |
| CD3 zeta (ezz) | RVKFSRSADERPPPVPNPDYEPIRKGQRDLYSGLNQRRGRDPEMGGKPRRKNPQEGLYNELQKDKMAEAYSEIGMKGERRRGKGHDGLYQGLSTATKDTYDALHMQALPPR | 27 |
| CD3 zeta (gzz) | RVKFSRSADDKQTLLPNDQLYQPLKDREDDQYSHLQGNRGRDPEMGGKPRRKNPQEGLYNELQKDKMAEAYSEIGMKGERRRGKGHDGLYQGLSTATKDTYDALHMQALPPR | 28 |
| CD3 zeta (deg) | RVKFSRSADDTQALLRNDQVYQPLRDRDDAQYSHLGGNRGRDPEMGGKERPPPVPNPDYEPIRKGQRDLYSGLNQRKGDKQTLLPNDQLYQPLKDREDDQYSHLQGNALPPR | 29 |
| CD3 zeta zeta (zdezg) | RVKFSRSADAPAYQQGQNQLYNELNLGRREEYDVLDKRRGRDPEMGGKDTQALLRNDQVYQPLRDRDDAQYSHLGGNKGPRRKNPQEGLYNELQKDKMAEAYSEIGMALPPRGRVKFSRSADERPPPVPNPDYEPIRKGQRDLYSGLNQRRGRDPEMGGKERRRGKGHDGLYQGLSTATKDTYDALHMQKGDKQTLLPNDQLYQPLKDREDDQYSHLQGNALPPR | 30 |
| CD3 zeta zeta (dzezgz) | RVKFSRSADDTQALLRNDQVYQPLRDRDDAQYSHLGGNRGRDPEMGGKAPAYQQGQNQLYNELNLGRREEYDVLDKRKGERPPPVPNPDYEPIRKGQRDLYSGLNQRALPPRGRVKFSRSADPRRKNPQEGLYNELQKDKMAEAYSEIGMRGRDPEMGGKDKQTLLPNDQLYQPLKDREDDQYSHLQGNKGERRRGKGHDGLYQGLSTATKDTYDALHMQALPPR | 31 |
| CD3 zeta zeta (zzzdeg) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGRVKFSRSADDTQALLRNDQVYQPLRDRDDAQYSHLGGNRGRDPEMGGKERPPPVPNPDYEPIRKGQRDLYSGLNQRKGDKQTLLPNDQLYQPLKDREDDQYSHLQGNALPPR | 32 |
| CD3 zeta zeta (degzzz) | RVKFSRSADDTQALLRNDQVYQPLRDRDDAQYSHLGGNRGRDPEMGGKERPPPVPNPDYEPIRKGQRDLYSGLNQRKGDKQTLLPNDQLYQPLKDREDDQYSHLQGNALPPRGRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 33 |
| CD3 zeta YA | RVKFSRSADAPAYQQGQNQLYAELNLGRREEYDVLDKRRGRDPEMGGKPRRKNPQEGLYNELQKDKMAEAYSEIGMKGERRRGKGHDGLYQGLSTATKDTYDALHMQALPPR | 34 |
| CD3 zeta YAYAYA | RVKFSRSADAPAYQQGQNQLYAELNLGRREEYDVLDKRRGRDPEMGGKPRRKNPQEGLYAELQKDKMAEAYSEIGMKGERRRGKGHDGLYAGLSTATKDTYDALHMQALPPR | 35 |

TABLE 1-continued

| Plasmid Feature | Amino acid sequence | SEQ ID NO: |
|---|---|---|
| CD3 zeta YAtrunc | RVKFSRSADAPAYQQGQNQLYAELNLGRREEYDVLDKRALPPR | 36 |
| CD3 zeta zeta (zdzezg-6xYA) | RVKFSRSADAPAYQQGQNQLYAELNLGRREEYDVLDKRRGRDPE MGGKDTQALLRNDQVYAPLRDRDDAQYSHLGGNKGPRRKNPQE GLYAELQKDKMAEAYSEIGMALPPRGRVKFSRSADERPPPVPNPD YAPIRKGQRDLYSGLNQRRGRDPEMGGKERRRGKGHDGLYAGLS TATKDTYDALHMQKGDKQTLLPNDQLYAPLKDREDDQYSHLQG NALPPR | 37 |
| CD3 zeta zeta (dzezgz-6xYA) | RVKFSRSADDTQALLRNDQVYAPLRDRDDAQYSHLGGNRGRDPE MGGKAPAYQQGQNQLYAELNLGRREEYDVLDKRKGERPPPVPNP DYAPIRKGQRDLYSGLNQRALPPRGRVKFSRSADPRRKNPQEGLY AELQKDKMAEAYSEIGMRGRDPEMGGKDKQTLLPNDQLYAPLK DREDDQYSHLQGNKGERRRGKGHDGLYAGLSTATKDTYDALHM QALPPR | 38 |
| BFP | MSELIKENMHMKLYMEGTVDNHHFKCTSEGEGKPYEGTQTMRIK VVEGGPLPFAFDILATSFLYGSKTFINHTQGIPDFFKQSFPEGFTWE RVTTYEDGGVLTATQDTSLQDGCLIYNVKIRGVNFTSNGPVMQKK TLGWEAFTETLYPADGGLEGRNDMALKLVGGSHLIANIKTTYRSK KPAKNLKMPGVYYVDYRLERIKEANNETYVEQHEVAVARYCDLP SKLGHKLN | 39 |
| Linker 1 (between BFP and Furin cleavage site) | GGSGG | 40 |
| Furin cleavage site | RAKR | 41 |
| P2A peptide | ATNFSLLKQAGDVEENPGP | 42 |
| 10G1-K scFv | EVQLLESGGGLVQPGGSLRLSCAASGFTFSSYAMNWVRQAPGKG LEWVSTISGSGGSTYYADSVKGRFTISRDNSKNTLYLQMNSLRAE DTAVFYCAIDPEYYDILTGGDYWGQGTLVTVSSGGGGSGGGGSG GGGSGGGGSDIQMTQSPSAMSASVGDRVTITCRASQGISNYLAWF QQKPGKVPKRLIYAASSLQSGVPSRFSGSGSGTEFTLTISSLQPEDF ATYFCLQHDSFPLTFGGGTKVEIK | 43 |
| 10G1-K VH | EVQLLESGGGLVQPGGSLRLSCAASGFTFSSYAMNWVRQAPGKG LEWVSTISGSGGSTYYADSVKGRFTISRDNSKNTLYLQMNSLRAE DTAVFYCAIDPEYYDILTGGDYWGQGTLVTVSS | 44 |
| 10G1-K VL | DIQMTQSPSAMSASVGDRVTITCRASQGISNYLAWFQQKPGKVPK RLIYAASSLQSGVPSRFSGSGSGTEFTLTISSLQPEDFATYFCLQHDS FPLTFGGGTKVEIK | 45 |
| 2G1 scFv | QLQLQESGPGLVKPSETLSLTCTVSGGSISSSSYYWGWIRQPPGKG LEWIGSIYYSGNIYHNPSLKSRVSISVDTSKNQFSLRLSSVTAADTA VYYCAREIIVGATHFDYWGQGTLVTVSSGGGGSGGGGSGGGGSG GGGSAIQMTQSPSSLSASVGDRVTITCRASQGIRNDLGWYQQKPG KAPELLIYAASSLQSGVPSRFSGSGSGTDFTLTISSLQPEDFATYYCL QDYNYPLTFGPGTKVDIK | 46 |
| 2G1 VH | QLQLQESGPGLVKPSETLSLTCTVSGGSISSSSYYWGWIRQPPGKG LEWIGSIYYSGNIYHNPSLKSRVSISVDTSKNQFSLRLSSVTAADTA VYYCAREIIVGATHFDYWGQGTLVTVSS | 47 |
| 2G1 VL | AIQMTQSPSSLSASVGDRVTITCRASQGIRNDLGWYQQKPGKAPEL LIYAASSLQSGVPSRFSGSGSGTDFTLTISSLQPEDFATYYCLQDYN YPLTFGPGTKVDIK | 48 |
| 4H8 scFv | QVQLQQSGPGLVKPSQTLSLTCAISGDSVSSNSATWNWIRQSPSRG LEWLGRTYYRSKWYDDYAVSVKSRITINPDTSKNHLSLHLNSVTP EDTAVYYCAGGGLVGAPDGFDWGQGTMVTVSSGGGGSGGGGS GGGGSGGGGSQSVLTQPPSASGTPGQRVTISCSGSSSNIGSDPVNW YQQLPGTAPKLLIYSNNQRPSGVPDRFSGSKSGTSASLAISGLQSED EADYYCSAWDDSLNGYVFGTGTKVTVL | 49 |
| 4H8 VH | QVQLQQSGPGLVKPSQTLSLTCAISGDSVSSNSATWNWIRQSPSRG LEWLGRTYYRSKWYDDYAVSVKSRITINPDTSKNHLSLHLNSVTP EDTAVYYCAGGGLVGAPDGFDWGQGTMVTVSS | 50 |

TABLE 1-continued

| Plasmid Feature | Amino acid sequence | SEQ ID NO: |
|---|---|---|
| 4H8 VL | QSVLTQPPSASGTPGQRVTISCSGSSSNIGSDPVNWYQQLPGTAPK LLIYSNNQRPSGVPDRFSGSKSGTSASLAISGLQSEDEADYYCSAW DDSLNGYVFGTGTKVTVL | 51 |
| Linker 2 (e.g. Between CAR and C-terminal LRM or between CAR and N-terminal LRM) | GGGGS | 52 |
| Linker 3 (e.g. Between CAR and N-terminal LRM or between CAR and C-terminal LRM) | GGGS | 53 |
| CD8 cytoplasmic domain (full length) | LYCNHRNRRRVCKCPRPVVKSGDKPSLSARYV | 54 |
| CD8LRM-1 | RRVCKCPR | 55 |
| 2XCD8LRM-1 | RRVCKCPRRRVCKCPR | 56 |
| CD8LRM-2 | RVCKCPRPV | 57 |
| CD28LRM | YQPYAPPRDFAAYRS | 58 |
| CD28LRMY3 | FQPFAPPRDFAAFRS | 59 |
| N-term Seq 1 | RVKFSRSAD | 60 |
| Intervening Seq 2 | RGRDPEMGGK | 61 |
| Intervening Seq 3 | KG | 62 |
| C-term Seq 4 | ALPPR | 63 |
| CD4LRM | RMSQIKRLLSEKKTCQCP | 64 |
| CD3 zeta ITAM zeta1 YA | APAYQQGQNQLYAELNLGRREEYDVLDKR | 65 |
| CD3 zeta ITAM zeta2 YA | PRRKNPQEGLYAELQKDKMAEAYSEIGM | 66 |
| CD3 zeta ITAM zeta3 YA | ERRRGKGHDGLYAGLSTATKDTYDALHMQ | 67 |
| CD3 delta ITAM delta YA | DTQALLRNDQVYAPLRDRDDAQYSHLGGN | 68 |
| CD3 epsilon ITAM epsilon YA | ERPPPVPNPDYAPIRKGQRDLYSGLNQR | 69 |
| CD3 gamma ITAM gamma YA | DKQTLLPNDQLYAPLKDREDDQYSHLQGN | 70 |

TABLE 1-continued

| Plasmid Feature | Amino acid sequence | SEQ ID NO: |
|---|---|---|
| 4H8-R2S Underlined is the CD8 signal sequence | <u>MALPVTALLLPLALLLHAARP</u>GGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCKRGRKKLLYIFKQPFMRPVQTTQEEDGCSCR<br>FPEEEEGGCELRVKFSRSADAPAYQQGQNQLYNELNLGRREEYDV<br>LDKRRGRDPEMGGKPRRKNPQEGLYNELQKDKMAEAYSEIGMK<br>GERRRGKGHDGLYQGLSTATKDTYDALHMQALPPR | 91 |
| 4H8-R2S-CD8 Full length (FL)-CD3ζWT | <u>MALPVTALLLPLALLLHAARP</u>GGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCNHRNRRRVCKCPRPVVKSGDKPSLSARYVK<br>RGRKKLLYIFKQPFMRPVQTTQEEDGCSCRFPEEEEGGCELRVKFS<br>RSADAPAYQQGQNQLYNELNLGRREEYDVLDKRRGRDPEMGGK<br>PRRKNPQEGLYNELQKDKMAEAYSEIGMKGERRRGKGHDGLYQ<br>GLSTATKDTYDALHMQALPPR | 92 |
| 4H8-R2S-2XCD8LRM-CD30ζWT | <u>MALPVTALLLPLALLLHAARP</u>GGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITRRVCKCPRRRVCKCPRKRGRKKLLYIFKQPFMRP<br>VQTTQEEDGCSCRFPEEEEGGCELRVKFSRSADAPAYQQGQNQLY<br>NELNLGRREEYDVLDKRRGRDPEMGGKPRRKNPQEGLYNELQKD<br>KMAEAYSEIGMKGERRRGKGHDGLYQGLSTATKDTYDALHMQA<br>LPPR | 93 |
| 4H8-R2S-CD28LRM-CD3ζWT | <u>MALPVTALLLPLALLLHAARP</u>GGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCGGGSYQPYAPPRDFAAYRSGGGSKRGRKKL<br>LYIFKQPFMRPVQTTQEEDGCSCRFPEEEEGGCELRVKFSRSADAP<br>AYQQGQNQLYNELNLGRREEYDVLDKRRGRDPEMGGKPRRKNP<br>QEGLYNELQKDKMAEAYSEIGMKGERRRGKGHDGLYQGLSTAT<br>KDTYDALHMQALPPR | 94 |
| 4H8-R2S-CD28LRMY3-CD3ζWT | <u>MALPVTALLLPLALLLHAARP</u>GGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCGGGSFQPFAPPRDFAAFRSGGGSKRGRKLL<br>YIFKQPFMRPVQTTQEEDGCSCRFPEEEEGGCELRVKFSRSADAPA<br>YQQGQNQLYNELNLGRREEYDVLDKRRGRDPEMGGKPRRKNPQ<br>EGLYNELQKDKMAEAYSEIGMKGERRRGKGHDGLYQGLSTATK<br>DTYDALHMQALPPR | 95 |
| 4H8-R2S-CD3ζ-CD8LRM | <u>MALPVTALLLPLALLLHAARP</u>GGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG | 96 |

TABLE 1-continued

| Plasmid Feature | Amino acid sequence | SEQ ID NO: |
|---|---|---|
| | TCGVLLLSLVITLYCKRGRKKLLYIFKQPFMRPVQTTQEEDGCSCR FPEEEEGGCELRVKFSRSADAPAYQQGQNQLYNELNLGRREEYDV LDKRRGRDPEMGGKPRRKNPQEGLYNELQKDKMAEAYSEIGMK GERRRGKGHDGLYQGLSTATKDTYDALHMQALPPRGGGGSRVC KCPRPV | |
| 4H8-R2S-CDζWT-CD28LRMY3 | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADAPAYQQGQNQLYNELNLGRREEYDV LDKRRGRDPEMGGKPRRKNPQEGLYNELQKDKMAEAYSEIGMK GERRRGKGHDGLYQGLSTATKDTYDALHMQALPPRGGGSFQPFA PPRDFAAFRS | 97 |
| 4H8-R2S-CDζWT-C2D8LRM | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADAPAYQQGQNQLYNELNLGRREEYDV LDKRRGRDPEMGGKPRRKNPQEGLYNELQKDKMAEAYSEIGMK GERRRGKGHDGLYQGLSTATKDTYDALHMQALPPRGGGSYQPY APPRDFAAYRS | 98 |
| 4H8-R2S-BB-FullCD8Cyto-CD3ζWT | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITKRGRKKLLYIFKQPFMRPVQTTQEEDGCSCRFPE EEEGGCELLYCNHRNRRRVCKCPRPVVKSGDKPSLSARYVRVKFS RSADAPAYQQGQNQLYNELNLGRREEYDVLDKRRGRDPEMGGK PRRKNPQEGLYNELQKDKMAEAYSEIGMKGERRRGKGHDGLYQ GLSTATKDTYDALHMQALPPR | 99 |
| 4H8-R2S-BB-2XCD8LRM-CD3ζWT | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITKRGRKKLLYIFKQPFMRPVQTTQEEDGCSCRFPE EEEGGCELRRVCKCPRRRVCKCPRRVKFSRSADAPAYQQGQNQL YNELNLGRREEYDVLDKRRGRDPEMGGKPRRKNPQEGLYNELQK DKMAEAYSEIGMKGERRRGKGHDGLYQGLSTATKDTYDALHMQ ALPPR | 100 |
| 4H8-R2S-CD3ζζ(zdzezg) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADAPAYQQGQNQLYNELNLGRREEYDV LDKRRGRDPEMGGKDTQALLRNDQVYQPLRDRDDAQYSHLGGN KGPRRKNPQEGLYNELQKDKMAEAYSEIGMALPPRGRVKFSRSA DERPPPVPNPDYEPIRKGQRDLYSGLNQRRGRDPEMGGKERRRGK GHDGLYQGLSTATKDTYDALHMQKGDKQTLLPNDQLYQPLKDR EDDQYSHLQGNALPPR | 101 |

TABLE 1-continued

| Plasmid Feature | Amino acid sequence | SEQ ID NO: |
|---|---|---|
| 4H8-R2S-CD3ζζ | MALPVTALLLPLALLLHAARPGGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCKRGRKKLLYIFKQPFMRPVQTTQEEDGCSCR<br>FPEEEEGGCELRVKFSRSADAPAYQQGQNQLYNELNLGRREEYDV<br>LDKRRGRDPEMGGKPRRKNPQEGLYNELQKDKMAEAYSEIGMK<br>GERRRGKGHDGLYQGLSTATKDTYDALHMQALPPRGRVKFSRSA<br>DAPAYQQGQNQLYNELNLGRREEYDVLDKRRGRDPEMGGKPRR<br>KNPQEGLYNELQKDKMAEAYSEIGMKGERRRGKGHDGLYQGLST<br>ATKDTYDALHMQALPPR | 102 |
| 4H8-R2S-CD3ζζ (YAYAYA) | MALPVTALLLPLALLLHAARPGGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCKRGRKKLLYIFKQPFMRPVQTTQEEDGCSCR<br>FPEEEEGGCELRVKFSRSADAPAYQQGQNQLYAELNLGRREEYDV<br>LDKRRGRDPEMGGKPRRKNPQEGLYAELQKDKMAEAYSEIGMK<br>GERRRGKGHDGLYAGLSTATKDTYDALHMQALPPRRVKFSRSAD<br>APAYQQGQNQLYAELNLGRREEYDVLDKRRGRDPEMGGKPRRK<br>NPQEGLYAELQKDKMAEAYSEIGMKGERRRGKGHDGLYAGLSTA<br>TKDTYDALHMQALPPR | 103 |
| 4H8-R2S-CD3ζζ (zdzezg-6xYA) | MALPVTALLLPLALLLHAARPGGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCKRGRKKLLYIFKQPFMRPVQTTQEEDGCSCR<br>FPEEEEGGCELRVKFSRSADAPAYQQGQNQLYAELNLGRREEYDV<br>LDKRRGRDPEMGGKDTQALLRNDQVYAPLRDRDDAQYSHLGGN<br>KGPRRKNPQEGLYAELQKDKMAEAYSEIGMALPPRGRVKFSRSA<br>DERPPPVPNPDYAPIRKGQRDLYSGLNQRRGRDPEMGGKERRGK<br>GHDGLYAGLSTATKDTYDALHMQKGDKQTLLPNDQLYAPLKDR<br>EDDQYSHLQGNALPPR | 104 |
| 4H8-R2S-CD3ζζ (dzezgz-6xYA) | MALPVTALLLPLALLLHAARPGGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCKRGRKKLLYIFKQPFMRPVQTTQEEDGCSCR<br>FPEEEEGGCELRVKFSRSADDTQALLRNDQVYAPLRDRDDAQYSH<br>LGGNRGRDPEMGGKAPAYQQGQNQLYAELNLGRREEYDVLDKR<br>KGERPPPVPNPDYAPIRKGQRDLYSGLNQRALPPRGRVKFSRSADP<br>RRKNPQEGLYAELQKDKMAEAYSEIGMRGRDPEMGGKDQTLLP<br>NDQLYAPLKDREDDQYSHLQGNKGERRRGKGHDGLYAGLSTAT<br>KDTYDALHMQALPPR | 105 |
| 4H8-R2S-CD3ζζ(dzezgz) | MALPVTALLLPLALLLHAARPGGGGSCPYSNPSLCGGGGSCPYSN<br>PSLCGGGGSQVQLQQSGPGLVKPSQTLSLTCAISGDSVSSNSATWN<br>WIRQSPSRGLEWLGRTYYRSKWYDDYAVSVKSRITINPDTSKNHL<br>SLHLNSVTPEDTAVYYCAGGGLVGAPDGFDVWGQGTMVTVSSG<br>GGGSGGGGSGGGGSGGGGSQSVLTQPPSASGTPGQRVTISCSGSSS<br>NIGSDPVNWYQQLPGTAPKLLIYSNNQRPSGVPDRFSGSKSGTSAS<br>LAISGLQSEDEADYYCSAWDDSLNGYVFGTGTKVTVLTTTPAPRP<br>PTPAPTIASQPLSLRPEACRPAAGGAVHTRGLDFACDIYIWAPLAG<br>TCGVLLLSLVITLYCKRGRKKLLYIFKQPFMRPVQTTQEEDGCSCR<br>FPEEEEGGCELRVKFSRSADDTQALLRNDQVYQPLRDRDDAQYSH<br>LGGNRGRDPEMGGKAPAYQQGQNQLYNELNLGRREEYDVLDKR<br>KGERPPPVPNPDYEPIRKGQRDLYSGLNQRALPPRGRVKFSRSADP | 106 |

TABLE 1-continued

| Plasmid Feature | Amino acid sequence | SEQ ID NO: |
|---|---|---|
| | RRKNPQEGLYNELQKDKMAEAYSEIGMRGRDPEMGGKDKQTLLP NDQLYQPLKDREDDQYSHLQGNKGERRRGKGHDGLYQGLSTAT KDTYDALHMQALPPR | |
| 4H8-R2S-CD3ζζ(degzzz) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADDTQALLRNDQVYQPLRDRDDAQYSH LGGNRGRDPEMGGKERPPPVPNPDYEPIRKGQRDLYSGLNQRKGD KQTLLPNDQLYQPLKDREDDQYSHLQGNALPPRGRVKFSRSADAP AYQQGQNQLYNELNLGRREEYDVLDKRRGRDPEMGGKPRRKNP QEGLYNELQKDKMAEAYSEIGMKGERRRGKGHDGLYQGLSTAT KDTYDALHMQALPPR | 107 |
| 4H8-R2S-CD3ζζ(zzzdeg) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADAPAYQQGQNQLYNELNLGRREEYDV LDKRRGRDPEMGGKPRRKNPQEGLYNELQKDKMAEAYSEIGMK GERRRGKGHDGLYQGLSTATKDTYDALHMQALPPRGRVKFSRSA DDTQALLRNDQVYQPLRDRDDAQYSHLGGNRGRDPEMGGKERP PPVPNPDYEPIRKGQRDLYSGLNQRKGDKQTLLPNDQLYQPLKDR EDDQYSHLQGNALPPR | 108 |
| 4H8-R2S-CD3ζ (YAYAYA) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADAPAYQQGQNQLYAELNLGRREEYDV LDKRRGRDPEMGGKPRRKNPQEGLYAELQKDKMAEAYSEIGMK GERRRGKGHDGLYAGLSTATKDTYDALHMQALPPR | 109 |
| 4H8-R2S-CD3ζ(dzz) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADDTQALLRNDQVYQPLRDRDDAQYSH LGGNRGRDPEMGGKPRRKNPQEGLYNELQKDKMAEAYSEIGMK GERRRGKGHDGLYQGLSTATKDTYDALHMQALPPR | 110 |
| 4H8-R2S-CD3ζ(ezz) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTQEEDGCSCR FPEEEEGGCELRVKFSRSADERPPPVPNPDYEPIRKGQRDLYSGLN QRRGRDPEMGGKPRRKNPQEGLYNELQKDKMAEAYSEIGMKGE RRRGKGHDGLYQGLSTATKDTYDALHMQALPPR | 111 |
| 4H8-R2S-CD3ζ(gzz) | MALPVTALLLPLALLLHAARPGGGGSCPYSNPSLCGGGGSCPYSN PSLCGGGGSQVQLQQSGPGLVKPSQTLSLTCAISGDSVSSNSATWN | 112 |

TABLE 1-continued

| Plasmid Feature | Amino acid sequence | SEQ ID NO: |
|---|---|---|
| | WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTEEDGCSCR FPEEEEGGCELRVKFSRSADDKQTLLPNDQLYQPLKDREDDQYSH LQGNRGRDPEMGGKPRRKNPQEGLYNELQKDKMAEAYSEIGMK GERRRGKGHDGLYQGLSTATKDTYDALHMQALPPR | |
| 4H8-R2S-CD3ζ(dzg) | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTEEDGCSCR FPEEEEGGCELRVKFSRSADDTQALLRNDQVYQPLRDRDDAQYSH LGGNRGRDPEMGGKERPPPVPNPDYEPIRKGQRDLYSGLNQRKGD KQTLLPNDQLYQPLKDREDDQYSHLQGNALPPR | 113 |
| 4H8-R2S-CD3ζYA | MALPVTALLLPLALLLHAARPGGGGSCPYSNPSLCGGGGSCPYSN PSLCGGGGSQVQLQQSGPGLVKPSQTLSLTCAISGDSVSSNSATWN WIRQSPSRGLEWLGRTYYRSKWYDDYAVSVKSRITINPDTSKNHL SLHLNSVTPEDTAVYYCAGGGLVGAPDGFDVWGQGTMVTVSSG GGGSGGGGSGGGGSGGGGSQSVLTQPPSASGTPGQRVTISCSGSSS NIGSDPVNWYQQLPGTAPKLLIYSNNQRPSGVPDRFSGSKSGTSAS LAISGLQSEDEADYYCSAWDDSLNGYVFGTGTKVTVLTTTPAPRP PTPAPTIASQPLSLRPEACRPAAGGAVHTRGLDFACDIYIWAPLAG TCGVLLLSLVITLYCKRGRKKLLYIFKQPFMRPVQTTEEDGCSCR FPEEEEGGCELRVKFSRSADAPAYQQGQNQLYAELNLGRREEYDV LDKRRGRDPEMGGKPRRKNPQEGLYNELQKDKMAEAYSEIGMK GERRRGKGHDGLYQGLSTATKDTYDALHMQALPPR | 114 |
| 2G1-RSR | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTEEDGCSCRFPEEEE GGCELRVKFSRSADAPAYQQGQNQLYNELNLGRREEYDVLDKRR GRDPEMGGKPRRKNPQEGLYNELQKDKMAEAYSEIGMKGERRR GKGHDGLYQGLSTATKDTYDALHMQALPPR | 115 |
| 2G1-RSR-CD8 FL-CD3ζWT | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCNHRNRRRVCKCPRPVVKSGDKPSLSARYVKRGRKKL LYIFKQPFMRPVQTTQEEDGCSCRFPEEEEGGCELRVKFSRSADAP AYQQGQNQLYNELNLGRREEYDVLDKRRGRDPEMGGKPRRKNP QEGLYNELQKDKMAEAYSEIGMKGERRRGKGHDGLYQGLSTAT KDTYDALHMQALPPR | 116 |
| 2G1-RSR-2XCD8LRM-CD3ζWT | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITRRVCKCPRRRVCKCPRKRGRKKLLYIFKQPFMRPVQTTQE EDGCSCRFPEEEEGGCELRVKFSRSADAPAYQQGQNQLYNELNLG RREEYDVLDKRRGRDPEMGGKPRRKNPQEGLYNELQKDKMAEA YSEIGMKGERRRGKGHDGLYQGLSTATKDTYDALHMQALPPR | 117 |

TABLE 1-continued

| Plasmid Feature | Amino acid sequence | SEQ ID NO: |
|---|---|---|
| 2G1-RSR-CD28LRM-CD3ζWT | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCGGGSYQPYAPPRDFAAYRSGGGSKRGRKKLLYIFKQP FMRPVQTTQEEDGCSCRFPEEEEGGCELRVKFSRSADAPAYQQGQ NQLYNELNLGRREEYDVLDKRRGRDPEMGGKPRRKNPQEGLYNE LQKDKMAEAYSEIGMKGERRRGKGHDGLYQGLSTATKDTYDAL HMQALPPR | 118 |
| 2G1-RSR-CD28LRMY3-CD3ζWT | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCGGGSFQPFAPPRDFAAFRSGGGSKRGRKKLLYIFKQPF MRPVQTTQEEDGCSCRFPEEEEGGCELRVKFSRSADAPAYQQGQN QLYNELNLGRREEYDVLDKRRGRDPEMGGKPRRKNPQEGLYNEL QKDKMAEAYSEIGMKGERRRGKGHDGLYQGLSTATKDTYDALH MQALPPR | 119 |
| 2G1-RSR-CD3ζ-CD8LRM | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYNELNLGRREEYDVLDKRR GRDPEMGGKPRRKNPQEGLYNELQKDKMAEAYSEIGMKGERRR GKGHDGLYQGLSTATKDTYDALHMQALPPRGGGGSRVCKCPRPV | 120 |
| 2G1-RSR-CD3ζWT-CD28LRMY3- | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYNELNLGRREEYDVLDKRR GRDPEMGGKPRRKNPQEGLYNELQKDKMAEAYSEIGMKGERRR GKGHDGLYQGLSTATKDTYDALHMQALPPRGGGSFQPFAPPRDF AAFRS | 121 |
| 2G1-RSR-CD3ζWT-CD28LRM | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYNELNLGRREEYDVLDKRR GRDPEMGGKPRRKNPQEGLYNELQKDKMAEAYSEIGMKGERRR GKGHDGLYQGLSTATKDTYDALHMQALPPRGGGSYQPYAPPRDF AAYRS | 122 |
| 2G1-RSR-BB-FullCD8Cyto-CD3ζWT | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL | 123 |

TABLE 1-continued

| Plasmid Feature | Amino acid sequence | SEQ ID NO: |
|---|---|---|
| | LSLVITKRGRKKLLYIFKQPFMRPVQTTQEEDGCSCRFPEEEEGGC ELLYCNHRNRRRVCKCPRPVVKSGDKPSLSARYVRVKFSRSADAP AYQQGQNQLYNELNLGRREEYDVLDKRRGRDPEMGGKPRRKNP QEGLYNELQKDKMAEAYSEIGMKGERRRGKGHDGLYQGLSTAT KDTYDALHMQALPPR | |
| 2G1-RSR-BB-2XCD8LRM-CD3ζWT | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITKRGRKKLLYIFKQPFMRPVQTTQEEDGCSCRFPEEEEGGC ELRRVCKCPRRRVCKCPRRVKFSRSADAPAYQQGQNQLYNELNL GRREEYDVLDKRRGRDPEMGGKPRRKNPQEGLYNELQKDKMAE AYSEIGMKGERRRGKGHDGLYQGLSTATKDTYDALHMQALPPR | 124 |
| 2G1-RSR-CD3ζζ | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYNELNLGRREEYDVLDKRR GRDPEMGGKPRRKNPQEGLYNELQKDKMAEAYSEIGMKGERRR GKGHDGLYQGLSTATKDTYDALHMQALPPRGRVKFSRSADAPAY QQGQNQLYNELNLGRREEYDVLDKRRGRDPEMGGKPRRKNPQE GLYNELQKDKMAEAYSEIGMKGERRRGKGHDGLYQGLSTATKD TYDALHMQALPPR | 125 |
| 2G1-RSR-CD3ζζ (YAYAYA) | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYAELNLGRREEYDVLDKRR GRDPEMGGKPRRKNPQEGLYAELQKDKMAEAYSEIGMKGERRR GKGHDGLYAGLSTATKDTYDALHMQALPPRRVKFSRSADAPAYQ QGQNQLYAELNLGRREEYDVLDKRRGRDPEMGGKPRRKNPQEGL YAELQKDKMAEAYSEIGMKGERRRGKGHDGLYAGLSTATKDTY DALHMQALPPR | 126 |
| 2G1-RSR-CD3ζζ (zdzezg-6xYA) | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYAELNLGRREEYDVLDKRR GRDPEMGGKDTQALLRNDQVYAPLRDRDDAQYSHLGGNKGPRR KNPQEGLYAELQKDKMAEAYSEIGMALPPRGRVKFSRSADERPPP VPNPDYAPIRKGQRDLYSGLNQRRGRDPEMGGKERRRGKGHDGL YAGLSTATKDTYDALHMQKGDKQTLLPNDQLYAPLKDREDDQY SHLQGNALPPR | 127 |
| 2G1-RSR-CD3ζζ(zdzezg) | MALPVTALLLPLALLLHAARPGGGGSCPYSNPSLCGGGGSQLQLQ ESGPGLVKPSETLSLTCTVSGGSISSSSYYWGWIRQPPGKGLEWIGS IYYSGNIYHNPSLKSRVSISVDTSKNQFSLRLSSVTAADTAVYYCA REIIVGATHFDYWGQGTLVTVSSGGGGSGGGGSGGGGSGGGGSAI QMTQSPSSLSASVGDRVTITCRASQGIRNDLGWYQQKPGKAPELLI YAASSLQSGVPSRFSGSGSGTDFTLTISSLQPEDFATYYCLQDYNY PLTFGPGTKVDIKGGGGSCPYSNPSLCGGGGSTTTPAPRPPTPAPTI ASQPLSLRPEACRPAAGGAVHTRGLDFACDIYIWAPLAGTCGVLL LSLVITLYCKRGRKKLLYIFKQPFMRPVQTTQEEDGCSCRFPEEEE GGCELRVKFSRSADAPAYQQGQNQLYNELNLGRREEYDVLDKRR | 128 |

TABLE 1-continued

| Plasmid Feature | Amino acid sequence | SEQ ID NO: |
|---|---|---|
| | GRDPEMGGKDTQALLRNDVYQPLRDRDDAQYSHLGGNKGPRR<br>KNPQEGLYNELQKDKMAEAYSEIGMALPPRGRVKFSRSADERPPP<br>VPNPDYEPIRKGQRDLYSGLNQRRGRDPEMGGKERRRGKHDGL<br>YQGLSTATKDTYDALHMQKGDKQTLLPNDQLYQPLKDREDDQY<br>SHLQGNALPPR | |
| 2G1-RSR-CD3ζζ (dzezgz-6xYA) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADDTQALLRNDVYAPLRDRDDAQYSHLGGNR<br>GRDPEMGGKAPAYQQGQNQLYAELNLGRREEYDVLDKRKGERP<br>PPVPNPDYAPIRKGQRDLYSGLNQRALPPRGRVKFSRSADPRRKN<br>PQEGLYAELQKDKMAEAYSEIGMRGRDPEMGGKDQTLLPNDQL<br>YAPLKDREDDQYSHLQGNKGERRRGKHDGLYAGLSTATKDTY<br>DALHMQALPPR | 129 |
| 2G1-RSR-CD3ζζ (dzezgz) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADDTQALLRNDVYQPLRDRDDAQYSHLGGNR<br>GRDPEMGGKAPAYQQGQNQLYNELNLGRREEYDVLDKRKGERP<br>PPVPNPDYEPIRKGQRDLYSGLNQRALPPRGRVKFSRSADPRRKN<br>PQEGLYNELQKDKMAEAYSEIGMRGRDPEMGGKDKQTLLPNDQL<br>YQPLKDREDDQYSHLQGNKGERRRGKHDGLYQGLSTATKDTY<br>DALHMQALPPR | 130 |
| 2G1-RSR-CD3ζζ (degzzz) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADDTQALLRNDVYQPLRDRDDAQYSHLGGNR<br>GRDPEMGGKERPPPVPNPDYEPIRKGQRDLYSGLNQRKGDKQTLL<br>PNDQLYQPLKDREDDQYSHLQGNALPPRGRVKFSRSADAPAYQQ<br>GQNQLYNELNLGRREEYDVLDKRRGRDPEMGGKPRRKNPQEGLY<br>NELQKDKMAEAYSEIGMKGERRRGKHDGLYQGLSTATKDTYD<br>ALHMQALPPR | 131 |
| 2G1-RSR-CD3ζζ (zzzdeg) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADAPAYQQGQNQLYNELNLGRREEYDVLDKRR<br>GRDPEMGGKPRRKNPQEGLYNELQKDKMAEAYSEIGMKGERRR<br>GKHDGLYQGLSTATKDTYDALHMQALPPRGRVKFSRSADDTQA<br>LLRNDVYQPLRDRDDAQYSHLGGNRGRDPEMGGKERPPPVPNP<br>DYEPIRKGQRDLYSGLNQRKGDKQTLLPNDQLYQPLKDREDDQY<br>SHLQGNALPPR | 132 |
| 2G1-RSR-CD3ζ (YAYAYA) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI | 133 |

TABLE 1-continued

| Plasmid Feature | Amino acid sequence | SEQ ID NO: |
|---|---|---|
| | ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADAPAYQQGQNQLYAELNLGRREEYDVLDKRR<br>GRDPEMGGKPRRKNPQEGLYAELQKDKMAEAYSEIGMKGERRR<br>GKGHDGLYAGLSTATKDTYDALHMQALPPR | |
| 2G1-RSR-<br>CD3ζ(dzz) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADDTQALLRNDQVYQPLRDRDDAQYSHLGGNR<br>GRDPEMGGKPRRKNPQEGLYNELQKDKMAEAYSEIGMKGERRR<br>GKGHDGLYQGLSTATKDTYDALHMQALPPR | 134 |
| 2G1-RSR-<br>CD3ζ(ezz) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADERPPPVPNPDYEPIRKGQRDLYSGLNQRRGR<br>DPEMGGKPRRKNPQEGLYNELQKDKMAEAYSEIGMKGERRRGK<br>GHDGLYQGLSTATKDTYDALHMQALPPR | 135 |
| 2G1-RSR-<br>CD3ζ(gzz) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADDKQTLLPNDQLYQPLKDREDDQYSHLQGNR<br>GRDPEMGGKPRRKNPQEGLYNELQKDKMAEAYSEIGMKGERRR<br>GKGHDGLYQGLSTATKDTYDALHMQALPPR | 136 |
| 2G1-RSR-<br>CD3ζ(deg) | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADDTQALLRNDQVYQPLRDRDDAQYSHLGGNR<br>GRDPEMGGKERPPPVPNPDYEPIRKGQRDLYSGLNQRKGDKQTLL<br>PNDQLYQPLKDREDDQYSHLQGNALPPR | 137 |
| 2G1-RSR-<br>CD3ζYA | MALPVTALLLPLALLLHAARPGGGGSCPYSNPSLCGGGGSQLQLQ<br>ESGPGLVKPSETLSLTCTVSGGSISSSSYYWGWIRQPPGKGLEWIGS<br>IYYSGNIYHNPSLKSRVSISVDTSKNQFSLRLSSVTAADTAVYYCA<br>REIIVGATHFDYWGQGTLVTVSSGGGGSGGGGSGGGGSGGGGSAI<br>QMTQSPSSLSASVGDRVTITCRASQGIRNDLGWYQQKPGKAPELLI<br>YAASSLQSGVPSRFSGSGSGTDFTLTISSLQPEDFATYYCLQDYNY<br>PLTFGPGTKVDIKGGGGSCPYSNPSLCGGGGSTTTPAPRPPTPAPTI<br>ASQPLSLRPEACRPAAGGAVHTRGLDFACDIYIWAPLAGTCGVLL<br>LSLVITLYCKRGRKKLLYIFKQPFMRPVQTTQEEDGCSCRFPEEEE<br>GGCELRVKFSRSADAPAYQQGQNQLYAELNLGRREEYDVLDKRR<br>GRDPEMGGKPRRKNPQEGLYNELQKDKMAEAYSEIGMKGERRR<br>GKGHDGLYQGLSTATKDTYDALHMQALPPR | 138 |
| 10G1-K-CD8<br>FL-CD3ζWT | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF<br>SGSGSGTEFTLTISSLQPEDFATYFCLQHDSFPLTFGGGTKVEIKTTT | 139 |

TABLE 1-continued

| Plasmid Feature | Amino acid sequence | SEQ ID NO: |
|---|---|---|
| | PAPRPPTPAPTIASQPLSLRPEACRPAAGGAVHTRGLDFACDIYIWA<br>PLAGTCGVLLLSLVITLYCNHRNRRRVCKCPRPVVKSGDKPSLSAR<br>YVKRGRKKLLYIFKQPFMRPVQTTQEEDGCSCRFPEEEEGGCELR<br>VKFSRSADAPAYQQGQNQLYNELNLGRREEYDVLDKRRGRDPEM<br>GGKPRRKNPQEGLYNELQKDKMAEAYSEIGMKGERRRGKGHDG<br>LYQGLSTATKDTYDALHMQALPPR | |
| 10G1-K-<br>2XCD8LRM-<br>CD3ζWT | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF<br>SGSGSGTEFTLTISSLQPEDFATYFCLQHDSFPLTFGGGTKVEIKTTT<br>PAPRPPTPAPTIASQPLSLRPEACRPAAGGAVHTRGLDFACDIYIWA<br>PLAGTCGVLLLSLVITRRVCKCPRRRVCKCPRKRGRKKLLYIFKQP<br>FMRPVQTTQEEDGCSCRFPEEEEGGCELRVKFSRSADAPAYQQGQ<br>NQLYNELNLGRREEYDVLDKRRGRDPEMGGKPRRKNPQEGLYNE<br>LQKDKMAEAYSEIGMKGERRRGKGHDGLYQGLSTATKDTYDAL<br>HMQALPPR | 140 |
| 10G1-K-<br>CD28LRM-<br>CD3ζWT | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF<br>SGSGSGTEFTLTISSLQPEDFATYFCLQHDSFPLTFGGGTKVEIKTTT<br>PAPRPPTPAPTIASQPLSLRPEACRPAAGGAVHTRGLDFACDIYIWA<br>PLAGTCGVLLLSLVITLYCGGGSYQPYAPPRDFAAYRSGGGSKRG<br>RKKLLYIFKQPFMRPVQTTQEEDGCSCRFPEEEEGGCELRVKFSRS<br>ADAPAYQQGQNQLYNELNLGRREEYDVLDKRRGRDPEMGGKPR<br>RKNPQEGLYNELQKDKMAEAYSEIGMKGERRRGKGHDGLYQGL<br>STATKDTYDALHMQALPPR | 141 |
| 10G1-K-<br>CD28LRMY3-<br>CD3ζWT | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF<br>SGSGSGTEFTLTISSLQPEDFATYFCLQHDSFPLTFGGGTKVEIKTTT<br>PAPRPPTPAPTIASQPLSLRPEACRPAAGGAVHTRGLDFACDIYIWA<br>PLAGTCGVLLLSLVITLYCGGGSFQPFAPPRDFAAFRSGGGSKRGR<br>KKLLYIFKQPFMRPVQTTQEEDGCSCRFPEEEEGGCELRVKFSRSA<br>DAPAYQQGQNQLYNELNLGRREEYDVLDKRRGRDPEMGGKPRR<br>KNPQEGLYNELQKDKMAEAYSEIGMKGERRRGKGHDGLYQGLST<br>ATKDTYDALHMQALPPR | 142 |
| 10G1-K-<br>CD3ζWT-<br>CD8LRM | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF<br>SGSGSGTEFTLTISSLQPEDFATYFCLQHDSFPLTFGGGTKVEIKTTT<br>PAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDG<br>CSCRFPEEEEGGCELRVKFSRSADAPAYQQGQNQLYNELNLGRRE<br>EYDVLDKRRGRDPEMGGKPRRKNPQEGLYNELQKDKMAEAYSEI<br>GMKGERRRGKGHDGLYQGLSTATKDTYDALHMQALPPRGGGGS<br>RVCKCPRPV | 143 |
| 10G1-K-<br>CD3ζWT-<br>CD28LRMY3 | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF<br>SGSGSGTEFTLTISSLQPEDFATYFCLQHDSFPLTFGGGTKVEIKTTT<br>PAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDG<br>CSCRFPEEEEGGCELRVKFSRSADAPAYQQGQNQLYNELNLGRRE<br>EYDVLDKRRGRDPEMGGKPRRKNPQEGLYNELQKDKMAEAYSEI<br>GMKGERRRGKGHDGLYQGLSTATKDTYDALHMQALPPRGGGSF<br>QPFAPPRDFAAFRS | 144 |
| 10G1-K-BB-<br>FullCD8TCyto-<br>CD3ζWT | MALPVTALLLPLALLLHAARPEVQLLESGGGLVQPGGSLRLSCAA<br>SGFTFSSYAMNWVRQAPGKGLEWVSTISGSGGSTYYADSVKGRFT<br>ISRDNSKNTLYLQMNSLRAEDTAVFYCAIDPEYYDILTGGDYWGQ<br>GTLVTVSSGGGGSGGGGSGGGGSGGGGSDIQMTQSPSAMSASVG<br>DRVTITCRASQGISNYLAWFQQKPGKVPKRLIYAASSLQSGVPSRF | 145 |

TABLE 1-continued

| Plasmid Feature | Amino acid sequence | SEQ ID NO: |
|---|---|---|
|  | SGSGSGTEFTLTISSLQPEDFATYFCLQHDSFPLTFGGGTKVEIKTTT PAPRPPTPAPTIASQPLSLRPEACRPAAGGAVHTRGLDFACDIYIWA PLAGTCGVLLLSLVITKRGRKKLLYIFKQPFMRPVQTTQEEDGCSC RFPEEEEGGCELLYCNHRNRRRVCKCPRPVVKSGDKPSLSARYVR VKFSRSADAPAYQQGQNQLYNELNLGRREEYDVLDKRRGRDPEM GGKPRRKNPQEGLYNELQKDKMAEAYSEIGMKGERRRGKGHDG LYQGLSTATKDTYDALHMQALPPR |  |
| 10G1-K-BB-2XCD8LRM-CD3ζWT | MALPVTALLLPLALLLHAARPEVQLLESGGGLVQPGGSLRLSCAA SGFTFSSYAMNWVRQAPGKGLEWVSTISGSGGSTYYADSVKGRFT ISRDNSKNTLYLQMNSLRAEDTAVFYCAIDPEYYDILTGGDYWGQ GTLVTVSSGGGGSGGGGSGGGGSGGGGSDIQMTQSPSAMSASVG DRVTITCRASQGISNYLAWFQQKPGKVPKRLIYAASSLQSGVPSRF SGSGSGTEFTLTISSLQPEDFATYFCLQHDSFPLTFGGGTKVEIKTTT PAPRPPTPAPTIASQPLSLRPEACRPAAGGAVHTRGLDFACDIYIWA PLAGTCGVLLLSLVITKRGRKKLLYIFKQPFMRPVQTTQEEDGCSC RFPEEEEGGCELRRVCKCPRRRVCKCPRRVKFSRSADAPAYQQGQ NQLYNELNLGRREEYDVLDKRRGRDPEMGGKPRRKNPQEGLYNE LQKDKMAEAYSEIGMKGERRRGKGHDGLYQGLSTATKDTYDAL HMQALPPR | 146 |

The recombinant antigen receptors of the present invention can be used to: (a) treat, prevent, ameliorate one or more symptoms of a condition associated with malignant cells expressing in a subject an antigen that the recombinant antigen receptor binds to (e.g., cancer); (b) inhibit tumor growth or progression in a subject (who has a malignant tumor expressing an antigen that the recombinant antigen receptor binds to); (c) inhibit metastasis of cancer (malignant) cells expressing an antigen that the recombinant antigen receptor binds to in a subject (who has one or more malignant cells expressing such an antigen); (d) induce regression (e.g., long-term regression) of a tumor expressing an antigen that the recombinant antigen receptor binds to; (e) exert cytotoxic activity in malignant cells expressing an antigen that the recombinant antigen receptor binds to; (f) block interaction between such an antigen and a factor yet to be identified; and/or (g) induce a bystander effect that kills or inhibits growth of malignant cells in the vicinity that do not express such an antigen.

The recombinant antigen receptors provided herein can encompass monoclonal antibodies, polyclonal antibodies, antibody fragments (e.g., Fab, Fab', F(ab')2, Fv, Fc, etc.), chimeric antibodies, single chain (ScFv), and/or humanized antibodies. The antibodies may be murine, rat, human, or any other origin (including chimeric or humanized antibodies).

The invention further provides a polynucleotide comprising a DNA sequence encoding the recombinant antigen receptor described herein. The invention further provides a vector comprising the polynucleotide. The invention further provides an engineered immune cell that comprises the polynucleotide and/or comprises the vector. The invention further provides an engineered immune cell comprising a first recombinant antigen receptor as described herein. Conventional molecular biology techniques may be used to produce these.

Additional Methods to Improve Signalling by the Recombinant Antigen Receptor.

In another aspect, the invention further provides an engineered immune cell comprising a first recombinant antigen receptor as described herein and further comprising a second recombinant antigen receptor comprising an extracellular antigen binding domain and an intracellular domain that comprises a Lck, LAT, ZAP70, or a variant thereof, e.g. a functional variant thereof. In an embodiment of this engineered immune cell, the antigen binding domain of the second recombinant antigen receptor binds to the same antigen as the first recombinant antigen receptor or the antigen binding domain of the second recombinant antigen receptor binds to a different antigen from the first recombinant antigen receptor. For example, the antigen binding domain of the first recombinant antigen receptor may bind to DLL3 on a target tumor cell, while the antigen binding domain of the second recombinant antigen receptor may bind to a second, different tumor antigen.

In an embodiment, the immune cell is a T cell. In an embodiment, the immune cell comprises one or more genomic modifications to the TCRa (TCR alpha) gene. In an embodiment, the immune cell expresses an exogenous downstream mediator of T cell signaling. In an embodiment, the exogenous downstream mediator of T cell signaling is one or more of ZAP70, Lck, Fyn, Syk, LAT or Unc119 (e.g. the downstream mediator comprises the amino acid sequence of SEQ ID NOs: 1 (ZAP70), 2 (Lck), 4 (Fyn), 6 (Syk), 8 (LAT), or 9 (Unc119)), or a variant thereof (e.g. the downstream mediator comprises the amino acid sequence of SEQ ID NOs: 3 (Truncated Lck), 5 (Truncated Fyn), or 7 (Truncated Syk)). In an embodiment, the antigen binding domain of the recombinant antigen receptor binds to an antigen characteristic of a disease or condition e.g. cancer. In an embodiment, the antigen binding domain of the recombinant antigen receptor binds to DLL3.

In another aspect, the invention further provides an engineered immune cell comprising a CAR and expressing one or more exogenous downstream mediators of T cell signaling. In an embodiment, the exogenous downstream mediator of T cell signaling is one or more of ZAP70, Lck, Fyn, Syk, LAT or Unc119 (e.g. the downstream mediator comprises the amino acid sequence of SEQ ID NOs: 1 (ZAP70), 2 (Lck), 4 (Fyn), 6 (Syk), 8 (LAT), or 9 (Unc119)), or a variant thereof, e.g. a functional variant thereof (e.g. the downstream mediator comprises the amino acid sequence of SEQ ID NOs: 3 (Truncated Lck), 5 (Truncated Fyn), or 7 (Truncated Syk)). In an embodiment, the immune cell is a T cell. In an embodiment, the immune cell comprises one or more genomic modifications to the TCRa (TCR alpha) gene. In an embodiment, the antigen binding domain of the recombinant antigen receptor binds to an antigen characteristic of a disease or condition e.g. cancer. In an embodiment, the antigen binding domain of the recombinant antigen receptor binds to DLL3.

In a further aspect, the invention provides an engineered immune cell comprising a first recombinant antigen receptor and a second recombinant antigen receptor, wherein the first recombinant antigen receptor comprises a CAR and the second recombinant antigen receptor comprises an extracellular antigen binding domain and an intracellular domain that comprises Lck, LAT, ZAP70, or a variant thereof. In an embodiment, the antigen binding domain of the second recombinant antigen receptor binds to the same antigen as the first recombinant antigen receptor or the antigen binding domain of the second recombinant antigen receptor binds to a different antigen from the first recombinant antigen receptor. In an embodiment, the immune cell is a T cell. In an embodiment, the immune cell comprises one or more genomic modifications to the TCRa (TCR alpha) gene. In an embodiment, the immune cell expresses an exogenous downstream mediator of T cell signaling. In an embodiment, the exogenous downstream mediator of T cell signaling is one or more of ZAP70, Lck, Fyn, Syk, LAT or Unc119 (e.g. the downstream mediator comprises the amino acid sequence of SEQ ID NOs: 1 (ZAP70), 2 (Lck), 4 (Fyn), 6 (Syk), 8 (LAT), or 9 (Unc119)), or a variant thereof, e.g. a functional variant thereof (e.g. the downstream mediator comprises the amino acid sequence of SEQ ID NOs: 3 (Truncated Lck), 5 (Truncated Fyn), or 7 (Truncated Syk)). In an embodiment, the antigen binding domain of the recombinant antigen receptor binds to an antigen characteristic of a disease or condition e.g. cancer. In an embodiment, the antigen binding domain of the recombinant antigen receptor binds to DLL3.

In a further aspect, the invention provides a pharmaceutical composition comprising any of the engineered immune cells described in this section. In a further aspect, the invention provides a method of treating cancer comprising administering to a patient in need thereof an effective amount of the pharmaceutical composition or an effective amount of any of the engineered immune cells described in this section.

Improved Recombinant Antigen Receptors e.g. Improved CARs and Methods of Making Thereof Provided herein are improved recombinant antigen receptors, e.g. improved CARs. CARs provided herein include single chain CARS and multichain CARs. The CARs have the ability to redirect T cell specificity and reactivity toward the antigen they bind e.g. DLL3 in a non-MHC-restricted manner, exploiting the antigen-binding properties of monoclonal antibodies. The non-MHC-restricted antigen recognition gives T cells expressing CARs the ability to recognize an antigen independent of antigen processing, thus bypassing a major mechanism of tumor escape.

In some embodiments, CARs provided herein comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain.

In some embodiments, the extracellular ligand-binding domain of the recombinant antigen receptor of the invention, e.g. CAR of the invention, comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence $(GGGGS)_3$ (SEQ ID NO: 147), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides, e.g. comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention encompasses modifications to the CARs and polypeptides of the invention shown in Table 2, including functionally equivalent CARs having modifications which do not significantly affect their properties and variants which have enhanced or decreased activity and/or affinity. For example, the amino acid sequence may be mutated to obtain an antibody with the desired binding affinity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 4 under the heading of "conservative substitutions." If such substitutions result in a change in biological activity, then more substantial changes, denominated "exemplary substitutions" in Table 4, or as further described below in reference to amino acid classes, may be introduced and the products screened.

TABLE 2

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

The binding affinity ($K_D$) of the ligand binding domain of the recombinant antigen receptor of the present invention e.g. a CAR of the present invention as described herein to its target antigen e.g. DLL3 (such as human DLL3) can be for example about 0.1 to about 1000 nM, for example between about 0.5 nM to about 500 nM, or for example between about 1 nM to about 250 nM. In some embodiments, the binding affinity is about any of 1000 nm, 750 nm, 500 nm, 400 nm, 300 nm, 250 nm, 200 nM, 100 nM, 90 nM, 80 nM, 70 nM, 60 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM or 0.1 nM.

In some embodiments, the binding affinity ($K_D$) of the scFv of the ligand binding domain of the recombinant antigen receptor as described herein to its target antigen e.g. DLL3 is about 10 nM to about 100 nM, about 10 nM to about 90 nM, about 10 nM to about 80 nM, about 20 nM to about 70 nM, about 25 nM to about 75 nM, or about 40 nM to about 110 nM. In one embodiment, the binding affinities of the scFv described in this paragraph are for human DLL3.

In some embodiments, the binding affinity is less than about any of 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM.

Monoclonal Antibody-Specific Epitopes

In some embodiments, the extracellular domain of any one of the improved recombinant antigen receptors disclosed herein may comprise one or more epitopes specific for (i.e., specifically recognized by) a monoclonal antibody. These epitopes are also referred to herein as mAb-specific epitopes. In these embodiments, the extracellular domain comprises the VH and VL polypeptides that specifically bind to the target antigen of choice e.g. DLL3 and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, this feature also promotes recovery of endogenous target antigen-expressing cells that were depleted by administration of engineered immune cells expressing the CARs.

Accordingly, in some embodiments, the present invention relates to a method for sorting and/or depleting the engineered immune cells endowed with the CARs comprising mAb-specific epitopes and a method for promoting recovery of endogenous target-antigen-expressing cells, such as bone marrow progenitor cells.

Several epitope-monoclonal antibody couples can be used to generate CARs comprising monoclonal antibody specific epitopes; in particular, those already approved for medical use, such as CD20 epitope/rituximab as a non-limiting example.

In some embodiments, the monoclonal antibody specific for the epitope may be conjugated with a cytotoxic drug. It is also possible to promote CDC cytotoxicity by using engineered antibodies on which are grafted component(s) of the complement system. In some embodiments, activation of the CAR-T cells can be modulated by depleting the cells using an antibody which recognizes the epitope.

The invention also encompasses methods for sorting the engineered immune cells endowed with the target-antigen-specific recombinant antigen receptors e.g. CARs expressing the mAb-specific epitope(s) and therapeutic methods where the activation of the engineered immune cells endowed with these target-antigen-specific recombinant antigen receptors is modulated by depleting the cells using an antibody that targets the external ligand binding domain of said CARs.

CARs comprising one or more epitopes specifically recognized by a monoclonal antibody are disclosed in WO2016/120216, which is hereby incorporated by reference in its entirety. The epitope can be selected from any number of epitopes known in the art. In some embodiments, the epitope can be a target of a monoclonal antibody approved for medical use, such as, for example without limitation, the CD20 epitope recognized by rituximab.

In some embodiments, the epitope can be located between the scFv and the hinge of a CAR. In some embodiments, two instances of the same epitope, separated by linkers, may be used in the CAR.

In some embodiments, the extracellular binding domain of the CAR comprising the VH and VL polypeptides and the mAb-specific epitope(s) may have different structures depending on the position of insertion of the epitope and the use of linkers. For example, the extracellular binding domain of the recombinant antigen receptor e.g. CAR of the present invention comprising mAb-specific epitopes may have one of the following structures:

$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;

(L)$_x$-Epitope1-(L)$_x$-V$_1$-L$_1$-V$_2$-(L)$_x$-Epitope2-(L)$_x$-Epitope3-(L)$_x$-;
(L)$_x$-Epitope1-(L)$_x$-V$_1$-L$_1$-V$_2$-(L)$_x$-Epitope2-(L)$_x$-Epitope3-(L)$_x$-Epitope4-(L)$_x$-;
(L)$_x$-Epitope1-(L)$_x$-Epitope2-(L)$_x$-V$_1$-L$_1$-V$_2$-(L)$_x$-Epitope3-(L)$_x$-;
(L)$_x$-Epitope1-(L)$_x$-Epitope2-(L)$_x$-V$_1$-L$_1$-V$_2$-(L)$_x$-Epitope3-(L)$_x$-Epitope4-(L)$_x$-;
V$_1$-(L)$_x$-Epitope1-(L)$_x$-V$_2$;
V$_1$-(L)$_x$-Epitope1-(L)$_x$-V$_2$-(L)$_x$-Epitope2-(L)$_x$;
V$_1$-(L)$_x$-Epitope1-(L)$_x$-V$_2$-(L)$_x$-Epitope2-(L)$_x$-Epitope3-(L)$_x$;
V$_1$-(L)$_x$-Epitope1-(L)$_x$-V$_2$-(L)$_x$-Epitope2-(L)$_x$-Epitope3-(L)$_x$-Epitope4-(L)$_x$;
(L)$_x$-Epitope1-(L TABLE 3-continued Examples of mAb-specific epitopes that can be used in the extracellular binding domain of the target-specific CAR of the invention such as for example mimotopes and epitope with their corresponding mAb.

| | QBEND-10 | |
|---|---|---|
| Epitope | SEQ ID NO: 89 | ELPTQGTFSNVSTNVSPAKPTTTA |
| | Alemtuzumab | |
| Epitope | SEQ ID NO: 90 | GQNDTSQTSSPS |

The recombinant antigen receptors e.g. CARs of the invention are expressed on the surface membrane of the cell. Thus, the CAR can comprise a transmembrane domain. Suitable transmembrane domains for a CAR disclosed herein have the ability to (a) be expressed at the surface of a cell, e.g. an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (α chain), p75 (β chain) or γ chain, subunit chain of Fc receptors, in particular Fcγ receptor III, or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1).

The transmembrane domain is linked to the extracellular ligand-binding domain by a stalk domain (also called hinge domain). A stalk domain may comprise up to 300 amino acids, e.g. 10 to 100 amino acids or 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In some embodiments, the stalk domain of recombinant antigen receptors e.g. CARs described herein comprises a CD8α hinge, an IgG1 hinge, or an FcγRIIIα hinge. In some embodiments, the stalk domain comprises a human CD8α hinge, a human IgG1 hinge, or a human FcγRIIIα hinge. In some embodiments, CARs disclosed herein can comprise an extracellular ligand-binding domain that specifically binds DLL3, a CD8α human hinge and transmembrane domains, the modified CD3t signaling domain as described herein, and 4-1BB co-stimulatory domain.

Downregulation or mutation of target antigens is commonly observed in cancer cells, creating antigen-loss escape variants. Thus, to offset tumor escape and render the immune cell more specific to target, the recombinant antigen receptor e.g. CAR of the invention can comprise one or more additional extracellular ligand-binding domains, to simultaneously bind different elements in target thereby augmenting immune cell activation and function. In some embodiments, the extracellular ligand-binding domains can be placed in tandem on the same transmembrane polypeptide, and optionally can be separated by a linker. In some embodiments, said different extracellular ligand-binding domains can be placed on different transmembrane polypeptides composing the recombinant antigen receptor e.g. CAR. In some embodiments, the invention relates to a population of recombinant antigen receptors, each comprising a different extracellular ligand-binding domain. In particular, the invention relates to a method of engineering immune cells comprising providing an immune cell and expressing at the surface of the cell a population of CARs, each CAR comprising different extracellular ligand-binding domains. In another particular embodiment, the invention relates to a method of engineering an immune cell comprising providing an immune cell and introducing into the cell polynucleotides encoding polypeptides composing a population of CAR each one comprising different extracellular ligand-binding domains. By population of CARs, it is meant at least two, three, four, five, six or more CARs each one comprising different extracellular ligand-binding domains. The different extracellular ligand-binding domains according to the invention can for example simultaneously bind different elements in the target thereby augmenting immune cell activation and function. The invention also relates to an isolated immune cell which comprises a population of CARs each one comprising different extracellular ligand-binding domains.

In another aspect, provided herein are polynucleotides encoding any of the recombinant antigen receptors e.g. CARs and polypeptides described herein. Polynucleotides can be made and expressed by procedures known in the art.

In another aspect, provided herein are compositions (such as a pharmaceutical compositions) comprising any of the cells of the invention. In some embodiments, the composition comprises a cell comprising a polynucleotide encoding any of the CARs described herein.

Expression vectors, and administration of polynucleotide compositions are further described herein.

In another aspect, provided herein is a method of making any of the polynucleotides described herein.

Polynucleotides complementary to any such sequences are also encompassed by the invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants generally exhibit at least about 70% identity, or at least about 80% identity, or even at least about 90% or 95% or greater than 95% identity e.g. at least 99% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Generally, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the invention. Further, alleles of the genes comprising the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell.

When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a recombinant antigen receptor e.g. CAR disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In some embodiments the signal peptide comprises the amino acid sequence MALPVTALLLPLALLLHAARP (SEQ ID NO: 150) (CD8 signal sequence) or MIPAVVLLLLLLVEQAAA (SEQ ID NO: 151) (FcεRIγ-signal peptide). Those skilled in the art will recognize that, in view of the degeneracy of the genetic code, considerable sequence variation is possible among these polynucleotide molecules. In some embodiments, nucleic acid sequences of the invention are codon-optimized for expression in mammalian cells, e.g. for expression in primate (e.g. human or monkey) cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering an Immune Cell

Methods of preparing immune cells for use in immunotherapy are provided herein. In some embodiments, the methods comprise obtaining immune cells, introducing a recombinant antigen receptor e.g. CAR according to the invention into immune cells, and expanding the cells. In some embodiments, the invention relates to a method of engineering an immune cell comprising: providing a cell and expressing at the surface of the cell at least one CAR as described herein. Methods for engineering immune cells are described in, for example, PCT Patent Application Publication Nos. WO/2014/039523, WO/2014/184741, WO/2014/191128, WO/2014/184744, and WO/2014/184143, each of which is incorporated herein by reference in its entirety. In some embodiments, the method comprises: transfecting the cell with at least one polynucleotide encoding CAR as described herein, and expressing the polynucleotides in the cell.

Prior to engineering of cells, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor or from a donor suffering from a disease or disorder, for example, an individual diagnosed with cancer or from an individual diagnosed with an infection. In some embodiments, cells can be part of a mixed population of cells which present different phenotypic characteristics.

In some embodiments, the polynucleotides are present in lentiviral vectors for stable expression in the cells.

In some embodiments, the method can further comprise a step of genetically modifying a cell by disrupting or inactivating at least one gene expressing, for example without limitation, a component of the TCR, a target for an immunosuppressive agent, an HLA gene, and/or an immune checkpoint protein such as, for example, PDCD1 or CTLA-4. By disruption or inactivating a gene it is intended that the gene of interest is not expressed in a functional protein form. In some embodiments, the gene to be disrupted or inactivated is selected from the group consisting of, for example without limitation, TCRα, TCRβ, CD52, glucocorticoid receptor (GR), deoxycytidine kinase (DCK), PD-1, and CTLA-4. In some embodiments, the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or Cas9 endonuclease.

In some embodiments, an additional catalytic domain is used with a rare-cutting endonuclease to enhance its capacity to inactivate targeted genes. For example, an additional catalytic domain can be a DNA end-processing enzyme. Non-limiting examples of DNA end-processing enzymes include 5-3' exonucleases, 3-5' exonucleases, 5-3' alkaline exonucleases, 5' flap endonucleases, helicases, phosphatase, hydrolases and template-independent DNA polymerases. Non-limiting examples of such catalytic domain comprise of a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In some embodiments, an additional catalytic domain can have a 3'-5'-exonuclease activity, and In some embodiments, said additional catalytic domain is TREX, e.g. a TREX2 catalytic domain (WO2012/058458). In some embodiments, said catalytic domain is encoded by a single chain TREX polypeptide. The additional catalytic domain may be fused to a nuclease fusion protein or chimeric protein. In some embodiments, the additional catalytic domain is fused using, for example, a peptide linker.

In some embodiments, the method further comprises a step of introducing into cells an exogeneous nucleic acid comprising at least a sequence homologous to a portion of the target nucleic acid sequence, such that homologous recombination occurs between the target nucleic acid sequence and the exogeneous nucleic acid. In some embodiments, said exogenous nucleic acid comprises first and second portions which are homologous to region 5' and 3' of the target nucleic acid sequence, respectively. The exogenous nucleic acid may also comprise a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogeneous nucleic acid. In some embodiments, homologous sequences of at least about 50 bp, greater than about 100 bp, or greater than about 200 bp can be used within the donor matrix. The exogenous nucleic acid can be, for example without limitation, from about 200 bp to about 6000 bp, e.g. from about 1000 bp to about 2000 bp. Shared nucleic acid homologies are located in regions flanking upstream and downstream the site of the break, and the nucleic acid sequence to be introduced is located between the two arms.

In some embodiments, a nucleic acid successively comprises a first region of homology to sequences upstream of said cleavage; a sequence to inactivate a targeted gene selected from the group consisting of TCRα, TCRβ, CD52, glucocorticoid receptor (GR), deoxycytidine kinase (DCK), and an immune checkpoint protein such as for example programmed death-1 (PD-1); and a second region of homology to sequences downstream of the cleavage. The polynucleotide introduction step can be simultaneous, before or after the introduction or expression of the rare-cutting endonuclease. Depending on the location of the target nucleic acid sequence wherein break event has occurred, such exogenous nucleic acid can be used to knock-out a gene, e.g. when exogenous nucleic acid is located within the open reading frame of the gene, or to introduce new sequences or genes of interest. Sequence insertions by using such exogenous nucleic acid can be used to modify a targeted existing gene, by correction or replacement of the gene (allele swap as a non-limiting example), or to up- or down-regulate the expression of the targeted gene (promoter swap as non-limiting example), the targeted gene correction or replacement. In some embodiments, inactivation of a gene selected from the group consisting of TCRα, TCRβ, CD52, GR, DCK, and immune checkpoint proteins, can be done at a precise genomic location targeted by a specific TALE-nuclease, wherein said specific TALE-nuclease catalyzes a cleavage and wherein the exogenous nucleic acid successively comprising at least a region of homology and a sequence to inactivate one targeted gene selected from the group consisting of TCRα, TCRβ, CD52, GR, DCK, immune checkpoint proteins which is integrated by homologous recombination. In some embodiments, several genes can be, successively or at the same time, inactivated by using several TALE-nucleases respectively and specifically targeting one defined gene and several specific polynucleotides for specific gene inactivation.

In some embodiments, the method comprises inactivation of one or more additional genes selected from the group consisting of TCRα, TCRβ, CD52, GR, DCK, and immune checkpoint proteins. In some embodiments, inactivation of a gene can be accomplished by introducing into the cells at least one rare-cutting endonuclease such that the rare-cutting endonuclease specifically catalyzes cleavage in a targeted sequence of the cell genome; and optionally, introducing into the cells an exogenous nucleic acid successively comprising a first region of homology to sequences upstream of the cleavage, a sequence to be inserted in the genome of the cell, and a second region of homology to sequences downstream of the cleavage; wherein the introduced exogenous nucleic acid inactivates a gene and integrates at least one exogenous polynucleotide sequence encoding at least one recombinant protein of interest. In some embodiments, the exogenous polynucleotide sequence is integrated within a gene encoding a protein selected from the group consisting of TCRα, TCRβ, CD52, GR, DCK, and immune checkpoint protein.

In another aspect, a step of genetically modifying cells can comprise: modifying T cells by inactivating at least one gene expressing a target for an immunosuppressive agent, and; expanding the cells, optionally in presence of the immunosuppressive agent. An immunosuppressive agent is an agent that suppresses immune function by one of several mechanisms of action. An immunosuppressive agent can diminish the extent and/or voracity of an immune response.

Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immunosuppressive antimetabolites. Some cytotoxic immunosuppressants act by inhibiting DNA synthesis. Others may act through activation of T cells or by inhibiting the activation of helper cells. The methods according to the invention allow conferring immunosuppressive resistance to T cells for immunotherapy by inactivating the target of the immunosuppressive agent in T cells. As non-limiting examples, targets for immunosuppressive agent can be a receptor for an immunosuppressive agent such as for example without limitation CD52, glucocorticoid receptor (GR), FKBP family gene members, and cyclophilin family gene members.

In some embodiments, the genetic modification of the method involves expression, in provided cells to engineer, of one rare-cutting endonuclease such that the rare-cutting endonuclease specifically catalyzes cleavage in one targeted gene, thereby inactivating the targeted gene. In some embodiments, a method of engineering cells comprises at least one of the following steps: providing a T cell, such as from a cell culture or from a blood sample; selecting a gene in the T cell expressing a target for an immunosuppressive agent; introducing into the T cell a rare-cutting endonuclease able to selectively inactivate by DNA cleavage, e.g. by double-strand break the gene encoding a target for the immunosuppressive agent, and expanding the cells, optionally in presence of the immunosuppressive agent.

In some embodiments, the method comprises: providing a T cell, such as from a cell culture or from a blood sample; selecting a gene in the T cell wherein the gene expresses a target for an immunosuppressive agent; transfecting the T cell with nucleic acid encoding a rare-cutting endonuclease able to selectively inactivate by DNA cleavage, for example by double-strand break the gene encoding a target for the immunosuppressive agent, and expressing the rare-cutting endonucleases into the T cells; and expanding the cells, optionally in presence of the immunosuppressive agent.

In some embodiments, the rare-cutting endonuclease specifically targets CD52 or GR. In some embodiments, the gene selected for inactivation encodes CD52, and the immunosuppressive treatment comprises a humanized antibody targeting CD52 antigen. In some embodiments, the gene selected for inactivation encodes GR, and the immunosuppressive treatment comprises a corticosteroid such as dexamethasone. In some embodiments, the gene selected for inactivation is a FKBP family gene member or a variant thereof and the immunosuppressive treatment comprises FK506, also known as Tacrolimus or fujimycin. In some embodiments, the FKBP family gene member is FKBP12 or a variant thereof. In some embodiments, gene selected for inactivation is a cyclophilin family gene member or a variant thereof and the immunosuppressive treatment comprises cyclosporine.

In some embodiments, the rare-cutting endonuclease can be, for example, a meganuclease, a zinc finger nuclease, or a TALE-nuclease (TALEN). In some embodiments, the rare-cutting endonuclease is a TALE-nuclease.

Also provided herein are methods of engineering T cells, suitable for immunotherapy, wherein the methods comprise: genetically modifying T cells by inactivating at least immune checkpoint protein. In some embodiments the immune checkpoint protein is, for example, PD-1 and/or CTLA-4. In some embodiments, methods of genetically modifying a cell comprises: modifying T cells by inactivating at least one immune checkpoint protein; and expanding the cells. Immune checkpoint proteins include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), B7H5 (also known as C10orf54, homolog of mouse vista gene, accession number: NM_022153.1), LAIR1 (also known as CD305, GenBank accession number: CR542051.1), SIGLEC10 (GeneBank accession number: AY358337.1), 2B4 (also known as CD244, accession number: NM_001166664.1), which directly inhibit immune cells. For example, CTLA-4 is a cell-surface protein expressed on certain CD4 and CD8 T cells; when engaged by its ligands (B7-1 and B7-2) on antigen presenting cells, T cell activation and effector function are inhibited.

In some embodiments, said method to engineer cells comprises at least one of the following steps: providing a T cell, such as from a cell culture or from a blood sample; introducing into the T cell a rare-cutting endonuclease able to selectively inactivate by DNA cleavage, for example by double-strand break one gene encoding a immune checkpoint protein; and expanding the cells. In some embodiments, the method comprises: providing a T cell, such as from a cell culture or from a blood sample; transfecting said T cell with nucleic acid encoding a rare-cutting endonuclease able to selectively inactivate by DNA cleavage, for example by double-strand break a gene encoding a immune checkpoint protein; expressing the rare-cutting endonucleases into the T cells; expanding the cells. In some embodiments, the rare-cutting endonuclease specifically targets a gene selected from the group consisting of: PD-1, CTLA-4, LAG3, Tim3, BTLA, BY55, TIGIT, B7H5, LAIR1, SIGLEC10, 2B4, TCRα, and TCRβ. In some embodiments, the rare-cutting endonuclease can be a meganuclease, a zinc finger nuclease or a TALE-nuclease. In some embodiments, the rare-cutting endonuclease is a TALE-nuclease.

In some embodiments, the present invention can be particularly suitable for allogeneic immunotherapy. In such embodiments, cells may be modified by a method comprising: inactivating at least one gene encoding a component of the T cell receptor (TCR) in T cells; and expanding the T cells. In some embodiments, the genetic modification of the method relies on the expression, in provided cells to engineer, of one rare-cutting endonuclease such that the rare-cutting endonuclease specifically catalyzes cleavage in one targeted gene thereby inactivating the targeted gene. In some embodiments, said method to engineer cells comprises at least one of the following steps: providing a T cell, such as from a cell culture or from a blood sample; introducing into the T cell a rare-cutting endonuclease able to selectively inactivate by DNA cleavage, for example by double-strand break at least one gene encoding a component of the T cell receptor (TCR), and expanding the cells.

In some embodiments, the method comprises: providing a T cell, such as from a cell culture or from a blood sample; transfecting said T cell with nucleic acid encoding a rare-cutting endonuclease able to selectively inactivate by DNA cleavage, for example by double-strand break at least one gene encoding a component of the T cell receptor (TCR);

expressing the rare-cutting endonucleases into the T cells; sorting the transformed T cells, which do not express TCR on their cell surface; and expanding the cells.

In some embodiments, the rare-cutting endonuclease can be a meganuclease, a zinc finger nuclease or a TALE-nuclease. In some embodiments, the rare-cutting endonuclease is a TALE-nuclease. In some embodiments, the TALE-nucleases recognize and cleave a sequence encoding TCRα or TCRβ. In some embodiments, a TALE-nuclease comprises a polypeptide sequence selected from the amino acid sequence shown in SEQ ID NOs: 71, 72, 73, 74, 75, 76, 77, and 78.

TALE-Nuclease Polypeptide Sequences:

```
Repeat TRAC_T01-L
                                                  (SEQ ID NO: 71)
LTPQQVVAIASNGGGKQALETVQRLLPVLCQAHGLTPQQVVAIASNNGGKQALET

VQRLLPVLCQAHGLTPQQVVAIASNGGGKQALETVQRLLPVLCQAHGLTPEQVVA

IASHDGGKQALETVQRLLPVLCQAHGLTPEQVVAIASHDGGKQALETVQRLLPVLC

QAHGLTPEQVVAIASHDGGKQALETVQRLLPVLCQAHGLTPEQVVAIASNIGGKQA

LETVQALLPVLCQAHGLTPEQVVAIASHDGGKQALETVQRLLPVLCQAHGLTPEQ

VVAIASNIGGKQALETVQALLPVLCQAHGLTPQQVVAIASNNGGKQALETVQRLLP

VLCQAHGLTPEQVVAIASNIGGKQALETVQALLPVLCQAHGLTPQQVVAIASNGGG

KQALETVQRLLPVLCQAHGLTPEQVVAIASNIGGKQALETVQALLPVLCQAHGLTP

QQVVAIASNGGGKQALETVQRLLPVLCQAHGLTPEQVVAIASHDGGKQALETVQR

LLPVLCQAHGLTPQQVVAIASNGGGRPALE.

Repeat TRAC_T01-R
                                                  (SEQ ID NO: 72)
LTPEQVVAIASHDGGKQALETVQRLLPVLCQAHGLTPQQVVAIASNGGGKQALET

VQRLLPVLCQAHGLTPEQVVAIASHDGGKQALETVQRLLPVLCQAHGLTPEQVVAI

ASNIGGKQALETVQALLPVLCQAHGLTPQQVVAIASNNGGKQALETVQRLLPVLC

QAHGLTPEQVVAIASHDGGKQALETVQRLLPVLCQAHGLTPQQVVAIASNGGGKQ

ALETVQRLLPVLCQAHGLTPQQVVAIASNNGGKQALETVQRLLPVLCQAHGLTPQ

QVVAIASNNGGKQALETVQRLLPVLCQAHGLTPQQVVAIASNGGGKQALETVQRL

LPVLCQAHGLTPEQVVAIASNIGGKQALETVQALLPVLCQAHGLTPEQVVAIASHD

GGKQALETVQRLLPVLCQAHGLTPEQVVAIASNIGGKQALETVQALLPVLCQAHG

LTPEQVVAIASHDGGKQALETVQRLLPVLCQAHGLTPQQVVAIASNNGGKQALET

VQRLLPVLCQAHGLTPQQVVAIASNGGGRPALE.

Repeat TRBC_T01-L
                                                  (SEQ ID NO: 73)
LTPQQVVAIASNNGGKQALETVQRLLPVLCQAHGLTPQQVVAIASNGGGKQALET

VQRLLPVLCQAHGLTPQQVVAIASNNGGKQALETVQRLLPVLCQAHGLTPQQVVA

IASNGGGKQALETVQRLLPVLCQAHGLTPQQVVAIASNGGGKQALETVQRLLPVL

CQAHGLTPQQVVAIASNGGGKQALETVQRLLPVLCQAHGLTPQQVVAIASNNGGK

QALETVQRLLPVLCQAHGLTPEQVVAIASNIGGKQALETVQALLPVLCQAHGLTPQ

QVVAIASNNGGKQALETVQRLLPVLCQAHGLTPEQVVAIASHDGGKQALETVQRL

LPVLCQAHGLTPEQVVAIASHDGGKQALETVQRLLPVLCQAHGLTPEQVVAIASNI

GGKQALETVQALLPVLCQAHGLTPQQVVAIASNGGGKQALETVQRLLPVLCQAHG

LTPEQVVAIASHDGGKQALETVQRLLPVLCQAHGLTPEQVVAIASNIGGKQALETV

QALLPVLCQAHGLTPQQVVAIASNGGGRPALE.

Repeat TRBC_T01-R
                                                  (SEQ ID NO: 74)
NPQRSTVWYLTPQQVVAIASNNGGKQALETVQRLLPVLCQAHGLTPQQVVAIASN

GGGKQALETVQRLLPVLCQAHGLTPQQVVAIASNNGGKQALETVQRLLPVLCQAH
```

-continued

GLTPQQVVAIASNNGGKQALETVQRLLPVLCQAHGLTPEQVVAIASHDGGKQALE

TVQRLLPVLCQAHGLTPEQVVAIASHDGGKQALETVQRLLPVLCQAHGLTPQQVV

AIASNGGGKQALETVQRLLPVLCQAHGLTPQQVVAIASNGGGKQALETVQRLLPV

LCQAHGLTPQQVVAIASNGGGKQALETVQRLLPVLCQAHGLTPQQVVAIASNGGG

KQALETVQRLLPVLCQAHGLTPQQVVAIASNNGGKQALETVQRLLPVLCQAHGLT

PQQVVAIASNNGGKQALETVQRLLPVLCQAHGLTPQQVVAIASNNGGKQALETVQ

RLLPVLCQAHGLTPQQVVAIASNGGGKQALETVQRLLPVLCQAHGLTPQQVVAIAS

NNGGKQALETVQRLLPVLCQAHGLTPQQVVAIASNGGGRPALE.

Repeat TRBC_T02-L
(SEQ ID NO: 75)
LTPEQVVAIASHDGGKQALETVQRLLPVLCQAHGLTPEQVVAIASHDGGKQALET

VQRLLPVLCQAHGLTPEQVVAIASHDGGKQALETVQRLLPVLCQAHGLTPEQVVAI

ASNIGGKQALETVQALLPVLCQAHGLTPEQVVAIASHDGGKQALETVQRLLPVLCQ

AHGLTPEQVVAIASHDGGKQALETVQRLLPVLCQAHGLTPEQVVAIASHDGGKQA

LETVQRLLPVLCQAHGLTPQQVVAIASNNGGKQALETVQRLLPVLCQAHGLTPEQ

VVAIASNIGGKQALETVQALLPVLCQAHGLTPQQVVAIASNNGGKQALETVQRLLP

VLCQAHGLTPQQVVAIASNNGGKQALETVQRLLPVLCQAHGLTPQQVVAIASNGG

GKQALETVQRLLPVLCQAHGLTPEQVVAIASHDGGKQALETVQRLLPVLCQAHGL

TPQQVVAIASNNGGKQALETVQRLLPVLCQAHGLTPEQVVAIASHDGGKQALETV

QRLLPVLCQAHGLTPQQVVAIASNGGGRPALE.

Repeat TRBC_T02-R
(SEQ ID NO: 76)
LTPQQVVAIASNNGGKQALETVQRLLPVLCQAHGLTPQQVVAIASNNGGKQALET

VQRLLPVLCQAHGLTPQQVVAIASNNGGKQALETVQRLLPVLCQAHGLTPEQVVA

IASNIGGKQALETVQALLPVLCQAHGLTPQQVVAIASNNGGKQALETVQRLLPVLC

QAHGLTPEQVVAIASNIGGKQALETVQALLPVLCQAHGLTPQQVVAIASNGGGKQ

ALETVQRLLPVLCQAHGLTPEQVVAIASHDGGKQALETVQRLLPVLCQAHGLTPQ

QVVAIASNGGGKQALETVQRLLPVLCQAHGLTPEQVVAIASHDGGKQALETVQRL

LPVLCQAHGLTPQQVVAIASNGGGKQALETVQRLLPVLCQAHGLTPQQVVAIASN

NGGKQALETVQRLLPVLCQAHGLTPEQVVAIASHDGGKQALETVQRLLPVLCQAH

GLTPQQVVAIASNGGGKQALETVQRLLPVLCQAHGLTPQQVVAIASNGGGKQALE

TVQRLLPVLCQAHGLTPQQVVAIASNGGGRPALE.

Repeat CD52_T02-L
(SEQ ID NO: 77)
LTPQQVVAIASNGGGKQALETVQRLLPVLCQAHGLTPEQVVAIASHDGGKQALET

VQRLLPVLCQAHGLTPEQVVAIASHDGGKQALETVQRLLPVLCQAHGLTPQQVVA

IASNGGGKQALETVQRLLPVLCQAHGLTPEQVVAIASHDGGKQALETVQRLLPVLC

QAHGLTPEQVVAIASHDGGKQALETVQRLLPVLCQAHGLTPQQVVAIASNGGGKQ

ALETVQRLLPVLCQAHGLTPEQVVAIASNIGGKQALETVQALLPVLCQAHGLTPEQ

VVAIASHDGGKQALETVQRLLPVLCQAHGLTPQQVVAIASNGGGKQALETVQRLL

PVLCQAHGLTPEQVVAIASHDGGKQALETVQRLLPVLCQAHGLTPEQVVAIASNIG

GKQALETVQALLPVLCQAHGLTPEQVVAIASHDGGKQALETVQRLLPVLCQAHGL

TPEQVVAIASHDGGKQALETVQRLLPVLCQAHGLTPEQVVAIASNIGGKQALETVQ

ALLPVLCQAHGLTPQQVVAIASNGGGRPALE.

```
Repeat CD52_T02-R
                                                        (SEQ ID NO: 78)
LTPQQVVAIASNGGGKQALETVQRLLPVLCQAHGLTPQQVVAIASNNGGKQALET

VQRLLPVLCQAHGLTPEQVVAIASHDGGKQALETVQRLLPVLCQAHGLTPQQVVA

IASNGGGKQALETVQRLLPVLCQAHGLTPEQVVAIASHDGGKQALETVQRLLPVLC

QAHGLTPQQVVAIASNGGGKQALETVQRLLPVLCQAHGLTPQQVVAIASNGGGKQ

ALETVQRLLPVLCQAHGLTPEQVVAIASNIGGKQALETVQALLPVLCQAHGLTPEQ

VVAIASHDGGKQALETVQRLLPVLCQAHGLTPEQVVAIASHDGGKQALETVQRLL

PVLCQAHGLTPQQVVAIASNGGGKQALETVQRLLPVLCQAHGLTPQQVVAIASNN

GGKQALETVQRLLPVLCQAHGLTPQQVVAIASNGGGKQALETVQRLLPVLCQAHG

LTPEQVVAIASNIGGKQALETVQALLPVLCQAHGLTPEQVVAIASHDGGKQALETV

QRLLPVLCQAHGLTPQQVVAIASNGGGRPALE.
```

In another aspect, another step of genetically modifying a cell can be a method of expanding TCRα deficient T cells comprising introducing into the T cell pTα (also known as preTCRα) or a functional variant thereof and expanding the cells, optionally through stimulation of the CD3 complex. In some embodiments, the method comprises: a) transfecting the cells with nucleic acid encoding at least a fragment of pTα to support CD3 surface expression; b) expressing said pTα into the cells; and c) expanding the cells, optionally through stimulation of the CD3 complex.

Also provided are methods of preparing T cells for immunotherapy comprising steps of the method for expansion for T cell. In some embodiments, the pTα polynucleotide sequence can be introduced randomly or by homologous recombination. In some embodiments, the insertion can be associated with the inactivation of the TCRα gene.

Different functional variants of pTα can be used. A "functional variant" of the peptide refers to a molecule substantially similar to either the entire peptide or a fragment thereof. A "fragment" of the pTα or functional variant thereof refers to any subset of the molecule, that is, a shorter peptide than the full-length pTα. In some embodiments, pTα or functional variants can be, for example, full-length pTα or a C-terminal truncated pTα version. C-terminal truncated pTα lacks in C-terminal end one or more residues. As non limiting examples, C-terminal truncated pTα version lacks 18, 48, 62, 78, 92, 110 or 114 residues from the C-terminus of the protein. Amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex. In an exemplary embodiment, at least one mutation is introduced in the different pTα versions as described herein to affect dimerization. As non limiting example, mutated residue can be at least W46R, D22A, K24A, R102A or R117A of the human pTα protein or aligned positions using CLUSTALW method on pTα family or homologue member. For example pTα or variant thereof as described herein comprise the mutated residue W46R or the mutated residues D22A, K24A, R102A and R117A. In some embodiments, said pTα or variants are also fused to a signal-transducing domain such as CD28, OX40, ICOS, CD27, CD137 (4-1BB) and CD8 as non limiting examples. The extracellular domain of pTα or variants as described herein can be fused to a fragment of the TCRα protein, particularly the transmembrane and intracellular domain of TCRα. pTα variants can also be fused to the intracellular domain of TCRα.

In some embodiments, pTα versions can be fused to an extracellular ligand-binding domain. In some embodiments, pTα or functional variant thereof is fused to a single chain antibody fragment (scFv) comprising the light and the heavy variable fragment of a target antigen specific monoclonal antibody joined by a flexible linker.

The term "TCRα deficient T cell" refers to an isolated T cell that lacks expression of a functional TCRα chain. Such cells may be prepared by various means, as non-limiting examples, by engineering a T cell such that it does not express any functional TCRα on its cell surface or by engineering a T cell such that it produces very little functional TCRα chain on its surface or by engineering a T cell to express mutated or truncated form of TCRα chain. TCRα deficient cells can no longer be expanded through CD3 complex. Thus, to overcome this problem and to allow proliferation of TCRα deficient cells, pTα or functional variant thereof is introduced into the cells, thus restoring a functional CD3 complex. In some embodiments, the method further comprises introducing into said T cells rare-cutting endonucleases able to selectively inactivate by DNA cleavage one gene encoding one component of the T cell receptor (TCR). In some embodiments, the rare-cutting endonuclease is a TALE-nuclease.

In some embodiments, polynucleotides encoding polypeptides according to the present invention can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Also provided herein are methods of transfecting T cell. In some embodiments, the method comprises: contacting a T cell with RNA and applying to T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V with a pulse width of about 100 ms and a pulse interval of about 100 ms between the electrical pulse of step (b) and the first electrical pulse of step (c); and (e) four electrical pulses with a voltage of about 325 V with a pulse width of about 0.2 ms and a pulse interval of 2 ms between each of 4 electrical pulses. In some embodiments, a method of transfecting T cell comprising contacting said T cell with RNA and applying to T cell an agile pulse sequence comprising: (a) an electrical pulse with a voltage of about 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (e) 4 electrical pulses with a voltage of about 325 V with a pulse width of about 0.2 ms and a pulse interval of about 2 ms between each of 4 electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, as non limiting examples, an RNA encodes a rare-cutting endonuclease, one monomer of the rare-cutting endonuclease such as half-TALE-nuclease, a CAR, at least one component of the multi-chain chimeric antigen receptor, a pTα or functional variant thereof, an exogenous nucleic acid, and/or one additional catalytic domain.

Engineered Immune Cells

The invention also provides engineered immune cells comprising any of the polynucleotides that encode the recombinant antigen receptors e.g. CARs described herein. In some embodiments, such an encoding polynucleotide can be introduced into an immune cell as a transgene via a plasmid vector. In some embodiments, the plasmid vector can also contain, for example, a selection marker which provides for identification and/or selection of cells which received the vector.

Recombinant antigen receptor e.g. CAR polypeptides may be synthesized in situ in the cell after introduction of polynucleotides encoding the polypeptides into the cell. Alternatively, the polypeptides may be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g. retroviruses, adenoviruses), liposomes, and the like. Transient transformation methods include, for example without limitation, microinjection, electroporation or particle bombardment. Polynucleotides may be included in vectors, such as for example plasmid vectors or viral vectors.

In some embodiments, the engineered immune cells disclosed herein further comprise one or more polynucleotides that express one or more polypeptides that enhance the efficacy, activity, proliferation and/or persistence of the engineered immune cell, In certain embodiments, the engineered immune cells further express one or more chimeric cytokine receptors that provide the signal 3 of TCR signaling. In some embodiments, the chimeric cytokine receptors are inducible or constitutively active. Exemplary chimeric cytoline receptors are described in WO2020/180694, WO2020/180664, and WO2021/041806, all of which are incorporated herein by reference.

In some embodiments, the engineered immune cells disclosed herein further comprise one or more polynucleotides that express one or more polypepties that reduce reactivity of the allogeneic engineered immune cells in a recipient. In certain embodiments, the engineered immune cells further express one or more autologous/allogeneic immune defense receptors. Exemplary autologous/allogeneic immune defense receptors are described in WO2019/210081, which is herein incorporated by reference.

Also provided herein are isolated cells and cell lines obtained by the herein-described methods of engineering cells provided herein. In some embodiments, an isolated cell comprises at least one recombinant antigen receptor e.g. CAR as described herein. In some embodiments, an isolated cell comprises a population of different recombinant antigen receptors e.g. CARs, each species of which comprises different extracellular ligand-binding domains.

Also provided herein are isolated immune cells obtained according to any one of the methods described herein. Any immune cell capable of expressing heterologous DNAs can be used for the purpose of expressing the polypeptide of interest. In some embodiments, the immune cell used for expressing any one of the recombinant antigen receptors e.g. CARs described herein is a T cell. In some embodiments, an immune cell used for expressing CARs can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human stem cells are CD34+ cells.

In some embodiments, the engineered immune cells expressing at their cell surface membrane a recombinant antigen receptor e.g. CAR of the invention comprise a percentage of stem cell memory and central memory cells greater than 10%, 20%, 30%, 40%, 50%, or 60%. In some embodiments, the engineered immune cells expressing at their cell surface membrane a recombinant antigen receptor e.g. CAR of the invention comprise a percentage of stem cell memory and central memory cells of about 10% to about 60%, about 10% to about 50%, about 10% to about 40%, about 15% to about 50%, about 15% to about 40%, about 20% to about 60%, or about 20% to about 70%.

The immune cell used for expressing any one of the recombinant antigen receptors e.g. CARs described herein can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes or helper T-lymphocytes. In some embodiments, the cell can be derived from the group consisting of CD4+ T-lymphocytes and CD8+ T-lymphocytes.

In one embodiment, the immune cell is an inflammatory T-lymphocyte that expresses any one of the CARs described herein. In one embodiment, the immune cell is a cytotoxic T-lymphocyte that expresses any one of the CARs described herein. In one embodiment, the immune cell is a regulatory T-lymphocyte that expresses any one of the CARs described herein. In one embodiment, the immune cell is a helper T-lymphocyte that expresses any one of the CARs described herein.

Also provided herein are cell lines obtained from a transformed T cell according to any of the herein-described methods. Also provided herein are modified cells resistant to an immunosuppressive treatment. In some embodiments, an isolated cell according to the invention comprises a polynucleotide encoding a CAR.

The immune cells of the invention can be activated and expanded, either prior to or after genetic modification of the T cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFp, and TNF, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics.

In some embodiments, the cells of the invention can be expanded by co-culturing with tissue or cells. The cells can also be expanded in vivo, for example in the subject's blood after administrating the cell into the subject.

In some embodiments, an isolated cell according to the present invention comprises one inactivated gene selected from the group consisting of CD52, GR, PD-1, CTLA-4, LAG3, Tim3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present invention comprises two inactivated genes selected from the group consisting of: CD52 and GR, CD52 and TCRα, CDR52 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, a multi-chain CAR and a pTα transgene.

In some embodiments, TCR is rendered not functional in the cells according to the invention by inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present invention. Modified cells disclosed herein can be used in for treating individuals in need thereof against Host versus Graft (HvG) rejection and Graft versus Host Disease (GvHD); therefore in the scope of the present invention is a method of treating individuals in need thereof against Host versus Graft (HvG) rejection and Graft versus Host Disease (GvHD) comprising treating said individual by administering to said individual an effective amount of modified cells comprising inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are target-specific CAR-T cells comprising an inactivated dCK gene. In some embodiments, the dCK knockout cells are made by transfection of T cells using polynucleotides encoding specific TAL-nuclease directed against dCK genes by, for example, electroporation of mRNA. The dCK knockout target-specific CAR-T cells are resistant to PNAs, including for example clorofarabine and/or fludarabine, and maintain T cell cytotoxic activity toward FLT3-expressing cells.

In some embodiments, isolated cells or cell lines of the invention can comprise a pTα or a functional variant thereof. In some embodiments, an isolated cell or cell line can be further genetically modified by inactivating the TCRα gene.

In some embodiments, the CAR-T cell comprises a polynucleotide encoding a suicide polypeptide, such as for example RQR8. See, e.g., WO2013153391A, which is hereby incorporated by reference in its entirety. In CAR-T cells comprising the polynucleotide, the suicide polypeptide is expressed at the surface of a CAR-T cell. In some embodiments, the suicide polypeptide comprises the amino acid sequence shown in SEQ ID NO: 79.

(SEQ ID NO: 79)
CPYSNPSLCSGGGGSELPTQGTFSNVSTNVSPAKPTTTACPYSNPSLCS

GGGGSPAPRPPTPAPTIASQPLSLRPEACRPAAGGAVHTRGLDFACDIY

IWAPLAGTCGVLLLSLVITLYCNHRNRRRVCKCPRPVV.

The suicide polypeptide may also comprise a signal peptide at the amino terminus. In some embodiments, the suicide polypeptide comprises the amino acid sequence shown in SEQ ID NO: 80.

(SEQ ID NO: 80)
MGTSLLCWMALCLLGADHADACPYSNPSLCSGGGGSELPTQGTFSNVST

NVSPAKPTTTACPYSNPSLCSGGGGSPAPRPPTPAPTIASQPLSLRPEA

CRPAAGGAVHTRGLDFACDIYIWAPLAGTCGVLLLSLVITLYCNHRNRR

RVCKCPRPVV.

When the suicide polypeptide is expressed at the surface of a CAR-T cell, binding of rituximab to the rituximab epitopes of the polypeptide causes lysis of the cell. More than one molecule of rituximab may bind per polypeptide expressed at the cell surface. Each rituximab epitope of the polypeptide may bind a separate molecule of rituximab. Deletion of target-specific CAR-T cells may occur in vivo, for example by administering rituximab to a subject. The decision to delete the transferred cells may arise from undesirable effects being detected in the subject which are attributable to the transferred cells, such as for example, when unacceptable levels of toxicity are detected.

In some embodiments, upon administration to a patient, engineered immune cells expressing at their cell surface any one of the recombinant antigen receptors e.g. CARs described herein may reduce, kill or lyse endogenous cells of the patient that express the target antigen (e.g. DLL3, BCMA, EGFRvIII, Flt-3, WT-1, CD20, CD23, CD30, CD38, CD70, CD33, CD133, LeY, NKG2D, CS1, CD44v6, ROR1, CD19, Claudin-18.2 (Claudin-18A2, or Claudin18 isoform 2), DLL3 (Delta-like protein 3, *Drosophila* Delta homolog 3, Delta3), Muc16, Muc17 (Mucin17, Muc3), FAP alpha (Fibroblast Activation Protein alpha), Ly6G6D (Lymphocyte antigen 6 complex locus protein G6d, c6orf23, G6D, MEGT1, NG25), and/or RNF43 (E3 ubiquitin-protein ligase RNF43, RING finger protein 43)) of the recombinant antigen receptor e.g. CAR. In one embodiment, a percentage reduction or lysis of such endogenous cells or cells of a cell line expressing the target antigen by engineered immune cells expressing any one of the recombinant antigen receptors e.g. CARs described herein is at least about or greater than 10%, 15%, 20%, 25%, 30%, 35%, 40%, 45%, 50%, 55%, 60%, 65%, 70%, 75%, 80%, 85%, 90%, or 95%. In one embodiment, a percentage reduction or lysis of such target antigen-expressing endogenous cells or cells of a cell line expressing the target antigen by engineered immune cells expressing any one of the target-specific CARs, such as DLL3 CAR described herein, is about 5% to about 95%, about 10% to about 95%, about 10% to about 90%, about 10% to about 80%, about 10% to about 70%, about 10% to about 60%, about 10% to about 50%, about 10% to about 40%, about 20% to about 90%, about 20% to about 80%, about 20% to about 70%, about 20% to about 60%, about 20% to about 50%, about 25% to about 75%, or about 25% to about 60%.

Method for Sorting Recombinant Antigen Receptor e.g. CAR-Positive Immune Cells

In one aspect, provided are methods for in vitro sorting of a population of immune cells, wherein a subset of the population of immune cells comprises engineered immune cells expressing any one of the recombinant antigen receptors e.g. CARs comprising epitopes specific for monoclonal antibodies described herein. The method comprises contacting the population of immune cells with a monoclonal antibody specific for the epitopes and selecting the immune cells that bind to the monoclonal antibody to obtain a population of cells enriched in engineered immune cells expressing the recombinant antigen receptor e.g. CAR.

In some embodiments, said monoclonal antibody specific for said epitope is optionally conjugated to a fluorophore. In this embodiment, the step of selecting the cells that bind to the monoclonal antibody can be done by Fluorescence Activated Cell Sorting (FACS). In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the population of recombinant antigen receptor-expressing e.g. CAR-expressing immune cells obtained when using the method for in vitro sorting of immune cells described herein, comprises at least 60%, 65%, 70%, 75%, 80%, 85%, 90%, or 95% of the recombinant antigen receptor-expressing e.g. CAR-expressing immune cells. In some embodiments, the population of expressing immune cells obtained when using the method for in vitro sorting of CAR-expressing immune cells described herein, comprises at least 85% of recombinant antigen receptor-expressing e.g. CAR-expressing immune cells.

In some embodiments, the mAbs used in the in vitro sorting method are previously bound onto a support such as a column or on beads such as routinely realized by the skilled in the art. In some embodiments, immune cells expressing CARs are T-cells.

According to the invention, cells to be administered to the recipient may be enriched in vitro from the source population. Methods of expanding source populations are well known in the art, and may include selecting cells that express an antigen such as CD34 antigen, using combinations of density centrifugation, immuno-magnetic bead purification, affinity chromatography, and fluorescent activated cell sorting, known to those skilled in the art.

Flow cytometry is widely used in the art and is a method well known to one of ordinary skill to sort and quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometric analysis involves two basic steps: 1) labeling selected cell types with one or more labeled markers, and 2) determining the number of labeled cells relative to the total number of cells in the population.

The primary method of labeling cell types is by binding labeled antibodies to markers expressed by the specific cell type. The antibodies are either directly labeled with a fluorescent compound or indirectly labeled using, for example, a fluorescent-labeled second antibody which recognizes the first antibody.

In some embodiments, the method used for sorting immune cells expressing a CAR is the Magnetic-Activated Cell Sorting (MACS).

Magnetic-activated cell sorting (MACS) is a method for separation of various cell populations depending on their surface antigens (CD molecules) by using superparamagnetic nanoparticles and columns. It takes a few simple steps to get pure cell populations. Cells in a single-cell suspension are magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a short washing step, the column is removed from the separator, and the magnetically labeled cells are eluted from the column.

In some embodiments, the mAb used in the method for sorting immune cells expressing the CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10.

Therapeutic Applications

Isolated cells obtained by the methods described herein, or cell lines derived from such isolated cells, expressing recombinant antigen receptors of the invention e.g. CARs of the invention can be used as a medicament. In some embodiments, such a medicament can be used for treating a disease or a condition associated with the target antigen of the recombinant antigen receptor e.g CAR of the invention. Because the target specificity of the recombinant antigen receptors e.g. CARs of the present invention can be engineered toward the target of choice, conditions treatable with the recombinant antigen receptors e.g. CARs of the invention are diverse. These include but are not limited to various forms of cancer, such as, for example, cancers associated with the expression of DLL3.

In some embodiments, an isolated cell according to the invention, or cell line derived from the isolated cells, or an antibody can be used in the manufacture of a medicament for treatment of a cancer in a subject in need thereof.

In some embodiments, immune cells containing a recombinant antigen receptor, e.g., a CAR, of the disclosure can be used to treat such malignancies as small cell lung cancer, melanoma, low grade gliomas, glioma, glioblastoma, medullary thyroid cancer, carcinoids, dispersed neuroendocrine tumors in the pancreas, bladder and prostate, testicular cancer, lymphoma, leukemia, Renal Cell Carcinoma (RCC), Non-Hodgkin's Lymphoma, Hodgkin's Disease (HD), Waldenstrom's macroglobulinemia, Acute Myeloid Leukemia, Multiple Myeloma, diffuse large-cell lymphoma, follicular lymphoma, and lung adenocarcinomas with neuroendocrine features. In exemplary embodiments, the CAR-containing immune cells, e.g., the anti-DLL3 CAR-T cells of the disclosure, are used to treat small cell lung cancer.

Also provided herein are methods for treating subjects. In some embodiments, the method comprises providing an immune cell of the invention to a subject in need thereof. In some embodiments, the method comprises a step of administering transformed immune cells of the invention to a subject in need thereof.

In some embodiments, T cells of the invention can undergo robust in vivo T cell expansion and can persist for an extended amount of time.

Methods of treatment of the invention can be ameliorating, curative or prophylactic. The method of the invention may be either part of an autologous immunotherapy or part of an allogeneic immunotherapy treatment. The invention is particularly suitable for allogeneic immunotherapy. T cells from donors can be transformed into non-alloreactive cells using standard protocols and reproduced as needed, thereby producing CAR-T cells which may be administered to one or several subjects. Such CAR-T cell therapy can be made available as an "off the shelf" therapeutic product.

Cells that can be used with the disclosed methods are described in the previous section. Treatment can be used to treat subjects diagnosed with, for example, cancer. Cancers that may be treated include, for example without limitation, adult tumors/cancers and pediatric tumors/cancers. In some embodiments, the treatment can be in combination with one or more therapies against cancer selected from the group of antibodies therapy, chemotherapy, cytokines therapy, dendritic cell therapy, gene therapy, hormone therapy, laser light therapy and radiation therapy.

In some embodiments, treatment can be adminstered into subjects undergoing an immunosuppressive treatment. Indeed, embodiments of the invention rely on cells or a population of cells, which have been made resistant to at least one immunosuppressive agent due to the inactivation of a gene encoding a receptor for such immunosuppressive agent. In this aspect, the immunosuppressive treatment should help the selection and expansion of the T cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. In some embodiments, the cell compositions of the invention are administered by intravenous injection.

In some embodiments, the administration of the cells or population of cells can comprise administration of, for example, about $10^4$ to about $10^9$ cells per kg body weight including all integer values of cell numbers within those ranges. In some embodiments the administration of the cells or population of cells can comprise administration of about $10^5$ to $10^6$ cells per kg body weight including all integer values of cell numbers within those ranges. The cells or population of cells can be administered in one or more doses. In some embodiments, said effective amount of cells can be administered as a single dose. In some embodiments, said effective amount of cells can be administered as more than one dose over a period time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administered parenterally. In some embodiments, administration can be an intravenous administration. In some embodiments, administration can be directly done by injection within a tumor.

In some embodiments of the invention, cells are administered to a subject in conjunction with (e.g., before, simultaneously or following) any number of relevant treatment modalities, including but not limited to treatment with agents such as monoclonal antibody therapy, CCR2 antagonist (e.g., INC-8761), antiviral therapy, cidofovir and interleukin-2, Cytarabine (also known as ARA-C) or nataliziimab treatment for MS patients or efaliztimab treatment for psoriasis patients or other treatments for PML patients. In some embodiments, target-specific CAR-T cells described herein with enhanced signaling, such as DLL3 CAR T cells described herein are administered to a subject in conjunction with one or more of the following: an anti-PD-1 antibody (e.g., nivolumab, pembrolizumab, or PF-06801591), an anti-PD-L1 antibody (e.g., avelumab, atezolizumab, or durvalumab), an anti-OX40 antibody (e.g., PF-04518600), an anti-4-1BB antibody (e.g., PF-05082566), an anti-MCSF antibody (e.g., PD-0360324), an anti-GITR antibody, and/or an anti-TIGIT antibody. In some embodiments, DLL3-specific CAR-T cells with enhanced signaling comprising the amino acid sequence shown in SEQ ID NOs: 43, 46 or 49, or other target-specific CAR-T cells, are administered to a subject in conjunction with anti-PD-L1 antibody avelumab. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In further embodiments, the T cells of the invention may be used in combination with Receptor Tyrosine Kinase inhibitors such as Midostaurin and Sunitinib, mTOR inhibitors such as Rapamacyn and Everolimus, epigenetic modulators such as Vormostat, proteasome inhibitors such as Bortezomib, immunomodulatory agents such as lenalidomide, Hedgehog inhibitors such as Erismodegib and PF-04449913 or Isocitrate Dehydrogenase (IDH) inhibitors such as AG-120 and AG-221. In a further embodiment, the cell compositions of the invention are administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In some embodiments, the cell compositions of the invention are administered following B-cell ablative therapy such as agents that react with CD20, e.g., Rituxan. For example, In some embodiments, subjects may undergo standard treatment with high dose chemotherapy followed by peripheral blood stem cell transplantation. In certain embodiments, following the transplant, subjects receive an infusion of the expanded immune cells of the invention. In some embodiments, expanded cells are administered before or following surgery.

In some embodiments, provided are methods for depleting engineered immune cells of the invention as described herein from a subject adminstered with said cells. Depletion can be by inhibition or elimination.

In one aspect, a method for depleting engineered immune cells expressing a recombinant antigen receptor of the invention e.g. CAR of the invention comprising an epitope specific for a monoclonal antibody comprises contacting said engineered immune cell with a monoclonal antibody specific for the epitope.

In some embodiments, a method for depleting from a subject administered with engineered immune cells of the invention comprising an epitope specific for a monoclonal antibody comprises administering to the subject a monoclonal antibody specific for the epitope. In these embodiments, administration of the monoclonal antibody specific for the epitope present in the extracellular domain of the recombinant antigen receptor e.g. CAR to the subject eliminates or inhibits the activity of engineered recombinant antigen receptor-expressing e.g. CAR-expressing immune cells from the subject. In one aspect, depletion of engineered immune cells allows for recovery of an endogenous population of cells that express the target antigen of the recombinant antigen receptor of the invention.

In one aspect, the invention relates to a method for promoting recovery of endogenous target antigen-expressing cells in a subject administered with engineered immune cells expressing at cell surface a recombinant antigen receptor e.g. CAR of the invention comprising an epitope specific for a monoclonal antibody, the method comprising administering a monoclonal antibody specific for the epitope to the subject. In one aspect, the term "recovery" refers to increasing the number of endogenous target antigen-expressing cells. The number of endogenous target antigen-expressing cells may increase due to increase in proliferation of endogenous target-expressing cells and/or due to reduction in elimination of such endogenous cells by the engineered immune cells. In some embodiments, administration of the monoclonal antibody to the subject depletes the engineered immune cells and increases the number of endogenous target antigen-expressing cells in the subject. In one embodiment, administration of the monoclonal antibody to the subject increases the number of endogenous target antigen-expressing cells by at least about 10%, 15%, 20%, 25%, 30%, 35%, 40%, 45%, 50%, 55%, 60%, 65%, 70%, 75%, 80%, 85%, 90%, or 95%, compared to the number of endogenous target antigen-expressing cells prior to administration of the monoclonal antibody.

In one aspect, provided is a method for treating a target antigen-mediated condition in a subject, the method comprising: (a) administering to the subject engineered immune cells expressing at cell surface recombinant antigen receptors e.g. CARs of the invention comprising one or more epitopes specific for one or more monoclonal antibodies; and (b) subsequently depleting the engineered immune cells from the subject by administering one or more monoclonal antibodies specific for the epitope to the subject.

In some embodiments, the mAbs used in the method for depleting CAR-expressing engineered immune cells are selected from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10, ustekinumab, and combinations thereof.

In some embodiments, the step of administering a monoclonal antibody to the subject comprises infusing the subject with the monoclonal antibody. In some embodiments, the amount of epitope-specific mAb administered to the subject is sufficient to eliminate at least 20%, 30%, 40%, 50%, 60%, 70%, 80% or 90% of the engineered immune cell in the subject.

In some embodiments, the step of administering a monoclonal antibody to the subject comprises infusing the subject with 375 mg/m$^2$ of rituximab, once or several times weekly.

In some embodiments, when immune cells expressing a CAR comprising an mAb-specific epitope (CAR-expressing immune cells) are depleted in a CDC assay using epitope-specific mAb, the amount of viable engineered immune cells decreases, e.g. by at least 10%, 20%, 30%, 40%, 50%, 60%, 70%, 80% or 90%.

In some embodiments, a cytotoxic drug is coupled to the epitope-specific mAbs which are used to deplete the engineered immune cells. By combining targeting capabilities of monoclonal antibodies with the cell-killing ability of cytotoxic drugs, antibody-drug conjugate (ADC) allows a sensitive discrimination between healthy and diseased tissue when compared to the use of the drug alone. Market approvals were received for several ADCs; the technology for making them—particularly on linkers—is abundantly presented in the following prior art (Payne, G. (2003) Cancer Cell 3:207-212; Trail et al (2003) Cancer Immunol. Immunother. 52:328-337; Syrigos and Epenetos (1999) Anticancer Research 19:605-614; Niculescu-Duvaz and Springer (1997) Adv. Drug Del. Rev. 26:151-172; U.S. Pat. No. 4,975,278).

In some embodiments, the epitope-specific mAb to be infused is conjugated beforehand with a molecule able to promote complement dependent cytotoxicity (CDC). Therefore, the complement system helps or complements the ability of antibodies to clear pathogens from the organism. When stimulated by one of several, is triggered an activation cascade as a massive amplification of the response and activation of the cell-killing membrane attack complex. Different molecules may be used to conjugate the mAb, such as glycans (Courtois, A, Gac-Breton, S., Berthou, C, Guezennec, J., Bordron, A. and Boisset, C. (2012), Complement dependent cytotoxicity activity of therapeutic antibody fragments is acquired by immunogenic glycan coupling, Electronic Journal of Biotechnology ISSN: 0717-3458; http://www.ejbiotechnology.info DOI: 10.2225/vol15-issue5).

Kits

The invention also provides kits for use in the instant methods. Kits of the invention include one or more containers comprising a polynucleotide encoding a recombinant antigen receptor e.g. CAR of the present invention or an engineered immune cell comprising a polynucleotide encoding the recombinant antigen receptor e.g. CAR of the invention, and instructions for use in accordance with any of the methods of the invention described herein. Generally, these instructions comprise a description of administration of the engineered immune cell for the herein-described therapeutic treatments.

The instructions relating to the use of the engineered immune cells or antibodies as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a recombinant antigen receptor e.g. CAR of the present invention. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the invention in any way. Indeed, various modifications of the invention in addition to those shown and described herein will become apparent to those skilled in the art from the foregoing description and fall within the scope of the appended claims.

EXAMPLES

Example 1: Altering the Quality and Quantity of CD3 ITAMs as a Strategy to Improve CAR Signaling A recombinant antigen receptor e.g. a CAR comprising a wildtype CD3ζ ITAM-containing domain has only 3 ITAMs, all of which derive from CD3ζ, whereas the naturally occurring TCR/CD3 holocomplex has 10 ITAMs comprising contributions from all four CD3 chains (delta, epsilon, gamma, and zeta). Reducing or increasing the number or diversity of ITAMs modulates both TCR and CAR function, underscoring the significance of these parameters. See, e.g., Bettini, M. L. et al. *Cutting Edge: CD3 ITAM Diversity Is Required for Optimal TCR Signaling and Thymocyte Development.* J. Immunol. 199, 1555-1560 (2017); Feucht, J. et al. *Calibration of CAR activation potential directs alternative T cell fates and therapeutic potency.* Nature Medicine 25, 82-88 (2019); Majzner, R. G. et al. *Low CD19 Antigen Density Diminishes Efficacy of CD19 CAR T Cells and Can be Overcome By Rational Redesign of CAR Signaling Domains.* Blood 132, 963 (2018). Thus, the quantity and quality of ITAMs and the complement of proximate signaling mediators differ between CARs and TCRs.

Figure 1B:
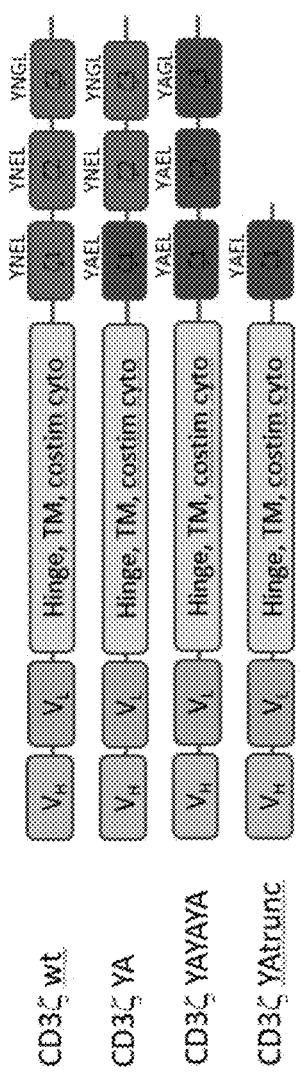
Figure 1C:
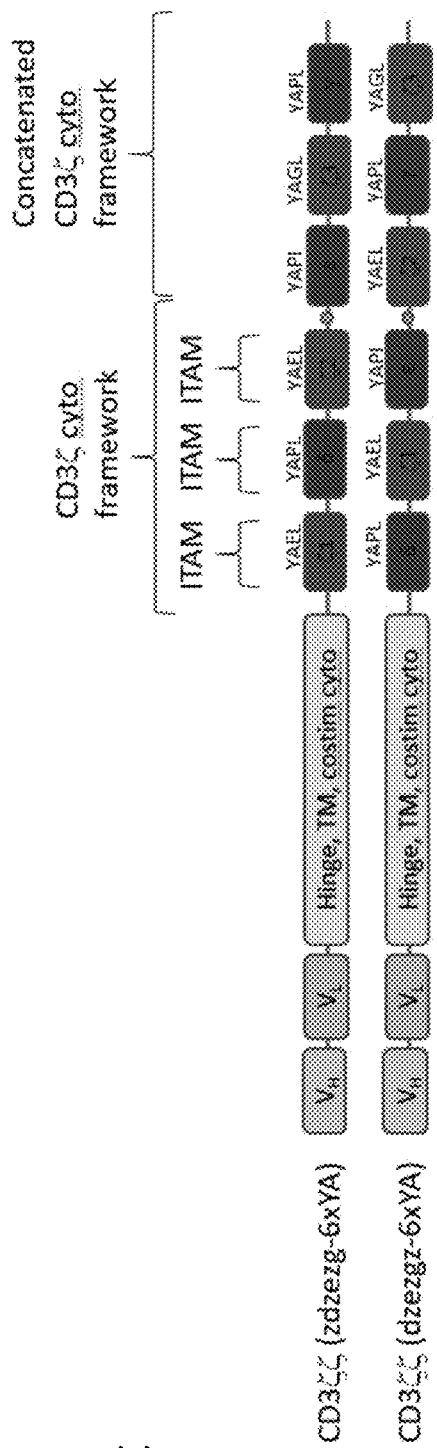

To test whether the sensitivity of CAR signaling can be improved by more closely mimicking TCR signaling, we altered the quality and quantity of CD3t ITAMs in a DLL3 CAR (10G1-K). In one set of constructs, the number of ITAMs affiliated with the CAR was decreased or increased (e.g. by truncating CAR after the first ITAM or by concatenating two copies of the CD3ζ cytoplasmic tail) (FIG. 1A). In addition, the character of the ITAMs in these constructs was varied by replacing them in the CD3ζ framework with ITAMs from other CD3 chains in various configurations (FIG. 1A). In a second set of constructs, the residue in the second position in the canonical YXX(L/I) ITAM motif was mutated to Ala, a mutation previously reported to reduce the degree of receptor clustering necessary to initiate signaling (FIG. 1B, Table 1). See, e.g., Sunder-Plassmann, R. et al. *Functional analysis of immunoreceptor tyrosine-based activation motif (ITAM)-mediated signal transduction: The two YxxL segments within a single CD3ζ-ITAM are functionally distinct*. Eur. J. Immunol. 27, 2001-2009 (1997). We reasoned that this mutation may therefore facilitate signaling in response to low density tumor antigens. Constructs that combine the strategies described for FIGS. 1A & 1B were also created (FIG. 1C).

Example 2: Overexpression of Downstream T Cell Signaling Mediators to Improve CAR Signaling CARs employing the 4-1BB costimulatory domain inefficiently recruit downstream mediators of T cell signaling (e.g. ZAP70) (see Gudipati, V. et al. *Inefficient CAR-proximal signaling blunts antigen sensitivity*. Nat. Immunol. (2020). doi:10.1038/s41590-020-0719-0) and overexpression of these mediators (e.g. Lck) has been shown to boost CAR function (see Sun, C. et al. *THEMIS-SHP1Recruitment by 4-1BB Tunes LCK-Mediated Priming of Chimeric Antigen Receptor-Redirected T Cells*. Cancer Cell 37, 216-225.e6 (2020)). We designed a series of constructs that employ an intervening 2A ribosomal skip sequence to couple CAR expression with overexpression of one of multiple downstream mediators of T cell signaling (see, e.g., Table 1, listing the following: SEQ ID NO: 1 (ZAP70), 2 (Lck), 4 (Fyn), 6 (Syk), 8 (LAT), and 9 (Unc119), SEQ ID NOs: 3 (Truncated Lck), 5 (Truncated Fyn), and 7 (Truncated Syk)). See FIGS. 3A-B.

Example 3: Comparison of CAR Constructs with Different Quality and Quantity of ITAMs In Vitro In this example, the constructs described in Example 1 were transduced in primary human T cells and tested for in vitro cytotoxic activity.

To make lentivirus expression constructs described in Example 1, HEK-293T cells were plated at 1.5 million cells per mL in 2 mL of DMEM (Gibco) supplemented with 10% FBS (Hyclone) per well of a 6-well plate on Day −1. On Day 0, the lentivirus was prepared by mixing together with lentiviral packaging vectors 1.5 ug psPAX2, 0.5 ug pMD2G, and 0.5 ug of the appropriate transfer CAR added to the DNA mix. The DLL3-specific CAR clone 10G1-K was used in this experiment. See WO2020/180591.

The mixture was incubated at room temperature for 20 minutes and the total volume of 500 uL was slowly added to the sides of the wells containing HEK-293T. Purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution). On Day 1, the media from each well of the 6-well plate was replaced with 2 mL per well of T cell transduction media, i.e., X-Vivo-15 supplemented with 10% FBS. On Day 2, T cells were resuspended at 0.4 million cells per mL in 1.5 mL of T cell transduction media per well of a Grex-24 plate (Wilson Wolf, cat #80192M). The lentiviral supernatants from HEK293T cells (about 1.5 ml) were harvested and passed through a 0.45 micron filter (EMD Millipore) to remove cell debris, and then added to the T cells along with 100 IU/mL human IL-2. On Day 5, 4.5 mL of T cell expansion media, i.e., X-Vivo-15 supplemented with 5% human AB serum (Gemini Bio) was added to each well of a Grex-24 plate. On Day 9 and Day 13, transduction efficiency was determined by detecting the percentage of T cells that express BFP and recognize recombinant DLL3 (Adipogen) using flow cytometry. Cells were expanded into larger flasks or G-Rex vessels (Wilson Wolf) as needed using T cell expansion media. On Day 14, DLL3 CAR-T cells were cryopreserved. Percentage of cells stained with recombinant DLL3 was normalized across clones right before cryopreservation.

Figure 2A:
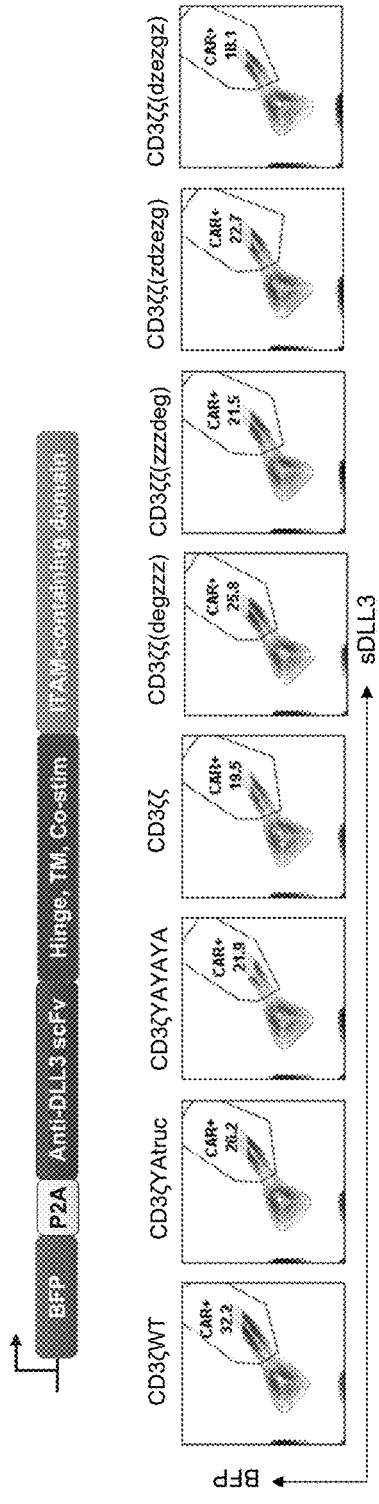
FIGS. 2A-2G show altering the quality and quantity of CD3ζ ITAMs improves CAR T function in a short-term kinetic killing assay with tumor cells expressing high or low antigen density.
Figure 2D:
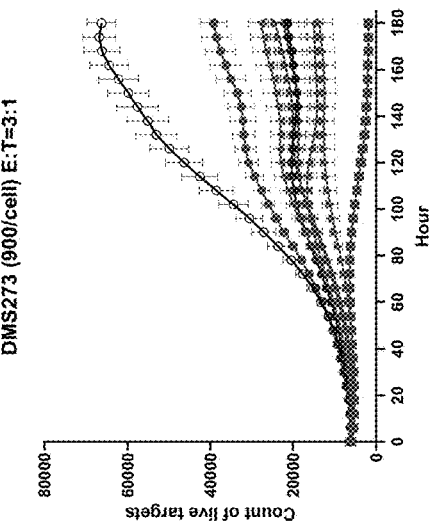
Figure 2C:
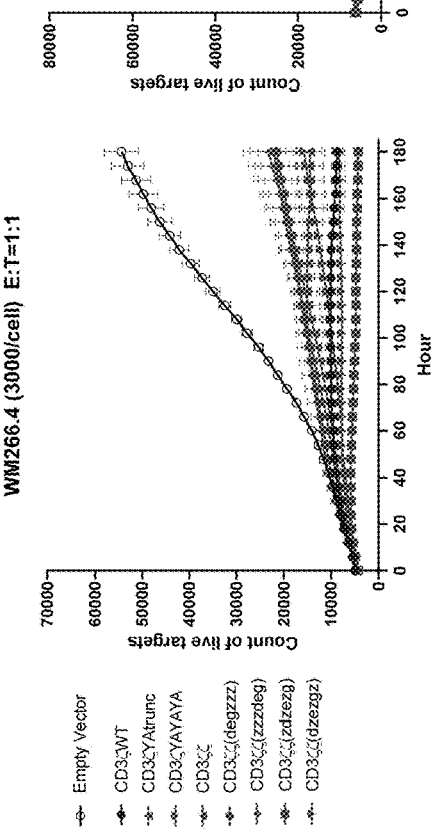
Figure 2B:
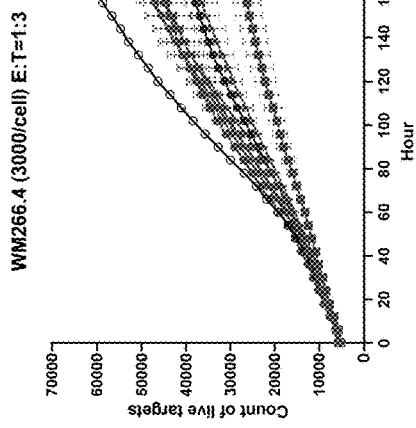
Figure 2E:
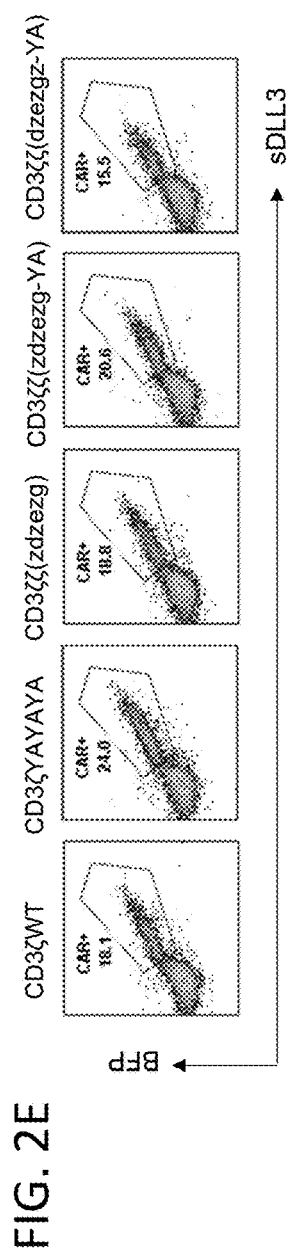

To determine the percentage of T cells that were successfully transduced with DLL3 CAR, T cells were first incubated with 1 ug/ml Flag tagged recombinant DLL3 (Adipogen) in PBS+1% BSA for 20 minutes at 4° C. Then cells were washed with PBS+1% BSA, stained with PE labelled anti-Flag antibodies (Biolegend, Cat #637310) and analyzed using flow cytometry. Examples of CAR T cells are shown in FIG. 2A-bottom panels. The results in FIG. 2A-bottom panels show that conventional (comprising wildtype CD3ζ ITAM-containing domain) or modified CARs (comprising a non-wildtype CD3ζ ITAM-containing domain) were expressed on the surface of primary T-cells. These results showed strong correlation between BFP expression and recombinant DLL3 staining, suggesting these constructs expressed properly and the proteins expressed had no major issues of folding or surface localization. The plots were gated on live CD3+ cells. The numbers on the plots are the percentage of cells that expressed each CAR construct. FIG. 2E shows the detection of conventional or modified CARs in a second human donor.

Figure 2G:
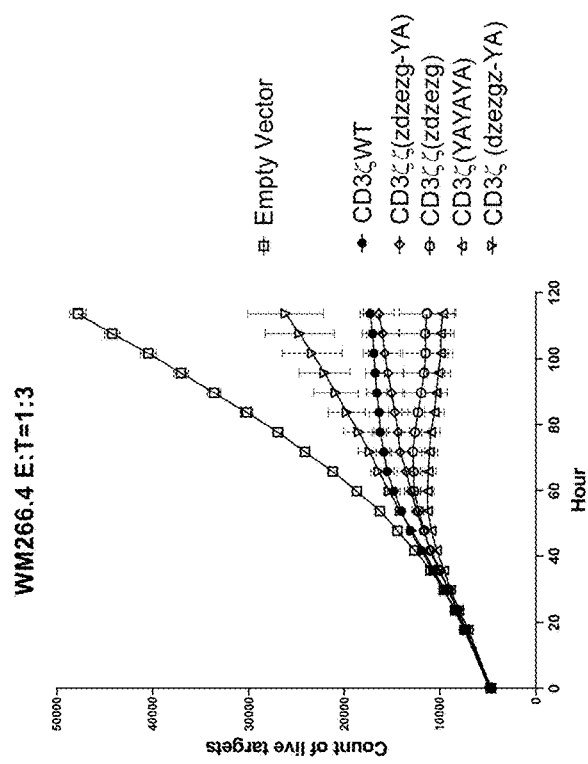
Figure 2F:
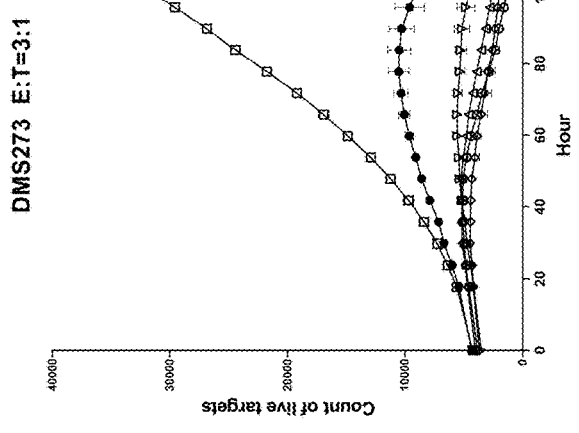

To compare the efficacy of conventional and modified CARs in a short-term kinetic killing assay, CAR T cells were incubated with DLL3 positive DMS273 (low antigen density) or WM266.4 (high antigen density) cells expressing nuclear GFP at indicated effector:target (E:T) ratio in T cell expansion media, i.e., X-Vivo-15 supplemented with 5% human AB serum (Gemini Bio). The tissue culture plates were placed in Incucyte and the number of GFP positive target cells was counted every 6 hours. FIGS. 2B-2D show in one human T cell donor, several constructs described in Example 1 improved CAR T cytotoxicity against both DMS273 and WM266.4 target cells (relative to CAR comprising a wildtype CD3t ITAM-containing domain). FIG. 2F-2G show that in CAR T cells derived from a second human donor, several constructs described in Example 1 also improved CAR T cell cytotoxicity (relative to CAR comprising a wildtype CD3t ITAM-containing domain).

To compare the efficacy of CARs described in Example 1 and Example 2 in a long-term cytotoxicity assay, CAR-T cells were exposed repeatedly to the target DLL3 every 2 to 3 days to promote CAR-T cells proliferation. On the first day of the assay, 5,000 firefly luciferase labelled WM266.4 or DMS273 cells were seeded in 96-well plates with black wall and flat clear bottom in 100 ul X-Vivo-15 medium with 5% of human serum. After target cells attached to the bottom of the plates, CAR T cells were thawed and added to plated target cells in X-VIVO medium with 5% of human serum. Every 2 to 3 days thereafter, 100 μl medium containing CAR T cells were transferred to freshly plated target cells and percentage lysis of previously plated target cells were determined using one-glo assay system (Promega). Each condition was assayed in 3 replicates. Average percentage of lysis and standard deviation were plotted in FIGS. 3A-3B. The experimental data of serial killing assay shows that after repeated exposure of CAR T cells to DLL3 positive target cells, some of the constructs performed better than the conventional CD3ζWT construct.

Example 4: Insertion of Lck Recruitment Motifs (LRM) as a Strategy to Enable Recruitment of Lck to CAR Synapses in a More TCR-Like Manner Synapse formation for CARs does not require co-receptor (CD8 or CD4) involvement. As a result, the co-receptor-associated Lck kinase that is central to TCR signaling is coordinated with target recognition for the TCR synapse but is not for the CAR synapse (FIG. 4A). See Davenport, A. J. et al. *Chimeric antigen receptor T cells form nonclassical and potent immune synapses driving rapid cytotoxicity.* Proc. Natl. Acad. Sci. U.S.A 115, E2068-E2076 (2018).

To facilitate Lck-mediated signaling events in CAR T cells, constructs were designed to deliver a CAR with a cytoplasmic domain modified to include a co-receptor-derived sequence motif that recruits T cell signaling mediators (FIG. 4B). In this example, a Lck recruitment motif (LRM) (derived, for example, from CD8, CD4, or CD28) was inserted between cytoplasmic domains and the intracellular domain of the CAR, between the co-stimulatory domain and the ITAM containing domain, or at the C-terminus of the CAR cytoplasmic tail, enabling directed recruitment of Lck to the CAR receptor (FIG. 5A). We hypothesized that the constructs will promote more efficient phosphorylation of the CAR ITAMs and ZAP70, and thus more efficient signaling of the CAR upon antigen binding and synapse formation. Exemplary LRM amino acid sequences of SEQ ID NOs: 55 (CD8LRM-1), 56 (2×CD8LRM-1), 57 (CD8LRM-2), 58 (CD28LRM), 59 (CD28LRMY3), 64 (CD4LRM)) are shown in Table 1.

Example 5: Comparison of CAR Constructs with LRM in an In Vitro Cytotoxicity Assay In this example, the constructs described in Example 4 were transduced in primary human T cells tested for in vitro cytotoxic activity. Lentivirus encoding constructs described in Example 4 and primary T cells transduced with these lentiviruses were produced using methods described in Example 3.

Figure 5B:
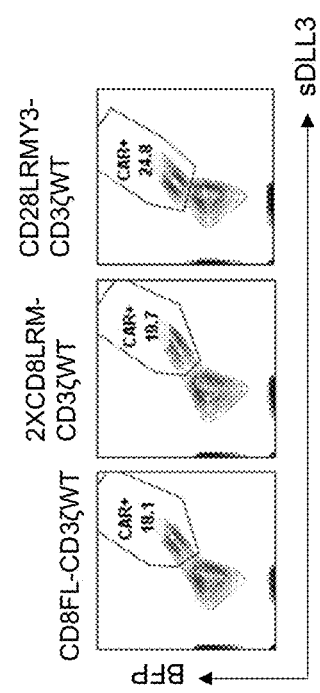

The results in FIG. 5B show that conventional CAR or CARs with an LRM insertion were expressed on the surface of primary T-cells. These T cells showed strong correlation between BFP expression and recombinant DLL3 staining, suggesting these constructs expressed properly and the proteins expressed had no major issues of folding or surface localization. The plots were gated on live CD3+ cells. The numbers on the plots are the percentage of cells expressing each CAR construct.

Figure 5C:
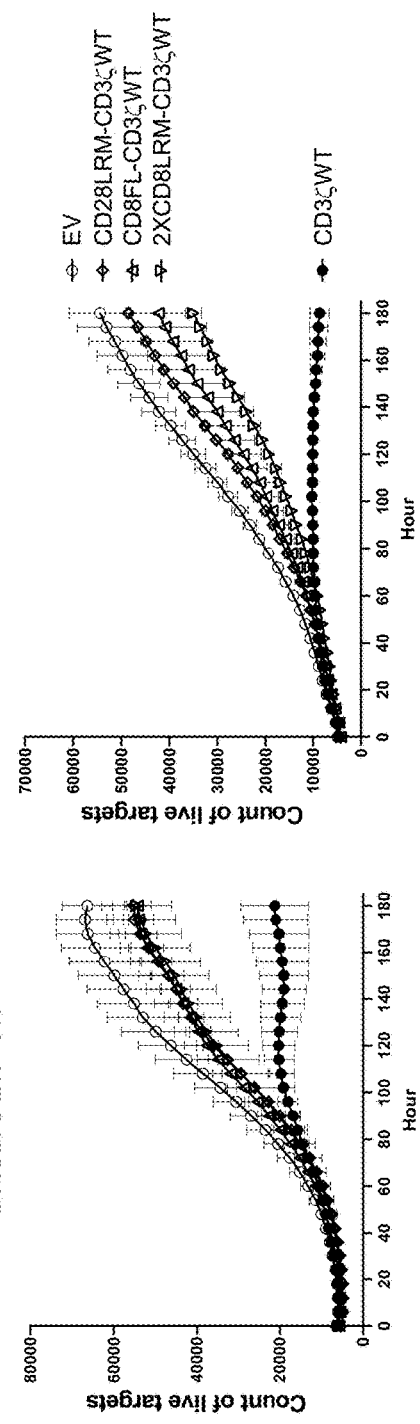
Figure 5D:
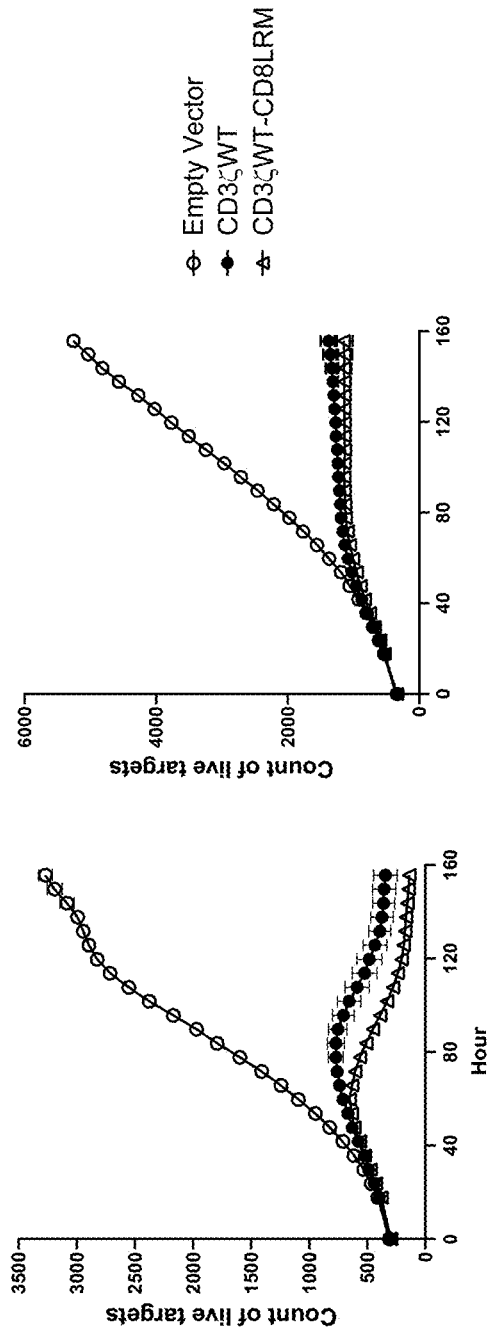
Figure 5E:
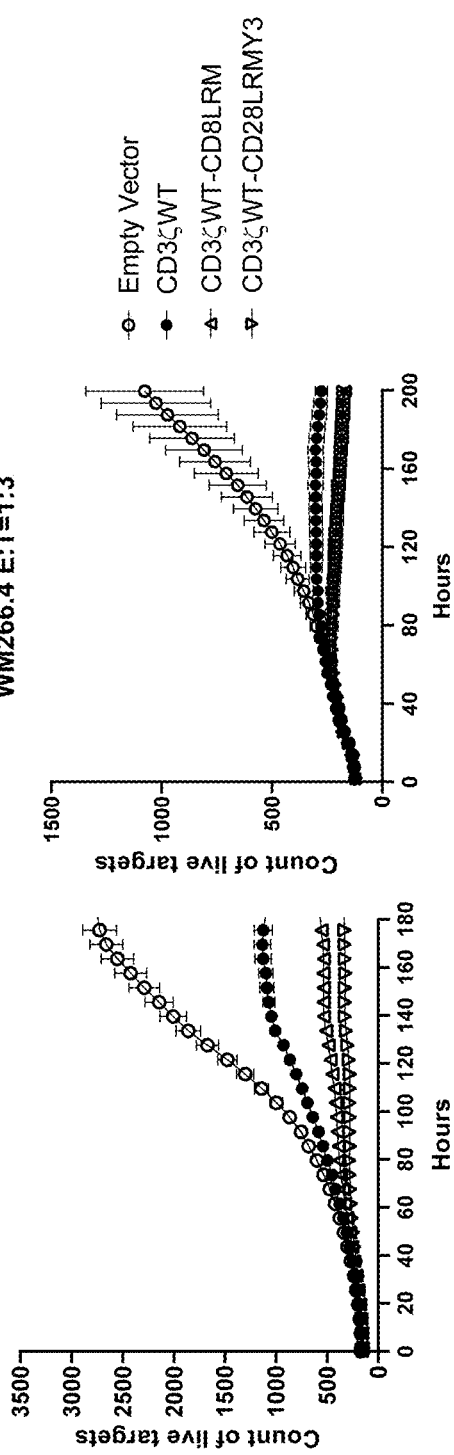
In FIG. 5E, DLL3 CAR T cells shown in FIG. 5D were produced with a different T cell donor. An additional construct having CD28LRMY3 instead of CD8LRM was also tested. These CARs once again showed better cytotoxicity against DMS273 and WM266.4 targets.

To compare the efficacy of conventional and modified CARs in a short-term kinetic killing assay, CAR T cells were incubated with DLL3 positive DMS273 (low antigen density) or WM266.4 (high antigen density) cells expressing nuclear GFP at indicated effector:target (E:T) ratio in T cell expansion media, i.e., X-Vivo-15 supplemented with 5% human AB serum (Gemini Bio). The tissue culture plates were placed in Incucyte and the number of GFP positive target cells was counted every 6 hours. FIG. 5C shows constructs with an LRM inserted between transmembrane domain and 4-1BB cytoplasmic domain did not perform as well as the conventional CAR construct. On the other hand, FIGS. 5D-5E show that several CAR constructs with an LRM inserted at the C-terminus of the CAR intracellular domain demonstrated comparable or better cytotoxicity against both DMS273 and WM266.4 target cells. The DLL3-specific CAR clone 10G1-K was used in this experiment.

Example 6: LckCARs as a Strategy to Boost Recruitment of Lck to the CAR Synapse and to Enable Combinatorial CAR Targeting A major obstacle to applying CAR T therapies to solid tumors has been the lack of suitable targets. Ideally, solid tumor targets can be identified that are expressed at high and relatively uniform levels across tumor cells but that are not expressed or expressed only at low levels on healthy tissues (as CD19 is in non-solid tumors). If solid tumor antigens cannot be identified with this auspicious confluence of characteristics, CAR design should accommodate the shortcomings of the less than ideal solid tumor target antigens. For instance, CAR-mediated targeting of solid tumor antigens that are also expressed in normal tissues may require combinatorial targeting (e.g. via logic gates) to de-risk these liabilities.

Figures 6A, 6B:
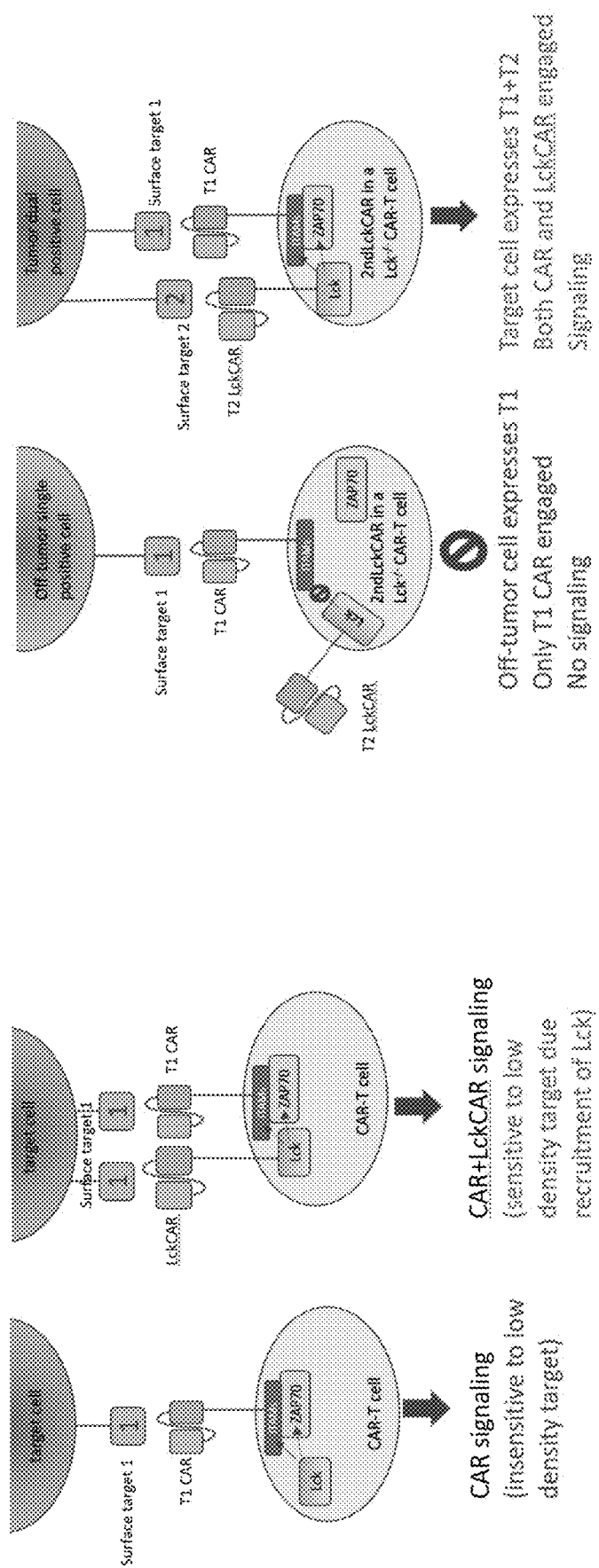
FIGS. 6A-6B are schematic representations showing "LckCARs" as a strategy to boost recruitment of Lck to the CAR synapse and to enable combinatorial CAR targeting.

To facilitate combinatorial targeting, a non-standard "CAR" or a second recombinant antigen receptor was designed, in which the intracellular domain of the non-standard CAR comprises, instead of domains that provide signal 1 and/or signal 2, a downstream mediator of T cell signaling or a functional variant thereof. As an example, such a non-standard "LckCAR" is shown in FIG. 6A. The LckCAR fuses an antigen recognition domain via the CD8 (or alternative) transmembrane domain to a protein comprising a Lck-recruitment motif (e.g. CD8 cytoplasmic tail) or directly to the Lck protein itself. Targeting of this Lck-CAR to the same target as a target-specific CAR may increase Lck recruitment to the synapse, juxtaposing Lck with ITAM substrates and thereby augmenting signaling efficiency (FIG. 6A). Targeting of the LckCAR to a second tumor-associated target antigen distinct from that recognized by the co-expressed CAR may enable AND-gated combinatorial targeting of solid tumor targets, thereby improving safety (FIG. 6B). There are many potential variations on this theme employing fusions of an extracellular antigen binding domain to different downstream T cell signaling mediators, such as ZAP70 and LAT.

Example 7: Comparison of CAR Constructs with Different ITAMs or LRM in the Context of DLL3 CAR 4118-R2S In this example, the constructs described in FIG. 1 were evaluated in the context of DLL3 CAR clone 4H8-R2S (see WO2020/180591) to demonstrate that the designs are broadly applicable.

To make lentivirus encoding constructs described in Example 1, HEK-293T cells were plated at 1.5 million cells per mL in 2 mL of DMEM (Gibco) supplemented with 10% FBS (Hyclone) per well of a 6-well plate on Day −1. On Day 0, the lentivirus was prepared by mixing together with lentiviral packaging vectors 1.5 ug psPAX2, 0.5 ug pMD2G, and 0.5 ug of the appropriate transfer CAR added to the DNA mix. The mixture was incubated at room temperature for 20 minutes and the total volume of 500 uL was slowly added to the sides of the wells containing HEK-293T. Purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution). On Day 1, the media from each well of the 6-well plate was replaced with 2 mL per well of T cell transduction media, i.e., X-Vivo-15 supplemented with 10% FBS. On Day 2, T cells were resuspended at 0.4 million cells per mL in 1.5 mL of T cell transduction media per well of a Grex-24 plate (Wilson Wolf, cat #80192M). The lentiviral supernatants from HEK293T cells (about 1.5 ml) were harvested and passed through a 0.45 micron filter (EMD Millipore) to remove cell debris, and then added to the T cells along with 100 IU/mL human IL-2. On Day 5, 4.5 mL of T cell expansion media, i.e., X-Vivo-15 supplemented with 5% human AB serum (Gemini Bio) was added to each well of a Grex-24 plate. On Day 9 and Day 13, transduction efficiency was determined by detecting the percentage of T cells that recognize recombinant Flag-DLL3 (Adipogen) using flow cytometry. Cells were expanded into larger flasks or G-Rex vessels (Wilson Wolf) as needed using T cell expansion media. On Day 14 or Day 16, DLL3 CAR-T cells were cryopreserved. Percentage of cells stained with recombinant DLL3 was normalized across clones right before cryopreservation.

To determine the percentage of T cells that were successfully transduced with the DLL3 CAR, T cells were first incubated with 1 ug/ml Flag tagged recombinant DLL3 (Adipogen) in PBS+1% BSA for 20 minutes at 4° C. The cells were then washed with PBS+1% BSA, stained with PE labelled anti-Flag antibodies (Biolegend, Cat #637310) and analyzed using flow cytometry.

Figure 7A:
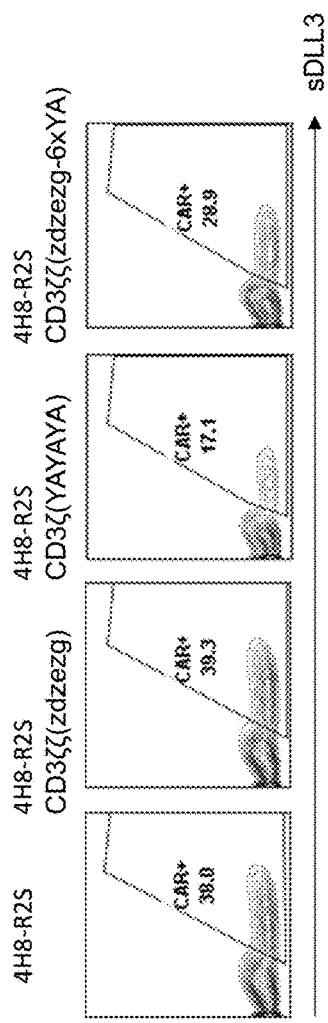
FIGS. 7A-7B show results of CAR expression and target cell killing assay of CAR T cells expressing the DLL3-specific CAR clone 4H8 with indicated intracellular signaling domains. Results from CAR T cells prepared from two other different donors are shown in FIGS. 8A-8C and FIGS. 9A-9B, respectively.
Figure 7B:
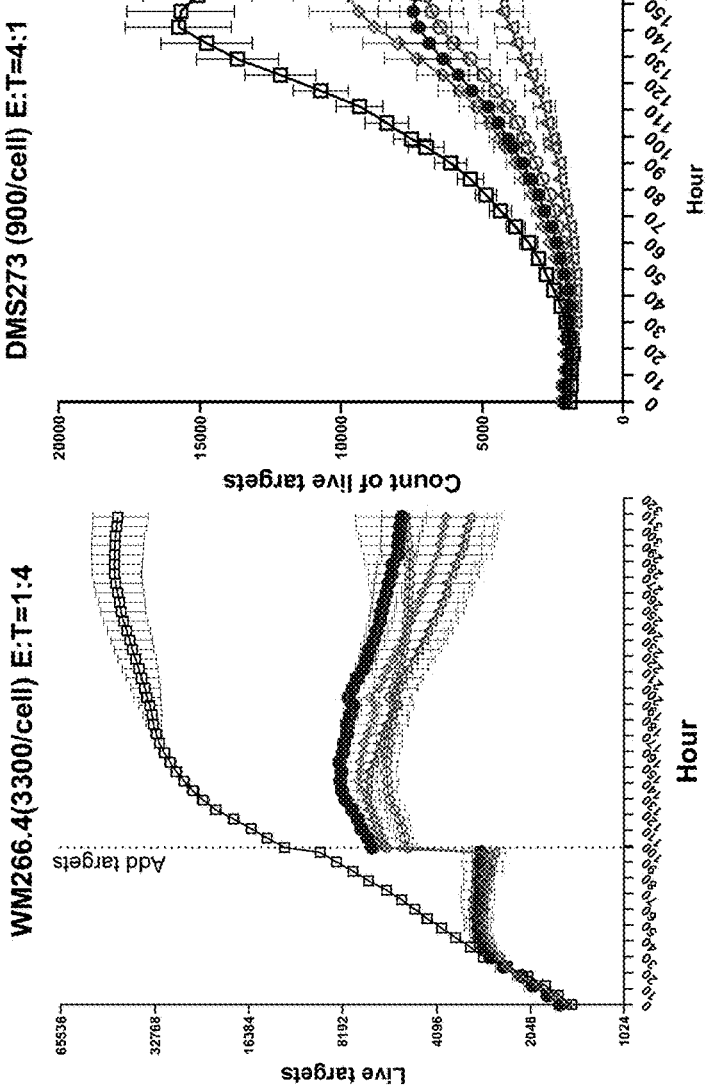
Figure 8A:
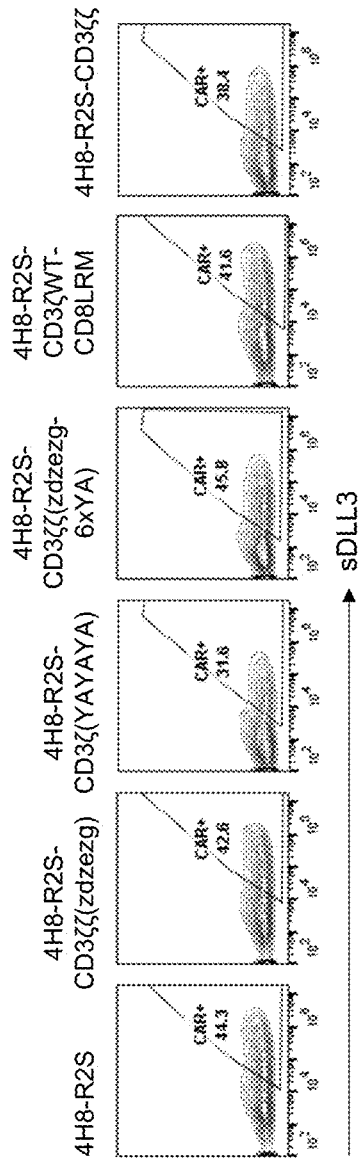
FIGS. 8D-8E show results of cytokine secretion from CAR T cells expressing DLL3 CARs with various intracellular domains.

FIGS. 7A-B, FIGS. 8A-E and FIGS. 9A-B show series of results of CAR T cells produced from three different human donors, respectively. FIGS. 7A, 8A and 9A show flow cytometry data exhibiting expression of various DLL3 CAR 4H8-R2S constructs on the surface of CAR T cells generated from three separate human donors. The plots are gated on live CD3+ cells. The numbers indicate the percentage of cells expressing each CAR construct. Most of the modified CART cells have similar percentage of CART cells compared to control CAR T cells. The activity data were normalized against transduction efficiency.

Figure 8B:
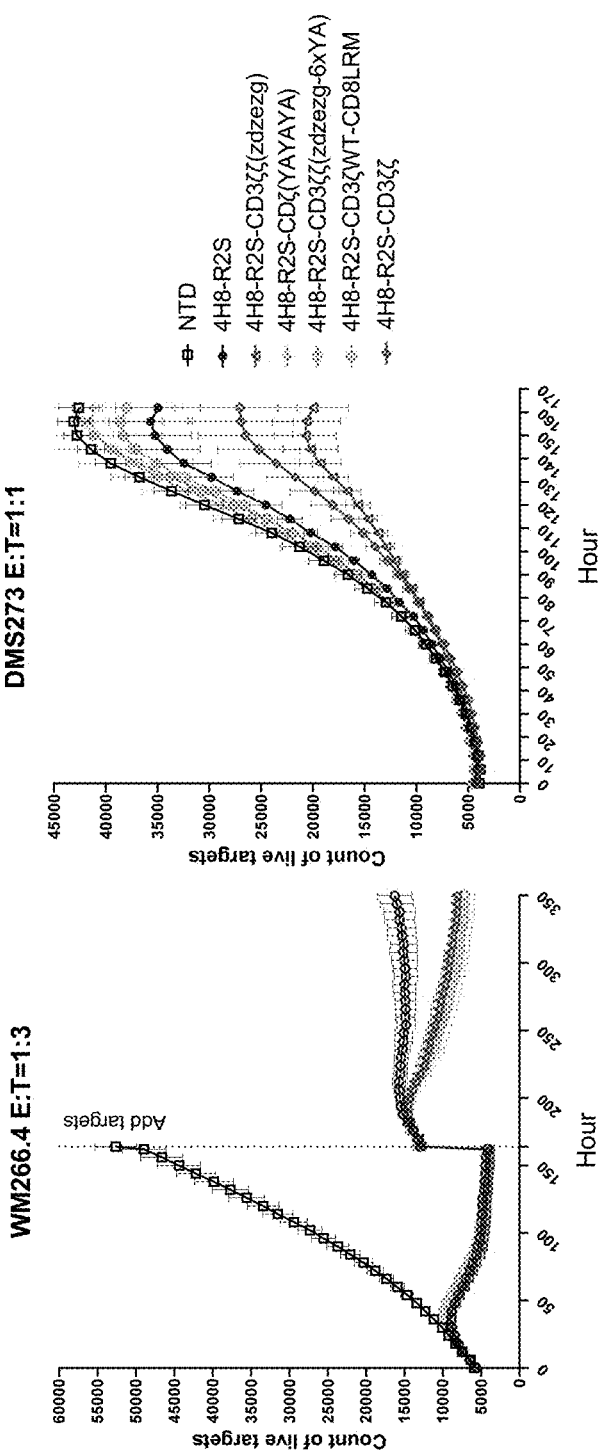

To compare the efficacy of various DLL3 CAR 4H8-R2S in a short-term kinetic killing assay, CAR T cells were incubated with DLL3 positive DMS273 cells (low antigen density cell line) or WM266.4 cells (high antigen density cell line) expressing nuclear GFP at indicated effector:target (E:T) ratio in RPMI (Gibco) supplemented with 10% FBS (Hyclone). The tissue culture plates were placed in Incucyte and the number of GFP positive target cells was counted every 6 hours. FIG. 7B shows CD3ζζ(zdzezg) construct in the context of DLL3 CAR 4H8-R2S performed better than the DLL3 CAR 4H8-R2S CD3∂WT construct, while CARs with the CD3ζ(YAYAYA) and CD3∂ζ(zdzezg-6xYA) modifications were comparable to CD3ζWT. FIG. 8B shows results of cytotoxicity assay where CAR T were prepared using primary T cells from a separate human donor. The results show that CD3ζζ(zdzezg) and CD3ζζ constructs were superior to CD3ζWT in cytotoxic activity.

Figure 8C:
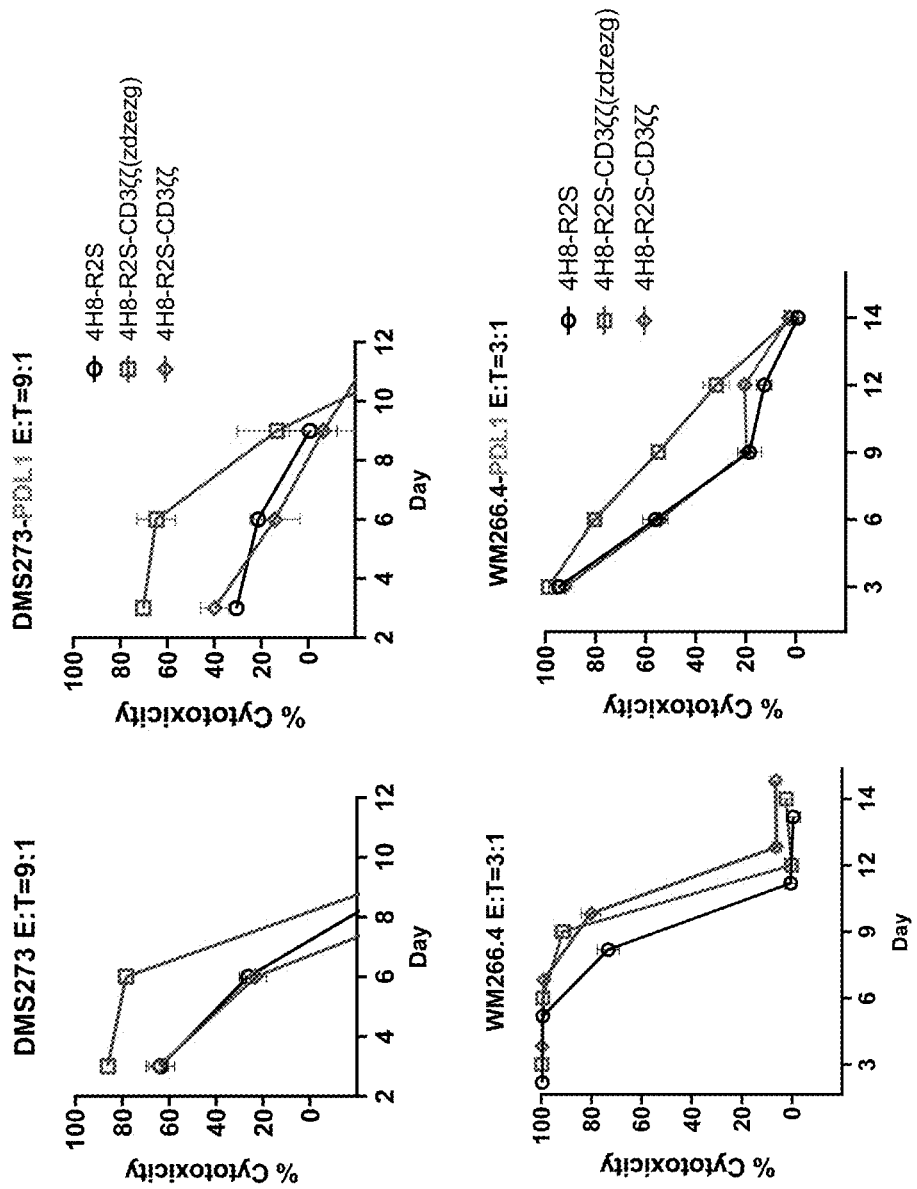

To compare the efficacy of CARs in a long-term cytotoxicity assay, CAR-T cells were exposed repeatedly to their targets every 2 to 3 days causing the CAR-T cells to undergo proliferation and in certain cases, differentiation and, in certain cases, exhaustion. PD-L1/PD-1 pathway has been shown to downregulate TCR and CAR signaling. To test if modified CAR constructs can resist the inhibition from PD-L1/PD-1 axis, 5,000 firefly luciferase labelled parental or PD-L1 overexpressed WM266.4 and DMS273 cells were seeded in 96-well plates with black wall and flat clear bottom in 50 ul RPMI (Gibco) supplemented with 10% FBS (Hyclone). After target cells attached to the bottom of the plates, CAR T cells were thawed and added to plated target cells. Every 2 to 3 days thereafter, 100 µl medium containing CAR T cells were transferred to freshly plated target cells and percentage lysis of previously plated target cells were determined using one-glo assay system (Promega). Each condition was assayed in 5 replicates. Average percentage of lysis and standard deviation were plotted. FIG. 8C and FIG. 9B show data of CAR T cells from two separate human donors. The results show that after repeated exposure of CAR T cells to DLL3 positive target cells, CD3ζζ(zdzezg) construct performed better than the CD3ζWT construct in the context of DLL3 CAR 4H8-R2S, against both parental DLL3-expressing target cells or target cells further overexpressing PD-L1. The CD3 ζζ construct was superior to the CD3ζWT construct in some settings and comparable to CD3ζWT in other settings.

To measure cytokines secreted from DLL3 CAR-T cells, CAR-T cells were incubated with WM266.4 and DMS273 at effector:target (E:T) ratio of 1:1 in RPMI (Gibco) supplemented 10% FBS (Hyclone). 24 hours later, tissue culture supernatant was collected and the levels of 3 cytokines [interferon gamma (IFN-γ), tumor necrosis factor alpha (TNF-α), and IL-2] in the supernatants were measured using human proinflammatory tissue culture 9-plex assay (MSD) following manufacturer's protocol.

Figure 8D:
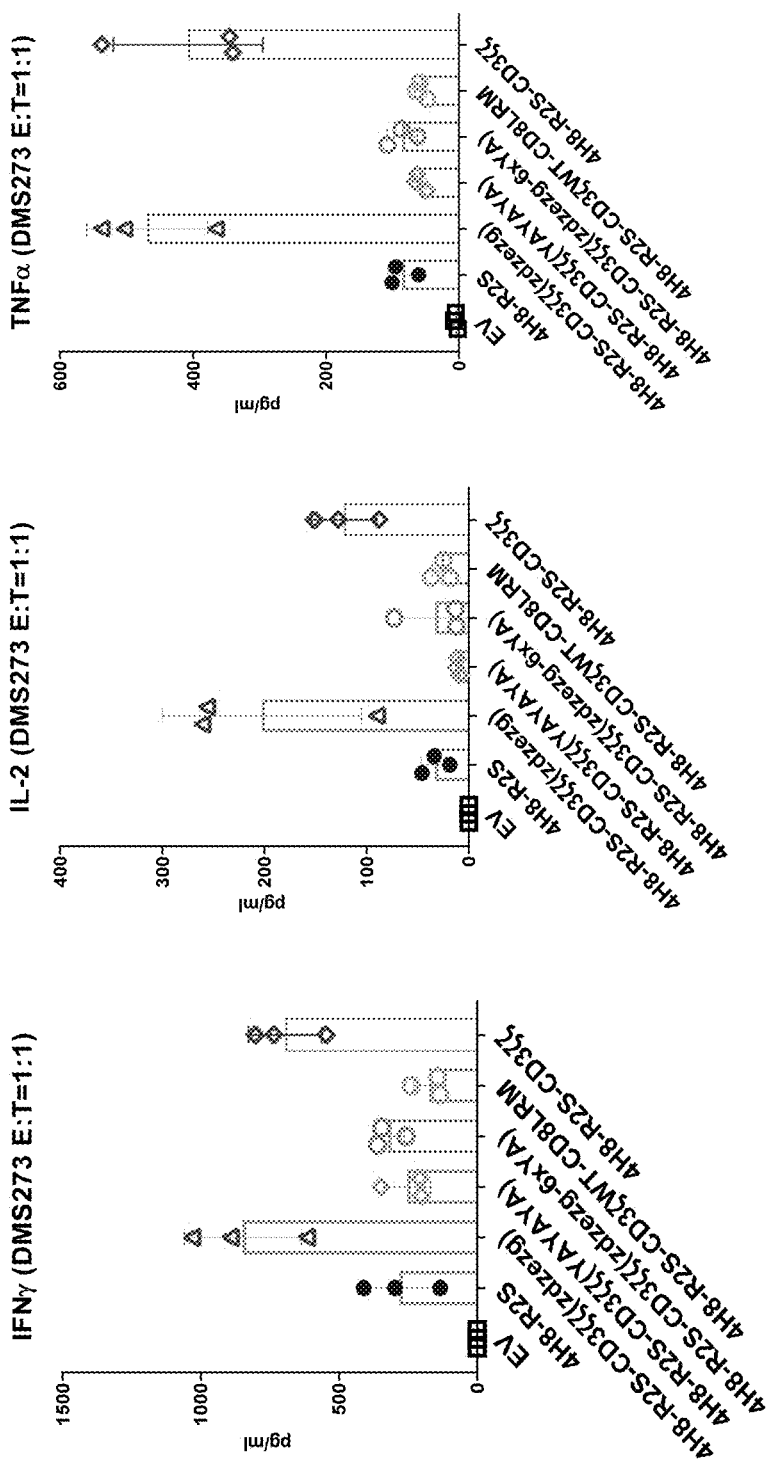

FIG. 8D shows CD3ζ∂(zdzezg) and CD3 CAR T cells secreted higher levels of IFN-γ, TNF-α and IL-2 than CD3ζWT CAR T cells when co-cultured with DMS273 (low DLL3 density) cell line, n=3.

Figure 8E:
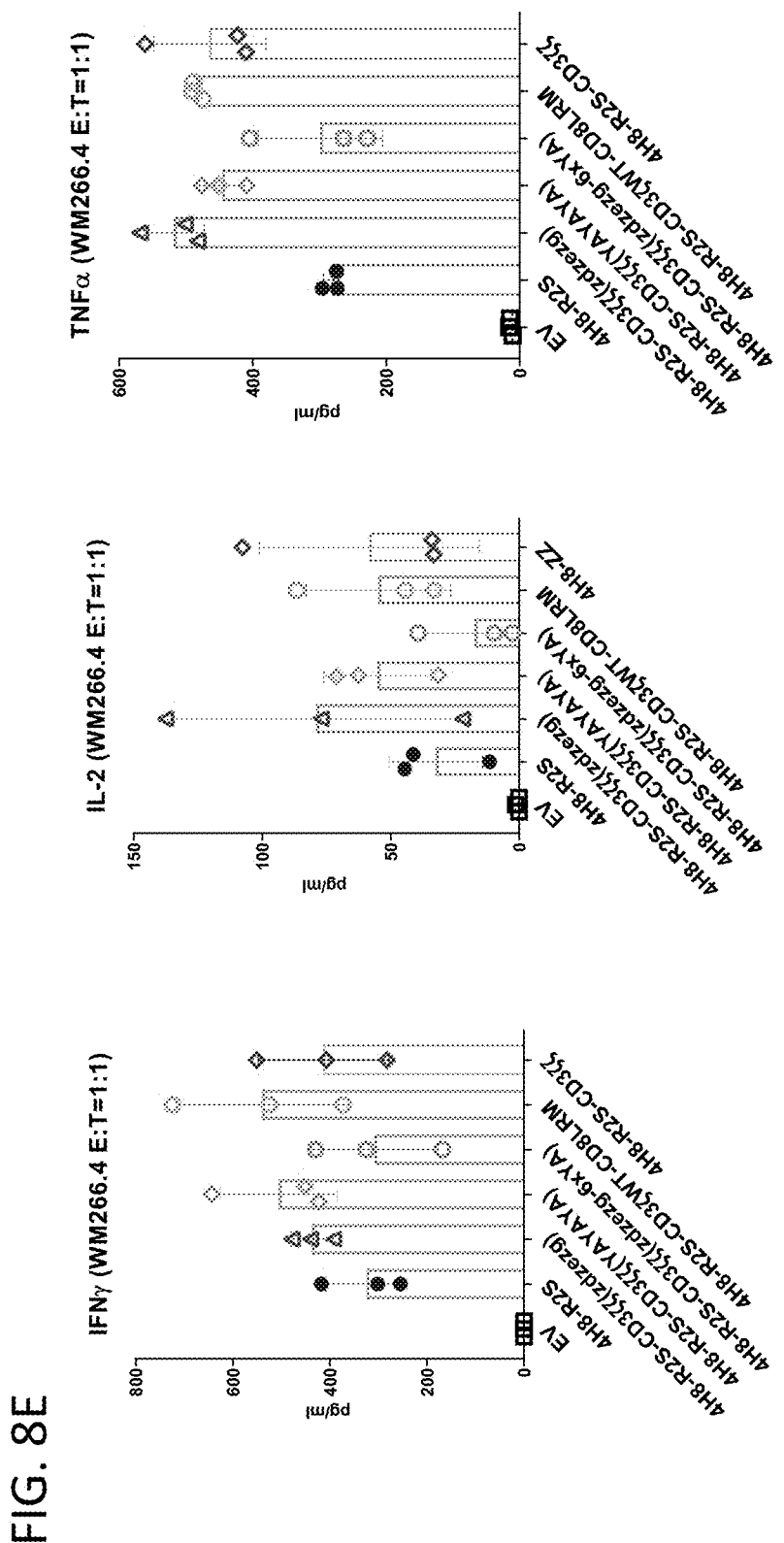

FIG. 8E shows CD3ζζ(zdzezg), CDζζ, CD3ζ(YAYAYA), and CD3ζWT-CD8LRM secret comparable or higher levels of cytokines than CD3ζWT CART cells when co-cultured with WM266.4 (high DLL3 density) cell line, n=3.

Example 8: Comparison of CAR Constructs with Different Quality and Quantity of ITAMs in the Context of DLL3 CAR 2G1-RSR In this example, the constructs described in FIG. 1 were evaluated in the context of DLL3 CAR clone 2G1-RSR (see WO2020/180591) to demonstrate the designs are broadly applicable.

Figure 10:
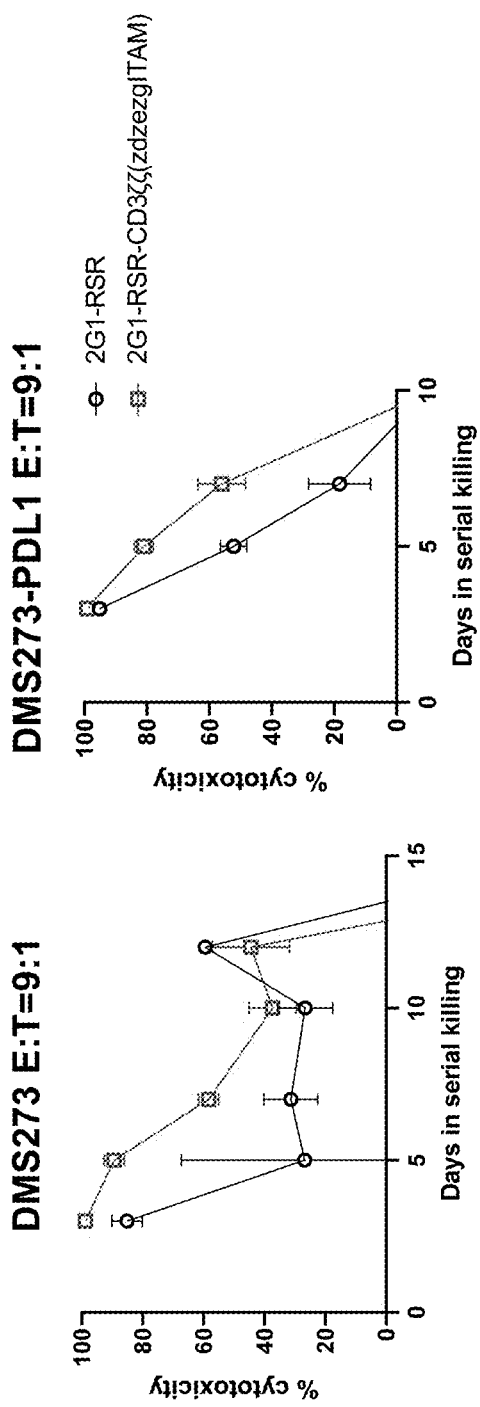
FIG. 10 shows results of long-term killing assay of CART cells expressing DLL3-specific CAR clone 2G1 cocultured with low density target cell line DMS273 with or without overexpression of PD-L1.

2G1-RSR DLL3 CAR T cells were produced as described and detected in Example 7. To compare the efficacy of CARs in a long-term cytotoxicity assay, CAR-T cells were exposed repeatedly to their targets every 2 to 3 days causing the CAR-T cells to undergo proliferation and in certain cases, differentiation and exhaustion. On the first day of the assay, 5,000 firefly luciferase labelled parental DMS273 or DMS273 overexpressing PD-L1 were seeded in 96-well plates with black wall and flat clear bottom in 50 ul RPMI (Gibco) supplemented with 10% FBS (Hyclone). After target cells attached to the bottom of the plates, CAR T cells were thawed and added to plated target cells. Every 2 to 3 days thereafter, 100 µl medium containing CAR T cells were transferred to freshly plated target cells and percentage lysis of previously plated target cells were determined using one-glo assay system (Promega). Each condition was assayed in 3 replicates. FIG. 10 shows data of long-term cytotoxicity assay, the CD3ζζ(zdzezg) construct performed better than the CD3ζWT construct in the context of DLL3 CAR 2G1-RSR on both parental and PD-L1-overexpressing DMS273 cells.

REFERENCES

Bettini, M. L. et al. Cutting Edge: CD3 ITAM Diversity Is Required for Optimal TCR Signaling and Thymocyte Development. *J. Immunol.* 199, 1555-1560 (2017).

Feucht, J. et al. Calibration of CAR activation potential directs alternative T cell fates and therapeutic potency. *Nature Medicine* 25, 82-88 (2019).

Majzner, R. G. et al. Low CD19 Antigen Density Diminishes Efficacy of CD19 CAR T Cells and Can be Overcome By Rational Redesign of CAR Signaling Domains. *Blood* 132, 963 (2018).

Sunder-Plassmann, R., Lialios, P., Madsen, M., Koyasu, S. & Reinherz, E. L. Functional analysis of immunoreceptor tyrosine-based activation motif (ITAM)-mediated signal transduction: The two YxxL segments within a single CD3ζ-ITAM are functionally distinct. *Eur. J. Immunol.* 27, 2001-2009 (1997).

Gudipati, V. et al. Inefficient CAR-proximal signaling blunts antigen sensitivity. *Nat. Immunol.* (2020). doi:10.1038/s41590-020-0719-0

Sun, C. et al. THEMIS-SHP1 Recruitment by 4-1BB Tunes LCK-Mediated Priming of Chimeric Antigen Receptor-Redirected T Cells. *Cancer Cell* 37, 216-225.e6 (2020).

Davenport, A. J. et al. Chimeric antigen receptor T cells form nonclassical and potent immune synapses driving rapid cytotoxicity. *Proc. Natl. Acad. Sci. U.S.A* 115, E2068-E2076 (2018).

What is claimed is:

1. A recombinant antigen receptor comprising an extracellular antigen binding domain, a transmembrane domain, and an intracellular domain that comprises a co-stimulatory domain and an ITAM-containing domain, wherein the ITAM-containing domain comprises from N-terminus to C-terminus (a) CD3z1 ITAM, CD3d ITAM, CD3z2 ITAM, CD3e ITAM, CD3z3 ITAM, CD3g ITAM, (b) CD3z1 (YAEL (SEQ ID NO: 152)) ITAM, CD3z2 (YAEL (SEQ ID NO: 152)) ITAM, CD3z3 (YAGL (SEQ ID NO: 153)) ITAM, or (c) CD3z1 (YAEL (SEQ ID NO: 152)) ITAM, CD3d (YAPL (SEQ ID NO: 154)) ITAM, CD3z2 (YAEL (SEQ ID NO: 152)) ITAM, CD3e (YAPI (SEQ ID NO: 155)) ITAM, CD3z3 (YAGL (SEQ ID NO: 153)) ITAM, CD3g (YAPL (SEQ ID NO: 154)) ITAM.

2. The recombinant antigen receptor of claim 1, wherein the recombinant antigen receptor is a chimeric antigen receptor (CAR).

3. The recombinant antigen receptor of claim 1, wherein the antigen binding domain comprises a heavy chain variable domain (VH) and a light chain variable domain (VL).

4. The recombinant antigen receptor of claim 1, wherein the co-stimulatory domain comprises 4-1BB co-stimulatory domain.

5. The recombinant antigen receptor of claim 1, wherein the intracellular domain comprises an amino acid sequence selected from the group consisting of SEQ ID NOs: 30, 35 and 37.

6. The recombinant antigen receptor of claim 5, wherein the intracellular domain comprises an amino acid sequence selected from the group consisting of SEQ ID NOs: 30 and 37.

7. The recombinant antigen receptor of claim 5, wherein the intracellular domain comprises an amino acid sequence of SEQ ID NO:35.

8. A polynucleotide comprising a DNA sequence encoding the recombinant antigen receptor of claim 1.

9. A vector comprising the polynucleotide of claim 8.

10. An engineered immune cell comprising the recombinant antigen receptor according to claim 1.

11. A pharmaceutical composition comprising the engineered immune cell of claim 10.

12. A recombinant antigen receptor comprising an extracellular antigen binding domain, a transmembrane domain, and an intracellular domain, wherein the intracellular domain comprises a 4-1BB co-stimulatory domain, a CD3z ITAM-containing domain, and further comprises an additional Lck recruiting motif (LRM), wherein the additional LRM is a CD8 LRM, and wherein the CD8 LRM comprises, consists of or consists essentially of the amino acid sequence of SEQ ID NO: 56.

* * * * *

UNITED STATES PATENT AND TRADEMARK OFFICE
CERTIFICATE OF CORRECTION

| | | |
|---|---|---|
| PATENT NO. | : 12,215,347 B2 | Page 1 of 1 |
| APPLICATION NO. | : 17/381693 | |
| DATED | : February 4, 2025 | |
| INVENTOR(S) | : Bethune et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 228 days.

Signed and Sealed this
Sixteenth Day of December, 2025

John A. Squires
*Director of the United States Patent and Trademark Office*

SEQUENCE LISTING

```
<160> NUMBER OF SEQ ID NOS: 157

<210> SEQ ID NO 1
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
        50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
    275                 280                 285

Ser Asp Gly Tyr Thr Pro Glu Pro Ala Arg Ile Thr Ser Pro Asp Lys
290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 2
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

-continued

```
Met Gly Cys Gly Cys Ser Ser His Pro Glu Asp Trp Met Glu Asn
 1               5                  10                  15

Ile Asp Val Cys Glu Asn Cys His Tyr Pro Ile Val Pro Leu Asp Gly
                 20                  25                  30

Lys Gly Thr Leu Leu Ile Arg Asn Gly Ser Glu Val Arg Asp Pro Leu
             35                  40                  45

Val Thr Tyr Glu Gly Ser Asn Pro Ala Ser Pro Leu Gln Asp Asn
 50                  55                  60

Leu Val Ile Ala Leu His Ser Tyr Glu Pro Ser His Asp Gly Asp Leu
 65              70                  75                  80

Gly Phe Glu Lys Gly Glu Gln Leu Arg Ile Leu Glu Gln Ser Gly Glu
                 85                  90                  95

Trp Trp Lys Ala Gln Ser Leu Thr Thr Gly Gln Glu Gly Phe Ile Pro
                100                 105                 110

Phe Asn Phe Val Ala Lys Ala Asn Ser Leu Glu Pro Glu Pro Trp Phe
            115                 120                 125

Phe Lys Asn Leu Ser Arg Lys Asp Ala Glu Arg Gln Leu Leu Ala Pro
130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
                180                 185                 190

Ile Ser Pro Arg Ile Thr Phe Pro Gly Leu His Glu Leu Val Arg His
            195                 200                 205

Tyr Thr Asn Ala Ser Asp Gly Leu Cys Thr Arg Leu Ser Arg Pro Cys
210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
                260                 265                 270

Lys Ser Leu Lys Gln Gly Ser Met Ser Pro Asp Ala Phe Leu Ala Glu
            275                 280                 285

Ala Asn Leu Met Lys Gln Leu Gln His Gln Arg Leu Val Arg Leu Tyr
290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
355                 360                 365

Asn Ile Leu Val Ser Asp Thr Leu Ser Cys Lys Ile Ala Asp Phe Gly
370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415
```

```
Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
            435                 440                 445

Val Ile Gln Asn Leu Glu Arg Gly Tyr Arg Met Val Arg Pro Asp Asn
450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505
```

<210> SEQ ID NO 3
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
210                 215                 220

Gln Thr Gln Lys Pro Gln Lys Pro Trp Trp Glu Asp Glu Trp Glu Val
225                 230                 235                 240

Pro Arg Glu Thr
```

<210> SEQ ID NO 4
<211> LENGTH: 537

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
            20                  25                  30

Asp Pro Thr Pro Gln His Tyr Pro Ser Phe Gly Val Thr Ser Ile Pro
        35                  40                  45

Asn Tyr Asn Asn Phe His Ala Ala Gly Gly Gln Gly Leu Thr Val Phe
    50                  55                  60

Gly Gly Val Asn Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
    130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
        195                 200                 205

Asp Asn Gly Gly Tyr Tyr Ile Thr Thr Arg Ala Gln Phe Glu Thr Leu
    210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
                245                 250                 255

Ser Val Lys Thr Lys Asp Val Trp Glu Ile Pro Arg Glu Ser Leu Gln
            260                 265                 270

Leu Ile Lys Arg Leu Gly Asn Gly Gln Phe Gly Glu Val Trp Met Gly
        275                 280                 285

Thr Trp Asn Gly Asn Thr Lys Val Ala Ile Lys Thr Leu Lys Pro Gly
    290                 295                 300

Thr Met Ser Pro Glu Ser Phe Leu Glu Glu Ala Gln Ile Met Lys Lys
305                 310                 315                 320

Leu Lys His Asp Lys Leu Val Gln Leu Tyr Ala Val Val Ser Glu Glu
                325                 330                 335

Pro Ile Tyr Ile Val Thr Glu Tyr Met Asn Lys Gly Ser Leu Leu Asp
            340                 345                 350

Phe Leu Lys Asp Gly Glu Gly Arg Ala Leu Lys Leu Pro Asn Leu Val
        355                 360                 365

Asp Met Ala Ala Gln Val Ala Ala Gly Met Ala Tyr Ile Glu Arg Met
    370                 375                 380
```

```
Asn Tyr Ile His Arg Asp Leu Arg Ser Ala Asn Ile Leu Val Gly Asn
385                 390                 395                 400

Gly Leu Ile Cys Lys Ile Ala Asp Phe Gly Leu Ala Arg Leu Ile Glu
            405                 410                 415

Asp Asn Glu Tyr Thr Ala Arg Gln Gly Ala Lys Phe Pro Ile Lys Trp
            420                 425                 430

Thr Ala Pro Glu Ala Ala Leu Tyr Gly Arg Phe Thr Ile Lys Ser Asp
            435                 440                 445

Val Trp Ser Phe Gly Ile Leu Leu Thr Glu Leu Val Thr Lys Gly Arg
        450                 455                 460

Val Pro Tyr Pro Gly Met Asn Asn Arg Glu Val Leu Glu Gln Val Glu
465                 470                 475                 480

Arg Gly Tyr Arg Met Pro Cys Pro Gln Asp Cys Pro Ile Ser Leu His
                485                 490                 495

Glu Leu Met Ile His Cys Trp Lys Lys Asp Pro Glu Glu Arg Pro Thr
            500                 505                 510

Phe Glu Tyr Leu Gln Ser Phe Leu Glu Asp Tyr Phe Thr Ala Thr Glu
            515                 520                 525

Pro Gln Tyr Gln Pro Gly Glu Asn Leu
        530                 535

<210> SEQ ID NO 5
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
            20                  25                  30

Asp Pro Thr Pro Gln His Tyr Pro Ser Phe Gly Val Thr Ser Ile Pro
        35                  40                  45

Asn Tyr Asn Asn Phe His Ala Ala Gly Gly Gln Gly Leu Thr Val Phe
    50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
    130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
```

```
                195                 200                 205
Asp Asn Gly Gly Tyr Tyr Ile Thr Thr Arg Ala Gln Phe Glu Thr Leu
    210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
                245                 250                 255

Ser Val Lys Thr Lys Asp Val Trp Glu Ile Pro Arg Glu Ser
            260                 265                 270

<210> SEQ ID NO 6
<211> LENGTH: 635
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
            20                  25                  30

Gly Met Ser Asp Gly Leu Tyr Leu Leu Arg Gln Ser Arg Asn Tyr Leu
        35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
    130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
    210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Thr Trp Ser Ala Gly Gly
        275                 280                 285
```

Ile Ile Ser Arg Ile Lys Ser Tyr Ser Phe Pro Lys Pro Gly His Arg
                290                 295                 300

Lys Ser Ser Pro Ala Gln Gly Asn Arg Gln Glu Ser Thr Val Ser Phe
305                 310                 315                 320

Asn Pro Tyr Glu Pro Glu Leu Ala Pro Trp Ala Ala Asp Lys Gly Pro
                325                 330                 335

Gln Arg Glu Ala Leu Pro Met Asp Thr Glu Val Tyr Glu Ser Pro Tyr
                340                 345                 350

Ala Asp Pro Glu Glu Ile Arg Pro Lys Glu Val Tyr Leu Asp Arg Lys
                355                 360                 365

Leu Leu Thr Leu Glu Asp Lys Glu Leu Gly Ser Gly Asn Phe Gly Thr
370                 375                 380

Val Lys Lys Gly Tyr Tyr Gln Met Lys Lys Val Val Lys Thr Val Ala
385                 390                 395                 400

Val Lys Ile Leu Lys Asn Glu Ala Asn Asp Pro Ala Leu Lys Asp Glu
                405                 410                 415

Leu Leu Ala Glu Ala Asn Val Met Gln Gln Leu Asp Asn Pro Tyr Ile
                420                 425                 430

Val Arg Met Ile Gly Ile Cys Glu Ala Glu Ser Trp Met Leu Val Met
                435                 440                 445

Glu Met Ala Glu Leu Gly Pro Leu Asn Lys Tyr Leu Gln Gln Asn Arg
450                 455                 460

His Val Lys Asp Lys Asn Ile Ile Glu Leu Val His Gln Val Ser Met
465                 470                 475                 480

Gly Met Lys Tyr Leu Glu Glu Ser Asn Phe Val His Arg Asp Leu Ala
                485                 490                 495

Ala Arg Asn Val Leu Leu Val Thr Gln His Tyr Ala Lys Ile Ser Asp
                500                 505                 510

Phe Gly Leu Ser Lys Ala Leu Arg Ala Asp Glu Asn Tyr Tyr Lys Ala
                515                 520                 525

Gln Thr His Gly Lys Trp Pro Val Lys Trp Tyr Ala Pro Glu Cys Ile
                530                 535                 540

Asn Tyr Tyr Lys Phe Ser Ser Lys Ser Asp Val Trp Ser Phe Gly Val
545                 550                 555                 560

Leu Met Trp Glu Ala Phe Ser Tyr Gly Gln Lys Pro Tyr Arg Gly Met
                565                 570                 575

Lys Gly Ser Glu Val Thr Ala Met Leu Glu Lys Gly Glu Arg Met Gly
                580                 585                 590

Cys Pro Ala Gly Cys Pro Arg Glu Met Tyr Asp Leu Met Asn Leu Cys
                595                 600                 605

Trp Thr Tyr Asp Val Glu Asn Arg Pro Gly Phe Ala Ala Val Glu Leu
610                 615                 620

Arg Leu Arg Asn Tyr Tyr Tyr Asp Val Val Asn
625                 630                 635

<210> SEQ ID NO 7
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Ser Ser Gly Met Ala Asp Ser Ala Asn His Leu Pro Phe Phe
1               5                   10                  15

Phe Gly Asn Ile Thr Arg Glu Ala Glu Asp Tyr Leu Val Gln Gly
                20                  25                  30

Gly Met Ser Asp Gly Leu Tyr Leu Arg Gln Ser Arg Asn Tyr Leu
            35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
            115                 120                 125

Arg Glu Tyr Val Lys Gln Thr Trp Asn Leu Gln Gly Gln Ala Leu Glu
130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
            195                 200                 205

His Glu Gly Lys Val Leu His Tyr Arg Ile Asp Lys Asp Lys Thr Gly
            210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Thr Trp Ser Ala Gly Gly
            275                 280                 285

Ile Ile Ser Arg Ile Lys Ser Tyr Ser Phe Pro Lys Pro Gly His Arg
            290                 295                 300

Lys Ser Ser Pro Ala Gln Gly Asn Arg Gln Glu Ser Thr Val Ser Phe
305                 310                 315                 320

Asn Pro Tyr Glu Pro Glu Leu Ala Pro Trp Ala Ala Asp Lys Gly Pro
                325                 330                 335

Gln Arg Glu Ala Leu Pro Met Asp Thr Glu Val Tyr Glu Ser Pro Tyr
            340                 345                 350

Ala Asp Pro Glu Glu Ile Arg Pro Lys Glu Val Tyr Leu Asp Arg Lys
            355                 360                 365

Leu Leu
    370

<210> SEQ ID NO 8
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 8

```
Met Glu Glu Ala Ile Leu Val Pro Cys Val Leu Gly Leu Leu Leu Leu
1               5                   10                  15

Pro Ile Leu Ala Met Leu Met Ala Leu Cys Val His Cys His Arg Leu
            20                  25                  30

Pro Gly Ser Tyr Asp Ser Thr Ser Ser Asp Ser Leu Tyr Pro Arg Gly
        35                  40                  45

Ile Gln Phe Lys Arg Pro His Thr Val Ala Pro Trp Pro Pro Ala Tyr
    50                  55                  60

Pro Pro Val Thr Ser Tyr Pro Pro Leu Ser Gln Pro Asp Leu Leu Pro
65                  70                  75                  80

Ile Pro Arg Ser Pro Gln Pro Leu Gly Gly Ser His Arg Thr Pro Ser
                85                  90                  95

Ser Arg Arg Asp Ser Asp Gly Ala Asn Ser Val Ala Ser Tyr Glu Asn
            100                 105                 110

Glu Gly Ala Ser Gly Ile Arg Gly Ala Gln Ala Gly Trp Gly Val Trp
        115                 120                 125

Gly Pro Ser Trp Thr Arg Leu Thr Pro Val Ser Leu Pro Pro Glu Pro
    130                 135                 140

Ala Cys Glu Asp Ala Asp Glu Asp Glu Asp Tyr His Asn Pro Gly
145                 150                 155                 160

Tyr Leu Val Val Leu Pro Asp Ser Thr Pro Ala Thr Ser Thr Ala Ala
                165                 170                 175

Pro Ser Ala Pro Ala Leu Ser Thr Pro Gly Ile Arg Asp Ser Ala Phe
            180                 185                 190

Ser Met Glu Ser Ile Asp Asp Tyr Val Asn Val Pro Glu Ser Gly Glu
        195                 200                 205

Ser Ala Glu Ala Ser Leu Asp Gly Ser Arg Glu Tyr Val Asn Val Ser
    210                 215                 220

Gln Glu Leu His Pro Gly Ala Ala Lys Thr Glu Pro Ala Ala Leu Ser
225                 230                 235                 240

Ser Gln Glu Ala Glu Glu Val Glu Glu Glu Gly Ala Pro Asp Tyr Glu
                245                 250                 255

Asn Leu Gln Glu Leu Asn
            260
```

<210> SEQ ID NO 9
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Lys Val Lys Lys Gly Gly Gly Ala Gly Thr Ala Thr Glu Ser
1               5                   10                  15

Ala Pro Gly Pro Ser Gly Gln Ser Val Ala Pro Ile Pro Gln Pro Pro
            20                  25                  30

Ala Glu Ser Glu Ser Gly Ser Glu Ser Glu Pro Asp Ala Gly Pro Gly
        35                  40                  45

Pro Arg Pro Gly Pro Leu Gln Arg Lys Gln Pro Ile Gly Pro Glu Asp
    50                  55                  60

Val Leu Gly Leu Gln Arg Ile Thr Gly Asp Tyr Leu Cys Ser Pro Glu
65                  70                  75                  80
```

```
Glu Asn Ile Tyr Lys Ile Asp Phe Val Arg Phe Lys Ile Arg Asp Met
             85                  90                  95

Asp Ser Gly Thr Val Leu Phe Glu Ile Lys Lys Pro Pro Val Ser Glu
            100                 105                 110

Arg Leu Pro Ile Asn Arg Arg Asp Leu Asp Pro Asn Ala Gly Arg Phe
            115                 120                 125

Val Arg Tyr Gln Phe Thr Pro Ala Phe Leu Arg Leu Arg Gln Val Gly
            130                 135                 140

Ala Thr Val Glu Phe Thr Val Gly Asp Lys Pro Val Asn Asn Phe Arg
145                 150                 155                 160

Met Ile Glu Arg His Tyr Phe Arg Asn Gln Leu Leu Lys Ser Phe Asp
                165                 170                 175

Phe His Phe Gly Phe Cys Ile Pro Ser Ser Lys Asn Thr Cys Glu His
                180                 185                 190

Ile Tyr Asp Phe Pro Pro Leu Ser Glu Glu Leu Ile Ser Glu Met Ile
                195                 200                 205

Arg His Pro Tyr Glu Thr Gln Ser Asp Ser Phe Tyr Phe Val Asp Asp
            210                 215                 220

Arg Leu Val Met His Asn Lys Ala Asp Tyr Ser Tyr Ser Gly Thr Pro
225                 230                 235                 240

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Ala Leu Pro Val Thr Ala Leu Leu Leu Pro Leu Ala Leu Leu Leu
1               5                   10                  15

His Ala Ala Arg Pro
            20

<210> SEQ ID NO 11
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Tyr Ile Trp Ala Pro Leu Ala Gly Thr Cys Gly Val Leu Leu Leu
```

```
                1               5                  10                 15
Ser Leu Val Ile Thr
                20

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Tyr Cys
1

<210> SEQ ID NO 14
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Arg Gly Arg Lys Lys Leu Leu Tyr Ile Phe Lys Gln Pro Phe Met
1               5                  10                 15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Arg Val Lys Phe Ser Arg Ser Ala Asp Ala Pro Ala Tyr Gln Gln Gly
1               5                  10                 15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 16
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

Gly Arg Val Lys Phe Ser Arg Ser Ala Asp Ala Pro Ala Tyr Gln Gln
        115                 120                 125

Gly Gln Asn Gln Leu Tyr Asn Glu Leu Asn Leu Gly Arg Arg Glu Glu
    130                 135                 140

Tyr Asp Val Leu Asp Lys Arg Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175

Lys Asp Lys Met Ala Glu Ala Tyr Ser Glu Ile Gly Met Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg
225

<210> SEQ ID NO 17
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly His Glu Thr Gly Arg Leu Ser Gly Ala Ala Asp Thr Gln Ala Leu
1               5                   10                  15

Leu Arg Asn Asp Gln Val Tyr Gln Pro Leu Arg Asp Arg Asp Asp Ala
            20                  25                  30

Gln Tyr Ser His Leu Gly Gly Asn Trp Ala Arg Asn Lys
        35                  40                  45

<210> SEQ ID NO 18
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55

<210> SEQ ID NO 19
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gln Asp Gly Val Arg Gln Ser Arg Ala Ser Asp Lys Gln Thr Leu
1               5                   10                  15

Leu Pro Asn Asp Gln Leu Tyr Gln Pro Leu Lys Asp Arg Glu Asp Asp
            20                  25                  30

Gln Tyr Ser His Leu Gln Gly Asn Gln Leu Arg Arg Asn
        35                  40                  45

<210> SEQ ID NO 20
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg
            20                  25

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Arg Arg Lys Asn Pro Gln Glu Gly Leu Tyr Asn Glu Leu Gln Lys
1               5                   10                  15

Asp Lys Met Ala Glu Ala Tyr Ser Glu Ile Gly Met
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Arg Arg Arg Gly Lys Gly His Asp Gly Leu Tyr Gln Gly Leu Ser
1               5                   10                  15
```

```
Thr Ala Thr Lys Asp Thr Tyr Asp Ala Leu His Met Gln
            20                  25
```

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Asp Thr Gln Ala Leu Leu Arg Asn Asp Gln Val Tyr Gln Pro Leu Arg
1               5                   10                  15

Asp Arg Asp Asp Ala Gln Tyr Ser His Leu Gly Gly Asn
            20                  25
```

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Glu Arg Pro Pro Pro Val Pro Asn Pro Asp Tyr Glu Pro Ile Arg Lys
1               5                   10                  15

Gly Gln Arg Asp Leu Tyr Ser Gly Leu Asn Gln Arg
            20                  25
```

<210> SEQ ID NO 25
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Asp Lys Gln Thr Leu Leu Pro Asn Asp Gln Leu Tyr Gln Pro Leu Lys
1               5                   10                  15

Asp Arg Glu Asp Asp Gln Tyr Ser His Leu Gln Gly Asn
            20                  25
```

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Arg Val Lys Phe Ser Arg Ser Ala Asp Asp Thr Gln Ala Leu Leu Arg
1               5                   10                  15

Asn Asp Gln Val Tyr Gln Pro Leu Arg Asp Arg Asp Asp Ala Gln Tyr
            20                  25                  30

Ser His Leu Gly Gly Asn Arg Gly Arg Asp Pro Glu Met Gly Gly Lys
            35                  40                  45

Pro Arg Arg Lys Asn Pro Gln Glu Gly Leu Tyr Asn Glu Leu Gln Lys
            50                  55                  60

Asp Lys Met Ala Glu Ala Tyr Ser Glu Ile Gly Met Lys Gly Glu Arg
```

65                  70                  75                  80
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 27
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Val Lys Phe Ser Arg Ser Ala Asp Glu Arg Pro Pro Val Pro
1               5                   10                  15

Asn Pro Asp Tyr Glu Pro Ile Arg Lys Gly Gln Arg Asp Leu Tyr Ser
                20                  25                  30

Gly Leu Asn Gln Arg Arg Gly Arg Asp Pro Glu Met Gly Gly Lys Pro
            35                  40                  45

Arg Arg Lys Asn Pro Gln Glu Gly Leu Tyr Asn Glu Leu Gln Lys Asp
50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Arg Val Lys Phe Ser Arg Ser Ala Asp Asp Lys Gln Thr Leu Leu Pro
1               5                   10                  15

Asn Asp Gln Leu Tyr Gln Pro Leu Lys Asp Arg Glu Asp Asp Gln Tyr
                20                  25                  30

Ser His Leu Gln Gly Asn Arg Gly Arg Asp Pro Glu Met Gly Gly Lys
            35                  40                  45

Pro Arg Arg Lys Asn Pro Gln Glu Gly Leu Tyr Asn Glu Leu Gln Lys
            50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Arg Val Lys Phe Ser Arg Ser Ala Asp Asp Thr Gln Ala Leu Leu Arg
1               5                   10                  15

Asn Asp Gln Val Tyr Gln Pro Leu Arg Asp Arg Asp Asp Ala Gln Tyr
            20                  25                  30

Ser His Leu Gly Gly Asn Arg Gly Arg Asp Pro Glu Met Gly Gly Lys
        35                  40                  45

Glu Arg Pro Pro Val Pro Asn Pro Asp Tyr Glu Pro Ile Arg Lys
    50                  55                  60

Gly Gln Arg Asp Leu Tyr Ser Gly Leu Asn Gln Arg Lys Gly Asp Lys
65                  70                  75                  80

Gln Thr Leu Leu Pro Asn Asp Gln Leu Tyr Gln Pro Leu Lys Asp Arg
                85                  90                  95

Glu Asp Asp Gln Tyr Ser His Leu Gln Gly Asn Ala Leu Pro Pro Arg
            100                 105                 110
```

<210> SEQ ID NO 30
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Asp Thr Gln Ala Leu Leu Arg Asn Asp Gln Val Tyr Gln Pro Leu Arg
    50                  55                  60

Asp Arg Asp Asp Ala Gln Tyr Ser His Leu Gly Gly Asn Lys Gly Pro
65                  70                  75                  80

Arg Arg Lys Asn Pro Gln Glu Gly Leu Tyr Asn Glu Leu Gln Lys Asp
                85                  90                  95

Lys Met Ala Glu Ala Tyr Ser Glu Ile Gly Met Ala Leu Pro Pro Arg
            100                 105                 110

Gly Arg Val Lys Phe Ser Arg Ser Ala Asp Glu Arg Pro Pro Val
        115                 120                 125

Pro Asn Pro Asp Tyr Glu Pro Ile Arg Lys Gly Gln Arg Asp Leu Tyr
    130                 135                 140

Ser Gly Leu Asn Gln Arg Arg Gly Arg Asp Pro Glu Met Gly Gly Lys
145                 150                 155                 160

Glu Arg Arg Arg Gly Lys Gly His Asp Gly Leu Tyr Gln Gly Leu Ser
                165                 170                 175

Thr Ala Thr Lys Asp Thr Tyr Asp Ala Leu His Met Gln Lys Gly Asp
            180                 185                 190

Lys Gln Thr Leu Leu Pro Asn Asp Gln Leu Tyr Gln Pro Leu Lys Asp
        195                 200                 205

Arg Glu Asp Asp Gln Tyr Ser His Leu Gln Gly Asn Ala Leu Pro Pro
    210                 215                 220

Arg
```

<210> SEQ ID NO 31
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Arg Val Lys Phe Ser Arg Ser Ala Asp Asp Thr Gln Ala Leu Leu Arg
1               5                   10                  15

Asn Asp Gln Val Tyr Gln Pro Leu Arg Asp Arg Asp Asp Ala Gln Tyr
            20                  25                  30

Ser His Leu Gly Gly Asn Arg Gly Arg Asp Pro Glu Met Gly Gly Lys
        35                  40                  45

Ala Pro Ala Tyr Gln Gln Gly Gln Asn Gln Leu Tyr Asn Glu Leu Asn
    50                  55                  60

Leu Gly Arg Arg Glu Glu Tyr Asp Val Leu Asp Lys Arg Lys Gly Glu
65                  70                  75                  80

Arg Pro Pro Pro Val Pro Asn Pro Asp Tyr Glu Pro Ile Arg Lys Gly
                85                  90                  95

Gln Arg Asp Leu Tyr Ser Gly Leu Asn Gln Arg Ala Leu Pro Pro Arg
            100                 105                 110

Gly Arg Val Lys Phe Ser Arg Ser Ala Asp Pro Arg Arg Lys Asn Pro
        115                 120                 125

Gln Glu Gly Leu Tyr Asn Glu Leu Gln Lys Asp Lys Met Ala Glu Ala
    130                 135                 140

Tyr Ser Glu Ile Gly Met Arg Gly Arg Asp Pro Glu Met Gly Gly Lys
145                 150                 155                 160

Asp Lys Gln Thr Leu Leu Pro Asn Asp Gln Leu Tyr Gln Pro Leu Lys
                165                 170                 175

Asp Arg Glu Asp Asp Gln Tyr Ser His Leu Gln Gly Asn Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg
225
```

<210> SEQ ID NO 32
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
```

```
                 50                  55                  60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

Gly Arg Val Lys Phe Ser Arg Ser Ala Asp Asp Thr Gln Ala Leu Leu
                115                 120                 125

Arg Asn Asp Gln Val Tyr Gln Pro Leu Arg Asp Arg Asp Asp Ala Gln
130                 135                 140

Tyr Ser His Leu Gly Gly Asn Arg Gly Arg Asp Pro Glu Met Gly Gly
145                 150                 155                 160

Lys Glu Arg Pro Pro Val Pro Asn Pro Asp Tyr Glu Pro Ile Arg
                165                 170                 175

Lys Gly Gln Arg Asp Leu Tyr Ser Gly Leu Asn Gln Arg Lys Gly Asp
                180                 185                 190

Lys Gln Thr Leu Leu Pro Asn Asp Gln Leu Tyr Gln Pro Leu Lys Asp
                195                 200                 205

Arg Glu Asp Asp Gln Tyr Ser His Leu Gln Gly Asn Ala Leu Pro Pro
                210                 215                 220

Arg
225

<210> SEQ ID NO 33
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Arg Val Lys Phe Ser Arg Ser Ala Asp Asp Thr Gln Ala Leu Leu Arg
 1               5                  10                  15

Asn Asp Gln Val Tyr Gln Pro Leu Arg Asp Arg Asp Asp Ala Gln Tyr
                20                  25                  30

Ser His Leu Gly Gly Asn Arg Gly Arg Asp Pro Glu Met Gly Gly Lys
                35                  40                  45

Glu Arg Pro Pro Val Pro Asn Pro Asp Tyr Glu Pro Ile Arg Lys
 50                  55                  60

Gly Gln Arg Asp Leu Tyr Ser Gly Leu Asn Gln Arg Lys Gly Asp Lys
 65                  70                  75                  80

Gln Thr Leu Leu Pro Asn Asp Gln Leu Tyr Gln Pro Leu Lys Asp Arg
                85                  90                  95

Glu Asp Asp Gln Tyr Ser His Leu Gln Gly Asn Ala Leu Pro Pro Arg
                100                 105                 110

Gly Arg Val Lys Phe Ser Arg Ser Ala Asp Ala Pro Ala Tyr Gln Gln
                115                 120                 125

Gly Gln Asn Gln Leu Tyr Asn Glu Leu Asn Leu Gly Arg Arg Glu Glu
130                 135                 140

Tyr Asp Val Leu Asp Lys Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175
```

```
Lys Asp Lys Met Ala Glu Ala Tyr Ser Glu Ile Gly Met Lys Gly Glu
                180                 185                 190

Arg Arg Arg Gly Lys Gly His Asp Gly Leu Tyr Gln Gly Leu Ser Thr
            195                 200                 205

Ala Thr Lys Asp Thr Tyr Asp Ala Leu His Met Gln Ala Leu Pro Pro
        210                 215                 220

Arg
225

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Ala Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Arg Val Lys Phe Ser Arg Ser Ala Asp Ala Pro Ala Tyr Gln Gln Gly
1               5                   10                  15

Gln Asn Gln Leu Tyr Ala Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Ala Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Ala Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 36
<211> LENGTH: 43
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

Arg Val Lys Phe Ser Arg Ser Ala Asp Ala Pro Ala Tyr Gln Gln Gly
1               5                   10                  15

Gln Asn Gln Leu Tyr Ala Glu Leu Asn Leu Gly Arg Arg Glu Glu Tyr
            20                  25                  30

Asp Val Leu Asp Lys Arg Ala Leu Pro Pro Arg
        35                  40

```
<210> SEQ ID NO 37
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37
```

Arg Val Lys Phe Ser Arg Ser Ala Asp Ala Pro Ala Tyr Gln Gln Gly
1               5                   10                  15

Gln Asn Gln Leu Tyr Ala Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Asp Thr Gln Ala Leu Leu Arg Asn Asp Gln Val Tyr Ala Pro Leu Arg
    50                  55                  60

Asp Arg Asp Asp Ala Gln Tyr Ser His Leu Gly Gly Asn Lys Gly Pro
65                  70                  75                  80

Arg Arg Lys Asn Pro Gln Glu Gly Leu Tyr Ala Glu Leu Gln Lys Asp
                85                  90                  95

Lys Met Ala Glu Ala Tyr Ser Glu Ile Gly Met Ala Leu Pro Pro Arg
            100                 105                 110

Gly Arg Val Lys Phe Ser Arg Ser Ala Asp Glu Arg Pro Pro Pro Val
        115                 120                 125

Pro Asn Pro Asp Tyr Ala Pro Ile Arg Lys Gly Gln Arg Asp Leu Tyr
    130                 135                 140

Ser Gly Leu Asn Gln Arg Arg Gly Arg Asp Pro Glu Met Gly Gly Lys
145                 150                 155                 160

Glu Arg Arg Arg Gly Lys Gly His Asp Gly Leu Tyr Ala Gly Leu Ser
                165                 170                 175

Thr Ala Thr Lys Asp Thr Tyr Asp Ala Leu His Met Gln Lys Gly Asp
            180                 185                 190

Lys Gln Thr Leu Leu Pro Asn Asp Gln Leu Tyr Ala Pro Leu Lys Asp
        195                 200                 205

Arg Glu Asp Asp Gln Tyr Ser His Leu Gln Gly Asn Ala Leu Pro Pro
    210                 215                 220

Arg
225

```
<210> SEQ ID NO 38
<211> LENGTH: 225
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 38

Arg Val Lys Phe Ser Arg Ser Ala Asp Asp Thr Gln Ala Leu Leu Arg
1               5                   10                  15

Asn Asp Gln Val Tyr Ala Pro Leu Arg Asp Arg Asp Ala Gln Tyr
            20                  25                  30

Ser His Leu Gly Gly Asn Arg Gly Arg Asp Pro Glu Met Gly Gly Lys
        35                  40                  45

Ala Pro Ala Tyr Gln Gln Gly Gln Asn Gln Leu Tyr Ala Glu Leu Asn
50                  55                  60

Leu Gly Arg Arg Glu Glu Tyr Asp Val Leu Asp Lys Arg Lys Gly Glu
65                  70                  75                  80

Arg Pro Pro Pro Val Pro Asn Pro Asp Tyr Ala Pro Ile Arg Lys Gly
                85                  90                  95

Gln Arg Asp Leu Tyr Ser Gly Leu Asn Gln Arg Ala Leu Pro Pro Arg
            100                 105                 110

Gly Arg Val Lys Phe Ser Arg Ser Ala Asp Pro Arg Arg Lys Asn Pro
        115                 120                 125

Gln Glu Gly Leu Tyr Ala Glu Leu Gln Lys Asp Lys Met Ala Glu Ala
130                 135                 140

Tyr Ser Glu Ile Gly Met Arg Gly Arg Asp Pro Glu Met Gly Gly Lys
145                 150                 155                 160

Asp Lys Gln Thr Leu Leu Pro Asn Asp Gln Leu Tyr Ala Pro Leu Lys
            165                 170                 175

Asp Arg Glu Asp Asp Gln Tyr Ser His Leu Gln Gly Asn Lys Gly Glu
        180                 185                 190

Arg Arg Arg Gly Lys Gly His Asp Gly Leu Tyr Ala Gly Leu Ser Thr
    195                 200                 205

Ala Thr Lys Asp Thr Tyr Asp Ala Leu His Met Gln Ala Leu Pro Pro
210                 215                 220

Arg
225

<210> SEQ ID NO 39
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
            85                  90                  95

```
Glu Asp Gly Gly Val Leu Thr Ala Thr Gln Asp Thr Ser Leu Gln Asp
                100                 105                 110
Gly Cys Leu Ile Tyr Asn Val Lys Ile Arg Gly Val Asn Phe Thr Ser
            115                 120                 125
Asn Gly Pro Val Met Gln Lys Lys Thr Leu Gly Trp Glu Ala Phe Thr
        130                 135                 140
Glu Thr Leu Tyr Pro Ala Asp Gly Gly Leu Glu Gly Arg Asn Asp Met
145                 150                 155                 160
Ala Leu Lys Leu Val Gly Gly Ser His Leu Ile Ala Asn Ile Lys Thr
                165                 170                 175
Thr Tyr Arg Ser Lys Lys Pro Ala Lys Asn Leu Lys Met Pro Gly Val
            180                 185                 190
Tyr Tyr Val Asp Tyr Arg Leu Glu Arg Ile Lys Glu Ala Asn Asn Glu
        195                 200                 205
Thr Tyr Val Glu Gln His Glu Val Ala Val Ala Arg Tyr Cys Asp Leu
210                 215                 220
Pro Ser Lys Leu Gly His Lys Leu Asn
225                 230

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Ser Gly Gly
1               5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ala Lys Arg
1

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Thr Asn Phe Ser Leu Leu Lys Gln Ala Gly Asp Val Glu Glu Asn
1               5                   10                  15

Pro Gly Pro

<210> SEQ ID NO 43
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 43

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Ile Asp Pro Glu Tyr Tyr Asp Ile Leu Thr Gly Gly Asp Tyr Trp
            100                 105                 110

Gly Gln Gly Thr Leu Val Thr Val Ser Gly Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Ser Ala Met Ser Ala Ser Val Gly Asp Arg
145                 150                 155                 160

Val Thr Ile Thr Cys Arg Ala Ser Gln Gly Ile Ser Asn Tyr Leu Ala
                165                 170                 175

Trp Phe Gln Gln Lys Pro Gly Lys Val Pro Lys Arg Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Glu Phe Thr Leu Thr Ile Ser Ser Leu Gln Pro Glu Asp
    210                 215                 220

Phe Ala Thr Tyr Phe Cys Leu Gln His Asp Ser Phe Pro Leu Thr Phe
225                 230                 235                 240

Gly Gly Gly Thr Lys Val Glu Ile Lys
                245
```

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 44

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95
```

Ala Ile Asp Pro Glu Tyr Tyr Asp Ile Leu Thr Gly Gly Asp Tyr Trp
            100                 105                 110

Gly Gln Gly Thr Leu Val Thr Val Ser Ser
        115                 120

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln His Asp Ser Phe Pro Leu
                85                  90                  95

Thr Phe Gly Gly Gly Thr Lys Val Glu Ile Lys
            100                 105

<210> SEQ ID NO 46
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Asn Ile Tyr His Asn Pro Ser
50                  55                  60

Leu Lys Ser Arg Val Ser Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Glu Ile Ile Val Gly Ala Thr His Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Ala Ile Gln
    130                 135                 140

Met Thr Gln Ser Pro Ser Ser Leu Ser Ala Ser Val Gly Asp Arg Val
145                 150                 155                 160

```
Thr Ile Thr Cys Arg Ala Ser Gln Gly Ile Arg Asn Asp Leu Gly Trp
                165                 170                 175

Tyr Gln Gln Lys Pro Gly Lys Ala Pro Glu Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Leu Gln Asp Tyr Asn Tyr Pro Leu Thr Phe Gly
225                 230                 235                 240

Pro Gly Thr Lys Val Asp Ile Lys
                245
```

<210> SEQ ID NO 47
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Asn Ile Tyr His Asn Pro Ser
    50                  55                  60

Leu Lys Ser Arg Val Ser Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Glu Ile Ile Val Gly Ala Thr His Phe Asp Tyr Trp Gly
            100                 105                 110

Gln Gly Thr Leu Val Thr Val Ser Ser
        115                 120
```

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Glu Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Leu Gln Asp Tyr Asn Tyr Pro Leu
                85                  90                  95

Thr Phe Gly Pro Gly Thr Lys Val Asp Ile Lys
            100                 105

<210> SEQ ID NO 49
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asp Asp Tyr Ala
    50                  55                  60

Val Ser Val Lys Ser Arg Ile Thr Ile Asn Pro Asp Thr Ser Lys Asn
65                  70                  75                  80

His Leu Ser Leu His Leu Asn Ser Val Thr Pro Glu Asp Thr Ala Val
                85                  90                  95

Tyr Tyr Cys Ala Gly Gly Leu Val Gly Ala Pro Asp Gly Phe Asp
            100                 105                 110

Val Trp Gly Gln Gly Thr Met Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gln Ser Val Leu Thr Gln Pro Pro Ser Ala Ser Gly Thr Pro Gly Gln
145                 150                 155                 160

Arg Val Thr Ile Ser Cys Ser Gly Ser Ser Ser Asn Ile Gly Ser Asp
                165                 170                 175

Pro Val Asn Trp Tyr Gln Gln Leu Pro Gly Thr Ala Pro Lys Leu Leu
            180                 185                 190

Ile Tyr Ser Asn Asn Gln Arg Pro Ser Gly Val Pro Asp Arg Phe Ser
        195                 200                 205

Gly Ser Lys Ser Gly Thr Ser Ala Ser Leu Ala Ile Ser Gly Leu Gln
    210                 215                 220

Ser Glu Asp Glu Ala Asp Tyr Tyr Cys Ser Ala Trp Asp Asp Ser Leu
225                 230                 235                 240

Asn Gly Tyr Val Phe Gly Thr Gly Thr Lys Val Thr Val Leu
                245                 250

<210> SEQ ID NO 50
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Gln Ser Gly Pro Gly Leu Val Lys Pro Ser Gln
1               5                   10                  15

```
Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asp Asp Tyr Ala
    50                  55                  60

Val Ser Val Lys Ser Arg Ile Thr Ile Asn Pro Asp Thr Ser Lys Asn
65                  70                  75                  80

His Leu Ser Leu His Leu Asn Ser Val Thr Pro Glu Asp Thr Ala Val
                85                  90                  95

Tyr Tyr Cys Ala Gly Gly Leu Val Gly Ala Pro Asp Gly Phe Asp
            100                 105                 110

Val Trp Gly Gln Gly Thr Met Val Thr Val Ser Ser
            115                 120

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asp
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser
1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

Gly Gly Gly Ser
1

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Leu Tyr Cys Asn His Arg Asn Arg Arg Val Cys Lys Cys Pro Arg
1               5                   10                  15

Pro Val Val Lys Ser Gly Asp Lys Pro Ser Leu Ser Ala Arg Tyr Val
            20                  25                  30

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Arg Val Cys Lys Cys Pro Arg
1               5

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Arg Val Cys Lys Cys Pro Arg Arg Arg Val Cys Lys Cys Pro Arg
1               5                   10                  15

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Val Cys Lys Cys Pro Arg Pro Val
1               5

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Gln Pro Tyr Ala Pro Pro Arg Asp Phe Ala Ala Tyr Arg Ser
1               5                   10                  15

<210> SEQ ID NO 59
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Gln Pro Phe Ala Pro Pro Arg Asp Phe Ala Ala Phe Arg Ser
1               5                   10                  15

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Val Lys Phe Ser Arg Ser Ala Asp
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Gly Arg Asp Pro Glu Met Gly Gly Lys
1               5                   10

<210> SEQ ID NO 62
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Gly
1

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Leu Pro Pro Arg
1               5

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Met Ser Gln Ile Lys Arg Leu Leu Ser Glu Lys Lys Thr Cys Gln
```

```
1               5                   10                  15

Cys Pro

<210> SEQ ID NO 65
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Pro Ala Tyr Gln Gln Gly Gln Asn Gln Leu Tyr Ala Glu Leu Asn
1               5                   10                  15

Leu Gly Arg Arg Glu Glu Tyr Asp Val Leu Asp Lys Arg
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Arg Arg Lys Asn Pro Gln Glu Gly Leu Tyr Ala Glu Leu Gln Lys
1               5                   10                  15

Asp Lys Met Ala Glu Ala Tyr Ser Glu Ile Gly Met
            20                  25

<210> SEQ ID NO 67
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Arg Arg Arg Gly Lys Gly His Asp Gly Leu Tyr Ala Gly Leu Ser
1               5                   10                  15

Thr Ala Thr Lys Asp Thr Tyr Asp Ala Leu His Met Gln
            20                  25

<210> SEQ ID NO 68
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Thr Gln Ala Leu Leu Arg Asn Asp Gln Val Tyr Ala Pro Leu Arg
1               5                   10                  15

Asp Arg Asp Asp Ala Gln Tyr Ser His Leu Gly Gly Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 69

Glu Arg Pro Pro Pro Val Pro Asn Pro Asp Tyr Ala Pro Ile Arg Lys
1               5                   10                  15

Gly Gln Arg Asp Leu Tyr Ser Gly Leu Asn Gln Arg
            20                  25

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Lys Gln Thr Leu Leu Pro Asn Asp Gln Leu Tyr Ala Pro Leu Lys
1               5                   10                  15

Asp Arg Glu Asp Asp Gln Tyr Ser His Leu Gln Gly Asn
            20                  25

<210> SEQ ID NO 71
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser Asn Ile Gly Gly Lys
    275                 280                 285

Gln Ala Leu Glu Thr Val Gln Ala Leu Leu Pro Val Leu Cys Gln Ala
290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
        340                 345                 350

Ile Gly Gly Lys Gln Ala Leu Glu Thr Val Gln Ala Leu Leu Pro Val
    355                 360                 365

Leu Cys Gln Ala His Gly Leu Thr Pro Gln Gln Val Val Ala Ile Ala
370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
        420                 425                 430

Leu Leu Pro Val Leu Cys Gln Ala His Gly Leu Thr Pro Gln Gln Val
    435                 440                 445

Val Ala Ile Ala Ser Asn Gly Gly Gly Lys Gln Ala Leu Glu Thr Val
450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
    515                 520                 525

Leu Glu
530

<210> SEQ ID NO 72
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly

```
            35                  40                  45
Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser His
 65                  70                  75                  80

Asp Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460
```

```
Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 73
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
```

```
                    275                 280                 285
Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 74
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asn Pro Gln Arg Ser Thr Val Trp Tyr Leu Thr Pro Gln Gln Val Val
1               5                   10                  15

Ala Ile Ala Ser Asn Asn Gly Gly Lys Gln Ala Leu Glu Thr Val Gln
            20                  25                  30

Arg Leu Leu Pro Val Leu Cys Gln Ala His Gly Leu Thr Pro Gln Gln
        35                  40                  45

Val Val Ala Ile Ala Ser Asn Gly Gly Gly Lys Gln Ala Leu Glu Thr
    50                  55                  60

Val Gln Arg Leu Leu Pro Val Leu Cys Gln Ala His Gly Leu Thr Pro
65                  70                  75                  80

Gln Gln Val Val Ala Ile Ala Ser Asn Asn Gly Gly Lys Gln Ala Leu
                85                  90                  95
```

```
Glu Thr Val Gln Arg Leu Leu Pro Val Leu Cys Gln Ala His Gly Leu
            100                 105                 110

Thr Pro Gln Gln Val Val Ala Ile Ala Ser Asn Asn Gly Gly Lys Gln
        115                 120                 125

Ala Leu Glu Thr Val Gln Arg Leu Leu Pro Val Leu Cys Gln Ala His
    130                 135                 140

Gly Leu Thr Pro Glu Gln Val Val Ala Ile Ala Ser His Asp Gly Gly
145                 150                 155                 160

Lys Gln Ala Leu Glu Thr Val Gln Arg Leu Leu Pro Val Leu Cys Gln
                165                 170                 175

Ala His Gly Leu Thr Pro Glu Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Ala His Gly Leu Thr Pro Gln Gln Val Val Ala Ile Ala Ser
    210                 215                 220

Asn Gly Gly Lys Gln Ala Leu Glu Thr Val Gln Arg Leu Leu Pro
225                 230                 235                 240

Val Leu Cys Gln Ala His Gly Leu Thr Pro Gln Gln Val Val Ala Ile
            245                 250                 255

Ala Ser Asn Gly Gly Lys Gln Ala Leu Glu Thr Val Gln Arg Leu
        260                 265                 270

Leu Pro Val Leu Cys Gln Ala His Gly Leu Thr Pro Gln Gln Val Val
            275                 280                 285

Ala Ile Ala Ser Asn Gly Gly Lys Gln Ala Leu Glu Thr Val Gln
    290                 295                 300

Arg Leu Leu Pro Val Leu Cys Gln Ala His Gly Leu Thr Pro Gln Gln
305                 310                 315                 320

Val Val Ala Ile Ala Ser Asn Gly Gly Lys Gln Ala Leu Glu Thr
                325                 330                 335

Val Gln Arg Leu Leu Pro Val Leu Cys Gln Ala His Gly Leu Thr Pro
            340                 345                 350

Gln Gln Val Val Ala Ile Ala Ser Asn Asn Gly Gly Lys Gln Ala Leu
        355                 360                 365

Glu Thr Val Gln Arg Leu Leu Pro Val Leu Cys Gln Ala His Gly Leu
    370                 375                 380

Thr Pro Gln Gln Val Val Ala Ile Ala Ser Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Gln Gln Val Val Ala Ile Ala Ser Asn Asn Gly Gly
            420                 425                 430

Lys Gln Ala Leu Glu Thr Val Gln Arg Leu Leu Pro Val Leu Cys Gln
        435                 440                 445

Ala His Gly Leu Thr Pro Gln Gln Val Val Ala Ile Ala Ser Asn Gly
    450                 455                 460

Gly Gly Lys Gln Ala Leu Glu Thr Val Gln Arg Leu Leu Pro Val Leu
465                 470                 475                 480

Cys Gln Ala His Gly Leu Thr Pro Gln Gln Val Val Ala Ile Ala Ser
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Gln Gln Val Val Ala Ile
```

```
                515                 520                 525
Ala Ser Asn Gly Gly Arg Pro Ala Leu Glu
    530                 535

<210> SEQ ID NO 75
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335
```

```
Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
            435                 440                 445

Val Ala Ile Ala Ser Asn Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
            515                 520                 525

Leu Glu
    530

<210> SEQ ID NO 76
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160
```

```
Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 77
<211> LENGTH: 530
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 77

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400
```

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Glu Gln Val
                435                 440                 445

Val Ala Ile Ala Ser His Asp Gly Gly Lys Gln Ala Leu Glu Thr Val
                450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
                515                 520                 525

Leu Glu
    530

<210> SEQ ID NO 78
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
                35                  40                  45

Gly Lys Gln Ala Leu Glu Thr Val Gln Arg Leu Leu Pro Val Leu Cys
50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
                115                 120                 125

Pro Val Leu Cys Gln Ala His Gly Leu Thr Pro Glu Gln Val Val Ala
                130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
                180                 185                 190

Gln Arg Leu Leu Pro Val Leu Cys Gln Ala His Gly Leu Thr Pro Gln
                195                 200                 205

Gln Val Val Ala Ile Ala Ser Asn Gly Gly Gly Lys Gln Ala Leu Glu

```
            210                 215                 220
Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 79
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30
```

```
Ala Lys Pro Thr Thr Thr Ala Cys Pro Tyr Ser Asn Pro Ser Leu Cys
            35                  40                  45

Ser Gly Gly Gly Gly Ser Pro Ala Pro Arg Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Arg Val
            115                 120                 125

Cys Lys Cys Pro Arg Pro Val Val
            130                 135

<210> SEQ ID NO 80
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Pro Tyr Ser Asn Pro Ser Leu Cys
1               5

<210> SEQ ID NO 82
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Gln Phe Asp Leu Ser Thr Arg Arg Leu Lys Cys
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Gln Tyr Asn Leu Ser Ser Arg Ala Leu Lys Cys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Val Trp Gln Arg Trp Gln Lys Ser Tyr Val Cys
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Met Trp Asp Arg Phe Ser Arg Trp Tyr Lys Cys
1               5                   10

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 87

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Gly Thr Tyr Leu Cys Gly Ala Ile Ser Leu Ala Pro Lys Ala Gln
1               5                   10                  15

Ile Lys Glu

<210> SEQ ID NO 89
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gln Asn Asp Thr Ser Gln Thr Ser Ser Pro Ser
1               5                   10

<210> SEQ ID NO 91
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Cys Pro Tyr Ser Asn Pro Ser Leu
            35                  40                  45

Cys Gly Gly Gly Ser Gln Val Gln Leu Gln Gln Ser Gly Pro Gly
        50                  55                  60

Leu Val Lys Pro Ser Gln Thr Leu Ser Leu Thr Cys Ala Ile Ser Gly
```

```
            65                  70                  75                  80
Asp Ser Val Ser Ser Asn Ser Ala Thr Trp Asn Trp Ile Arg Gln Ser
                85                  90                  95
Pro Ser Arg Gly Leu Glu Trp Leu Gly Arg Thr Tyr Tyr Arg Ser Lys
               100                 105                 110
Trp Tyr Asp Asp Tyr Ala Val Ser Val Lys Ser Arg Ile Thr Ile Asn
               115                 120                 125
Pro Asp Thr Ser Lys Asn His Leu Ser Leu His Leu Asn Ser Val Thr
               130                 135                 140
Pro Glu Asp Thr Ala Val Tyr Tyr Cys Ala Gly Gly Leu Val Gly
145                150                 155                 160
Ala Pro Asp Gly Phe Asp Val Trp Gly Gln Gly Thr Met Val Thr Val
                   165                 170                 175
Ser Ser Gly Gly Gly Gly Ser Gly Gly Gly Ser Gly Gly Gly Gly
               180                 185                 190
Ser Gly Gly Gly Gly Ser Gln Ser Val Leu Thr Gln Pro Pro Ser Ala
               195                 200                 205
Ser Gly Thr Pro Gly Gln Arg Val Thr Ile Ser Cys Ser Gly Ser Ser
    210                 215                 220
Ser Asn Ile Gly Ser Asp Pro Val Asn Trp Tyr Gln Gln Leu Pro Gly
225                 230                 235                 240
Thr Ala Pro Lys Leu Leu Ile Tyr Ser Asn Asn Gln Arg Pro Ser Gly
                245                 250                 255
Val Pro Asp Arg Phe Ser Gly Ser Lys Ser Gly Thr Ser Ala Ser Leu
                260                 265                 270
Ala Ile Ser Gly Leu Gln Ser Glu Asp Glu Ala Asp Tyr Tyr Cys Ser
            275                 280                 285
Ala Trp Asp Asp Ser Leu Asn Gly Tyr Val Phe Gly Thr Gly Thr Lys
            290                 295                 300
Val Thr Val Leu Thr Thr Thr Pro Ala Pro Arg Pro Pro Thr Pro Ala
305                 310                 315                 320
Pro Thr Ile Ala Ser Gln Pro Leu Ser Leu Arg Pro Glu Ala Cys Arg
                325                 330                 335
Pro Ala Ala Gly Gly Ala Val His Thr Arg Gly Leu Asp Phe Ala Cys
                340                 345                 350
Asp Ile Tyr Ile Trp Ala Pro Leu Ala Gly Thr Cys Gly Val Leu Leu
            355                 360                 365
Leu Ser Leu Val Ile Thr Leu Tyr Cys Lys Arg Gly Arg Lys Lys Leu
    370                 375                 380
Leu Tyr Ile Phe Lys Gln Pro Phe Met Arg Pro Val Gln Thr Thr Gln
385                 390                 395                 400
Glu Glu Asp Gly Cys Ser Cys Arg Phe Pro Glu Glu Glu Glu Gly Gly
                405                 410                 415
Cys Glu Leu Arg Val Lys Phe Ser Arg Ser Ala Asp Ala Pro Ala Tyr
                420                 425                 430
Gln Gln Gly Gln Asn Gln Leu Tyr Asn Glu Leu Asn Leu Gly Arg Arg
            435                 440                 445
Glu Glu Tyr Asp Val Leu Asp Lys Arg Arg Gly Arg Asp Pro Glu Met
            450                 455                 460
Gly Gly Lys Pro Arg Arg Lys Asn Pro Gln Glu Gly Leu Tyr Asn Glu
465                 470                 475                 480
Leu Gln Lys Asp Lys Met Ala Glu Ala Tyr Ser Glu Ile Gly Met Lys
                485                 490                 495
```

```
Gly Glu Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg
    530

<210> SEQ ID NO 92
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Cys Pro Tyr Ser Asn Pro Ser Leu
        35                  40                  45

Cys Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
```

```
                305                 310                 315                 320
Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
                355                 360                 365

Leu Ser Leu Val Ile Thr Leu Tyr Cys Asn His Arg Asn Arg Arg
370                 375                 380

Val Cys Lys Cys Pro Arg Pro Val Val Lys Ser Gly Asp Lys Pro Ser
385                 390                 395                 400

Leu Ser Ala Arg Tyr Val Lys Arg Gly Lys Lys Leu Leu Tyr Ile
                405                 410                 415

Phe Lys Gln Pro Phe Met Arg Pro Val Gln Thr Thr Gln Glu Glu Asp
                420                 425                 430

Gly Cys Ser Cys Arg Phe Pro Glu Glu Glu Gly Cys Glu Leu
                435                 440                 445

Arg Val Lys Phe Ser Arg Ser Ala Asp Ala Pro Ala Tyr Gln Gln Gly
    450                 455                 460

Gln Asn Gln Leu Tyr Asn Glu Leu Asn Leu Gly Arg Arg Glu Glu Tyr
465                 470                 475                 480

Asp Val Leu Asp Lys Arg Arg Gly Arg Asp Pro Glu Met Gly Gly Lys
                485                 490                 495

Pro Arg Arg Lys Asn Pro Gln Glu Gly Leu Tyr Asn Glu Leu Gln Lys
                500                 505                 510

Asp Lys Met Ala Glu Ala Tyr Ser Glu Ile Gly Met Lys Gly Glu Arg
            515                 520                 525

Arg Arg Gly Lys Gly His Asp Gly Leu Tyr Gln Gly Leu Ser Thr Ala
                530                 535                 540

Thr Lys Asp Thr Tyr Asp Ala Leu His Met Gln Ala Leu Pro Pro Arg
545                 550                 555                 560

<210> SEQ ID NO 93
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
                35                  40                  45

Cys Gly Gly Gly Gly Ser Gln Val Gln Leu Gln Gln Ser Gly Pro Gly
        50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
                100                 105                 110
```

-continued

```
Trp Tyr Asp Tyr Ala Val Ser Val Lys Ser Arg Ile Thr Ile Asn
            115                 120                 125
Pro Asp Thr Ser Lys Asn His Leu Ser Leu His Leu Asn Ser Val Thr
130                 135                 140
Pro Glu Asp Thr Ala Val Tyr Tyr Cys Ala Gly Gly Leu Val Gly
145                 150                 155                 160
Ala Pro Asp Gly Phe Asp Val Trp Gly Gln Gly Thr Met Val Thr Val
            165                 170                 175
Ser Ser Gly Gly Gly Gly Ser Gly Gly Gly Ser Gly Gly Gly Gly
            180                 185                 190
Ser Gly Gly Gly Gly Ser Gln Ser Val Leu Thr Gln Pro Pro Ser Ala
            195                 200                 205
Ser Gly Thr Pro Gly Gln Arg Val Thr Ile Ser Cys Ser Gly Ser Ser
            210                 215                 220
Ser Asn Ile Gly Ser Asp Pro Val Asn Trp Tyr Gln Gln Leu Pro Gly
225                 230                 235                 240
Thr Ala Pro Lys Leu Leu Ile Tyr Ser Asn Asn Gln Arg Pro Ser Gly
            245                 250                 255
Val Pro Asp Arg Phe Ser Gly Ser Lys Ser Gly Thr Ser Ala Ser Leu
            260                 265                 270
Ala Ile Ser Gly Leu Gln Ser Glu Asp Glu Ala Asp Tyr Tyr Cys Ser
            275                 280                 285
Ala Trp Asp Asp Ser Leu Asn Gly Tyr Val Phe Gly Thr Gly Thr Lys
            290                 295                 300
Val Thr Val Leu Thr Thr Thr Pro Ala Pro Arg Pro Pro Thr Pro Ala
305                 310                 315                 320
Pro Thr Ile Ala Ser Gln Pro Leu Ser Leu Arg Pro Glu Ala Cys Arg
            325                 330                 335
Pro Ala Ala Gly Gly Ala Val His Thr Arg Gly Leu Asp Phe Ala Cys
            340                 345                 350
Asp Ile Tyr Ile Trp Ala Pro Leu Ala Gly Thr Cys Gly Val Leu Leu
            355                 360                 365
Leu Ser Leu Val Ile Thr Arg Arg Val Cys Lys Cys Pro Arg Arg Arg
370                 375                 380
Val Cys Lys Cys Pro Arg Lys Arg Gly Arg Lys Lys Leu Leu Tyr Ile
385                 390                 395                 400
Phe Lys Gln Pro Phe Met Arg Pro Val Gln Thr Thr Gln Glu Glu Asp
            405                 410                 415
Gly Cys Ser Cys Arg Phe Pro Glu Glu Glu Gly Gly Cys Glu Leu
            420                 425                 430
Arg Val Lys Phe Ser Arg Ser Ala Asp Ala Pro Ala Tyr Gln Gln Gly
            435                 440                 445
Gln Asn Gln Leu Tyr Asn Glu Leu Asn Leu Gly Arg Arg Glu Glu Tyr
            450                 455                 460
Asp Val Leu Asp Lys Arg Arg Gly Arg Asp Pro Glu Met Gly Gly Lys
465                 470                 475                 480
Pro Arg Arg Lys Asn Pro Gln Glu Gly Leu Tyr Asn Glu Leu Gln Lys
            485                 490                 495
Asp Lys Met Ala Glu Ala Tyr Ser Glu Ile Gly Met Lys Gly Glu Arg
            500                 505                 510
Arg Arg Gly Lys Gly His Asp Gly Leu Tyr Gln Gly Leu Ser Thr Ala
            515                 520                 525
Thr Lys Asp Thr Tyr Asp Ala Leu His Met Gln Ala Leu Pro Pro Arg
```

<210> SEQ ID NO 94
<211> LENGTH: 554
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350
```

```
Asp Ile Tyr Ile Trp Ala Pro Leu Ala Gly Thr Cys Gly Val Leu Leu
            355                 360                 365

Leu Ser Leu Val Ile Thr Leu Tyr Cys Gly Gly Gly Ser Tyr Gln Pro
    370                 375                 380

Tyr Ala Pro Pro Arg Asp Phe Ala Ala Tyr Arg Ser Gly Gly Gly Ser
385                 390                 395                 400

Lys Arg Gly Arg Lys Lys Leu Leu Tyr Ile Phe Lys Gln Pro Phe Met
                405                 410                 415

Arg Pro Val Gln Thr Thr Gln Glu Glu Asp Gly Cys Ser Cys Arg Phe
                420                 425                 430

Pro Glu Glu Glu Glu Gly Gly Cys Glu Leu Arg Val Lys Phe Ser Arg
            435                 440                 445

Ser Ala Asp Ala Pro Ala Tyr Gln Gln Gly Gln Asn Gln Leu Tyr Asn
    450                 455                 460

Glu Leu Asn Leu Gly Arg Arg Glu Glu Tyr Asp Val Leu Asp Lys Arg
465                 470                 475                 480

Arg Gly Arg Asp Pro Glu Met Gly Gly Lys Pro Arg Arg Lys Asn Pro
                485                 490                 495

Gln Glu Gly Leu Tyr Asn Glu Leu Gln Lys Asp Lys Met Ala Glu Ala
            500                 505                 510

Tyr Ser Glu Ile Gly Met Lys Gly Glu Arg Arg Arg Gly Lys Gly His
    515                 520                 525

Asp Gly Leu Tyr Gln Gly Leu Ser Thr Ala Thr Lys Asp Thr Tyr Asp
    530                 535                 540

Ala Leu His Met Gln Ala Leu Pro Pro Arg
545                 550

<210> SEQ ID NO 95
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
                100                 105                 110

Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Gly Leu Val Gly
145                 150                 155                 160
```

Ala Pro Asp Gly Phe Asp Val Trp Gly Gln Gly Thr Met Val Thr Val
                165                 170                 175

Ser Ser Gly Gly Gly Ser Gly Gly Gly Ser Gly Gly Gly Gly
            180                 185                 190

Ser Gly Gly Gly Ser Gln Ser Val Leu Thr Gln Pro Pro Ser Ala
            195                 200                 205

Ser Gly Thr Pro Gly Gln Arg Val Thr Ile Ser Cys Ser Gly Ser Ser
        210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
                260                 265                 270

Ala Ile Ser Gly Leu Gln Ser Glu Asp Glu Ala Asp Tyr Tyr Cys Ser
            275                 280                 285

Ala Trp Asp Asp Ser Leu Asn Gly Tyr Val Phe Gly Thr Gly Thr Lys
            290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
            355                 360                 365

Leu Ser Leu Val Ile Thr Leu Tyr Cys Gly Gly Ser Phe Gln Pro
370                 375                 380

Phe Ala Pro Pro Arg Asp Phe Ala Ala Phe Arg Ser Gly Gly Gly Ser
385                 390                 395                 400

Lys Arg Gly Arg Lys Lys Leu Leu Tyr Ile Phe Lys Gln Pro Phe Met
                405                 410                 415

Arg Pro Val Gln Thr Thr Gln Glu Glu Asp Gly Cys Ser Cys Arg Phe
            420                 425                 430

Pro Glu Glu Glu Glu Gly Gly Cys Glu Leu Arg Val Lys Phe Ser Arg
            435                 440                 445

Ser Ala Asp Ala Pro Ala Tyr Gln Gln Gly Gln Asn Gln Leu Tyr Asn
450                 455                 460

Glu Leu Asn Leu Gly Arg Arg Glu Glu Tyr Asp Val Leu Asp Lys Arg
465                 470                 475                 480

Arg Gly Arg Asp Pro Glu Met Gly Gly Lys Pro Arg Arg Lys Asn Pro
                485                 490                 495

Gln Glu Gly Leu Tyr Asn Glu Leu Gln Lys Asp Lys Met Ala Glu Ala
            500                 505                 510

Tyr Ser Glu Ile Gly Met Lys Gly Glu Arg Arg Arg Gly Lys Gly His
            515                 520                 525

Asp Gly Leu Tyr Gln Gly Leu Ser Thr Ala Thr Lys Asp Thr Tyr Asp
            530                 535                 540

Ala Leu His Met Gln Ala Leu Pro Pro Arg
545                 550

<210> SEQ ID NO 96
<211> LENGTH: 545

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
                35                  40                  45

Cys Gly Gly Gly Gly Ser Gln Val Gln Leu Gln Gln Ser Gly Pro Gly
50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
                100                 105                 110

Trp Tyr Asp Asp Tyr Ala Val Ser Val Lys Ser Arg Ile Thr Ile Asn
                115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
                180                 185                 190

Ser Gly Gly Gly Gly Ser Gln Ser Val Leu Thr Gln Pro Pro Ser Ala
                195                 200                 205

Ser Gly Thr Pro Gly Gln Arg Val Thr Ile Ser Cys Ser Gly Ser Ser
210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
                260                 265                 270

Ala Ile Ser Gly Leu Gln Ser Glu Asp Glu Ala Asp Tyr Tyr Cys Ser
                275                 280                 285

Ala Trp Asp Asp Ser Leu Asn Gly Tyr Val Phe Gly Thr Gly Thr Lys
                290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
                355                 360                 365

Leu Ser Leu Val Ile Thr Leu Tyr Cys Lys Arg Gly Arg Lys Lys Leu
                370                 375                 380
```

```
Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
            405                 410                 415

Cys Glu Leu Arg Val Lys Phe Ser Arg Ser Ala Asp Ala Pro Ala Tyr
        420                 425                 430

Gln Gln Gly Gln Asn Gln Leu Tyr Asn Glu Leu Asn Leu Gly Arg Arg
    435                 440                 445

Glu Glu Tyr Asp Val Leu Asp Lys Arg Arg Gly Arg Asp Pro Glu Met
450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg Gly Gly Gly Ser Arg Val Cys Lys Cys Pro Arg Pro
    530                 535                 540

Val
545

<210> SEQ ID NO 97
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
                100                 105                 110

Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Gly Ser Gly Gly Gly Gly
```

```
              180                 185                 190
Ser Gly Gly Gly Gly Ser Gln Ser Val Leu Thr Gln Pro Pro Ser Ala
        195                 200                 205
Ser Gly Thr Pro Gly Gln Arg Val Thr Ile Ser Cys Ser Gly Ser Ser
        210                 215                 220
Ser Asn Ile Gly Ser Asp Pro Val Asn Trp Tyr Gln Gln Leu Pro Gly
225                 230                 235                 240
Thr Ala Pro Lys Leu Leu Ile Tyr Ser Asn Asn Gln Arg Pro Ser Gly
        245                 250                 255
Val Pro Asp Arg Phe Ser Gly Ser Lys Ser Gly Thr Ser Ala Ser Leu
        260                 265                 270
Ala Ile Ser Gly Leu Gln Ser Glu Asp Glu Ala Asp Tyr Tyr Cys Ser
        275                 280                 285
Ala Trp Asp Asp Ser Leu Asn Gly Tyr Val Phe Gly Thr Gly Thr Lys
        290                 295                 300
Val Thr Val Leu Thr Thr Thr Pro Ala Pro Arg Pro Pro Thr Pro Ala
305                 310                 315                 320
Pro Thr Ile Ala Ser Gln Pro Leu Ser Leu Arg Pro Glu Ala Cys Arg
        325                 330                 335
Pro Ala Ala Gly Gly Ala Val His Thr Arg Gly Leu Asp Phe Ala Cys
        340                 345                 350
Asp Ile Tyr Ile Trp Ala Pro Leu Ala Gly Thr Cys Gly Val Leu Leu
        355                 360                 365
Leu Ser Leu Val Ile Thr Leu Tyr Cys Lys Arg Gly Arg Lys Lys Leu
        370                 375                 380
Leu Tyr Ile Phe Lys Gln Pro Phe Met Arg Pro Val Gln Thr Thr Gln
385                 390                 395                 400
Glu Glu Asp Gly Cys Ser Cys Arg Phe Pro Glu Glu Glu Glu Gly Gly
        405                 410                 415
Cys Glu Leu Arg Val Lys Phe Ser Arg Ser Ala Asp Ala Pro Ala Tyr
        420                 425                 430
Gln Gln Gly Gln Asn Gln Leu Tyr Asn Glu Leu Asn Leu Gly Arg Arg
        435                 440                 445
Glu Glu Tyr Asp Val Leu Asp Lys Arg Arg Gly Arg Asp Pro Glu Met
        450                 455                 460
Gly Gly Lys Pro Arg Arg Lys Asn Pro Gln Glu Gly Leu Tyr Asn Glu
465                 470                 475                 480
Leu Gln Lys Asp Lys Met Ala Glu Ala Tyr Ser Glu Ile Gly Met Lys
        485                 490                 495
Gly Glu Arg Arg Arg Gly Lys Gly His Asp Gly Leu Tyr Gln Gly Leu
        500                 505                 510
Ser Thr Ala Thr Lys Asp Thr Tyr Asp Ala Leu His Met Gln Ala Leu
        515                 520                 525
Pro Pro Arg Gly Gly Gly Ser Phe Gln Pro Phe Ala Pro Pro Arg Asp
        530                 535                 540
Phe Ala Ala Phe Arg Ser
545                 550

<210> SEQ ID NO 98
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 98

```
Met Ala Leu Pro Val Thr Ala Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Ser Gly Pro Gly
    50                  55                  60

Leu Val Lys Pro Ser Gln Thr Leu Ser Leu Thr Cys Ala Ile Ser Gly
65              70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Gly Ser Gly Gly Gly Gly
            180                 185                 190

Ser Gly Gly Gly Gly Ser Gln Ser Val Leu Thr Gln Pro Pro Ser Ala
            195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
            245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
            325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365

Leu Ser Leu Val Ile Thr Leu Tyr Cys Lys Arg Gly Arg Lys Lys Leu
    370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
```

```
                405                 410                 415
Cys Glu Leu Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
            435                 440                 445

Glu Glu Tyr Asp Val Leu Asp Lys Arg Arg Gly Arg Asp Pro Glu Met
            450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
            485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
            515                 520                 525

Pro Pro Arg Gly Gly Gly Ser Tyr Gln Pro Tyr Ala Pro Pro Arg Asp
            530                 535                 540

Phe Ala Ala Tyr Arg Ser
545                 550

<210> SEQ ID NO 99
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
            50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
            85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
            165                 170                 175

Ser Ser Gly Gly Gly Gly Ser Gly Gly Gly Gly Ser Gly Gly Gly Gly
            180                 185                 190

Ser Gly Gly Gly Gly Ser Gln Ser Val Leu Thr Gln Pro Pro Ser Ala
            195                 200                 205
```

```
Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
            245                 250                 255

Val Pro Asp Arg Phe Ser Gly Ser Lys Ser Gly Thr Ser Ala Ser Leu
                260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
            355                 360                 365

Leu Ser Leu Val Ile Thr Lys Arg Gly Arg Lys Lys Leu Leu Tyr Ile
370                 375                 380

Phe Lys Gln Pro Phe Met Arg Pro Val Gln Thr Thr Gln Glu Glu Asp
385                 390                 395                 400

Gly Cys Ser Cys Arg Phe Pro Glu Glu Glu Glu Gly Gly Cys Glu Leu
                405                 410                 415

Leu Tyr Cys Asn His Arg Asn Arg Arg Arg Val Cys Lys Cys Pro Arg
                420                 425                 430

Pro Val Val Lys Ser Gly Asp Lys Pro Ser Leu Ser Ala Arg Tyr Val
            435                 440                 445

Arg Val Lys Phe Ser Arg Ser Ala Asp Ala Pro Ala Tyr Gln Gln Gly
        450                 455                 460

Gln Asn Gln Leu Tyr Asn Glu Leu Asn Leu Gly Arg Arg Glu Glu Tyr
465                 470                 475                 480

Asp Val Leu Asp Lys Arg Arg Gly Arg Asp Pro Glu Met Gly Gly Lys
                485                 490                 495

Pro Arg Arg Lys Asn Pro Gln Glu Gly Leu Tyr Asn Glu Leu Gln Lys
                500                 505                 510

Asp Lys Met Ala Glu Ala Tyr Ser Glu Ile Gly Met Lys Gly Glu Arg
            515                 520                 525

Arg Arg Gly Lys Gly His Asp Gly Leu Tyr Gln Gly Leu Ser Thr Ala
530                 535                 540

Thr Lys Asp Thr Tyr Asp Ala Leu His Met Gln Ala Leu Pro Pro Arg
545                 550                 555                 560

<210> SEQ ID NO 100
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Ala Leu Pro Val Thr Ala Leu Leu Leu Pro Leu Ala Leu Leu Leu
1               5                   10                  15
```

His Ala Ala Arg Pro Gly Gly Gly Ser Cys Pro Tyr Ser Asn Pro
                20              25              30

Ser Leu Cys Gly Gly Gly Ser Cys Pro Tyr Ser Asn Pro Ser Leu
            35              40              45

Cys Gly Gly Gly Ser Gln Val Gln Leu Gln Ser Gly Pro Gly
50              55              60

Leu Val Lys Pro Ser Gln Thr Leu Ser Leu Thr Cys Ala Ile Ser Gly
65              70              75              80

Asp Ser Val Ser Ser Asn Ser Ala Thr Trp Asn Trp Ile Arg Gln Ser
                85              90              95

Pro Ser Arg Gly Leu Glu Trp Leu Gly Arg Thr Tyr Tyr Arg Ser Lys
            100             105             110

Trp Tyr Asp Asp Tyr Ala Val Ser Val Lys Ser Arg Ile Thr Ile Asn
                115             120             125

Pro Asp Thr Ser Lys Asn His Leu Ser Leu His Leu Asn Ser Val Thr
130             135             140

Pro Glu Asp Thr Ala Val Tyr Tyr Cys Ala Gly Gly Leu Val Gly
145             150             155             160

Ala Pro Asp Gly Phe Asp Val Trp Gly Gln Gly Thr Met Val Thr Val
                165             170             175

Ser Ser Gly Gly Gly Gly Ser Gly Gly Gly Gly Ser Gly Gly Gly Gly
            180             185             190

Ser Gly Gly Gly Gly Ser Gln Ser Val Leu Thr Gln Pro Pro Ser Ala
            195             200             205

Ser Gly Thr Pro Gly Gln Arg Val Thr Ile Ser Cys Ser Gly Ser Ser
            210             215             220

Ser Asn Ile Gly Ser Asp Pro Val Asn Trp Tyr Gln Gln Leu Pro Gly
225             230             235             240

Thr Ala Pro Lys Leu Leu Ile Tyr Ser Asn Asn Gln Arg Pro Ser Gly
            245             250             255

Val Pro Asp Arg Phe Ser Gly Ser Lys Ser Gly Thr Ser Ala Ser Leu
            260             265             270

Ala Ile Ser Gly Leu Gln Ser Glu Asp Glu Ala Asp Tyr Tyr Cys Ser
            275             280             285

Ala Trp Asp Asp Ser Leu Asn Gly Tyr Val Phe Gly Thr Gly Thr Lys
            290             295             300

Val Thr Val Leu Thr Thr Thr Pro Ala Pro Arg Pro Pro Thr Pro Ala
305             310             315             320

Pro Thr Ile Ala Ser Gln Pro Leu Ser Leu Arg Pro Glu Ala Cys Arg
            325             330             335

Pro Ala Ala Gly Gly Ala Val His Thr Arg Gly Leu Asp Phe Ala Cys
            340             345             350

Asp Ile Tyr Ile Trp Ala Pro Leu Ala Gly Thr Cys Gly Val Leu Leu
            355             360             365

Leu Ser Leu Val Ile Thr Lys Arg Gly Arg Lys Lys Leu Leu Tyr Ile
            370             375             380

Phe Lys Gln Pro Phe Met Arg Pro Val Gln Thr Thr Gln Glu Glu Asp
385             390             395             400

Gly Cys Ser Cys Arg Phe Pro Glu Glu Glu Gly Gly Cys Glu Leu
                405             410             415

Arg Arg Val Cys Lys Cys Pro Arg Arg Val Cys Lys Cys Pro Arg
            420             425             430

```
Arg Val Lys Phe Ser Arg Ser Ala Asp Ala Pro Ala Tyr Gln Gln Gly
            435                 440                 445

Gln Asn Gln Leu Tyr Asn Glu Leu Asn Leu Gly Arg Arg Glu Tyr
    450                 455                 460

Asp Val Leu Asp Lys Arg Arg Gly Arg Asp Pro Glu Met Gly Gly Lys
465                 470                 475                 480

Pro Arg Arg Lys Asn Pro Gln Glu Gly Leu Tyr Asn Glu Leu Gln Lys
                485                 490                 495

Asp Lys Met Ala Glu Ala Tyr Ser Glu Ile Gly Met Lys Gly Glu Arg
            500                 505                 510

Arg Arg Gly Lys Gly His Asp Gly Leu Tyr Gln Gly Leu Ser Thr Ala
            515                 520                 525

Thr Lys Asp Thr Tyr Asp Ala Leu His Met Gln Ala Leu Pro Pro Arg
530                 535                 540

<210> SEQ ID NO 101
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
            180                 185                 190

Ser Gly Gly Gly Gly Ser Gln Ser Val Leu Thr Gln Pro Ser Ala
            195                 200                 205

Ser Gly Thr Pro Gly Gln Arg Val Thr Ile Ser Cys Ser Gly Ser Ser
210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255
```

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365

Leu Ser Leu Val Ile Thr Leu Tyr Cys Lys Arg Gly Arg Lys Lys Leu
    370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
        435                 440                 445

Glu Glu Tyr Asp Val Leu Asp Lys Arg Arg Gly Arg Asp Pro Glu Met
    450                 455                 460

Gly Gly Lys Asp Thr Gln Ala Leu Leu Arg Asn Asp Gln Val Tyr Gln
465                 470                 475                 480

Pro Leu Arg Asp Arg Asp Asp Ala Gln Tyr Ser His Leu Gly Gly Asn
                485                 490                 495

Lys Gly Pro Arg Arg Lys Asn Pro Gln Glu Gly Leu Tyr Asn Glu Leu
            500                 505                 510

Gln Lys Asp Lys Met Ala Glu Ala Tyr Ser Glu Ile Gly Met Ala Leu
        515                 520                 525

Pro Pro Arg Gly Arg Val Lys Phe Ser Arg Ser Ala Asp Glu Arg Pro
    530                 535                 540

Pro Pro Val Pro Asn Pro Asp Tyr Glu Pro Ile Arg Lys Gly Gln Arg
545                 550                 555                 560

Asp Leu Tyr Ser Gly Leu Asn Gln Arg Arg Gly Arg Asp Pro Glu Met
                565                 570                 575

Gly Gly Lys Glu Arg Arg Arg Gly Lys Gly His Asp Gly Leu Tyr Gln
            580                 585                 590

Gly Leu Ser Thr Ala Thr Lys Asp Thr Tyr Asp Ala Leu His Met Gln
        595                 600                 605

Lys Gly Asp Lys Gln Thr Leu Leu Pro Asn Asp Gln Leu Tyr Gln Pro
    610                 615                 620

Leu Lys Asp Arg Glu Asp Asp Gln Tyr Ser His Leu Gln Gly Asn Ala
625                 630                 635                 640

Leu Pro Pro Arg

<210> SEQ ID NO 102
<211> LENGTH: 644
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 102

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
            165                 170                 175

Ser Ser Gly Gly Gly Gly Ser Gly Gly Gly Gly Ser Gly Gly Gly Gly
            180                 185                 190

Ser Gly Gly Gly Gly Ser Gln Ser Val Leu Thr Gln Pro Pro Ser Ala
            195                 200                 205

Ser Gly Thr Pro Gly Gln Arg Val Thr Ile Ser Cys Ser Gly Ser Ser
210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
            245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
            325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365

Leu Ser Leu Val Ile Thr Leu Tyr Cys Lys Arg Gly Arg Lys Lys Leu
    370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
            405                 410                 415

Cys Glu Leu Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
            435                 440                 445

Glu Glu Tyr Asp Val Leu Asp Lys Arg Arg Gly Arg Asp Pro Glu Met
            450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
            485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
            515                 520                 525

Pro Pro Arg Gly Arg Val Lys Phe Ser Arg Ser Ala Asp Ala Pro Ala
            530                 535                 540

Tyr Gln Gln Gly Gln Asn Gln Leu Tyr Asn Glu Leu Asn Leu Gly Arg
545                 550                 555                 560

Arg Glu Glu Tyr Asp Val Leu Asp Lys Arg Arg Gly Arg Asp Pro Glu
            565                 570                 575

Met Gly Gly Lys Pro Arg Arg Lys Asn Pro Gln Glu Gly Leu Tyr Asn
            580                 585                 590

Glu Leu Gln Lys Asp Lys Met Ala Glu Ala Tyr Ser Glu Ile Gly Met
            595                 600                 605

Lys Gly Glu Arg Arg Arg Gly Lys Gly His Asp Gly Leu Tyr Gln Gly
            610                 615                 620

Leu Ser Thr Ala Thr Lys Asp Thr Tyr Asp Ala Leu His Met Gln Ala
625                 630                 635                 640

Leu Pro Pro Arg

<210> SEQ ID NO 103
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
            50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
            85                  90                  95

-continued

```
Pro Ser Arg Gly Leu Glu Trp Leu Gly Arg Thr Tyr Tyr Arg Ser Lys
            100                 105                 110
Trp Tyr Asp Asp Tyr Ala Val Ser Val Lys Ser Arg Ile Thr Ile Asn
        115                 120                 125
Pro Asp Thr Ser Lys Asn His Leu Ser Leu His Leu Asn Ser Val Thr
    130                 135                 140
Pro Glu Asp Thr Ala Val Tyr Tyr Cys Ala Gly Gly Leu Val Gly
145                 150                 155                 160
Ala Pro Asp Gly Phe Asp Val Trp Gly Gln Gly Thr Met Val Thr Val
                165                 170                 175
Ser Ser Gly Gly Gly Gly Ser Gly Gly Gly Ser Gly Gly Gly Gly
            180                 185                 190
Ser Gly Gly Gly Gly Ser Gln Ser Val Leu Thr Gln Pro Pro Ser Ala
        195                 200                 205
Ser Gly Thr Pro Gly Gln Arg Val Thr Ile Ser Cys Ser Gly Ser Ser
    210                 215                 220
Ser Asn Ile Gly Ser Asp Pro Val Asn Trp Tyr Gln Gln Leu Pro Gly
225                 230                 235                 240
Thr Ala Pro Lys Leu Leu Ile Tyr Ser Asn Asn Gln Arg Pro Ser Gly
                245                 250                 255
Val Pro Asp Arg Phe Ser Gly Ser Lys Ser Gly Thr Ser Ala Ser Leu
            260                 265                 270
Ala Ile Ser Gly Leu Gln Ser Glu Asp Glu Ala Asp Tyr Tyr Cys Ser
        275                 280                 285
Ala Trp Asp Asp Ser Leu Asn Gly Tyr Val Phe Gly Thr Gly Thr Lys
    290                 295                 300
Val Thr Val Leu Thr Thr Thr Pro Ala Pro Arg Pro Pro Thr Pro Ala
305                 310                 315                 320
Pro Thr Ile Ala Ser Gln Pro Leu Ser Leu Arg Pro Glu Ala Cys Arg
                325                 330                 335
Pro Ala Ala Gly Gly Ala Val His Thr Arg Gly Leu Asp Phe Ala Cys
            340                 345                 350
Asp Ile Tyr Ile Trp Ala Pro Leu Ala Gly Thr Cys Gly Val Leu Leu
        355                 360                 365
Leu Ser Leu Val Ile Thr Leu Tyr Cys Lys Arg Gly Arg Lys Lys Leu
    370                 375                 380
Leu Tyr Ile Phe Lys Gln Pro Phe Met Arg Pro Val Gln Thr Thr Gln
385                 390                 395                 400
Glu Glu Asp Gly Cys Ser Cys Arg Phe Pro Glu Glu Glu Glu Gly Gly
                405                 410                 415
Cys Glu Leu Arg Val Lys Phe Ser Arg Ser Ala Asp Ala Pro Ala Tyr
            420                 425                 430
Gln Gln Gly Gln Asn Gln Leu Tyr Ala Glu Leu Asn Leu Gly Arg Arg
        435                 440                 445
Glu Glu Tyr Asp Val Leu Asp Lys Arg Arg Gly Arg Asp Pro Glu Met
    450                 455                 460
Gly Gly Lys Pro Arg Arg Lys Asn Pro Gln Glu Gly Leu Tyr Ala Glu
465                 470                 475                 480
Leu Gln Lys Asp Lys Met Ala Glu Ala Tyr Ser Glu Ile Gly Met Lys
                485                 490                 495
Gly Glu Arg Arg Arg Gly Lys Gly His Asp Gly Leu Tyr Ala Gly Leu
            500                 505                 510
Ser Thr Ala Thr Lys Asp Thr Tyr Asp Ala Leu His Met Gln Ala Leu
```

```
                515                 520                 525
Pro Pro Arg Arg Val Lys Phe Ser Arg Ser Ala Asp Ala Pro Ala Tyr
    530                 535                 540
Gln Gln Gly Gln Asn Gln Leu Tyr Ala Glu Leu Asn Leu Gly Arg Arg
545                 550                 555                 560
Glu Glu Tyr Asp Val Leu Asp Lys Arg Gly Arg Asp Pro Glu Met
            565                 570                 575
Gly Gly Lys Pro Arg Arg Lys Asn Pro Gln Glu Gly Leu Tyr Ala Glu
            580                 585                 590
Leu Gln Lys Asp Lys Met Ala Glu Ala Tyr Ser Glu Ile Gly Met Lys
        595                 600                 605
Gly Glu Arg Arg Arg Gly Lys Gly His Asp Gly Leu Tyr Ala Gly Leu
    610                 615                 620
Ser Thr Ala Thr Lys Asp Thr Tyr Asp Ala Leu His Met Gln Ala Leu
625                 630                 635                 640
Pro Pro Arg

<210> SEQ ID NO 104
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Ala Leu Pro Val Thr Ala Leu Leu Leu Pro Leu Ala Leu Leu Leu
1               5                   10                  15
His Ala Ala Arg Pro Gly Gly Gly Gly Ser Cys Pro Tyr Ser Asn Pro
            20                  25                  30
Ser Leu Cys Gly Gly Gly Gly Ser Cys Pro Tyr Ser Asn Pro Ser Leu
        35                  40                  45
Cys Gly Gly Gly Gly Ser Gln Val Gln Leu Gln Gln Ser Gly Pro Gly
    50                  55                  60
Leu Val Lys Pro Ser Gln Thr Leu Ser Leu Thr Cys Ala Ile Ser Gly
65                  70                  75                  80
Asp Ser Val Ser Ser Asn Ser Ala Thr Trp Asn Trp Ile Arg Gln Ser
                85                  90                  95
Pro Ser Arg Gly Leu Glu Trp Leu Gly Arg Thr Tyr Tyr Arg Ser Lys
            100                 105                 110
Trp Tyr Asp Asp Tyr Ala Val Ser Val Lys Ser Arg Ile Thr Ile Asn
        115                 120                 125
Pro Asp Thr Ser Lys Asn His Leu Ser Leu His Leu Asn Ser Val Thr
    130                 135                 140
Pro Glu Asp Thr Ala Val Tyr Tyr Cys Ala Gly Gly Leu Val Gly
145                 150                 155                 160
Ala Pro Asp Gly Phe Asp Val Trp Gly Gln Gly Thr Met Val Thr Val
                165                 170                 175
Ser Ser Gly Gly Gly Gly Ser Gly Gly Gly Gly Ser Gly Gly Gly Gly
            180                 185                 190
Ser Gly Gly Gly Gly Ser Gln Ser Val Leu Thr Gln Pro Pro Ser Ala
        195                 200                 205
Ser Gly Thr Pro Gly Gln Arg Val Thr Ile Ser Cys Ser Gly Ser Ser
    210                 215                 220
Ser Asn Ile Gly Ser Asp Pro Val Asn Trp Tyr Gln Gln Leu Pro Gly
```

```
            225                 230                 235                 240
        Thr Ala Pro Lys Leu Leu Ile Tyr Ser Asn Asn Gln Arg Pro Ser Gly
                        245                 250                 255
        Val Pro Asp Arg Phe Ser Gly Ser Lys Ser Gly Thr Ser Ala Ser Leu
                        260                 265                 270
        Ala Ile Ser Gly Leu Gln Ser Glu Asp Glu Ala Asp Tyr Tyr Cys Ser
                        275                 280                 285
        Ala Trp Asp Asp Ser Leu Asn Gly Tyr Val Phe Gly Thr Gly Thr Lys
                        290                 295                 300
        Val Thr Val Leu Thr Thr Thr Pro Ala Pro Arg Pro Pro Thr Pro Ala
        305                 310                 315                 320
        Pro Thr Ile Ala Ser Gln Pro Leu Ser Leu Arg Pro Glu Ala Cys Arg
                        325                 330                 335
        Pro Ala Ala Gly Gly Ala Val His Thr Arg Gly Leu Asp Phe Ala Cys
                        340                 345                 350
        Asp Ile Tyr Ile Trp Ala Pro Leu Ala Gly Thr Cys Gly Val Leu Leu
                        355                 360                 365
        Leu Ser Leu Val Ile Thr Leu Tyr Cys Lys Arg Gly Arg Lys Lys Leu
                        370                 375                 380
        Leu Tyr Ile Phe Lys Gln Pro Phe Met Arg Pro Val Gln Thr Thr Gln
        385                 390                 395                 400
        Glu Glu Asp Gly Cys Ser Cys Arg Phe Pro Glu Glu Glu Glu Gly Gly
                        405                 410                 415
        Cys Glu Leu Arg Val Lys Phe Ser Arg Ser Ala Asp Ala Pro Ala Tyr
                        420                 425                 430
        Gln Gln Gly Gln Asn Gln Leu Tyr Ala Glu Leu Asn Leu Gly Arg Arg
                        435                 440                 445
        Glu Glu Tyr Asp Val Leu Asp Lys Arg Arg Gly Arg Asp Pro Glu Met
                        450                 455                 460
        Gly Gly Lys Asp Thr Gln Ala Leu Leu Arg Asn Asp Gln Val Tyr Ala
        465                 470                 475                 480
        Pro Leu Arg Asp Arg Asp Asp Ala Gln Tyr Ser His Leu Gly Gly Asn
                        485                 490                 495
        Lys Gly Pro Arg Arg Lys Asn Pro Gln Glu Gly Leu Tyr Ala Glu Leu
                        500                 505                 510
        Gln Lys Asp Lys Met Ala Glu Ala Tyr Ser Glu Ile Gly Met Ala Leu
                        515                 520                 525
        Pro Pro Arg Gly Arg Val Lys Phe Ser Arg Ser Ala Asp Glu Arg Pro
        530                 535                 540
        Pro Pro Val Pro Asn Pro Asp Tyr Ala Pro Ile Arg Lys Gly Gln Arg
        545                 550                 555                 560
        Asp Leu Tyr Ser Gly Leu Asn Gln Arg Arg Gly Arg Asp Pro Glu Met
                        565                 570                 575
        Gly Gly Lys Glu Arg Arg Arg Gly Lys Gly His Asp Gly Leu Tyr Ala
                        580                 585                 590
        Gly Leu Ser Thr Ala Thr Lys Asp Thr Tyr Asp Ala Leu His Met Gln
                        595                 600                 605
        Lys Gly Asp Lys Gln Thr Leu Leu Pro Asn Asp Gln Leu Tyr Ala Pro
                        610                 615                 620
        Leu Lys Asp Arg Glu Asp Asp Gln Tyr Ser His Leu Gln Gly Asn Ala
        625                 630                 635                 640
        Leu Pro Pro Arg
```

<210> SEQ ID NO 105
<211> LENGTH: 644
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Ser Gly Pro Gly
50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205

Ser Gly Thr Pro Gly Gln Arg Val Thr Ile Ser Cys Ser Gly Ser Ser
210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365
```

```
Leu Ser Leu Val Ile Thr Leu Tyr Cys Lys Arg Gly Arg Lys Lys Leu
        370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Asp Thr Gln Ala
                420                 425                 430

Leu Leu Arg Asn Asp Gln Val Tyr Ala Pro Leu Arg Asp Arg Asp Asp
            435                 440                 445

Ala Gln Tyr Ser His Leu Gly Gly Asn Arg Gly Arg Asp Pro Glu Met
        450                 455                 460

Gly Gly Lys Ala Pro Ala Tyr Gln Gln Gly Gln Asn Gln Leu Tyr Ala
465                 470                 475                 480

Glu Leu Asn Leu Gly Arg Arg Glu Glu Tyr Asp Val Leu Asp Lys Arg
                485                 490                 495

Lys Gly Glu Arg Pro Pro Pro Val Pro Asn Pro Asp Tyr Ala Pro Ile
                500                 505                 510

Arg Lys Gly Gln Arg Asp Leu Tyr Ser Gly Leu Asn Gln Arg Ala Leu
            515                 520                 525

Pro Pro Arg Gly Arg Val Lys Phe Ser Arg Ser Ala Asp Pro Arg Arg
        530                 535                 540

Lys Asn Pro Gln Glu Gly Leu Tyr Ala Glu Leu Gln Lys Asp Lys Met
545                 550                 555                 560

Ala Glu Ala Tyr Ser Glu Ile Gly Met Arg Gly Arg Asp Pro Glu Met
                565                 570                 575

Gly Gly Lys Asp Lys Gln Thr Leu Leu Pro Asn Asp Gln Leu Tyr Ala
            580                 585                 590

Pro Leu Lys Asp Arg Glu Asp Asp Gln Tyr Ser His Leu Gln Gly Asn
        595                 600                 605

Lys Gly Glu Arg Arg Arg Gly Lys Gly His Asp Gly Leu Tyr Ala Gly
    610                 615                 620

Leu Ser Thr Ala Thr Lys Asp Thr Tyr Asp Ala Leu His Met Gln Ala
625                 630                 635                 640

Leu Pro Pro Arg

<210> SEQ ID NO 106
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
        50                  55                  60

Leu Val Lys Pro Ser Gln Thr Leu Ser Leu Thr Cys Ala Ile Ser Gly
65                  70                  75                  80
```

```
Asp Ser Val Ser Ser Asn Ser Ala Thr Trp Asn Trp Ile Arg Gln Ser
                85                  90                  95
Pro Ser Arg Gly Leu Glu Trp Leu Gly Arg Thr Tyr Tyr Arg Ser Lys
            100                 105                 110
Trp Tyr Asp Asp Tyr Ala Val Ser Val Lys Ser Arg Ile Thr Ile Asn
        115                 120                 125
Pro Asp Thr Ser Lys Asn His Leu Ser Leu His Leu Asn Ser Val Thr
130                 135                 140
Pro Glu Asp Thr Ala Val Tyr Tyr Cys Ala Gly Gly Gly Leu Val Gly
145                 150                 155                 160
Ala Pro Asp Gly Phe Asp Val Trp Gly Gln Gly Thr Met Val Thr Val
                165                 170                 175
Ser Ser Gly Gly Gly Gly Ser Gly Gly Gly Gly Ser Gly Gly Gly Gly
            180                 185                 190
Ser Gly Gly Gly Gly Ser Gln Ser Val Leu Thr Gln Pro Pro Ser Ala
        195                 200                 205
Ser Gly Thr Pro Gly Gln Arg Val Thr Ile Ser Cys Ser Gly Ser Ser
    210                 215                 220
Ser Asn Ile Gly Ser Asp Pro Val Asn Trp Tyr Gln Gln Leu Pro Gly
225                 230                 235                 240
Thr Ala Pro Lys Leu Leu Ile Tyr Ser Asn Asn Gln Arg Pro Ser Gly
                245                 250                 255
Val Pro Asp Arg Phe Ser Gly Ser Lys Ser Gly Thr Ser Ala Ser Leu
            260                 265                 270
Ala Ile Ser Gly Leu Gln Ser Glu Asp Glu Ala Asp Tyr Tyr Cys Ser
        275                 280                 285
Ala Trp Asp Asp Ser Leu Asn Gly Tyr Val Phe Gly Thr Gly Thr Lys
        290                 295                 300
Val Thr Val Leu Thr Thr Thr Pro Ala Pro Arg Pro Pro Thr Pro Ala
305                 310                 315                 320
Pro Thr Ile Ala Ser Gln Pro Leu Ser Leu Arg Pro Glu Ala Cys Arg
                325                 330                 335
Pro Ala Ala Gly Gly Ala Val His Thr Arg Gly Leu Asp Phe Ala Cys
            340                 345                 350
Asp Ile Tyr Ile Trp Ala Pro Leu Ala Gly Thr Cys Gly Val Leu Leu
        355                 360                 365
Leu Ser Leu Val Ile Thr Leu Tyr Cys Lys Arg Gly Arg Lys Lys Leu
370                 375                 380
Leu Tyr Ile Phe Lys Gln Pro Phe Met Arg Pro Val Gln Thr Thr Gln
385                 390                 395                 400
Glu Glu Asp Gly Cys Ser Cys Arg Phe Pro Glu Glu Glu Glu Gly Gly
                405                 410                 415
Cys Glu Leu Arg Val Lys Phe Ser Arg Ser Ala Asp Asp Thr Gln Ala
            420                 425                 430
Leu Leu Arg Asn Asp Gln Val Tyr Gln Pro Leu Arg Asp Arg Asp Asp
        435                 440                 445
Ala Gln Tyr Ser His Leu Gly Gly Asn Arg Gly Arg Asp Pro Glu Met
450                 455                 460
Gly Gly Lys Ala Pro Ala Tyr Gln Gln Gly Gln Asn Gln Leu Tyr Asn
465                 470                 475                 480
Glu Leu Asn Leu Gly Arg Arg Glu Glu Tyr Asp Val Leu Asp Lys Arg
                485                 490                 495
```

```
Lys Gly Glu Arg Pro Pro Pro Val Pro Asn Pro Asp Tyr Glu Pro Ile
            500                 505                 510

Arg Lys Gly Gln Arg Asp Leu Tyr Ser Gly Leu Asn Gln Arg Ala Leu
        515                 520                 525

Pro Pro Arg Gly Arg Val Lys Phe Ser Arg Ser Ala Asp Pro Arg Arg
    530                 535                 540

Lys Asn Pro Gln Glu Gly Leu Tyr Asn Glu Leu Gln Lys Asp Lys Met
545                 550                 555                 560

Ala Glu Ala Tyr Ser Glu Ile Gly Met Arg Gly Arg Asp Pro Glu Met
                565                 570                 575

Gly Gly Lys Asp Lys Gln Thr Leu Leu Pro Asn Asp Gln Leu Tyr Gln
            580                 585                 590

Pro Leu Lys Asp Arg Glu Asp Asp Gln Tyr Ser His Leu Gln Gly Asn
        595                 600                 605

Lys Gly Glu Arg Arg Arg Gly Lys Gly His Asp Gly Leu Tyr Gln Gly
    610                 615                 620

Leu Ser Thr Ala Thr Lys Asp Thr Tyr Asp Ala Leu His Met Gln Ala
625                 630                 635                 640

Leu Pro Pro Arg

<210> SEQ ID NO 107
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205
```

Ser Gly Thr Pro Gly Gln Arg Val Thr Ile Ser Cys Ser Gly Ser Ser
210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
                260                 265                 270

Ala Ile Ser Gly Leu Gln Ser Glu Asp Glu Ala Asp Tyr Tyr Cys Ser
                275                 280                 285

Ala Trp Asp Asp Ser Leu Asn Gly Tyr Val Phe Gly Thr Gly Thr Lys
                290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
                355                 360                 365

Leu Ser Leu Val Ile Thr Leu Tyr Cys Lys Arg Gly Arg Lys Lys Leu
370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Asp Thr Gln Ala
                420                 425                 430

Leu Leu Arg Asn Asp Gln Val Tyr Gln Pro Leu Arg Asp Arg Asp Asp
                435                 440                 445

Ala Gln Tyr Ser His Leu Gly Gly Asn Arg Gly Arg Asp Pro Glu Met
450                 455                 460

Gly Gly Lys Glu Arg Pro Pro Val Pro Asn Pro Asp Tyr Glu Pro
465                 470                 475                 480

Ile Arg Lys Gly Gln Arg Asp Leu Tyr Ser Gly Leu Asn Gln Arg Lys
                485                 490                 495

Gly Asp Lys Gln Thr Leu Leu Pro Asn Asp Gln Leu Tyr Gln Pro Leu
                500                 505                 510

Lys Asp Arg Glu Asp Asp Gln Tyr Ser His Leu Gln Gly Asn Ala Leu
                515                 520                 525

Pro Pro Arg Gly Arg Val Lys Phe Ser Arg Ser Ala Asp Ala Pro Ala
                530                 535                 540

Tyr Gln Gln Gly Gln Asn Gln Leu Tyr Asn Glu Leu Asn Leu Gly Arg
545                 550                 555                 560

Arg Glu Glu Tyr Asp Val Leu Asp Lys Arg Gly Arg Asp Pro Glu
                565                 570                 575

Met Gly Gly Lys Pro Arg Arg Lys Asn Pro Gln Glu Gly Leu Tyr Asn
                580                 585                 590

Glu Leu Gln Lys Asp Lys Met Ala Glu Ala Tyr Ser Glu Ile Gly Met
                595                 600                 605

Lys Gly Glu Arg Arg Arg Gly Lys Gly His Asp Gly Leu Tyr Gln Gly
                610                 615                 620

Leu Ser Thr Ala Thr Lys Asp Thr Tyr Asp Ala Leu His Met Gln Ala

```
625                 630                 635                 640
Leu Pro Pro Arg

<210> SEQ ID NO 108
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
```

-continued

```
                340                 345                 350
Asp Ile Tyr Ile Trp Ala Pro Leu Ala Gly Thr Cys Gly Val Leu Leu
            355                 360                 365

Leu Ser Leu Val Ile Thr Leu Tyr Cys Lys Arg Gly Arg Lys Lys Leu
        370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
        435                 440                 445

Glu Glu Tyr Asp Val Leu Asp Lys Arg Arg Gly Arg Asp Pro Glu Met
        450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg Gly Arg Val Lys Phe Ser Arg Ser Ala Asp Asp Thr Gln
        530                 535                 540

Ala Leu Leu Arg Asn Asp Gln Val Tyr Gln Pro Leu Arg Asp Arg Asp
545                 550                 555                 560

Asp Ala Gln Tyr Ser His Leu Gly Gly Asn Arg Gly Arg Asp Pro Glu
                565                 570                 575

Met Gly Gly Lys Glu Arg Pro Pro Val Pro Asn Pro Asp Tyr Glu
            580                 585                 590

Pro Ile Arg Lys Gly Gln Arg Asp Leu Tyr Ser Gly Leu Asn Gln Arg
        595                 600                 605

Lys Gly Asp Lys Gln Thr Leu Leu Pro Asn Asp Gln Leu Tyr Gln Pro
        610                 615                 620

Leu Lys Asp Arg Glu Asp Asp Gln Tyr Ser His Leu Gln Gly Asn Ala
625                 630                 635                 640

Leu Pro Pro Arg
```

```
<210> SEQ ID NO 109
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109
```

```
Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
```

```
            50                  55                  60
Leu Val Lys Pro Ser Gln Thr Leu Ser Leu Thr Cys Ala Ile Ser Gly
 65                  70                  75                  80

Asp Ser Val Ser Ser Asn Ser Ala Thr Trp Asn Trp Ile Arg Gln Ser
                     85                  90                  95

Pro Ser Arg Gly Leu Glu Trp Leu Gly Arg Thr Tyr Tyr Arg Ser Lys
                100                 105                 110

Trp Tyr Asp Asp Tyr Ala Val Ser Val Lys Ser Arg Ile Thr Ile Asn
                115                 120                 125

Pro Asp Thr Ser Lys Asn His Leu Ser Leu His Leu Asn Ser Val Thr
            130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Gly Ser Gly Gly Gly Gly
                180                 185                 190

Ser Gly Gly Gly Gly Ser Gln Ser Val Leu Thr Gln Pro Pro Ser Ala
            195                 200                 205

Ser Gly Thr Pro Gly Gln Arg Val Thr Ile Ser Cys Ser Gly Ser Ser
            210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
                260                 265                 270

Ala Ile Ser Gly Leu Gln Ser Glu Asp Glu Ala Asp Tyr Tyr Cys Ser
                275                 280                 285

Ala Trp Asp Asp Ser Leu Asn Gly Tyr Val Phe Gly Thr Gly Thr Lys
                290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
                355                 360                 365

Leu Ser Leu Val Ile Thr Leu Tyr Cys Lys Arg Gly Arg Lys Lys Leu
            370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Ala Pro Ala Tyr
                420                 425                 430

Gln Gln Gly Gln Asn Gln Leu Tyr Ala Glu Leu Asn Leu Gly Arg Arg
            435                 440                 445

Glu Glu Tyr Asp Val Leu Asp Lys Arg Arg Gly Arg Asp Pro Glu Met
            450                 455                 460

Gly Gly Lys Pro Arg Arg Lys Asn Pro Gln Glu Gly Leu Tyr Ala Glu
465                 470                 475                 480
```

Leu Gln Lys Asp Lys Met Ala Glu Ala Tyr Ser Glu Ile Gly Met Lys
                485                 490                 495

Gly Glu Arg Arg Gly Lys Gly His Asp Gly Leu Tyr Ala Gly Leu
            500                 505                 510

Ser Thr Ala Thr Lys Asp Thr Tyr Asp Ala Leu His Met Gln Ala Leu
        515                 520                 525

Pro Pro Arg
    530

<210> SEQ ID NO 110
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Cys Pro Tyr Ser Asn Pro Ser Leu
        35                  40                  45

Cys Gly Gly Gly Ser Gln Val Gln Leu Gln Gln Ser Gly Pro Gly
50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys

```
                290                 295                 300
Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
                340                 345                 350

Asp Ile Tyr Ile Trp Ala Pro Leu Ala Gly Thr Cys Gly Val Leu Leu
                355                 360                 365

Leu Ser Leu Val Ile Thr Leu Tyr Cys Lys Arg Gly Arg Lys Lys Leu
370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Asp Thr Gln Ala
                420                 425                 430

Leu Leu Arg Asn Asp Gln Val Tyr Gln Pro Leu Arg Asp Arg Asp Asp
                435                 440                 445

Ala Gln Tyr Ser His Leu Gly Gly Asn Arg Gly Arg Asp Pro Glu Met
                450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
                500                 505                 510

Ser Thr Ala Thr Lys Asp Thr Tyr Asp Ala Leu His Met Gln Ala Leu
                515                 520                 525

Pro Pro Arg
    530

<210> SEQ ID NO 111
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Gln Ser Gly Pro Gly
        50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
                100                 105                 110
```

```
Trp Tyr Asp Asp Tyr Ala Val Ser Val Lys Ser Arg Ile Thr Ile Asn
            115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Ser Gly Gly Gly Gly
            180                 185                 190

Ser Gly Gly Gly Gly Ser Gln Ser Val Leu Thr Gln Pro Pro Ser Ala
            195                 200                 205

Ser Gly Thr Pro Gly Gln Arg Val Thr Ile Ser Cys Ser Gly Ser Ser
            210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
275                 280                 285

Ala Trp Asp Asp Ser Leu Asn Gly Tyr Val Phe Gly Thr Gly Thr Lys
            290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
            355                 360                 365

Leu Ser Leu Val Ile Thr Leu Tyr Cys Lys Arg Gly Arg Lys Lys Leu
370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Glu Arg Pro Pro
            420                 425                 430

Pro Val Pro Asn Pro Asp Tyr Glu Pro Ile Arg Lys Gly Gln Arg Asp
            435                 440                 445

Leu Tyr Ser Gly Leu Asn Gln Arg Arg Gly Arg Asp Pro Glu Met Gly
450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
515                 520                 525

Pro Arg
```

530

<210> SEQ ID NO 112
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Gly Ser Gly Gly Gly Gly Ser Gly Gly Gly Gly
            180                 185                 190

Ser Gly Gly Gly Gly Ser Gln Ser Val Leu Thr Gln Pro Pro Ser Ala
        195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
    290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
            355                 360                 365

Leu Ser Leu Val Ile Thr Leu Tyr Cys Lys Arg Gly Arg Lys Lys Leu
    370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Asp Lys Gln Thr
            420                 425                 430

Leu Leu Pro Asn Asp Gln Leu Tyr Gln Pro Leu Lys Asp Arg Glu Asp
        435                 440                 445

Asp Gln Tyr Ser His Leu Gln Gly Asn Arg Gly Arg Asp Pro Glu Met
    450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg
    530

<210> SEQ ID NO 113
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Cys Pro Tyr Ser Asn Pro Ser Leu
    35                  40                  45

Cys Gly Gly Gly Ser Gln Val Gln Leu Gln Gln Ser Gly Pro Gly
50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
    130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
                165                 170                 175

Ser Ser Gly Gly Gly Ser Gly Gly Gly Ser Gly Gly Gly
          180                 185                 190

Ser Gly Gly Gly Ser Gln Ser Val Leu Thr Gln Pro Ser Ala
        195                 200                 205

Ser Gly Thr Pro Gly Gln Arg Val Thr Ile Ser Cys Ser Gly Ser
    210                 215                 220

Ser Asn Ile Gly Ser Asp Pro Val Asn Trp Tyr Gln Leu Pro Gly
225                 230                 235                 240

Thr Ala Pro Lys Leu Leu Ile Tyr Ser Asn Asn Gln Arg Pro Ser Gly
                245                 250                 255

Val Pro Asp Arg Phe Ser Gly Ser Lys Ser Gly Thr Ser Ala Ser Leu
            260                 265                 270

Ala Ile Ser Gly Leu Gln Ser Glu Asp Glu Ala Asp Tyr Tyr Cys Ser
        275                 280                 285

Ala Trp Asp Asp Ser Leu Asn Gly Tyr Val Phe Gly Thr Gly Thr Lys
        290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365

Leu Ser Leu Val Ile Thr Leu Tyr Cys Lys Arg Gly Arg Lys Lys Leu
370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
                405                 410                 415

Cys Glu Leu Arg Val Lys Phe Ser Arg Ser Ala Asp Asp Thr Gln Ala
            420                 425                 430

Leu Leu Arg Asn Asp Gln Val Tyr Gln Pro Leu Arg Asp Arg Asp Asp
        435                 440                 445

Ala Gln Tyr Ser His Leu Gly Gly Asn Arg Gly Arg Asp Pro Glu Met
    450                 455                 460

Gly Gly Lys Glu Arg Pro Pro Val Pro Asn Pro Asp Tyr Glu Pro
465                 470                 475                 480

Ile Arg Lys Gly Gln Arg Asp Leu Tyr Ser Gly Leu Asn Gln Arg Lys
                485                 490                 495

Gly Asp Lys Gln Thr Leu Leu Pro Asn Asp Gln Leu Tyr Gln Pro Leu
            500                 505                 510

Lys Asp Arg Glu Asp Asp Gln Tyr Ser His Leu Gln Gly Asn Ala Leu
        515                 520                 525

Pro Pro Arg
    530

<210> SEQ ID NO 114
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Cys Pro Tyr Ser Asn Pro Ser Leu
        35                  40                  45

Cys Gly Gly Gly Gly Ser Gln Val Gln Leu Gln Ser Gly Pro Gly
    50                  55                  60

Leu Val Lys Pro Ser Gln Thr Leu Ser Leu Thr Cys Ala Ile Ser Gly
65                  70                  75                  80

Asp Ser Val Ser Ser Asn Ser Ala Thr Trp Asn Trp Ile Arg Gln Ser
                85                  90                  95

Pro Ser Arg Gly Leu Glu Trp Leu Gly Arg Thr Tyr Tyr Arg Ser Lys
            100                 105                 110

Trp Tyr Asp Asp Tyr Ala Val Ser Val Lys Ser Arg Ile Thr Ile Asn
        115                 120                 125

Pro Asp Thr Ser Lys Asn His Leu Ser Leu His Leu Asn Ser Val Thr
130                 135                 140

Pro Glu Asp Thr Ala Val Tyr Tyr Cys Ala Gly Gly Leu Val Gly
145                 150                 155                 160

Ala Pro Asp Gly Phe Asp Val Trp Gly Gln Gly Thr Met Val Thr Val
            165                 170                 175

Ser Ser Gly Gly Gly Gly Ser Gly Gly Gly Ser Gly Gly Gly Gly
        180                 185                 190

Ser Gly Gly Gly Gly Ser Gln Ser Val Leu Thr Gln Pro Pro Ser Ala
    195                 200                 205

Ser Gly Thr Pro Gly Gln Arg Val Thr Ile Ser Cys Ser Gly Ser Ser
    210                 215                 220

Ser Asn Ile Gly Ser Asp Pro Val Asn Trp Tyr Gln Gln Leu Pro Gly
225                 230                 235                 240

Thr Ala Pro Lys Leu Leu Ile Tyr Ser Asn Asn Gln Arg Pro Ser Gly
            245                 250                 255

Val Pro Asp Arg Phe Ser Gly Ser Lys Ser Gly Thr Ser Ala Ser Leu
        260                 265                 270

Ala Ile Ser Gly Leu Gln Ser Glu Asp Glu Ala Asp Tyr Tyr Cys Ser
    275                 280                 285

Ala Trp Asp Asp Ser Leu Asn Gly Tyr Val Phe Gly Thr Gly Thr Lys
290                 295                 300

Val Thr Val Leu Thr Thr Thr Pro Ala Pro Arg Pro Pro Thr Pro Ala
305                 310                 315                 320

Pro Thr Ile Ala Ser Gln Pro Leu Ser Leu Arg Pro Glu Ala Cys Arg
            325                 330                 335

Pro Ala Ala Gly Gly Ala Val His Thr Arg Gly Leu Asp Phe Ala Cys
        340                 345                 350

Asp Ile Tyr Ile Trp Ala Pro Leu Ala Gly Thr Cys Gly Val Leu Leu
    355                 360                 365

Leu Ser Leu Val Ile Thr Leu Tyr Cys Lys Arg Gly Arg Lys Lys Leu
370                 375                 380

Leu Tyr Ile Phe Lys Gln Pro Phe Met Arg Pro Val Gln Thr Thr Gln
385                 390                 395                 400

Glu Glu Asp Gly Cys Ser Cys Arg Phe Pro Glu Glu Glu Glu Gly Gly
            405                 410                 415

```
Cys Glu Leu Arg Val Lys Phe Ser Arg Ser Ala Asp Ala Pro Ala Tyr
            420                 425                 430

Gln Gln Gly Gln Asn Gln Leu Tyr Ala Glu Leu Asn Leu Gly Arg Arg
            435                 440                 445

Glu Glu Tyr Asp Val Leu Asp Lys Arg Gly Arg Asp Pro Glu Met
450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
                500                 505                 510

Ser Thr Ala Thr Lys Asp Thr Tyr Asp Ala Leu His Met Gln Ala Leu
                515                 520                 525

Pro Pro Arg
        530

<210> SEQ ID NO 115
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Tyr Ser
            85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
        130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
```

```
                225                 230                 235                 240
        Ser Arg Phe Ser Gly Ser Gly Ser Gly Thr Asp Phe Thr Leu Thr Ile
                        245                 250                 255

Ser Ser Leu Gln Pro Glu Asp Phe Ala Thr Tyr Tyr Cys Leu Gln Asp
                        260                 265                 270

Tyr Asn Tyr Pro Leu Thr Phe Gly Pro Gly Thr Lys Val Asp Ile Lys
                        275                 280                 285

Gly Gly Gly Gly Ser Cys Pro Tyr Ser Asn Pro Ser Leu Cys Gly Gly
                        290                 295                 300

Gly Gly Ser Thr Thr Thr Pro Ala Pro Arg Pro Pro Thr Pro Ala Pro
        305                 310                 315                 320

Thr Ile Ala Ser Gln Pro Leu Ser Leu Arg Pro Glu Ala Cys Arg Pro
                        325                 330                 335

Ala Ala Gly Gly Ala Val His Thr Arg Gly Leu Asp Phe Ala Cys Asp
                        340                 345                 350

Ile Tyr Ile Trp Ala Pro Leu Ala Gly Thr Cys Gly Val Leu Leu Leu
                        355                 360                 365

Ser Leu Val Ile Thr Leu Tyr Cys Lys Arg Gly Arg Lys Lys Leu Leu
                370                 375                 380

Tyr Ile Phe Lys Gln Pro Phe Met Arg Pro Val Gln Thr Thr Gln Glu
        385                 390                 395                 400

Glu Asp Gly Cys Ser Cys Arg Phe Pro Glu Glu Glu Glu Gly Gly Cys
                        405                 410                 415

Glu Leu Arg Val Lys Phe Ser Arg Ser Ala Asp Ala Pro Ala Tyr Gln
                        420                 425                 430

Gln Gly Gln Asn Gln Leu Tyr Asn Glu Leu Asn Leu Gly Arg Arg Glu
                        435                 440                 445

Glu Tyr Asp Val Leu Asp Lys Arg Arg Gly Arg Asp Pro Glu Met Gly
                        450                 455                 460

Gly Lys Pro Arg Arg Lys Asn Pro Gln Glu Gly Leu Tyr Asn Glu Leu
        465                 470                 475                 480

Gln Lys Asp Lys Met Ala Glu Ala Tyr Ser Glu Ile Gly Met Lys Gly
                        485                 490                 495

Glu Arg Arg Arg Gly Lys Gly His Asp Gly Leu Tyr Gln Gly Leu Ser
                        500                 505                 510

Thr Ala Thr Lys Asp Thr Tyr Asp Ala Leu His Met Gln Ala Leu Pro
                        515                 520                 525

Pro Arg
            530

<210> SEQ ID NO 116
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Ala Leu Pro Val Thr Ala Leu Leu Leu Pro Leu Ala Leu Leu Leu
        1               5                   10                  15

His Ala Ala Arg Pro Gly Gly Gly Gly Ser Cys Pro Tyr Ser Asn Pro
                        20                  25                  30

Ser Leu Cys Gly Gly Gly Gly Ser Gln Leu Gln Leu Gln Glu Ser Gly
                        35                  40                  45
```

```
Pro Gly Leu Val Lys Pro Ser Glu Thr Leu Ser Leu Thr Cys Thr Val
 50                  55                  60

Ser Gly Gly Ser Ile Ser Ser Ser Tyr Tyr Trp Gly Trp Ile Arg
 65                  70                  75                  80

Gln Pro Pro Gly Lys Gly Leu Glu Trp Ile Gly Ser Ile Tyr Tyr Ser
                 85                  90                  95

Gly Asn Ile Tyr His Asn Pro Ser Leu Lys Ser Arg Val Ser Ile Ser
                100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
        130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Asn His Arg Asn Arg Arg Arg Val
370                 375                 380

Cys Lys Cys Pro Arg Pro Val Val Lys Ser Gly Asp Lys Pro Ser Leu
385                 390                 395                 400

Ser Ala Arg Tyr Val Lys Arg Gly Arg Lys Lys Leu Leu Tyr Ile Phe
                405                 410                 415

Lys Gln Pro Phe Met Arg Pro Val Gln Thr Thr Gln Glu Glu Asp Gly
            420                 425                 430

Cys Ser Cys Arg Phe Pro Glu Glu Glu Glu Gly Gly Cys Glu Leu Arg
        435                 440                 445

Val Lys Phe Ser Arg Ser Ala Asp Ala Pro Ala Tyr Gln Gln Gly Gln
    450                 455                 460

Asn Gln Leu Tyr Asn Glu Leu Asn Leu Gly Arg Arg Glu Glu Tyr Asp
```

```
                465                 470                 475                 480
Val Leu Asp Lys Arg Arg Gly Arg Asp Pro Glu Met Gly Gly Lys Pro
                    485                 490                 495

Arg Arg Lys Asn Pro Gln Glu Gly Leu Tyr Asn Glu Leu Gln Lys Asp
                500                 505                 510

Lys Met Ala Glu Ala Tyr Ser Glu Ile Gly Met Lys Gly Glu Arg Arg
                515                 520                 525

Arg Gly Lys Gly His Asp Gly Leu Tyr Gln Gly Leu Ser Thr Ala Thr
            530                 535                 540

Lys Asp Thr Tyr Asp Ala Leu His Met Gln Ala Leu Pro Pro Arg
545                 550                 555

<210> SEQ ID NO 117
<211> LENGTH: 543
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
50                  55                  60

Ser Gly Gly Ser Ile Ser Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270
```

-continued

Tyr Asn Tyr Pro Leu Thr Phe Gly Pro Gly Thr Lys Val Asp Ile Lys
            275                 280                 285

Gly Gly Gly Gly Ser Cys Pro Tyr Ser Asn Pro Ser Leu Cys Gly Gly
        290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Arg Arg Val Cys Lys Cys Pro Arg Arg Arg Val
370                 375                 380

Cys Lys Cys Pro Arg Lys Arg Gly Arg Lys Lys Leu Leu Tyr Ile Phe
385                 390                 395                 400

Lys Gln Pro Phe Met Arg Pro Val Gln Thr Thr Gln Glu Glu Asp Gly
                405                 410                 415

Cys Ser Cys Arg Phe Pro Glu Glu Glu Glu Gly Gly Cys Glu Leu Arg
            420                 425                 430

Val Lys Phe Ser Arg Ser Ala Asp Ala Pro Ala Tyr Gln Gln Gly Gln
        435                 440                 445

Asn Gln Leu Tyr Asn Glu Leu Asn Leu Gly Arg Arg Glu Glu Tyr Asp
    450                 455                 460

Val Leu Asp Lys Arg Arg Gly Arg Asp Pro Glu Met Gly Gly Lys Pro
465                 470                 475                 480

Arg Arg Lys Asn Pro Gln Glu Gly Leu Tyr Asn Glu Leu Gln Lys Asp
                485                 490                 495

Lys Met Ala Glu Ala Tyr Ser Glu Ile Gly Met Lys Gly Glu Arg Arg
            500                 505                 510

Arg Gly Lys Gly His Asp Gly Leu Tyr Gln Gly Leu Ser Thr Ala Thr
        515                 520                 525

Lys Asp Thr Tyr Asp Ala Leu His Met Gln Ala Leu Pro Pro Arg
    530                 535                 540

<210> SEQ ID NO 118
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Tyr Ser
            85                  90                  95

```
Gly Asn Ile Tyr His Asn Pro Ser Leu Lys Ser Arg Val Ser Ile Ser
                100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
            195                 200                 205

Gly Ile Arg Asn Asp Leu Gly Trp Tyr Gln Gln Lys Pro Gly Lys Ala
            210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
            275                 280                 285

Gly Gly Gly Gly Ser Cys Pro Tyr Ser Asn Pro Ser Leu Cys Gly Gly
            290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
            355                 360                 365

Ser Leu Val Ile Thr Leu Tyr Cys Gly Gly Ser Tyr Gln Pro Tyr
370                 375                 380

Ala Pro Pro Arg Asp Phe Ala Ala Tyr Arg Ser Gly Gly Gly Ser Lys
385                 390                 395                 400

Arg Gly Arg Lys Lys Leu Leu Tyr Ile Phe Lys Gln Pro Phe Met Arg
                405                 410                 415

Pro Val Gln Thr Thr Gln Glu Glu Asp Gly Cys Ser Cys Arg Phe Pro
            420                 425                 430

Glu Glu Glu Glu Gly Gly Cys Glu Leu Arg Val Lys Phe Ser Arg Ser
            435                 440                 445

Ala Asp Ala Pro Ala Tyr Gln Gln Gly Gln Asn Gln Leu Tyr Asn Glu
450                 455                 460

Leu Asn Leu Gly Arg Arg Glu Glu Tyr Asp Val Leu Asp Lys Arg Arg
465                 470                 475                 480

Gly Arg Asp Pro Glu Met Gly Gly Lys Pro Arg Arg Lys Asn Pro Gln
                485                 490                 495

Glu Gly Leu Tyr Asn Glu Leu Gln Lys Asp Lys Met Ala Glu Ala Tyr
            500                 505                 510
```

```
Ser Glu Ile Gly Met Lys Gly Glu Arg Arg Gly Lys Gly His Asp
            515                 520                 525

Gly Leu Tyr Gln Gly Leu Ser Thr Ala Thr Lys Asp Thr Tyr Asp Ala
530                 535                 540

Leu His Met Gln Ala Leu Pro Pro Arg
545                 550

<210> SEQ ID NO 119
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
    290                 295                 300

Gly Gly Ser Thr Thr Thr Pro Ala Pro Arg Pro Pro Thr Pro Ala Pro
305                 310                 315                 320
```

```
Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Gly Gly Ser Phe Gln Pro Phe
    370                 375                 380

Ala Pro Pro Arg Asp Phe Ala Ala Phe Arg Ser Gly Gly Ser Lys
385                 390                 395                 400

Arg Gly Arg Lys Lys Leu Leu Tyr Ile Phe Lys Gln Pro Phe Met Arg
                405                 410                 415

Pro Val Gln Thr Thr Gln Glu Glu Asp Gly Cys Ser Cys Arg Phe Pro
            420                 425                 430

Glu Glu Glu Glu Gly Gly Cys Glu Leu Arg Val Lys Phe Ser Arg Ser
        435                 440                 445

Ala Asp Ala Pro Ala Tyr Gln Gln Gly Gln Asn Gln Leu Tyr Asn Glu
    450                 455                 460

Leu Asn Leu Gly Arg Arg Glu Glu Tyr Asp Val Leu Asp Lys Arg Arg
465                 470                 475                 480

Gly Arg Asp Pro Glu Met Gly Gly Lys Pro Arg Arg Lys Asn Pro Gln
                485                 490                 495

Glu Gly Leu Tyr Asn Glu Leu Gln Lys Asp Lys Met Ala Glu Ala Tyr
            500                 505                 510

Ser Glu Ile Gly Met Lys Gly Glu Arg Arg Gly Lys Gly His Asp
        515                 520                 525

Gly Leu Tyr Gln Gly Leu Ser Thr Ala Thr Lys Asp Thr Tyr Asp Ala
    530                 535                 540

Leu His Met Gln Ala Leu Pro Pro Arg
545                 550

<210> SEQ ID NO 120
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
        50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
```

```
                115                 120                 125
Ala Ala Asp Thr Ala Val Tyr Tyr Cys Ala Arg Glu Ile Ile Val Gly
            130                 135                 140
Ala Thr His Phe Asp Tyr Trp Gly Gln Gly Thr Leu Val Thr Val Ser
145                 150                 155                 160
Ser Gly Gly Gly Gly Ser Gly Gly Gly Ser Gly Gly Gly Gly Ser
                165                 170                 175
Gly Gly Gly Gly Ser Ala Ile Gln Met Thr Gln Ser Pro Ser Ser Leu
            180                 185                 190
Ser Ala Ser Val Gly Asp Arg Val Thr Ile Thr Cys Arg Ala Ser Gln
            195                 200                 205
Gly Ile Arg Asn Asp Leu Gly Trp Tyr Gln Gln Lys Pro Gly Lys Ala
            210                 215                 220
Pro Glu Leu Leu Ile Tyr Ala Ala Ser Ser Leu Gln Ser Gly Val Pro
225                 230                 235                 240
Ser Arg Phe Ser Gly Ser Gly Ser Gly Thr Asp Phe Thr Leu Thr Ile
                245                 250                 255
Ser Ser Leu Gln Pro Glu Asp Phe Ala Thr Tyr Tyr Cys Leu Gln Asp
            260                 265                 270
Tyr Asn Tyr Pro Leu Thr Phe Gly Pro Gly Thr Lys Val Asp Ile Lys
            275                 280                 285
Gly Gly Gly Gly Ser Cys Pro Tyr Ser Asn Pro Ser Leu Cys Gly Gly
            290                 295                 300
Gly Gly Ser Thr Thr Thr Pro Ala Pro Arg Pro Pro Thr Pro Ala Pro
305                 310                 315                 320
Thr Ile Ala Ser Gln Pro Leu Ser Leu Arg Pro Glu Ala Cys Arg Pro
                325                 330                 335
Ala Ala Gly Gly Ala Val His Thr Arg Gly Leu Asp Phe Ala Cys Asp
            340                 345                 350
Ile Tyr Ile Trp Ala Pro Leu Ala Gly Thr Cys Gly Val Leu Leu Leu
            355                 360                 365
Ser Leu Val Ile Thr Leu Tyr Cys Lys Arg Gly Arg Lys Lys Leu Leu
            370                 375                 380
Tyr Ile Phe Lys Gln Pro Phe Met Arg Pro Val Gln Thr Thr Gln Glu
385                 390                 395                 400
Glu Asp Gly Cys Ser Cys Arg Phe Pro Glu Glu Glu Glu Gly Gly Cys
                405                 410                 415
Glu Leu Arg Val Lys Phe Ser Arg Ser Ala Asp Ala Pro Ala Tyr Gln
            420                 425                 430
Gln Gly Gln Asn Gln Leu Tyr Asn Glu Leu Asn Leu Gly Arg Arg Glu
            435                 440                 445
Glu Tyr Asp Val Leu Asp Lys Arg Arg Gly Arg Asp Pro Glu Met Gly
            450                 455                 460
Gly Lys Pro Arg Arg Lys Asn Pro Gln Glu Gly Leu Tyr Asn Glu Leu
465                 470                 475                 480
Gln Lys Asp Lys Met Ala Glu Ala Tyr Ser Glu Ile Gly Met Lys Gly
                485                 490                 495
Glu Arg Arg Arg Gly Lys Gly His Asp Gly Leu Tyr Gln Gly Leu Ser
            500                 505                 510
Thr Ala Thr Lys Asp Thr Tyr Asp Ala Leu His Met Gln Ala Leu Pro
            515                 520                 525
Pro Arg Gly Gly Gly Ser Arg Val Cys Lys Cys Pro Arg Pro Val
            530                 535                 540
```

<210> SEQ ID NO 121
<211> LENGTH: 549
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
    290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
```

```
                355                 360                 365
Ser Leu Val Ile Thr Leu Tyr Cys Lys Arg Gly Arg Lys Lys Leu Leu
370                 375                 380
Tyr Ile Phe Lys Gln Pro Phe Met Arg Pro Val Gln Thr Thr Gln Glu
385                 390                 395                 400
Glu Asp Gly Cys Ser Cys Arg Phe Pro Glu Glu Glu Gly Gly Cys
            405                 410                 415
Glu Leu Arg Val Lys Phe Ser Arg Ser Ala Asp Ala Pro Ala Tyr Gln
            420                 425                 430
Gln Gly Gln Asn Gln Leu Tyr Asn Glu Leu Asn Leu Gly Arg Arg Glu
            435                 440                 445
Glu Tyr Asp Val Leu Asp Lys Arg Arg Gly Arg Asp Pro Glu Met Gly
    450                 455                 460
Gly Lys Pro Arg Arg Lys Asn Pro Gln Glu Gly Leu Tyr Asn Glu Leu
465                 470                 475                 480
Gln Lys Asp Lys Met Ala Glu Ala Tyr Ser Glu Ile Gly Met Lys Gly
            485                 490                 495
Glu Arg Arg Arg Gly Lys Gly His Asp Gly Leu Tyr Gln Gly Leu Ser
            500                 505                 510
Thr Ala Thr Lys Asp Thr Tyr Asp Ala Leu His Met Gln Ala Leu Pro
            515                 520                 525
Pro Arg Gly Gly Gly Ser Phe Gln Pro Phe Ala Pro Pro Arg Asp Phe
    530                 535                 540
Ala Ala Phe Arg Ser
545

<210> SEQ ID NO 122
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Ala Leu Pro Val Thr Ala Leu Leu Leu Pro Leu Ala Leu Leu Leu
1               5                   10                  15
His Ala Ala Arg Pro Gly Gly Gly Ser Cys Pro Tyr Ser Asn Pro
            20                  25                  30
Ser Leu Cys Gly Gly Gly Ser Gln Leu Gln Leu Gln Glu Ser Gly
        35                  40                  45
Pro Gly Leu Val Lys Pro Ser Glu Thr Leu Ser Leu Thr Cys Thr Val
    50                  55                  60
Ser Gly Gly Ser Ile Ser Ser Ser Tyr Tyr Trp Gly Trp Ile Arg
65                  70                  75                  80
Gln Pro Pro Gly Lys Gly Leu Glu Trp Ile Gly Ser Ile Tyr Tyr Ser
            85                  90                  95
Gly Asn Ile Tyr His Asn Pro Ser Leu Lys Ser Arg Val Ser Ile Ser
            100                 105                 110
Val Asp Thr Ser Lys Asn Gln Phe Ser Leu Arg Leu Ser Ser Val Thr
            115                 120                 125
Ala Ala Asp Thr Ala Val Tyr Tyr Cys Ala Arg Glu Ile Ile Val Gly
        130                 135                 140
Ala Thr His Phe Asp Tyr Trp Gly Gln Gly Thr Leu Val Thr Val Ser
145                 150                 155                 160
```

```
Ser Gly Gly Gly Gly Ser Gly Gly Gly Ser Gly Gly Gly Ser
                165                 170                 175
Gly Gly Gly Gly Ser Ala Ile Gln Met Thr Gln Ser Pro Ser Ser Leu
            180                 185                 190
Ser Ala Ser Val Gly Asp Arg Val Thr Ile Thr Cys Arg Ala Ser Gln
            195                 200                 205
Gly Ile Arg Asn Asp Leu Gly Trp Tyr Gln Gln Lys Pro Gly Lys Ala
            210                 215                 220
Pro Glu Leu Leu Ile Tyr Ala Ala Ser Ser Leu Gln Ser Gly Val Pro
225                 230                 235                 240
Ser Arg Phe Ser Gly Ser Gly Ser Gly Thr Asp Phe Thr Leu Thr Ile
                245                 250                 255
Ser Ser Leu Gln Pro Glu Asp Phe Ala Thr Tyr Tyr Cys Leu Gln Asp
            260                 265                 270
Tyr Asn Tyr Pro Leu Thr Phe Gly Pro Gly Thr Lys Val Asp Ile Lys
            275                 280                 285
Gly Gly Gly Gly Ser Cys Pro Tyr Ser Asn Pro Ser Leu Cys Gly Gly
            290                 295                 300
Gly Gly Ser Thr Thr Thr Pro Ala Pro Arg Pro Pro Thr Pro Ala Pro
305                 310                 315                 320
Thr Ile Ala Ser Gln Pro Leu Ser Leu Arg Pro Glu Ala Cys Arg Pro
                325                 330                 335
Ala Ala Gly Gly Ala Val His Thr Arg Gly Leu Asp Phe Ala Cys Asp
            340                 345                 350
Ile Tyr Ile Trp Ala Pro Leu Ala Gly Thr Cys Gly Val Leu Leu Leu
            355                 360                 365
Ser Leu Val Ile Thr Leu Tyr Cys Lys Arg Gly Arg Lys Lys Leu Leu
370                 375                 380
Tyr Ile Phe Lys Gln Pro Phe Met Arg Pro Val Gln Thr Thr Gln Glu
385                 390                 395                 400
Glu Asp Gly Cys Ser Cys Arg Phe Pro Glu Glu Glu Gly Gly Cys
                405                 410                 415
Glu Leu Arg Val Lys Phe Ser Arg Ser Ala Asp Ala Pro Ala Tyr Gln
            420                 425                 430
Gln Gly Gln Asn Gln Leu Tyr Asn Glu Leu Asn Leu Gly Arg Arg Glu
            435                 440                 445
Glu Tyr Asp Val Leu Asp Lys Arg Arg Gly Arg Asp Pro Glu Met Gly
            450                 455                 460
Gly Lys Pro Arg Arg Lys Asn Pro Gln Glu Gly Leu Tyr Asn Glu Leu
465                 470                 475                 480
Gln Lys Asp Lys Met Ala Glu Ala Tyr Ser Glu Ile Gly Met Lys Gly
            485                 490                 495
Glu Arg Arg Arg Gly Lys Gly His Asp Gly Leu Tyr Gln Gly Leu Ser
            500                 505                 510
Thr Ala Thr Lys Asp Thr Tyr Asp Ala Leu His Met Gln Ala Leu Pro
            515                 520                 525
Pro Arg Gly Gly Gly Ser Tyr Gln Pro Tyr Ala Pro Pro Arg Asp Phe
            530                 535                 540
Ala Ala Tyr Arg Ser
545

<210> SEQ ID NO 123
<211> LENGTH: 559
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 123

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
        130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
        180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
    290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
        340                 345                 350

Ile Tyr Ile Trp Ala Pro Leu Ala Gly Thr Cys Gly Val Leu Leu Leu
    355                 360                 365

Ser Leu Val Ile Thr Lys Arg Gly Arg Lys Lys Leu Leu Tyr Ile Phe
    370                 375                 380

```
Lys Gln Pro Phe Met Arg Pro Val Gln Thr Thr Gln Glu Glu Asp Gly
385                 390                 395                 400

Cys Ser Cys Arg Phe Pro Glu Glu Glu Gly Gly Cys Glu Leu Leu
            405                 410                 415

Tyr Cys Asn His Arg Asn Arg Arg Val Cys Lys Cys Pro Arg Pro
        420                 425                 430

Val Val Lys Ser Gly Asp Lys Pro Ser Leu Ser Ala Arg Tyr Val Arg
        435                 440                 445

Val Lys Phe Ser Arg Ser Ala Asp Ala Pro Ala Tyr Gln Gln Gly Gln
        450                 455                 460

Asn Gln Leu Tyr Asn Glu Leu Asn Leu Gly Arg Arg Glu Glu Tyr Asp
465                 470                 475                 480

Val Leu Asp Lys Arg Arg Gly Arg Asp Pro Glu Met Gly Gly Lys Pro
            485                 490                 495

Arg Arg Lys Asn Pro Gln Glu Gly Leu Tyr Asn Glu Leu Gln Lys Asp
                500                 505                 510

Lys Met Ala Glu Ala Tyr Ser Glu Ile Gly Met Lys Gly Glu Arg Arg
            515                 520                 525

Arg Gly Lys Gly His Asp Gly Leu Tyr Gln Gly Leu Ser Thr Ala Thr
        530                 535                 540

Lys Asp Thr Tyr Asp Ala Leu His Met Gln Ala Leu Pro Pro Arg
545                 550                 555

<210> SEQ ID NO 124
<211> LENGTH: 543
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190
```

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
            245                 250                 255

Ser Ser Leu Gln Pro Glu Asp Phe Ala Thr Tyr Tyr Cys Leu Gln Asp
        260                 265                 270

Tyr Asn Tyr Pro Leu Thr Phe Gly Pro Gly Thr Lys Val Asp Ile Lys
    275                 280                 285

Gly Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
        340                 345                 350

Ile Tyr Ile Trp Ala Pro Leu Ala Gly Thr Cys Gly Val Leu Leu Leu
    355                 360                 365

Ser Leu Val Ile Thr Lys Arg Gly Arg Lys Lys Leu Leu Tyr Ile Phe
370                 375                 380

Lys Gln Pro Phe Met Arg Pro Val Gln Thr Thr Gln Glu Glu Asp Gly
385                 390                 395                 400

Cys Ser Cys Arg Phe Pro Glu Glu Glu Gly Gly Cys Glu Leu Arg
            405                 410                 415

Arg Val Cys Lys Cys Pro Arg Arg Val Cys Lys Cys Pro Arg Arg
                420                 425                 430

Val Lys Phe Ser Arg Ser Ala Asp Ala Pro Ala Tyr Gln Gln Gly Gln
        435                 440                 445

Asn Gln Leu Tyr Asn Glu Leu Asn Leu Gly Arg Arg Glu Glu Tyr Asp
    450                 455                 460

Val Leu Asp Lys Arg Arg Gly Arg Asp Pro Glu Met Gly Gly Lys Pro
465                 470                 475                 480

Arg Arg Lys Asn Pro Gln Glu Gly Leu Tyr Asn Glu Leu Gln Lys Asp
            485                 490                 495

Lys Met Ala Glu Ala Tyr Ser Glu Ile Gly Met Lys Gly Glu Arg Arg
        500                 505                 510

Arg Gly Lys Gly His Asp Gly Leu Tyr Gln Gly Leu Ser Thr Ala Thr
    515                 520                 525

Lys Asp Thr Tyr Asp Ala Leu His Met Gln Ala Leu Pro Pro Arg
530                 535                 540

<210> SEQ ID NO 125
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Ala Leu Pro Val Thr Ala Leu Leu Leu Pro Leu Ala Leu Leu Leu

```
1               5                   10                  15
His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
            50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
            130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
            195                 200                 205

Gly Ile Arg Asn Asp Leu Gly Trp Tyr Gln Gln Lys Pro Gly Lys Ala
            210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
            245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
            275                 280                 285

Gly Gly Gly Gly Ser Cys Pro Tyr Ser Asn Pro Ser Leu Cys Gly Gly
            290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
            355                 360                 365

Ser Leu Val Ile Thr Leu Tyr Cys Lys Arg Gly Arg Lys Lys Leu Leu
            370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Gln
            420                 425                 430
```

```
Gln Gly Gln Asn Gln Leu Tyr Asn Glu Leu Asn Leu Gly Arg Arg Glu
        435                 440                 445

Glu Tyr Asp Val Leu Asp Lys Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
        485                 490                 495

Glu Arg Arg Arg Gly Lys Gly His Asp Gly Leu Tyr Gln Gly Leu Ser
        500                 505                 510

Thr Ala Thr Lys Asp Thr Tyr Asp Ala Leu His Met Gln Ala Leu Pro
        515                 520                 525

Pro Arg Gly Arg Val Lys Phe Ser Arg Ser Ala Asp Ala Pro Ala Tyr
        530                 535                 540

Gln Gln Gly Gln Asn Gln Leu Tyr Asn Glu Leu Asn Leu Gly Arg Arg
545                 550                 555                 560

Glu Glu Tyr Asp Val Leu Asp Lys Arg Gly Arg Asp Pro Glu Met
                    565                 570                 575

Gly Gly Lys Pro Arg Arg Lys Asn Pro Gln Glu Gly Leu Tyr Asn Glu
                580                 585                 590

Leu Gln Lys Asp Lys Met Ala Glu Ala Tyr Ser Glu Ile Gly Met Lys
        595                 600                 605

Gly Glu Arg Arg Arg Gly Lys Gly His Asp Gly Leu Tyr Gln Gly Leu
        610                 615                 620

Ser Thr Ala Thr Lys Asp Thr Tyr Asp Ala Leu His Met Gln Ala Leu
625                 630                 635                 640

Pro Pro Arg

<210> SEQ ID NO 126
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Tyr Ser
            85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140
```

```
Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
            165                 170                 175

Gly Gly Gly Gly Ser Ala Ile Gln Met Thr Gln Ser Pro Ser Ser Leu
        180                 185                 190

Ser Ala Ser Val Gly Asp Arg Val Thr Ile Thr Cys Arg Ala Ser Gln
            195                 200                 205

Gly Ile Arg Asn Asp Leu Gly Trp Tyr Gln Gln Lys Pro Gly Lys Ala
        210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
            245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
            355                 360                 365

Ser Leu Val Ile Thr Leu Tyr Cys Lys Arg Gly Arg Lys Lys Leu Leu
            370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
            405                 410                 415

Glu Leu Arg Val Lys Phe Ser Arg Ser Ala Asp Ala Pro Ala Tyr Gln
            420                 425                 430

Gln Gly Gln Asn Gln Leu Tyr Ala Glu Leu Asn Leu Gly Arg Arg Glu
            435                 440                 445

Glu Tyr Asp Val Leu Asp Lys Arg Arg Gly Arg Asp Pro Glu Met Gly
            450                 455                 460

Gly Lys Pro Arg Arg Lys Asn Pro Gln Glu Gly Leu Tyr Ala Glu Leu
465                 470                 475                 480

Gln Lys Asp Lys Met Ala Glu Ala Tyr Ser Glu Ile Gly Met Lys Gly
            485                 490                 495

Glu Arg Arg Arg Gly Lys Gly His Asp Gly Leu Tyr Ala Gly Leu Ser
            500                 505                 510

Thr Ala Thr Lys Asp Thr Tyr Asp Ala Leu His Met Gln Ala Leu Pro
            515                 520                 525

Pro Arg Arg Val Lys Phe Ser Arg Ser Ala Asp Ala Pro Ala Tyr Gln
            530                 535                 540

Gln Gly Gln Asn Gln Leu Tyr Ala Glu Leu Asn Leu Gly Arg Arg Glu
545                 550                 555                 560
```

```
Glu Tyr Asp Val Leu Asp Lys Arg Arg Gly Arg Asp Pro Glu Met Gly
            565                 570                 575

Gly Lys Pro Arg Arg Lys Asn Pro Gln Glu Gly Leu Tyr Ala Glu Leu
        580                 585                 590

Gln Lys Asp Lys Met Ala Glu Ala Tyr Ser Glu Ile Gly Met Lys Gly
    595                 600                 605

Glu Arg Arg Arg Gly Lys Gly His Asp Gly Leu Tyr Ala Gly Leu Ser
610                 615                 620

Thr Ala Thr Lys Asp Thr Tyr Asp Ala Leu His Met Gln Ala Leu Pro
625                 630                 635                 640

Pro Arg

<210> SEQ ID NO 127
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
50                  55                  60

Ser Gly Gly Ser Ile Ser Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270
```

Tyr Asn Tyr Pro Leu Thr Phe Gly Pro Gly Thr Lys Val Asp Ile Lys
            275                 280                 285

Gly Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
            355                 360                 365

Ser Leu Val Ile Thr Leu Tyr Cys Lys Arg Gly Arg Lys Lys Leu Leu
370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Gln
            420                 425                 430

Gln Gly Gln Asn Gln Leu Tyr Ala Glu Leu Asn Leu Gly Arg Arg Glu
        435                 440                 445

Glu Tyr Asp Val Leu Asp Lys Arg Gly Arg Asp Pro Glu Met Gly
    450                 455                 460

Gly Lys Asp Thr Gln Ala Leu Leu Arg Asn Asp Gln Val Tyr Ala Pro
465                 470                 475                 480

Leu Arg Asp Arg Asp Asp Ala Gln Tyr Ser His Leu Gly Gly Asn Lys
                485                 490                 495

Gly Pro Arg Arg Lys Asn Pro Gln Glu Gly Leu Tyr Ala Glu Leu Gln
            500                 505                 510

Lys Asp Lys Met Ala Glu Ala Tyr Ser Glu Ile Gly Met Ala Leu Pro
        515                 520                 525

Pro Arg Gly Arg Val Lys Phe Ser Arg Ser Ala Asp Glu Arg Pro Pro
    530                 535                 540

Pro Val Pro Asn Pro Asp Tyr Ala Pro Ile Arg Lys Gly Gln Arg Asp
545                 550                 555                 560

Leu Tyr Ser Gly Leu Asn Gln Arg Arg Gly Arg Asp Pro Glu Met Gly
                565                 570                 575

Gly Lys Glu Arg Arg Gly Lys Gly His Asp Gly Leu Tyr Ala Gly
            580                 585                 590

Leu Ser Thr Ala Thr Lys Asp Thr Tyr Asp Ala Leu His Met Gln Lys
        595                 600                 605

Gly Asp Lys Gln Thr Leu Leu Pro Asn Asp Gln Leu Tyr Ala Pro Leu
610                 615                 620

Lys Asp Arg Glu Asp Asp Gln Tyr Ser His Leu Gln Gly Asn Ala Leu
625                 630                 635                 640

Pro Pro Arg

<210> SEQ ID NO 128
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Met Ala Leu Pro Val Thr Ala Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
                100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
                180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
        210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
                260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
                340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Lys Arg Gly Arg Lys Lys Leu Leu
        370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
```

-continued

```
                405                 410                 415
Glu Leu Arg Val Lys Phe Ser Arg Ser Ala Asp Ala Pro Ala Tyr Gln
                420                 425                 430

Gln Gly Gln Asn Gln Leu Tyr Asn Glu Leu Asn Leu Gly Arg Arg Glu
            435                 440                 445

Glu Tyr Asp Val Leu Asp Lys Arg Gly Arg Asp Pro Glu Met Gly
    450                 455                 460

Gly Lys Asp Thr Gln Ala Leu Leu Arg Asn Asp Gln Val Tyr Gln Pro
465                 470                 475                 480

Leu Arg Asp Arg Asp Asp Ala Gln Tyr Ser His Leu Gly Gly Asn Lys
                485                 490                 495

Gly Pro Arg Arg Lys Asn Pro Gln Glu Gly Leu Tyr Asn Glu Leu Gln
            500                 505                 510

Lys Asp Lys Met Ala Glu Ala Tyr Ser Glu Ile Gly Met Ala Leu Pro
        515                 520                 525

Pro Arg Gly Arg Val Lys Phe Ser Arg Ser Ala Asp Glu Arg Pro Pro
    530                 535                 540

Pro Val Pro Asn Pro Asp Tyr Glu Pro Ile Arg Lys Gly Gln Arg Asp
545                 550                 555                 560

Leu Tyr Ser Gly Leu Asn Gln Arg Arg Gly Arg Asp Pro Glu Met Gly
                565                 570                 575

Gly Lys Glu Arg Arg Gly Lys Gly His Asp Gly Leu Tyr Gln Gly
            580                 585                 590

Leu Ser Thr Ala Thr Lys Asp Thr Tyr Asp Ala Leu His Met Gln Lys
        595                 600                 605

Gly Asp Lys Gln Thr Leu Leu Pro Asn Asp Gln Leu Tyr Gln Pro Leu
    610                 615                 620

Lys Asp Arg Glu Asp Asp Gln Tyr Ser His Leu Gln Gly Asn Ala Leu
625                 630                 635                 640

Pro Pro Arg
```

<210> SEQ ID NO 129
<211> LENGTH: 643
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
        50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
```

```
                115                 120                 125
Ala Ala Asp Thr Ala Val Tyr Tyr Cys Ala Arg Glu Ile Ile Val Gly
            130                 135                 140
Ala Thr His Phe Asp Tyr Trp Gly Gln Gly Thr Leu Val Thr Val Ser
145                 150                 155                 160
Ser Gly Gly Gly Gly Ser Gly Gly Gly Gly Ser Gly Gly Gly Gly Ser
                165                 170                 175
Gly Gly Gly Gly Ser Ala Ile Gln Met Thr Gln Ser Pro Ser Ser Leu
            180                 185                 190
Ser Ala Ser Val Gly Asp Arg Val Thr Ile Thr Cys Arg Ala Ser Gln
                195                 200                 205
Gly Ile Arg Asn Asp Leu Gly Trp Tyr Gln Gln Lys Pro Gly Lys Ala
            210                 215                 220
Pro Glu Leu Leu Ile Tyr Ala Ala Ser Ser Leu Gln Ser Gly Val Pro
225                 230                 235                 240
Ser Arg Phe Ser Gly Ser Gly Ser Gly Thr Asp Phe Thr Leu Thr Ile
                245                 250                 255
Ser Ser Leu Gln Pro Glu Asp Phe Ala Thr Tyr Tyr Cys Leu Gln Asp
            260                 265                 270
Tyr Asn Tyr Pro Leu Thr Phe Gly Pro Gly Thr Lys Val Asp Ile Lys
            275                 280                 285
Gly Gly Gly Gly Ser Cys Pro Tyr Ser Asn Pro Ser Leu Cys Gly Gly
            290                 295                 300
Gly Gly Ser Thr Thr Thr Pro Ala Pro Arg Pro Pro Thr Pro Ala Pro
305                 310                 315                 320
Thr Ile Ala Ser Gln Pro Leu Ser Leu Arg Pro Glu Ala Cys Arg Pro
                325                 330                 335
Ala Ala Gly Gly Ala Val His Thr Arg Gly Leu Asp Phe Ala Cys Asp
            340                 345                 350
Ile Tyr Ile Trp Ala Pro Leu Ala Gly Thr Cys Gly Val Leu Leu Leu
            355                 360                 365
Ser Leu Val Ile Thr Leu Tyr Cys Lys Arg Gly Arg Lys Lys Leu Leu
370                 375                 380
Tyr Ile Phe Lys Gln Pro Phe Met Arg Pro Val Gln Thr Thr Gln Glu
385                 390                 395                 400
Glu Asp Gly Cys Ser Cys Arg Phe Pro Glu Glu Glu Glu Gly Gly Cys
                405                 410                 415
Glu Leu Arg Val Lys Phe Ser Arg Ser Ala Asp Asp Thr Gln Ala Leu
            420                 425                 430
Leu Arg Asn Asp Gln Val Tyr Ala Pro Leu Arg Asp Arg Asp Asp Ala
            435                 440                 445
Gln Tyr Ser His Leu Gly Gly Asn Arg Gly Arg Asp Pro Glu Met Gly
            450                 455                 460
Gly Lys Ala Pro Ala Tyr Gln Gln Gly Gln Asn Gln Leu Tyr Ala Glu
465                 470                 475                 480
Leu Asn Leu Gly Arg Arg Glu Glu Tyr Asp Val Leu Asp Lys Arg Lys
                485                 490                 495
Gly Glu Arg Pro Pro Pro Val Pro Asn Pro Asp Tyr Ala Pro Ile Arg
            500                 505                 510
Lys Gly Gln Arg Asp Leu Tyr Ser Gly Leu Asn Gln Arg Ala Leu Pro
            515                 520                 525
Pro Arg Gly Arg Val Lys Phe Ser Arg Ser Ala Asp Pro Arg Arg Lys
            530                 535                 540
```

-continued

```
Asn Pro Gln Glu Gly Leu Tyr Ala Glu Leu Gln Lys Asp Lys Met Ala
545                 550                 555                 560

Glu Ala Tyr Ser Glu Ile Gly Met Arg Gly Arg Asp Pro Glu Met Gly
            565                 570                 575

Gly Lys Asp Lys Gln Thr Leu Leu Pro Asn Asp Gln Leu Tyr Ala Pro
        580                 585                 590

Leu Lys Asp Arg Glu Asp Asp Gln Tyr Ser His Leu Gln Gly Asn Lys
    595                 600                 605

Gly Glu Arg Arg Arg Gly Lys Gly His Asp Gly Leu Tyr Ala Gly Leu
610                 615                 620

Ser Thr Ala Thr Lys Asp Thr Tyr Asp Ala Leu His Met Gln Ala Leu
625                 630                 635                 640

Pro Pro Arg

<210> SEQ ID NO 130
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255
```

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
    290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Asp Thr Gln Ala Leu
            420                 425                 430

Leu Arg Asn Asp Gln Val Tyr Gln Pro Leu Arg Asp Arg Asp Asp Ala
        435                 440                 445

Gln Tyr Ser His Leu Gly Gly Asn Arg Gly Arg Asp Pro Glu Met Gly
    450                 455                 460

Gly Lys Ala Pro Ala Tyr Gln Gln Gly Gln Asn Gln Leu Tyr Asn Glu
465                 470                 475                 480

Leu Asn Leu Gly Arg Arg Glu Glu Tyr Asp Val Leu Asp Lys Arg Lys
                485                 490                 495

Gly Glu Arg Pro Pro Val Pro Asn Pro Asp Tyr Glu Pro Ile Arg
            500                 505                 510

Lys Gly Gln Arg Asp Leu Tyr Ser Gly Leu Asn Gln Arg Ala Leu Pro
        515                 520                 525

Pro Arg Gly Arg Val Lys Phe Ser Arg Ser Ala Asp Pro Arg Arg Lys
    530                 535                 540

Asn Pro Gln Glu Gly Leu Tyr Asn Glu Leu Gln Lys Asp Lys Met Ala
545                 550                 555                 560

Glu Ala Tyr Ser Glu Ile Gly Met Arg Gly Arg Asp Pro Glu Met Gly
                565                 570                 575

Gly Lys Asp Lys Gln Thr Leu Leu Pro Asn Asp Gln Leu Tyr Gln Pro
            580                 585                 590

Leu Lys Asp Arg Glu Asp Asp Gln Tyr Ser His Leu Gln Gly Asn Lys
        595                 600                 605

Gly Glu Arg Arg Arg Gly Lys Gly His Asp Gly Leu Tyr Gln Gly Leu
    610                 615                 620

Ser Thr Ala Thr Lys Asp Thr Tyr Asp Ala Leu His Met Gln Ala Leu
625                 630                 635                 640

Pro Pro Arg

<210> SEQ ID NO 131
<211> LENGTH: 643
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 131

```
Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
    275                 280                 285

Gly Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
        340                 345                 350

Ile Tyr Ile Trp Ala Pro Leu Ala Gly Thr Cys Gly Val Leu Leu Leu
    355                 360                 365

Ser Leu Val Ile Thr Leu Tyr Cys Lys Arg Gly Arg Lys Lys Leu Leu
370                 375                 380
```

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Gly Cys
            405                 410                 415

Glu Leu Arg Val Lys Phe Ser Arg Ser Ala Asp Asp Thr Gln Ala Leu
            420                 425                 430

Leu Arg Asn Asp Gln Val Tyr Gln Pro Leu Arg Asp Arg Asp Asp Ala
            435                 440                 445

Gln Tyr Ser His Leu Gly Gly Asn Arg Gly Arg Pro Glu Met Gly
    450                 455                 460

Gly Lys Glu Arg Pro Pro Val Pro Asn Pro Asp Tyr Glu Pro Ile
465                 470                 475                 480

Arg Lys Gly Gln Arg Asp Leu Tyr Ser Gly Leu Asn Gln Arg Lys Gly
            485                 490                 495

Asp Lys Gln Thr Leu Leu Pro Asn Asp Gln Leu Tyr Gln Pro Leu Lys
            500                 505                 510

Asp Arg Glu Asp Gln Tyr Ser His Leu Gly Asn Ala Leu Pro
            515                 520                 525

Pro Arg Gly Arg Val Lys Phe Ser Arg Ser Ala Asp Ala Pro Ala Tyr
530                 535                 540

Gln Gln Gly Gln Asn Gln Leu Tyr Asn Glu Leu Asn Leu Gly Arg Arg
545                 550                 555                 560

Glu Glu Tyr Asp Val Leu Asp Lys Arg Gly Arg Asp Pro Glu Met
            565                 570                 575

Gly Gly Lys Pro Arg Arg Lys Asn Pro Gln Glu Gly Leu Tyr Asn Glu
            580                 585                 590

Leu Gln Lys Asp Lys Met Ala Glu Ala Tyr Ser Glu Ile Gly Met Lys
            595                 600                 605

Gly Glu Arg Arg Arg Gly Lys Gly His Asp Gly Leu Tyr Gln Gly Leu
            610                 615                 620

Ser Thr Ala Thr Lys Asp Thr Tyr Asp Ala Leu His Met Gln Ala Leu
625                 630                 635                 640

Pro Pro Arg

<210> SEQ ID NO 132
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Ala Leu Pro Val Thr Ala Leu Leu Leu Pro Leu Ala Leu Leu Leu
1                   5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
            50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
            85                  90                  95

```
Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
            130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
            195                 200                 205

Gly Ile Arg Asn Asp Leu Gly Trp Tyr Gln Gln Lys Pro Gly Lys Ala
            210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
            245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
            275                 280                 285

Gly Gly Gly Gly Ser Cys Pro Tyr Ser Asn Pro Ser Leu Cys Gly Gly
            290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
            355                 360                 365

Ser Leu Val Ile Thr Leu Tyr Cys Lys Arg Gly Arg Lys Lys Leu Leu
            370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
            405                 410                 415

Glu Leu Arg Val Lys Phe Ser Arg Ser Ala Asp Ala Pro Ala Tyr Gln
            420                 425                 430

Gln Gly Gln Asn Gln Leu Tyr Asn Glu Leu Asn Leu Gly Arg Arg Glu
            435                 440                 445

Glu Tyr Asp Val Leu Asp Lys Arg Arg Gly Arg Asp Pro Glu Met Gly
            450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
            485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
```

```
                    515                 520                 525
Pro Arg Gly Arg Val Lys Phe Ser Arg Ser Ala Asp Asp Thr Gln Ala
            530                 535                 540

Leu Leu Arg Asn Asp Gln Val Tyr Gln Pro Leu Arg Asp Arg Asp Asp
545                 550                 555                 560

Ala Gln Tyr Ser His Leu Gly Gly Asn Arg Gly Arg Asp Pro Glu Met
                565                 570                 575

Gly Gly Lys Glu Arg Pro Pro Val Pro Asn Pro Asp Tyr Glu Pro
            580                 585                 590

Ile Arg Lys Gly Gln Arg Asp Leu Tyr Ser Gly Leu Asn Gln Arg Lys
                595                 600                 605

Gly Asp Lys Gln Thr Leu Leu Pro Asn Asp Gln Leu Tyr Gln Pro Leu
            610                 615                 620

Lys Asp Arg Glu Asp Asp Gln Tyr Ser His Leu Gln Gly Asn Ala Leu
625                 630                 635                 640

Pro Pro Arg

<210> SEQ ID NO 133
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
```

```
                225                 230                 235                 240
        Ser Arg Phe Ser Gly Ser Gly Ser Gly Thr Asp Phe Thr Leu Thr Ile
                        245                 250                 255

Ser Ser Leu Gln Pro Glu Asp Phe Ala Thr Tyr Tyr Cys Leu Gln Asp
                        260                 265                 270

Tyr Asn Tyr Pro Leu Thr Phe Gly Pro Gly Thr Lys Val Asp Ile Lys
                        275                 280                 285

Gly Gly Gly Gly Ser Cys Pro Tyr Ser Asn Pro Ser Leu Cys Gly Gly
                        290                 295                 300

Gly Gly Ser Thr Thr Thr Pro Ala Pro Arg Pro Pro Thr Pro Ala Pro
        305                 310                 315                 320

Thr Ile Ala Ser Gln Pro Leu Ser Leu Arg Pro Glu Ala Cys Arg Pro
                        325                 330                 335

Ala Ala Gly Gly Ala Val His Thr Arg Gly Leu Asp Phe Ala Cys Asp
                        340                 345                 350

Ile Tyr Ile Trp Ala Pro Leu Ala Gly Thr Cys Gly Val Leu Leu Leu
                        355                 360                 365

Ser Leu Val Ile Thr Leu Tyr Cys Lys Arg Gly Arg Lys Lys Leu Leu
                        370                 375                 380

Tyr Ile Phe Lys Gln Pro Phe Met Arg Pro Val Gln Thr Thr Gln Glu
        385                 390                 395                 400

Glu Asp Gly Cys Ser Cys Arg Phe Pro Glu Glu Glu Glu Gly Gly Cys
                        405                 410                 415

Glu Leu Arg Val Lys Phe Ser Arg Ser Ala Asp Ala Pro Ala Tyr Gln
                        420                 425                 430

Gln Gly Gln Asn Gln Leu Tyr Ala Glu Leu Asn Leu Gly Arg Arg Glu
                        435                 440                 445

Glu Tyr Asp Val Leu Asp Lys Arg Arg Gly Arg Asp Pro Glu Met Gly
                        450                 455                 460

Gly Lys Pro Arg Arg Lys Asn Pro Gln Glu Gly Leu Tyr Ala Glu Leu
        465                 470                 475                 480

Gln Lys Asp Lys Met Ala Glu Ala Tyr Ser Glu Ile Gly Met Lys Gly
                        485                 490                 495

Glu Arg Arg Arg Gly Lys Gly His Asp Gly Leu Tyr Ala Gly Leu Ser
                        500                 505                 510

Thr Ala Thr Lys Asp Thr Tyr Asp Ala Leu His Met Gln Ala Leu Pro
                        515                 520                 525

Pro Arg
            530

<210> SEQ ID NO 134
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Ala Leu Pro Val Thr Ala Leu Leu Leu Pro Leu Ala Leu Leu Leu
        1               5                   10                  15

His Ala Ala Arg Pro Gly Gly Gly Gly Ser Cys Pro Tyr Ser Asn Pro
                        20                  25                  30

Ser Leu Cys Gly Gly Gly Gly Ser Gln Leu Gln Leu Gln Glu Ser Gly
                        35                  40                  45
```

-continued

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
                100                 105                 110

Val Asp Thr Ser Lys Asn Gln Phe Ser Leu Arg Leu Ser Ser Val Thr
            115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
                180                 185                 190

Ser Ala Ser Val Gly Asp Arg Val Thr Ile Thr Cys Arg Ala Ser Gln
    195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
                260                 265                 270

Tyr Asn Tyr Pro Leu Thr Phe Gly Pro Gly Thr Lys Val Asp Ile Lys
    275                 280                 285

Gly Gly Gly Gly Ser Cys Pro Tyr Ser Asn Pro Ser Leu Cys Gly Gly
    290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
                340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Asp Thr Gln Ala Leu
                420                 425                 430

Leu Arg Asn Asp Gln Val Tyr Gln Pro Leu Arg Asp Arg Asp Asp Ala
            435                 440                 445

Gln Tyr Ser His Leu Gly Gly Asn Arg Gly Arg Asp Pro Glu Met Gly
    450                 455                 460

Gly Lys Pro Arg Arg Lys Asn Pro Gln Glu Gly Leu Tyr Asn Glu Leu

```
               465                 470                 475                 480
Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
                500                 505                 510

Thr Ala Thr Lys Asp Thr Tyr Asp Ala Leu His Met Gln Ala Leu Pro
                515                 520                 525

Pro Arg
    530

<210> SEQ ID NO 135
<211> LENGTH: 529
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285
```

Gly Gly Gly Ser Cys Pro Tyr Ser Asn Pro Ser Leu Cys Gly Gly
290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Lys Arg Gly Arg Lys Lys Leu Leu
370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Glu Arg Pro Pro Pro
            420                 425                 430

Val Pro Asn Pro Asp Tyr Glu Pro Ile Arg Lys Gly Gln Arg Asp Leu
        435                 440                 445

Tyr Ser Gly Leu Asn Gln Arg Arg Gly Arg Asp Pro Glu Met Gly Gly
450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510

Ala Thr Lys Asp Thr Tyr Asp Ala Leu His Met Gln Ala Leu Pro Pro
        515                 520                 525

Arg

<210> SEQ ID NO 136
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Gln Leu Gln Leu Gln Glu Ser Gly
            35                  40                  45

Pro Gly Leu Val Lys Pro Ser Glu Thr Leu Ser Leu Thr Cys Thr Val
        50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

```
Val Asp Thr Ser Lys Asn Gln Phe Ser Leu Arg Leu Ser Val Thr
            115                 120                 125
Ala Ala Asp Thr Ala Val Tyr Tyr Cys Ala Arg Glu Ile Ile Val Gly
130                 135                 140
Ala Thr His Phe Asp Tyr Trp Gly Gln Gly Thr Leu Val Thr Val Ser
145                 150                 155                 160
Ser Gly Gly Gly Gly Ser Gly Gly Gly Ser Gly Gly Gly Gly Ser
            165                 170                 175
Gly Gly Gly Gly Ser Ala Ile Gln Met Thr Gln Ser Pro Ser Ser Leu
            180                 185                 190
Ser Ala Ser Val Gly Asp Arg Val Thr Ile Thr Cys Arg Ala Ser Gln
            195                 200                 205
Gly Ile Arg Asn Asp Leu Gly Trp Tyr Gln Gln Lys Pro Gly Lys Ala
            210                 215                 220
Pro Glu Leu Leu Ile Tyr Ala Ala Ser Ser Leu Gln Ser Gly Val Pro
225                 230                 235                 240
Ser Arg Phe Ser Gly Ser Gly Ser Gly Thr Asp Phe Thr Leu Thr Ile
            245                 250                 255
Ser Ser Leu Gln Pro Glu Asp Phe Ala Thr Tyr Tyr Cys Leu Gln Asp
            260                 265                 270
Tyr Asn Tyr Pro Leu Thr Phe Gly Pro Gly Thr Lys Val Asp Ile Lys
            275                 280                 285
Gly Gly Gly Gly Ser Cys Pro Tyr Ser Asn Pro Ser Leu Cys Gly Gly
            290                 295                 300
Gly Gly Ser Thr Thr Thr Pro Ala Pro Arg Pro Pro Thr Pro Ala Pro
305                 310                 315                 320
Thr Ile Ala Ser Gln Pro Leu Ser Leu Arg Pro Glu Ala Cys Arg Pro
            325                 330                 335
Ala Ala Gly Gly Ala Val His Thr Arg Gly Leu Asp Phe Ala Cys Asp
            340                 345                 350
Ile Tyr Ile Trp Ala Pro Leu Ala Gly Thr Cys Gly Val Leu Leu Leu
            355                 360                 365
Ser Leu Val Ile Thr Leu Tyr Cys Lys Arg Gly Arg Lys Lys Leu Leu
            370                 375                 380
Tyr Ile Phe Lys Gln Pro Phe Met Arg Pro Val Gln Thr Thr Gln Glu
385                 390                 395                 400
Glu Asp Gly Cys Ser Cys Arg Phe Pro Glu Glu Glu Glu Gly Gly Cys
            405                 410                 415
Glu Leu Arg Val Lys Phe Ser Arg Ser Ala Asp Asp Lys Gln Thr Leu
            420                 425                 430
Leu Pro Asn Asp Gln Leu Tyr Gln Pro Leu Lys Asp Arg Glu Asp Asp
            435                 440                 445
Gln Tyr Ser His Leu Gln Gly Asn Arg Gly Arg Asp Pro Glu Met Gly
            450                 455                 460
Gly Lys Pro Arg Arg Lys Asn Pro Gln Glu Gly Leu Tyr Asn Glu Leu
465                 470                 475                 480
Gln Lys Asp Lys Met Ala Glu Ala Tyr Ser Glu Ile Gly Met Lys Gly
            485                 490                 495
Glu Arg Arg Arg Gly Lys Gly His Asp Gly Leu Tyr Gln Gly Leu Ser
            500                 505                 510
Thr Ala Thr Lys Asp Thr Tyr Asp Ala Leu His Met Gln Ala Leu Pro
            515                 520                 525
Pro Arg
```

<210> SEQ ID NO 137
<211> LENGTH: 530
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
            20                  25                  30

Ser Leu Cys Gly Gly Gly Ser Gln Leu Gln Leu Gln Glu Ser Gly
        35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65              70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Ser Leu Gln Ser Gly Val Pro
225                 230                 235                 240

Ser Arg Phe Ser Gly Ser Gly Ser Gly Thr Asp Phe Thr Leu Thr Ile
                245                 250                 255

Ser Ser Leu Gln Pro Glu Asp Phe Ala Thr Tyr Tyr Cys Leu Gln Asp
            260                 265                 270

Tyr Asn Tyr Pro Leu Thr Phe Gly Pro Gly Thr Lys Val Asp Ile Lys
        275                 280                 285

Gly Gly Gly Gly Ser Cys Pro Tyr Ser Asn Pro Ser Leu Cys Gly Gly
    290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu
            355                 360                 365

Ser Leu Val Ile Thr Leu Tyr Cys Lys Arg Gly Arg Lys Lys Leu Leu
370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
            405                 410                 415

Glu Leu Arg Val Lys Phe Ser Arg Ser Ala Asp Ala Pro Ala Tyr Gln
            420                 425                 430

Leu Arg Asn Asp Gln Val Tyr Gln Pro Leu Arg Asp Arg Asp Asp Ala
            435                 440                 445

Gln Tyr Ser His Leu Gly Gly Asn Arg Gly Arg Asp Pro Glu Met Gly
            450                 455                 460

Gly Lys Glu Arg Pro Pro Val Pro Asn Pro Asp Tyr Glu Pro Ile
465                 470                 475                 480

Arg Lys Gly Gln Arg Asp Leu Tyr Ser Gly Leu Asn Gln Arg Lys Gly
                485                 490                 495

Asp Lys Gln Thr Leu Leu Pro Asn Asp Gln Leu Tyr Gln Pro Leu Lys
            500                 505                 510

Asp Arg Glu Asp Asp Gln Tyr Ser His Leu Gln Gly Asn Ala Leu Pro
            515                 520                 525

Pro Arg
    530

<210> SEQ ID NO 138
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Gly Gly Gly Gly Ser Gln Leu Gln Leu Gln Glu Ser Gly
                35                  40                  45

Pro Gly Leu Val Lys Pro Ser Glu Thr Leu Ser Leu Thr Cys Thr Val
    50                  55                  60

Ser Gly Gly Ser Ile Ser Ser Ser Tyr Tyr Trp Gly Trp Ile Arg
65                  70                  75                  80

Gln Pro Pro Gly Lys Gly Leu Glu Trp Ile Gly Ser Ile Tyr Tyr Ser
                85                  90                  95

Gly Asn Ile Tyr His Asn Pro Ser Leu Lys Ser Arg Val Ser Ile Ser
            100                 105                 110

Val Asp Thr Ser Lys Asn Gln Phe Ser Leu Arg Leu Ser Ser Val Thr
        115                 120                 125

Ala Ala Asp Thr Ala Val Tyr Tyr Cys Ala Arg Glu Ile Ile Val Gly
    130                 135                 140

Ala Thr His Phe Asp Tyr Trp Gly Gln Gly Thr Leu Val Thr Val Ser
145                 150                 155                 160

Ser Gly Gly Gly Gly Ser Gly Gly Gly Gly Ser Gly Gly Gly Gly Ser
                165                 170                 175

Gly Gly Gly Gly Ser Ala Ile Gln Met Thr Gln Ser Pro Ser Ser Leu
            180                 185                 190

Ser Ala Ser Val Gly Asp Arg Val Thr Ile Thr Cys Arg Ala Ser Gln
        195                 200                 205

Gly Ile Arg Asn Asp Leu Gly Trp Tyr Gln Gln Lys Pro Gly Lys Ala
    210                 215                 220

Pro Glu Leu Leu Ile Tyr Ala Ala Ser Leu Gln Ser Gly Val Pro
225                 230                 235                 240

Ser Arg Phe Ser Gly Ser Gly Ser Gly Thr Asp Phe Thr Leu Thr Ile
            245                 250                 255

Ser Ser Leu Gln Pro Glu Asp Phe Ala Thr Tyr Tyr Cys Leu Gln Asp
        260                 265                 270

Tyr Asn Tyr Pro Leu Thr Phe Gly Pro Gly Thr Lys Val Asp Ile Lys
    275                 280                 285

Gly Gly Gly Gly Ser Cys Pro Tyr Ser Asn Pro Ser Leu Cys Gly Gly
            290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
        340                 345                 350

Ile Tyr Ile Trp Ala Pro Leu Ala Gly Thr Cys Gly Val Leu Leu Leu
    355                 360                 365

Ser Leu Val Ile Thr Leu Tyr Cys Lys Arg Gly Arg Lys Lys Leu Leu
370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Gly Cys
            405                 410                 415

Glu Leu Arg Val Lys Phe Ser Arg Ser Ala Asp Ala Pro Ala Tyr Gln
        420                 425                 430

Gln Gly Gln Asn Gln Leu Tyr Ala Glu Leu Asn Leu Gly Arg Arg Glu
    435                 440                 445

Glu Tyr Asp Val Leu Asp Lys Arg Arg Gly Arg Asp Pro Glu Met Gly
450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
            485                 490                 495

Glu Arg Arg Arg Gly Lys Gly His Asp Gly Leu Tyr Gln Gly Leu Ser
        500                 505                 510

Thr Ala Thr Lys Asp Thr Tyr Asp Ala Leu His Met Gln Ala Leu Pro
    515                 520                 525

Pro Arg
    530

<210> SEQ ID NO 139
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 139

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Thr Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Phe Tyr Cys Ala Ile Asp Pro Glu Tyr Tyr Asp Ile Leu Thr
        115                 120                 125

Gly Gly Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ala Met Ser Ala
                165                 170                 175

Ser Val Gly Asp Arg Val Thr Ile Thr Cys Arg Ala Ser Gln Gly Ile
            180                 185                 190

Ser Asn Tyr Leu Ala Trp Phe Gln Gln Lys Pro Gly Lys Val Pro Lys
        195                 200                 205

Arg Leu Ile Tyr Ala Ala Ser Ser Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Asn His Arg Asn Arg Arg Val Cys Lys Cys Pro Arg
            340                 345                 350

Pro Val Val Lys Ser Gly Asp Lys Pro Ser Leu Ser Ala Arg Tyr Val
        355                 360                 365

Lys Arg Gly Arg Lys Lys Leu Leu Tyr Ile Phe Lys Gln Pro Phe Met
    370                 375                 380

Arg Pro Val Gln Thr Thr Gln Glu Glu Asp Gly Cys Ser Cys Arg Phe
385                 390                 395                 400

Pro Glu Glu Glu Glu Gly Gly Cys Glu Leu Arg Val Lys Phe Ser Arg
                405                 410                 415
```

```
Ser Ala Asp Ala Pro Ala Tyr Gln Gln Gly Gln Asn Gln Leu Tyr Asn
                420                 425                 430

Glu Leu Asn Leu Gly Arg Arg Glu Glu Tyr Asp Val Leu Asp Lys Arg
            435                 440                 445

Arg Gly Arg Asp Pro Glu Met Gly Gly Lys Pro Arg Arg Lys Asn Pro
450                 455                 460

Gln Glu Gly Leu Tyr Asn Glu Leu Gln Lys Asp Lys Met Ala Glu Ala
465                 470                 475                 480

Tyr Ser Glu Ile Gly Met Lys Gly Glu Arg Arg Arg Gly Lys Gly His
                485                 490                 495

Asp Gly Leu Tyr Gln Gly Leu Ser Thr Ala Thr Lys Asp Thr Tyr Asp
                500                 505                 510

Ala Leu His Met Gln Ala Leu Pro Pro Arg
            515                 520

<210> SEQ ID NO 140
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Thr Ile Ser Gly Ser Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Phe Tyr Cys Ala Ile Asp Pro Glu Tyr Tyr Asp Ile Leu Thr
        115                 120                 125

Gly Gly Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ala Met Ser Ala
                165                 170                 175

Ser Val Gly Asp Arg Val Thr Ile Thr Cys Arg Ala Ser Gln Gly Ile
            180                 185                 190

Ser Asn Tyr Leu Ala Trp Phe Gln Gln Lys Pro Gly Lys Val Pro Lys
        195                 200                 205

Arg Leu Ile Tyr Ala Ala Ser Ser Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
```

```
                    245                 250                 255
Phe Pro Leu Thr Phe Gly Gly Thr Lys Val Glu Ile Lys Thr Thr
                260                 265                 270

Thr Pro Ala Pro Arg Pro Pro Thr Pro Ala Pro Thr Ile Ala Ser Gln
                275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Arg Arg Val Cys Lys Cys Pro Arg Arg Val Cys Lys Cys Pro Arg
                340                 345                 350

Lys Arg Gly Arg Lys Lys Leu Leu Tyr Ile Phe Lys Gln Pro Phe Met
                355                 360                 365

Arg Pro Val Gln Thr Thr Gln Glu Glu Asp Gly Cys Ser Cys Arg Phe
            370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Gln Gln Gly Gln Asn Gln Leu Tyr Asn
                    405                 410                 415

Glu Leu Asn Leu Gly Arg Arg Glu Glu Tyr Asp Val Leu Asp Lys Arg
                420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
        450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
                500                 505

<210> SEQ ID NO 141
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
        50                  55                  60

Gly Leu Glu Trp Val Ser Thr Ile Ser Gly Ser Gly Ser Thr Tyr
65                  70                  75                  80

Tyr Ala Asp Ser Val Lys Gly Arg Phe Thr Ile Ser Arg Asp Asn Ser
                85                  90                  95
```

```
Lys Asn Thr Leu Tyr Leu Gln Met Asn Ser Leu Arg Ala Glu Asp Thr
                100                 105                 110

Ala Val Phe Tyr Cys Ala Ile Asp Pro Glu Tyr Tyr Asp Ile Leu Thr
            115                 120                 125

Gly Gly Asp Tyr Trp Gly Gln Gly Thr Leu Val Thr Val Ser Ser Gly
        130                 135                 140

Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ala Met Ser Ala
            165                 170                 175

Ser Val Gly Asp Arg Val Thr Ile Thr Cys Arg Ala Ser Gln Gly Ile
            180                 185                 190

Ser Asn Tyr Leu Ala Trp Phe Gln Gln Lys Pro Gly Lys Val Pro Lys
        195                 200                 205

Arg Leu Ile Tyr Ala Ala Ser Ser Leu Gln Ser Gly Val Pro Ser Arg
210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Gly Thr Lys Val Glu Ile Lys Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Gly Gly Gly Ser Tyr Gln Pro Tyr Ala Pro Pro Arg Asp
            340                 345                 350

Phe Ala Ala Tyr Arg Ser Gly Gly Gly Ser Lys Arg Gly Arg Lys Lys
            355                 360                 365

Leu Leu Tyr Ile Phe Lys Gln Pro Phe Met Arg Pro Val Gln Thr Thr
        370                 375                 380

Gln Glu Glu Asp Gly Cys Ser Cys Arg Phe Pro Glu Glu Glu Glu Gly
385                 390                 395                 400

Gly Cys Glu Leu Arg Val Lys Phe Ser Arg Ser Ala Asp Ala Pro Ala
                405                 410                 415

Tyr Gln Gln Gly Gln Asn Gln Leu Tyr Asn Glu Leu Asn Leu Gly Arg
            420                 425                 430

Arg Glu Glu Tyr Asp Val Leu Asp Lys Arg Arg Gly Arg Asp Pro Glu
        435                 440                 445

Met Gly Gly Lys Pro Arg Arg Lys Asn Pro Gln Glu Gly Leu Tyr Asn
        450                 455                 460

Glu Leu Gln Lys Asp Lys Met Ala Glu Ala Tyr Ser Glu Ile Gly Met
465                 470                 475                 480

Lys Gly Glu Arg Arg Arg Gly Lys Gly His Asp Gly Leu Tyr Gln Gly
                485                 490                 495

Leu Ser Thr Ala Thr Lys Asp Thr Tyr Asp Ala Leu His Met Gln Ala
            500                 505                 510

Leu Pro Pro Arg
```

<210> SEQ ID NO 142
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Thr Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Phe Tyr Cys Ala Ile Asp Pro Glu Tyr Tyr Asp Ile Leu Thr
        115                 120                 125

Gly Gly Asp Tyr Trp Gly Gln Gly Thr Leu Val Thr Val Ser Ser Gly
    130                 135                 140

Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ala Met Ser Ala
                165                 170                 175

Ser Val Gly Asp Arg Val Thr Ile Thr Cys Arg Ala Ser Gln Gly Ile
            180                 185                 190

Ser Asn Tyr Leu Ala Trp Phe Gln Gln Lys Pro Gly Lys Val Pro Lys
        195                 200                 205

Arg Leu Ile Tyr Ala Ala Ser Ser Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Gly Gly Ser Phe Gln Pro Phe Ala Pro Pro Arg Asp
            340                 345                 350
```

```
Phe Ala Ala Phe Arg Ser Gly Gly Ser Lys Arg Gly Arg Lys Lys
                355                 360                 365

Leu Leu Tyr Ile Phe Lys Gln Pro Phe Met Arg Pro Val Gln Thr Thr
    370                 375                 380

Gln Glu Glu Asp Gly Cys Ser Cys Arg Phe Pro Glu Glu Glu Glu Gly
385                 390                 395                 400

Gly Cys Glu Leu Arg Val Lys Phe Ser Arg Ser Ala Asp Ala Pro Ala
                405                 410                 415

Tyr Gln Gln Gly Gln Asn Gln Leu Tyr Asn Glu Leu Asn Leu Gly Arg
                420                 425                 430

Arg Glu Glu Tyr Asp Val Leu Asp Lys Arg Arg Gly Arg Asp Pro Glu
            435                 440                 445

Met Gly Gly Lys Pro Arg Arg Lys Asn Pro Gln Glu Gly Leu Tyr Asn
            450                 455                 460

Glu Leu Gln Lys Asp Lys Met Ala Glu Ala Tyr Ser Glu Ile Gly Met
465                 470                 475                 480

Lys Gly Glu Arg Arg Arg Gly Lys Gly His Asp Gly Leu Tyr Gln Gly
                485                 490                 495

Leu Ser Thr Ala Thr Lys Asp Thr Tyr Asp Ala Leu His Met Gln Ala
                500                 505                 510

Leu Pro Pro Arg
            515

<210> SEQ ID NO 143
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
    50                  55                  60

Gly Leu Glu Trp Val Ser Thr Ile Ser Gly Gly Ser Thr Tyr
65              70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Phe Tyr Cys Ala Ile Asp Pro Glu Tyr Tyr Asp Ile Leu Thr
        115                 120                 125

Gly Gly Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ala Met Ser Ala
                165                 170                 175

Ser Val Gly Asp Arg Val Thr Ile Thr Cys Arg Ala Ser Gln Gly Ile
                180                 185                 190
```

```
Ser Asn Tyr Leu Ala Trp Phe Gln Gln Lys Pro Gly Lys Val Pro Lys
        195                 200                 205

Arg Leu Ile Tyr Ala Ala Ser Ser Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Thr Lys Val Glu Ile Lys Thr Thr
                260                 265                 270

Thr Pro Ala Pro Arg Pro Pro Thr Pro Ala Pro Thr Ile Ala Ser Gln
                275                 280                 285

Pro Leu Ser Leu Arg Pro Glu Ala Cys Arg Pro Ala Ala Gly Gly Ala
                290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
                450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Gly Gly
                485                 490                 495

Gly Ser Arg Val Cys Lys Cys Pro Arg Pro Val
                500                 505

<210> SEQ ID NO 144
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
```

-continued

```
                35                  40                  45
Thr Phe Ser Ser Tyr Ala Met Asn Trp Val Arg Gln Ala Pro Gly Lys
 50                  55                  60

Gly Leu Glu Trp Val Ser Thr Ile Ser Gly Ser Gly Gly Ser Thr Tyr
 65                  70                  75                  80

Tyr Ala Asp Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Phe Tyr Cys Ala Ile Asp Pro Glu Tyr Tyr Asp Ile Leu Thr
            115                 120                 125

Gly Gly Asp Tyr Trp Gly Gln Gly Thr Leu Val Thr Val Ser Ser Gly
            130                 135                 140

Gly Gly Gly Ser Gly Gly Gly Ser Gly Gly Gly Ser Gly Gly Gly Gly
145                 150                 155                 160

Gly Gly Ser Asp Ile Gln Met Thr Gln Ser Pro Ser Ala Met Ser Ala
                165                 170                 175

Ser Val Gly Asp Arg Val Thr Ile Thr Cys Arg Ala Ser Gln Gly Ile
                180                 185                 190

Ser Asn Tyr Leu Ala Trp Phe Gln Gln Lys Pro Gly Lys Val Pro Lys
            195                 200                 205

Arg Leu Ile Tyr Ala Ala Ser Ser Leu Gln Ser Gly Val Pro Ser Arg
210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Gly Thr Lys Val Glu Ile Lys Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460
```

```
Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Gly Gly
                485                 490                 495

Ser Phe Gln Pro Phe Ala Pro Pro Arg Asp Phe Ala Ala Phe Arg Ser
            500                 505                 510

<210> SEQ ID NO 145
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Thr Ile Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Phe Tyr Cys Ala Ile Asp Pro Glu Tyr Tyr Asp Ile Leu Thr
        115                 120                 125

Gly Gly Asp Tyr Trp Gly Gln Gly Thr Leu Val Thr Val Ser Ser Gly
    130                 135                 140

Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ala Met Ser Ala
                165                 170                 175

Ser Val Gly Asp Arg Val Thr Ile Thr Cys Arg Ala Ser Gln Gly Ile
            180                 185                 190

Ser Asn Tyr Leu Ala Trp Phe Gln Gln Lys Pro Gly Lys Val Pro Lys
        195                 200                 205

Arg Leu Ile Tyr Ala Ala Ser Ser Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
```

```
                305                 310                 315                 320
        Pro Leu Ala Gly Thr Cys Gly Val Leu Leu Ser Leu Val Ile Thr
                        325                 330                 335
        Lys Arg Gly Arg Lys Leu Leu Tyr Ile Phe Lys Gln Pro Phe Met
                        340                 345                 350
        Arg Pro Val Gln Thr Thr Gln Glu Asp Gly Cys Ser Cys Arg Phe
                        355                 360                 365
        Pro Glu Glu Glu Gly Gly Cys Glu Leu Leu Tyr Cys Asn His Arg
                370                 375                 380
        Asn Arg Arg Arg Val Cys Lys Cys Pro Arg Pro Val Val Lys Ser Gly
        385                 390                 395                 400
        Asp Lys Pro Ser Leu Ser Ala Arg Tyr Val Arg Val Lys Phe Ser Arg
                        405                 410                 415
        Ser Ala Asp Ala Pro Ala Tyr Gln Gln Gly Gln Asn Gln Leu Tyr Asn
                        420                 425                 430
        Glu Leu Asn Leu Gly Arg Arg Glu Glu Tyr Asp Val Leu Asp Lys Arg
                        435                 440                 445
        Arg Gly Arg Asp Pro Glu Met Gly Gly Lys Pro Arg Arg Lys Asn Pro
                        450                 455                 460
        Gln Glu Gly Leu Tyr Asn Glu Leu Gln Lys Asp Lys Met Ala Glu Ala
        465                 470                 475                 480
        Tyr Ser Glu Ile Gly Met Lys Gly Glu Arg Arg Arg Gly Lys Gly His
                        485                 490                 495
        Asp Gly Leu Tyr Gln Gly Leu Ser Thr Ala Thr Lys Asp Thr Tyr Asp
                        500                 505                 510
        Ala Leu His Met Gln Ala Leu Pro Pro Arg
                        515                 520

<210> SEQ ID NO 146
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Met Ala Leu Pro Val Thr Ala Leu Leu Leu Pro Leu Ala Leu Leu Leu
        1               5                   10                  15
        His Ala Ala Arg Pro Glu Val Gln Leu Leu Glu Ser Gly Gly Gly Leu
                        20                  25                  30
        Val Gln Pro Gly Gly Ser Leu Arg Leu Ser Cys Ala Ala Ser Gly Phe
                        35                  40                  45
        Thr Phe Ser Ser Tyr Ala Met Asn Trp Val Arg Gln Ala Pro Gly Lys
                        50                  55                  60
        Gly Leu Glu Trp Val Ser Thr Ile Ser Gly Ser Gly Gly Ser Thr Tyr
        65                  70                  75                  80
        Tyr Ala Asp Ser Val Lys Gly Arg Phe Thr Ile Ser Arg Asp Asn Ser
                        85                  90                  95
        Lys Asn Thr Leu Tyr Leu Gln Met Asn Ser Leu Arg Ala Glu Asp Thr
                        100                 105                 110
        Ala Val Phe Tyr Cys Ala Ile Asp Pro Glu Tyr Tyr Asp Ile Leu Thr
                        115                 120                 125
        Gly Gly Asp Tyr Trp Gly Gln Gly Thr Leu Val Thr Val Ser Ser Gly
                        130                 135                 140
```

```
Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ala Met Ser Ala
            165                 170                 175

Ser Val Gly Asp Arg Val Thr Ile Thr Cys Arg Ala Ser Gln Gly Ile
        180                 185                 190

Ser Asn Tyr Leu Ala Trp Phe Gln Gln Lys Pro Gly Lys Val Pro Lys
    195                 200                 205

Arg Leu Ile Tyr Ala Ala Ser Ser Leu Gln Ser Gly Val Pro Ser Arg
210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Phe Cys Leu Gln His Asp Ser
                245                 250                 255

Phe Pro Leu Thr Phe Gly Gly Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
370                 375                 380

Pro Arg Arg Val Cys Lys Cys Pro Arg Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147
```

```
Gly Gly Gly Gly Ser Gly Gly Gly Ser Gly Gly Gly Ser
1               5                   10                  15

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Gly Gly Gly Gly
1               5

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Gly Gly Gly Gly Ser
1               5

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Met Ala Leu Pro Val Thr Ala Leu Leu Leu Pro Leu Ala Leu Leu Leu
1               5                   10                  15

His Ala Ala Arg Pro
            20

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Met Ile Pro Ala Val Val Leu Leu Leu Leu Leu Leu Val Glu Gln Ala
1               5                   10                  15

Ala Ala

<210> SEQ ID NO 152
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Ala Glu Leu
1
```

```
<210> SEQ ID NO 153
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Ala Gly Leu
1

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Tyr Ala Pro Leu
1

<210> SEQ ID NO 155
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Tyr Ala Pro Ile
1

<210> SEQ ID NO 156
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Tyr Asn Glu Leu
1

<210> SEQ ID NO 157
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Asn Gly Leu
1
```